United States Patent
Anderson et al.

(10) Patent No.: US 9,540,324 B2
(45) Date of Patent: Jan. 10, 2017

(54) SELECTIVE OCTAHYDRO-CYCLOPENTA[C] PYRROLE NEGATIVE MODULATORS OF NR2B

(71) Applicant: Mnemosyne Pharmaceuticals, Inc., Providence, RI (US)

(72) Inventors: David R. Anderson, Salem, CT (US); Robert A. Volkmann, Mystic, CT (US); Frank S. Menniti, Mystic, CT (US)

(73) Assignee: LUC THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/498,462

(22) Filed: Sep. 26, 2014

(65) Prior Publication Data

US 2015/0225342 A1    Aug. 13, 2015

Related U.S. Application Data

(60) Provisional application No. 61/883,050, filed on Sep. 26, 2013.

(51) Int. Cl.

| | | |
|---|---|---|
| C07D 209/52 | (2006.01) |
| C07D 403/12 | (2006.01) |
| C07D 401/04 | (2006.01) |
| C07D 401/06 | (2006.01) |
| C07D 401/10 | (2006.01) |
| C07D 401/12 | (2006.01) |
| C07D 403/04 | (2006.01) |
| C07D 403/06 | (2006.01) |
| C07D 403/10 | (2006.01) |
| C07D 403/14 | (2006.01) |
| C07D 413/06 | (2006.01) |
| C07D 205/04 | (2006.01) |
| C07D 401/14 | (2006.01) |
| C07D 487/04 | (2006.01) |

(52) U.S. Cl.
CPC ........... *C07D 209/52* (2013.01); *C07D 205/04* (2013.01); *C07D 401/04* (2013.01); *C07D 401/06* (2013.01); *C07D 401/10* (2013.01); *C07D 401/12* (2013.01); *C07D 401/14* (2013.01); *C07D 403/04* (2013.01); *C07D 403/06* (2013.01); *C07D 403/10* (2013.01); *C07D 403/12* (2013.01); *C07D 403/14* (2013.01); *C07D 413/06* (2013.01); *C07D 487/04* (2013.01)

(58) Field of Classification Search
CPC .................................................. C07D 209/52
USPC ................... 548/515; 514/412, 421
See application file for complete search history.

(56) References Cited

U.S. PATENT DOCUMENTS

| | | | |
|---|---|---|---|
| 5,262,564 | A | 11/1993 | Kun et al. |
| 5,532,243 | A | 7/1996 | Gilligan |
| 5,541,217 | A | 7/1996 | Carmosin et al. |
| 7,164,019 | B2 | 1/2007 | Lee et al. |
| 2004/0254376 | A1 | 12/2004 | Suzuki et al. |
| 2012/0095040 | A1 | 4/2012 | Abouabdellah et al. |
| 2012/0136026 | A1 | 5/2012 | Abouabdellah et al. |
| 2013/0012705 | A1 | 1/2013 | Tang et al. |

FOREIGN PATENT DOCUMENTS

| | | |
|---|---|---|
| WO | WO 93/16050 | 8/1993 |
| WO | WO 95/15327 | 6/1995 |
| WO | WO 2005/086735 A2 | 9/2005 |
| WO | WO 2006/012396 A1 | 9/2006 |
| WO | WO 2007/128458 A1 | 11/2007 |
| WO | WO 2007/128459 A1 | 11/2007 |
| WO | WO 2008/121686 A1 | 10/2008 |
| WO | WO 2009/055331 A2 | 4/2009 |
| WO | WO 2010/068851 A1 | 6/2010 |
| WO | WO 2011/085170 A1 | 7/2011 |
| WO | WO 2011/149993 A2 | 12/2011 |
| WO | WO 2012/156339 A1 | 11/2012 |
| WO | WO 2012/174199 A1 | 12/2012 |
| WO | WO 2013/013308 A1 | 1/2013 |
| WO | WO 2013/021054 A1 | 2/2013 |
| WO | WO 2013/091539 A1 | 6/2013 |
| WO | WO 2014/048865 A1 | 4/2014 |
| WO | WO 2015/048507 A1 | 4/2015 |

OTHER PUBLICATIONS

Stec et al., "Tandem Insertion, etc.," Chem. Eur. J. 2011, 17, 4896-4904.*
Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*

(Continued)

*Primary Examiner* — Patricia L Morris
(74) *Attorney, Agent, or Firm* — Brinks Gilson & Lione

(57) ABSTRACT

Compounds that selectively negatively modulate NMDA receptors containing an NR1/NR2B subunit, pharmaceutical compositions comprising the compounds, and methods of treating a disease using the compounds are disclosed.

18 Claims, No Drawings

(56) References Cited

OTHER PUBLICATIONS

Dean "Analytical Chem . . . " p. 10.24-10.26 (1995).*
Invanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*
Wolff, ed., Burger's Medicinal Chemistry and Drug Discovery, 5th edition, NY: John Wiley & Sons, 1996, vol. 1, pp. 949-976.*
Bhattarai, Deepak et al., "*Synthesis and in Vitro Evaluation of the Antitubercular and Antibacterial Activity of Novel Oxazolidinones Bearing Octahydrocyclopenta[c]pyrrol-2-yl Moieties*", Chem. Pharm. Bull. Vo. 62, No. 12, (2014), pp. 1214-1224.
Borza, Istvan, et al., "*NR2B Selective NMDA Antagonists: The Evolution of the Ifenprodil-Type Pharmacophore*", Current Topics in Medicinal Chemistry, vol. 6 (2006), pp. 687-695.
Mony, Laetitia, et al., "*Allosteric Modulators of NR2B-Containing NMDA Receptors: Molecular Mechanisms and Therapeutic Potential*", British Journal of Pharmacology, vol. 57 (2009), pp. 1301-1317.
Taylor, Albert, et al., "*Synthesis of Putative Metabolites and Investigation of the Metabolic Fate of Gliclazide, [1-(3-Azabicyclo(3,3,0)oct-3-yl)-3-(4-Methylphenylsulfonyl)Urea], in Diabetic Patients*", Drug Metabolism and Disposition, vol. 24, No. 1, (1995), 10p.
International Search Report to PCT Application No. PCT/US2014/057800 dated Feb. 24, 2015, 13p.

\* cited by examiner

SELECTIVE OCTAHYDRO-CYCLOPENTA[C] PYRROLE NEGATIVE MODULATORS OF NR2B

PRIORITY

This application claims priority to provisional application No. 61/883,050, filed Sep. 26, 2013. The entire disclosure of which is hereby incorporated by reference.
m

FIELD

The present disclosure relates to compounds that selectively negatively modulate the activity of an NR1/NR2B receptor.

BACKGROUND

The NMDA receptor is arguably an important signaling mechanism in the human brain. The brain processes a complex array of information to allow humans to function, storing information from the past and analyzing this information in the context of the present to respond and plan for the future. These incredibly complex computations are mediated at the molecular level by the continual adjustment of the strength of synapses, the nodes for communication between nerve cells (estimated at about 60 trillion in the human brain).

Glutamate is the major excitatory neurotransmitter in the brain, utilized at 80% of these synapses. NMDA receptors are one of three classes that mediate synaptic transmission using glutamate. NMDA receptors play a critical role in regulating the strength of synapses, that is, in regulating synaptic plasticity. Thus, the NMDA receptor is at the molecular core of brain function, and in particular the cognitive functions of learning and memory. These facts underlie the tremendous therapeutic utility of modulating NMDA receptor function with new drugs to treat a broad range of neuropsychiatric disease and cognitive dysfunction.

The molecular basis of NMDA receptor function is increasingly well understood. The NMDA receptor is composed of four protein subunits, two NR1 subunits and two NR2 subunits. An NR1 subunit derived from a single gene is ubiquitously expressed throughout the brain and is common to all NMDA receptors. However, the four different NR2 subunits, NR2A-D, are derived from separate genes that are differentially expressed in different brain regions and by distinct populations of neurons within a particular region. Furthermore, individual neurons may express more than one NR2 subunit and individual NMDA receptors expressed by such neurons may contain two of the same NR2 subunits (for example, 2 NR2B subunits) or two different subunits (one NR2A and one NR2B subunit). Therefore, a drug that selectively modulates the activity of one NR2 subunit may do so at receptors that express two of the targeted subunits, or only one of the targeted subunits. Thus there is a need for new treatments for diseases related to the NR1/NR2B receptor.

SUMMARY

In an aspect, compounds of Formula I are described:

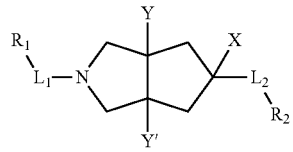

(I)

and pharmaceutically acceptable salts, prodrugs, solvates, hydrates, tautomers or stereoisomers thereof
wherein:
$L_1$ is straight or branched $C_2$-$C_4$ alkyl substituted with one or more substituents selected from the group consisting of OH, D, $OR_{10}$, $NH_2$, $NHR_{10}$, and $N(R_{10})(R_{10'})$, provided that no more than one oxygen or nitrogen is attached to any carbon; or
$L_1$ is selected from the group consisting of —CO—$C_1$-$C_2$alkylenyl-, —S(O)$_2$—, —S(O)$_2$NH—, —C(O)NH—, —C(O)NR$_{10}$—, —$C_1$-$C_3$alkylenyl-C(O)—$C_1$-$C_3$alkylenyl-, and a bond, wherein the $C_1$-$C_2$alkylenyl or $C_1$-$C_3$alkylenyl is optionally substituted with $C_1$-$C_4$ alkyl;
  each $R_{10}$ and $R_{10'}$ is independently selected from the group consisting of H; O—$C_1$-$C_5$ alkyl; $C_1$-$C_6$ alkyl optionally substituted with one or more substituents selected from the group consisting of OH, O—$C_1$-$C_5$ alkyl, —OP(O)(OH)$_2$, OP(O)O$_2^{-2}$M$_2$, —OC(O)alkyl, —OC(O)Oalkyl, aryl, and heteroaryl; and cycloalkyl optionally substituted with one or more substituents selected from the group consisting of OH and O—$C_1$-$C_5$ alkyl;
  provided that no more than one oxygen is attached to any carbon of $R_{10}$ and $R_{10'}$;
  M is a monovalent metal cation;
  or $R_{10}$ and $R_{10'}$, together with the nitrogen to which they are attached, may form a heterocycle;
$R_1$ is aryl or heteroaryl, both of which optionally substituted with one or more substituents selected from the group consisting of OH, CN, halogen, —O—$R_{10}$, —OP(O)(OH)$_2$, OP(O)O$_2^{-2}$M$_2$, —SH, —S—$R_{10}$, $C_1$-$C_5$ alkyl, branched alkyl, —$C_1$-$C_6$haloalkyl, $NH_2$, $NHR_{10}$, —$C_1$-$C_6$hydroxyalkyl, $N(R_{10})(NR_{10'})$, —NHS(O)$_2$R$_{10}$, —O-alkylaryl, —O—(CH$_2$)$_n$—C(O)-aryl, and NHCOR$_{10}$; M is a monovalent metal cation; or
$R_1$ is cycloalkyl;
X is selected from the group consisting of H, halogen, OH, O—$C_1$-$C_6$ alkyl, O-branched alkyl, $C_1$-$C_5$ straight alkyl and $C_1$-$C_5$ branched alkyl;
Y and Y' are independently H, F, or methyl;
$L_2$ is —(CH$_2$)$_n$— or —(CHR$_{11}$)$_n$—, or a bond;
  Each $R_{11}$ is independently selected from the group consisting of H, —$C_1$-$C_5$ alkylenyl-, —C(O)—$C_1$-$C_5$alkylenyl-, and -alkylenyl-CO-alkylenyl-;
$R_2$ is $C_3$-$C_8$cycloalkyl; $C_3$-$C_8$heterocyclyl, phenyl, naphthyl, heteroaryl, or bicyclic heteroaryl, each of which is optionally substituted with one or more substituents selected from the group consisting of halogen, OH, $C_1$-$C_6$alkyl, $OR_{10}$, CN, $NH_2$, $NHR_{10}$, $N(R_{10})(R_{10'})$, SH, $SR_{10}$, $SOR_{10}$, $SO_2R_{10}$, $SO_2NHR_{10}$, $SO_2N(R_{10})(R_{10'})$, $CONH_2$, $CONR_{10}$, and $CON(R_{10})(R_{10'})$; and
n is 1, 2, or 3.

In another aspect, compounds of Formula II are described:

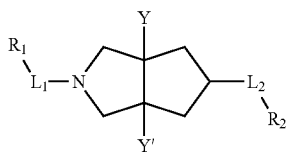

(II)

and pharmaceutically acceptable salts, prodrugs, solvates, hydrates, tautomers, or stereoisomers thereof
wherein:
$L_1$ is straight or branched $C_1$-$C_5$ alkyl optionally substituted with one or more substituents selected from the group consisting of H, OH, $OR_{10}$, $NH_2$, $NHR_{10}$, and $N(R_{10})(R_{10'})$ provided that no more than one oxygen or nitrogen is attached to any carbon; or
$L_1$ is selected from the group consisting of —C(O)—, —C(O)—$C_1$-$C_3$alkylenyl-, —S(O)$_2$—, —S(O)$_2$NH—, —CONH—, —CON($R_{10}$)—, and a bond;
  Each $R_{10}$ and $R_{10'}$ is independently selected from the group consisting of H; $C_1$-$C_6$ alkyl optionally substituted with one or more substituents selected from the group consisting of OH, O—$C_1$-$C_5$ alkyl, $OPO_3^{-2}M_2$, OP(O)(OH)$_2$, OCOalkyl, and OC(O)Oalkyl where M is a monovalent metal cation; and cycloalkyl optionally substituted with one or more substituents selected from the group consisting of OH and O—$C_1$-$C_5$ alkyl provided that no more than one oxygen is attached to any carbon; or $R_{10}$ and $R_{10'}$, together with the nitrogen to which they are attached, may form a heterocycle;
$R_1$ is aryl or heteroaryl, both of which optionally substituted with one or more substituents selected from the group consisting of OH, CN, halogen, O—$R_{10}$, $OPO_3^{-2}M_2$, OP(O)(OH)$_2$, SH, S—$R_{10}$, $C_1$-$C_5$ alkyl, branched alkyl, $NH_2$, $NHR_{10}$, $N(R_{10})(NR_{10'})$, and $NHCOR_{10}$ where M is a monovalent metal cation; or
$R_1$ is cycloalkyl;
Y and Y' are independently H, F or methyl;
$L_2$ is a bond, $(CH_2)_n$ or $(CHR_{11})_n$;
  Each $R_{11}$ is independently selected from the group consisting of H, —$C_1$-$C_5$ alkylenyl-, —CO—$C_1$-$C_5$alkylenyl-, and -alkylenyl-CO-alkylenyl-;
$R_2$ is phenyl, naphthyl, heteroaryl or bicyclic heteroaryl, each of which is optionally substituted with one or more substituents selected from the group consisting of halogen, OH, $OR_{10}$, CN, $NH_2$, $NHR_{10}$, $N(R_{10})(R_{10'})$, SH, $SR_{10}$, —S(O)$R_{10}$, —S(O)$_2R_{10}$, —S(O)$_2NHR_{10}$, —S(O)$_2N(R_{10})(R_{10'})$, —C(O)NH$_2$, —C(O)NR$_{10}$, and —C(O)N($R_{10}$)($R_{10'}$); and
n is 1, 2, or 3.
In another aspect, compounds of Formula III are described:

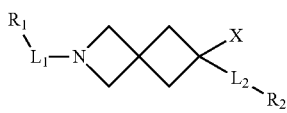

(III)

and pharmaceutically acceptable salts, prodrugs, solvates, hydrates, tautomers, or stereoisomers thereof
wherein:
$L_1$ is straight or branched $C_1$-$C_5$ alkyl optionally substituted with one or more substituents selected from the group consisting of H, OH, $OR_{10}$, $NH_2$, $NHR_{10}$, and $N(R_{10})(R_{10'})$ provided that no more than one oxygen or nitrogen is attached to any carbon; or
$L_1$ is selected from the group consisting of —C(O)—, —C(O)O—, —C(O)—$C_1$-$C_3$alkylenyl-, —S(O)$_2$—, —S(O)$_2$NH—, —C(O)NH—, —C(O)NR$_{10}$—, and a bond;
  Each $R_{10}$ and $R_{10'}$ is independently selected from the group consisting of H; $C_1$-$C_6$ alkyl optionally substituted with one or more substituents selected from the group consisting of OH, O—$C_1$-$C_5$ alkyl, $OPO_3^{-2}M_2$, OP(O)(OH)$_2$, OC(O)alkyl, and OC(O)Oalkyl where M is a monovalent metal cation; and cycloalkyl optionally substituted with one or more substituents selected from the group consisting of OH and O—$C_1$-$C_5$ alkyl provided that no more than one oxygen is attached to any carbon; or $R_{10}$ and $R_{10'}$, together with the nitrogen to which they are attached, may form a heterocycle;
$R_1$ is aryl or heteroaryl, both of which optionally substituted with one or more substituents selected from the group consisting of OH, CN, halogen, O—$R_{10}$, $OPO_3^{-2}M_2$, OP(O)(OH)$_2$, SH, S—$R_{10}$, $C_1$-$C_5$ alkyl, branched alkyl, $NH_2$, $NHR_{10}$, $N(R_{10})(NR_{10'})$, and $NHCOR_{10}$ where M is a monovalent metal cation; or
$R_1$ is straight or branched $C_1$-$C_6$ alkyl or cycloalkyl;
X is selected from the group consisting of H, halogen, OH, O—$C_1$-$C_6$ alkyl, O-branched alkyl, $C_1$-$C_5$ straight alkyl and $C_1$-$C_5$ branched alkyl;
$L_2$ is —$(CH_2)_n$— or —$(CHR_{11})_n$—, or a bond;
  Each $R_{11}$ is independently selected from the group consisting of H, —$C_1$-$C_5$ alkylenyl-, —CO—$C_1$-$C_5$alkylenyl-, and -alkylenyl-CO-alkylenyl-;
$R_2$ is phenyl, naphthyl, heteroaryl or bicyclic heteroaryl, each of which is optionally substituted with one or more substituents selected from the group consisting of halogen, OH, $OR_{10}$, CN, $NH_2$, $NHR_{10}$, $N(R_{10})(R_{10'})$, SH, $SR_{10}$, —S(O)$R_{10}$, —S(O)$_2R_{10}$, —S(O)$_2NHR_{10}$, —S(O)$_2N(R_{10})(R_{10'})$, —C(O)NH$_2$, —C(O)NHR$_{10}$, and CON($R_{10}$)($R_{10'}$); and
n is 1, 2, or 3.

The present disclosure further pertains to compounds that selectively modulate the activity of NMDA receptors that contain an NR2B subunit, which encompasses receptors containing two NR2B subunits or one NR2B subunit in combination with one other NR2 subunit (ie., NR2A/NR2B, NR2B/NR2C, or NR2B/NR2D receptors). Such compounds may either increase or decrease the activity of NR2B-containing NMDA receptors. The present invention also pertains to the therapeutic uses of such compounds. Also described are pharmaceutical formulations comprising at least a disclosed compound.

Also described herein are methods of treating a disease susceptible to treatment with a disclosed compound in a patient in need thereof by administering to the patient an effective amount of a disclosed compound. Such diseases include, without limitation, neurological dysfunction such as Parkinson's disease, Huntington's disease, amyotrophic lateral sclerosis, multiple sclerosis, and seizure disorders; emotional disorders; depression; bipolar disorder; obsessive-compulsive disorder; and other anxiety disorders.

Compounds or pharmaceutical compositions of the present invention may be used to treat individuals that experience dysfunction caused by abnormal brain development, including but not limited to those suffering from autism and autism spectrum disorders, Fragile X syndrome, Rett Syndrome, Angelman syndrome, tuberous sclerosis, Down's syndrome and other forms of mental retardation.

The invention further pertains to pharmaceutical compositions that comprise an effective amount of a disclosed compound and a pharmaceutically acceptable carrier. The compositions are useful for treating or preventing a disease or disorder. The invention includes a disclosed compound provided as a pharmaceutically acceptable prodrug, hydrate, salt, stereoisomer, or mixtures thereof.

The invention also includes the use of a compound or pharmaceutical composition as described herein in the manufacture of a medicament for the treatment of a disease mediated by the NR1/NR2B receptor.

The invention also includes any compound described herein or a pharmaceutically acceptable salt thereof for use in treating a disease mediated by the NR1/NR2B receptor.

DETAILED DESCRIPTION

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DEFINITIONS

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, $C_1$-$C_6$alkyl, —O$C_1$-$C_6$alkenyl, —O$C_1$-$C_6$alkynyl, —$C_1$-$C_6$alkenyl, —$C_1$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, NH$_2$, NH($C_1$-$C_6$alkyl), N($C_1$-$C_6$alkyl)$_2$, —S(O)$_2$—$C_1$-$C_6$alkyl, —S(O)NH$C_1$-$C_6$alkyl, and S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

"$C_1$-$C_3$ alkyl" refers to a straight or branched chain saturated hydrocarbon containing 1-3 carbon atoms. Examples of a $C_1$-C3alkyl group include, but are not limited to, methyl, ethyl, propyl and isopropyl.

"$C_1$-$C_5$ alkyl" refers to a straight or branched chain saturated hydrocarbon containing 1-5 carbon atoms. Examples of a $C_1$-$C_5$alkyl group include, but are not limited to, methyl, ethyl, propyl, butyl, pentyl, isopropyl, isobutyl, sec-butyl and tert-butyl, isopentyl and neopentyl.

Alkyl is generally lower alkyl, or $C_1$-$C_6$ alkyl. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkylenyl" as herein defined refers to groups of general formula —(CH$_2$)$_n$— where n is an integer from 1 to 6. Suitable examples of alkylenyl groups include methylenyl, ethylenyl, and propylenyl.

The term "haloalkyl" refers to straight or branched saturated hydrocarbon chains containing 1-5 carbon atoms which are substituted at least one of the carbon with halogen groups such fluorine, chlorine, bromine, iodide. Examples of haloalkyl groups as herein defined include without limitation trifluoromethyl, tribromomethyl, and 1,1,1-trifluoroethyl.

The term "hydroalkyl" refers to straight or branched saturated hydrocarbon chains containing 1-5 carbon atoms which are substituted at least one of the carbon with the hydroxyl group.

The term "-alkylaryl" refers to aryl groups connected to an adjacent C1-C6alkyl wherein the linkage is located at the alkyl end. For examples, groups such as benzyl, phenylethyl, or mesitylenyl.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, 10sethio[2.2.2]octanyl, or 10sethio[2.2.2]octenyl.

"Heterocyclyl" or "heterocycloalkyl" or "heterocycle" monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl.

"Spirocycle" means bicyclic ring system with both rings connected through a single atom. The ring can be different in size, nature, or identical. Examples include spiropentane, spriohexane, spiroheptane, spirooctane, spirononane, or spirodecane.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, 10sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "monovalent metal cation" refers to atomic elements that positively charged (atoms which have more protons than electrons because they have lost electrons). Examples of metal cations include, without limitation, monovalent metal and metalloids of the periodic table. These metal cations include monovalent alkaline metals such Li, K, Na, Rb, or Cs, monovalent transition metals such as Cu, Au, or Ag.

The term "stereoisomers" refers to the set of compounds which have the same number and type of atoms and share the same bond connectivity between those atoms, but differ in three dimensional structure. The term "stereoisomer" refers to any member of this set of compounds.

The term "diasteromers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diasteromers. The term "diasteromer" refers to any member of this set of compounds. In some examples presented, the synthetic route may produce a single diateromer or a mixture of diasteromers. In some cases these diasteromers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

A "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

Compounds

In an embodiment, compounds of Formula I are described:

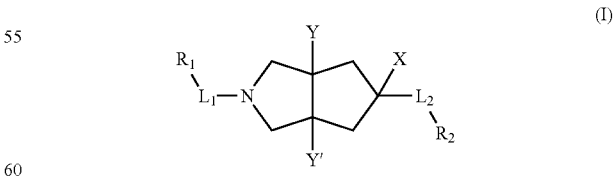

(I)

and pharmaceutically acceptable salts, prodrugs, solvates, hydrates, tautomers, or stereoisomers thereof, wherein $R_1$, $L_1$, Y, Y', X, $L_2$, and $R_2$ are described as above in formula I.

In one embodiment of the compounds of Formula I, $R_1$ is aryl or heteroaryl each of which is substituted with one or more substituents selected from the group consisting of OH, halogen, $OR_{10}$, SH, $SR_{10}$, $NH_2$, $NHR_{10}$ and $NHCOR_{10}$.

In another embodiment of Formula I compounds, wherein $R_1$ is aryl substituted with one substituent selected from the group consisting of OH, halogen, $OR_{10}$, SH, $SR_{10}$, $NH_2$, $NHR_{10}$ and $NHCOR_{10}$.

In another embodiment of Formula I compounds, Y and Y' are hydrogen.

In another embodiment of Formula I compounds, $L_2$ is a bond.

In another embodiment of Formula I compounds, n is 1.

In another embodiment of Formula I compounds, n is 2.

In another embodiment of Formula I compounds, $R_2$ is phenyl optionally substituted with one or more halogen, OH, $OR_{10}$, CN, $NH_2$, $NHR_{10}$, $N(R_{10})(R_{10'})$, SH, $SR_{10}$, $SOR_{10}$, $SO_2R_{10}$, $SO_2NHR_{10}$, $SO_2N(R_{10})(R_{10'})$, $CONH_2$, $CONR_{10}$, $CON(R_{10})(R_{10'})$.

In another embodiment of Formula I compounds, $R_2$ is phenyl substituted with one or more halogen.

In another embodiment of Formula I compounds, $L_1$ is branched $C_2$-$C_4$ alkyl substituted with one or more substituents selected from the group consisting of OH, $OR_{10}$, $NH_2$, $NHR_{10}$, and $N(R_{10})(R_{10'})$ provided that no more than one oxygen or nitrogen is attached to any carbon of $L_1$.

In another embodiment of Formula I compounds, $L_1$ is straight $C_2$-$C_4$ alkyl substituted with one or more substituents selected from the group consisting of OH, $OR_{10}$, $NH_2$, $NHR_{10}$, and $N(R_{10})(R_{10'})$ provided that no more than one oxygen or nitrogen is attached to any carbon of $L_1$.

In another embodiment of the invention, compounds of Formula (Ia) are disclosed:

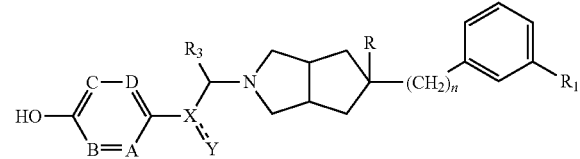

(Ia)

and pharmaceutically acceptable salts, prodrugs, solvates, hydrates, tautomers, or stereoisomers thereof;
wherein:
  A, B, C, and D are independently N or CH;
  X is CH or C;
  Y is OH or O;
  $R_3$ is H or $CH_3$;
  n is 0, 1, or 2;
  R is H, OH or R; and
  $R_1$ is H or F.

In another embodiment of Formula Ia compounds, A, B, C, and D are CH.

In another embodiment of Formula Ia compounds, X and Y form a carbonyl.

In another embodiment of Formula Ia compounds, X is CH and Y is OH.

In another embodiment of Formula Ia compounds, $R_3$ is H.

In another embodiment of Formula Ia compounds, R is H.

In another embodiment of Formula Ia compounds, R is OH.

In another embodiment of Formula Ia compounds, n is 0.

In another embodiment of Formula Ia compounds, n is 1.

In another embodiment of Formula Ia compounds, n is 2.

In another embodiment of Formula Ia compounds, $R_1$ is H.

In another embodiment of Formula Ia compounds, $R_1$ is F.

In another embodiment of the invention, compounds of Formula (Ib) are disclosed:

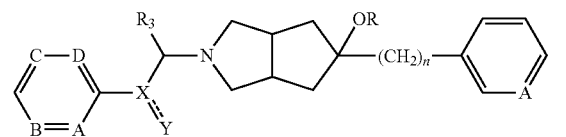

(Ib)

and pharmaceutically acceptable salts, prodrugs, solvates, hydrates, tautomers, or stereoisomers thereof
wherein:
  A, B, C, and D are independently N or $CR_x$;
  X is CH or C;
  Y is OH or O;
  $R_3$ is H;
  n is 0, 1, or 2;
  R is H, or $CH_3$; and
  $R_x$ is H, $C_{1-6}$ alkyl, halogen, —OH, or —$OC_{1-6}$ alkyl.

In another embodiment, compounds of Formula (Ic) are disclosed:

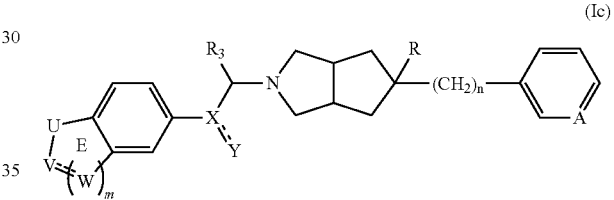

(Ic)

and pharmaceutically acceptable salts, prodrugs, solvates, hydrates, tautomers, or stereoisomers thereof;
wherein:
  A is independently N or $CR_x$;
  U is O, S, $NR_y$, C=O, or $C(R_x)_m$;
  V is O, S, N, $NR_y$, C=O, or $C(R_x)_m$;
  each W is independently selected from O, S, C=O, N, $NR_y$, or $C(R_x)_m$;
  ------ is an optional double bond which allows the E ring to be partially or fully saturated;
  X is CH or C;
  Y is OH or O;
  $R_3$ is H;
  n is 0, 1, or 2;
  each m is independently 1, or 2;
  R is H, OH, or $CH_3$;
  $R_x$ is H, $C_{1-6}$ alkyl, halogen, —OH, or —$OC_{1-6}$ alkyl; and
  $R_y$ is H, or $C_{1-6}$ alkyl.

In another embodiment, compounds of Formula (Id) are disclosed:

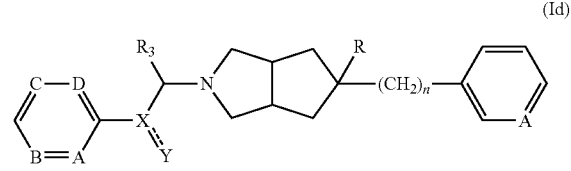

(Id)

and pharmaceutically acceptable salts, prodrugs, solvates, hydrates, tautomers, or stereoisomers thereof;
wherein:
A, B, C, and D are independently N or $CR_x$;
X is CH or C;
Y is OH or O;
$R_3$ is H;
n is 0, 1, or 2;
R is F; and
$R_x$ is H, $C_{1-6}$ alkyl, halogen, —OH, or —$OC_{1-6}$ alkyl.

In another aspect, compounds of Formula (Ie) are disclosed:

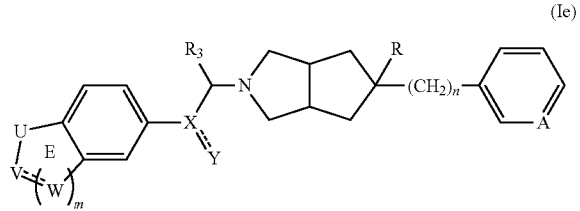

(Ie)

and pharmaceutically acceptable salts, prodrugs, solvates, hydrates, tautomers, or stereoisomers thereof;
wherein:
A is independently N or $CR_x$;
U is O, S, $NR_y$, C=O, or $C(R_x)_m$;
V is O, S, N, $NR_y$, C=O, or $C(R_x)_m$;
each W is independently selected from O, S, C=O, N, $NR_x$ or $C(R_x)_m$;
------ is an optional double bond which allows the E ring to be partially or fully saturated;
X is CH or C;
Y is OH or O;
$R_3$ is H;
n is 0, 1 or 2;
each m is independently 1, or 2;
R is H, OH, or $CH_3$;
$R_x$ is H, $C_{1-6}$ alkyl, halogen, —OH, or —$OC_{1-6}$ alkyl; and
$R_y$ is H, or $C_{1-6}$ alkyl.

In an illustrative embodiment, the compound of Formula I is
5-hydroxy-N-(4-methoxyphenyl)-5-phenylhexahydrocyclopenta[c]pyrrole-2(1H)-carboxamide;
5-(4-cyanophenyl)-5-hydroxy-N-(4-methoxyphenyl)-octahydrocyclopenta[c]pyrrole-2-carboxamide;
5-hydroxy-N-(4-methylphenyl)-5-phenyl-octahydrocyclopenta[c]pyrrole-2-carboxamide;
N-(3-chlorophenyl)-5-hydroxy-5-phenyl-octahydrocyclopenta[c]pyrrole-2-carboxamide;
5-hydroxy-5-phenyl-N-[3-(trifluoromethyl)phenyl]-octahydrocyclopenta[c]pyrrole-2-carboxamide;
N-(4-fluorophenyl)-5-hydroxy-5-phenyl-octahydrocyclopenta[c]pyrrole-2-carboxamide;
5-hydroxy-N-(3-methoxyphenyl)-5-phenyl-octahydrocyclopenta[c]pyrrole-2-carboxamide;
5-hydroxy-N-(4-methoxyphenyl)-5-(2-methylphenyl)-octahydrocyclopenta[c]pyrrole-2-carboxamide;
5-hydroxy-5-(2-methylphenyl)-N-(4-methylphenyl)-octahydrocyclopenta[c]pyrrole-2-carboxamide;
5-hydroxy-N-(3-methoxyphenyl)-5-(2-methylphenyl)-octahydrocyclopenta[c]pyrrole-2-carboxamide;
N-(3-chlorophenyl)-5-hydroxy-5-(2-methylphenyl)-octahydrocyclopenta[c]pyrrole-2-carboxamide;
5-hydroxy-5-(2-methylphenyl)-N-[3-(trifluoromethyl)phenyl]-octahydrocyclopenta[c]pyrrole-2-carboxamide;
N-(4-fluorophenyl)-5-hydroxy-5-(2-methylphenyl)-octahydrocyclopenta[c]pyrrole-2-carboxamide;
5-hydroxy-5-(3-methoxyphenyl)-N-(4-methylphenyl)-octahydrocyclopenta[c]pyrrole-2-carboxamide;
N-(3-chlorophenyl)-5-hydroxy-5-(3-methoxyphenyl)-octahydrocyclopenta[c]pyrrole-2-carboxamide;
5-hydroxy-5-(3-methoxyphenyl)-N-[3-(trifluoromethyl)phenyl]-octahydrocyclopenta[c]pyrrole-2-carboxamide;
5-hydroxy-5-(3-methoxyphenyl)-N-(4-methoxyphenyl)-octahydrocyclopenta[c]pyrrole-2-carboxamide;
5-hydroxy-N,5-bis(3-methoxyphenyl)-octahydrocyclopenta[c]pyrrole-2-carboxamide;
N-(2,4-difluorophenyl)-5-hydroxy-5-phenyl-octahydrocyclopenta[c]pyrrole-2-carboxamide;
N-[(1R)-1-(4-chlorophenyl)ethyl]-5-hydroxy-5-phenyl-octahydrocyclopenta[c]pyrrole-2-carboxamide;
5-hydroxy-N-[(2-methoxyphenyl)methyl]-5-phenyl-octahydrocyclopenta[c]pyrrole-2-carboxamide;
Methyl 4-(5-hydroxy-5-(o-tolyl)octahydrocyclopenta[c]pyrrole-2-carboxamido)benzoate;
5-hydroxy-N-(2-methoxy-5-methylphenyl)-5-(2-methylphenyl)-octahydrocyclopenta[c]pyrrole-2-carboxamide;
N-[4-chloro-3-(trifluoromethyl)phenyl]-5-hydroxy-5-(2-methylphenyl)-octahydrocyclopenta[c]pyrrole-2-carboxamide;
5-hydroxy-N,5-diphenyl-octahydrocyclopenta[c]pyrrole-2-carboxamide;
N-(3-cyanophenyl)-5-hydroxy-5-phenyl-octahydrocyclopenta[c]pyrrole-2-carboxamide;
5-hydroxy-N-(2-methoxy-5-methylphenyl)-5-phenyl-octahydrocyclopenta[c]pyrrole-2-carboxamide;
methyl 4-[({5-hydroxy-5-phenyloctahydrocyclopenta[c]pyrrol-2-yl}carbonyl)amino]benzoate;
5-hydroxy-5-(3-methoxyphenyl)-N-phenyl-octahydrocyclopenta[c]pyrrole-2-carboxamide;
5-hydroxy-5-(2-methylphenyl)-N-phenyl-octahydrocyclopenta[c]pyrrole-2-carboxamide;
N-(3-cyanophenyl)-5-hydroxy-5-(2-methylphenyl)-octahydrocyclopenta[c]pyrrole-2-carboxamide;
N-[4-chloro-3-(trifluoromethyl)phenyl]-5-hydroxy-5-phenyl-octahydrocyclopenta[c]pyrrole-2-carboxamide;
5-hydroxy-N-(2-methoxy-5-methylphenyl)-5-(3-methoxyphenyl)-octahydrocyclopenta[c]pyrrole-2-carboxamide;
N-[4-chloro-3-(trifluoromethyl)phenyl]-5-hydroxy-5-(3-methoxyphenyl)-octahydrocyclopenta[c]pyrrole-2-carboxamide;
N,5-bis(4-fluorophenyl)-5-hydroxy-octahydrocyclopenta[c]pyrrole-2-carboxamide;
5-(4-fluorophenyl)-5-hydroxy-N-(4-methylphenyl)-octahydrocyclopenta[c]pyrrole-2-carboxamide;
5-(4-fluorophenyl)-5-hydroxy-N-(3-methoxyphenyl)-octahydrocyclopenta[c]pyrrole-2-carboxamide;
5-(4-fluorophenyl)-5-hydroxy-N-[3-(trifluoromethyl)phenyl]-octahydrocyclopenta[c]pyrrole-2-carboxamide;
N-(3-chlorophenyl)-5-(4-fluorophenyl)-5-hydroxy-octahydrocyclopenta[c]pyrrole-2-carboxamide;
N-(3-cyanophenyl)-5-(4-fluorophenyl)-5-hydroxy-octahydrocyclopenta[c]pyrrole-2-carboxamide;
5-(4-fluorophenyl)-5-hydroxy-N-(pyridin-3-yl)-octahydrocyclopenta[c]pyrrole-2-carboxamide;
5-(4-fluorophenyl)-5-hydroxy-N-(2-methoxy-5-methylphenyl)-octahydrocyclopenta[c]pyrrole-2-carboxamide;
N-[4-chloro-3-(trifluoromethyl)phenyl]-5-(4-fluorophenyl)-5-hydroxy-octahydrocyclopenta[c]pyrrole-2-carboxamide;

5-hydroxy-5-phenyl-N-(pyridin-3-yl)-octahydrocyclopenta[c]pyrrole-2-carboxamide;
methyl 4-({[5-hydroxy-5-(3-methoxyphenyl)-octahydrocyclopenta[c]pyrrol-2-yl]carbonyl}amino)benzoate;
5-hydroxy-5-(3-methoxyphenyl)-N-(pyridin-3-yl)-octahydrocyclopenta[c]pyrrole-2-carboxamide
N-(2,4-dimethylphenyl)-5-hydroxy-5-phenyl-octahydrocyclopenta[c]pyrrole-2-carboxamide;
N-(2,4-dimethylphenyl)-5-hydroxy-5-(2-methylphenyl)-octahydrocyclopenta[c]pyrrole-2-carboxamide;
N-(2,4-dimethylphenyl)-5-hydroxy-5-(3-methoxyphenyl)-octahydrocyclopenta[c]pyrrole-2-carboxamide;
methyl 4-({[5-(4-tert-butylphenyl)-5-hydroxy-octahydrocyclopenta[c]pyrrol-2-yl]carbonyl}amino)benzoate;
5-(4-tert-butylphenyl)-5-hydroxy-N-(3-methoxyphenyl)-octahydrocyclopenta[c]pyrrole-2-carboxamide;
5-(4-tert-butylphenyl)-N-(3-cyanophenyl)-5-hydroxy-octahydrocyclopenta[c]pyrrole-2-carboxamide;
5-(4-tert-butylphenyl)-N-[4-chloro-3-(trifluoromethyl)phenyl]-5-hydroxy-octahydrocyclopenta[c]pyrrole-2-carboxamide;
5-(4-tert-butylphenyl)-5-hydroxy-N-phenyl-octahydrocyclopenta[c]pyrrole-2-carboxamide;
5-(4-tert-butylphenyl)-5-hydroxy-N-[3-(trifluoromethyl)phenyl]-octahydrocyclopenta[c]pyrrole-2-carboxamide;
5-(4-tert-butylphenyl)-N-(3-chlorophenyl)-5-hydroxy-octahydrocyclopenta[c]pyrrole-2-carboxamide;
2-(5-hydroxy-5-phenylhexahydrocyclopenta[c]pyrrol-2(1H)-yl)-1-phenylethanone;
rac-2-(2-hydroxy-2-phenylethyl)-5-phenyloctahydrocyclopenta[c]pyrrol-5-ol;
2-[5-hydroxy-5-(3-methoxyphenyl)-octahydrocyclopenta[c]pyrrol-2-yl]-1-phenylethan-1-one;
rac-2-(2-hydroxy-2-phenylethyl)-5-(3-methoxyphenyl)-octahydrocyclopenta[c]pyrrol-5-ol;
1-(3-fluorophenyl)-2-{5-hydroxy-5-phenyl-octahydrocyclopenta[c]pyrrol-2-yl}ethan-1-one;
1-(3-fluorophenyl)-2-[5-hydroxy-5-(3-methoxyphenyl)-octahydrocyclopenta[c]pyrrol-2-yl]ethan-1-one;
rac-2-[2-(3-fluorophenyl)-2-hydroxyethyl]-5-(3-methoxyphenyl)-octahydrocyclopenta[c]pyrrol-5-ol;
rac-2-[2-(3-fluorophenyl)-2-hydroxyethyl]-5-phenyl-octahydrocyclopenta[c]pyrrol-5-ol;
2-{5-hydroxy-5-phenyl-octahydrocyclopenta[c]pyrrol-2-yl}-1-(4-hydroxyphenyl)ethan-1-one;
2-{5-hydroxy-5-phenyl-octahydrocyclopenta[c]pyrrol-2-yl}-1-(4-methoxyphenyl)ethan-1-one;
rac-2-[2-hydroxy-2-(4-methoxyphenyl)ethyl]-5-phenyl-octahydrocyclopenta[c]pyrrol-5-ol;
rac-2-[2-hydroxy-2-(4-hydroxyphenyl)ethyl]-5-phenyl-octahydrocyclopenta[c]pyrrol-5-ol;
2-(5-hydroxy-5-phenylhexahydrocyclopenta[c]pyrrol-2(1H)-yl)-1-(4-(2-hydroxypropan-2-yl)phenyl)ethanone;
rac-2-(2-hydroxy-2-(4-(2-hydroxypropan-2-yl)phenyl)ethyl)-5-phenyloctahydrocyclopenta[c]pyrrol-5-ol;
rac-5-(4-(tert-butyl)phenyl)-2-(2-hydroxy-2-(3-(trifluoromethyl)phenyl)ethyl)octahydrocyclopenta[c]pyrrol-5-ol;
rac-5-(4-tert-butylphenyl)-2-[2-(3-fluorophenyl)-2-hydroxyethyl]-octahydrocyclopenta[c]pyrrol-5-ol;
rac-2-{2-hydroxy-2-[3-(trifluoromethyl)phenyl]ethyl}-5-(2-methylphenyl)-octahydrocyclopenta[c]pyrrol-5-ol;
rac-2-{2-hydroxy-2-[3-(trifluoromethyl)phenyl]ethyl}-5-(3-methoxyphenyl)-octahydrocyclopenta[c]pyrrol-5-ol;
rac-2-[2-(2,4-dichlorophenyl)-2-hydroxyethyl]-5-(3-methoxyphenyl)-octahydrocyclopenta[c]pyrrol-5-ol;
rac-5-(4-fluorophenyl)-2-{2-hydroxy-2-[3-(trifluoromethyl)phenyl]ethyl}-octahydrocyclopenta[c]pyrrol-5-ol;
rac-2-[2-(2,4-dichlorophenyl)-2-hydroxyethyl]-5-(4-fluorophenyl)-octahydrocyclopenta[c]pyrrol-5-ol;
rac-2-[2-hydroxy-2-(3-methoxyphenyl)ethyl]-5-(3-methoxyphenyl)-octahydrocyclopenta[c]pyrrol-5-ol;
rac-2-(1-hydroxy-1-(4-hydroxyphenyl)propan-2-yl)-5-(3-methoxyphenyl)octahydrocyclopenta[c]pyrrol-5-ol;
2-(4-fluorobenzyl)-5-(4-fluorophenyl)octahydrocyclopenta[c]pyrrol-5-ol;
5-(4-fluorophenyl)-2-(pyridin-2-yl)-octahydrocyclopenta[c]pyrrol-5-ol;
5-(4-fluorophenyl)-2-[6-(trifluoromethyl)pyridin-2-yl]-octahydrocyclopenta[c]pyrrol-5-ol;
5-(2-methylphenyl)-2-(pyridin-2-yl)-octahydrocyclopenta[c]pyrrol-5-ol;
5-phenyl-2-[6-(trifluoromethyl)pyridin-2-yl]-octahydrocyclopenta[c]pyrrol-5-ol;
5-(2-methylphenyl)-2-[6-(trifluoromethyl)pyridin-2-yl]-octahydrocyclopenta[c]pyrrol-5-ol;
2-(6-methylpyridin-2-yl)-5-phenyl-octahydrocyclopenta[c]pyrrol-5-ol;
5-(2-methylphenyl)-2-(6-methylpyridin-2-yl)-octahydrocyclopenta[c]pyrrol-5-ol;
5-(4-fluorophenyl)-2-(6-methylpyridin-2-yl)-octahydrocyclopenta[c]pyrrol-5-ol;
5-(4-tert-butylphenyl)-2-(pyridin-2-yl)-octahydrocyclopenta[c]pyrrol-5-ol;
5-(4-tert-butylphenyl)-2-(6-methylpyridin-2-yl)-octahydrocyclopenta[c]pyrrol-5-ol;
rac-2-(5-hydroxy-5-phenylhexahydrocyclopenta[c]pyrrol-2(1H)-yl)-1-(4-hydroxyphenyl)propan-1-one;
rac-2-(1-hydroxy-1-(4-hydroxyphenyl)propan-2-yl)-5-phenyloctahydrocyclopenta[c]pyrrol-5-ol;
rac-2-[5-(4-fluorophenyl)-5-hydroxy-octahydrocyclopenta[c]pyrrol-2-yl]-1-(4-hydroxyphenyl)propan-1-one;
rac-2-[5-(4-tert-butylphenyl)-5-hydroxy-octahydrocyclopenta[c]pyrrol-2-yl]-1-(4-hydroxyphenyl)propan-1-one;
rac-2-[5-hydroxy-5-(2-methylphenyl)-octahydrocyclopenta[c]pyrrol-2-yl]-1-(4-hydroxyphenyl)propan-1-one;
rac-2-[1-hydroxy-1-(4-hydroxyphenyl)propan-2-yl]-5-(2-methylphenyl)-octahydrocyclopenta[c]pyrrol-5-ol;
rac-5-(4-tert-butylphenyl)-2-[1-hydroxy-1-(4-hydroxyphenyl)propan-2-yl]-octahydrocyclopenta[c]pyrrol-5-ol;
(5-hydroxy-5-phenylhexahydrocyclopenta[c]pyrrol-2(1H)-yl)(4-hydroxyphenyl)methanone;
3-(5-hydroxy-5-phenylhexahydrocyclopenta[c]pyrrol-2(1H)-yl)-1-(4-hydroxyphenyl)propan-1-one;
2-(3-hydroxy-3-(4-hydroxyphenyl)propyl)-5-phenyloctahydrocyclopenta[c]pyrrol-5-ol;
2N-(4-methoxyphenyl)-5-phenylhexahydrocyclopenta[c]pyrrole-2(1H)-carboxamide;
N-(4-hydroxyphenyl)-5-phenyl-octahydrocyclopenta[c]pyrrole-2-carboxamide;
N-(4-fluorophenyl)-5-phenyl-octahydrocyclopenta[c]pyrrole-2-carboxamide;
N,5-diphenyl-octahydrocyclopenta[c]pyrrole-2-carboxamide;
methyl 4-[({5-phenyl-octahydrocyclopenta[c]pyrrol-2-yl}carbonyl)amino]benzoate;
N-(3-methoxyphenyl)-5-phenyl-octahydrocyclopenta[c]pyrrole-2-carboxamide;
5-phenyl-N-[3-(trifluoromethyl)phenyl]-octahydrocyclopenta[c]pyrrole-2-carboxamide;
N-(3-chlorophenyl)-5-phenyl-octahydrocyclopenta[c]pyrrole-2-carboxamide;
N-(3-cyanophenyl)-5-phenyl-octahydrocyclopenta[c]pyrrole-2-carboxamide;

N-[4-chloro-3-(trifluoromethyl)phenyl]-5-phenyl-octahydrocyclopenta[c]pyrrole-2-carboxamide;
N-(2-methoxy-5-methylphenyl)-5-phenyl-octahydrocyclopenta[c]pyrrole-2-carboxamide;
N-(2,4-dimethylphenyl)-5-phenyl-octahydrocyclopenta[c]pyrrole-2-carboxamide;
5-phenyl-N-(pyridin-3-yl)-octahydrocyclopenta[c]pyrrole-2-carboxamide;
N-[(2-methoxyphenyl)methyl]-5-phenyl-octahydrocyclopenta[c]pyrrole-2-carboxamide;
N-[(1R)-1-(4-chlorophenyl)ethyl]-5-phenyl-octahydrocyclopenta[c]pyrrole-2-carboxamide;
1-(4-hydroxyphenyl)-2-(5-phenylhexahydrocyclopenta[c]pyrrol-2(1H)-yl)ethanone;
4-(1-hydroxy-2-(5-phenylhexahydrocyclopenta[c]pyrrol-2(1H)-yl)ethyl)phenol;
rac-2-(5-phenylhexahydrocyclopenta[c]pyrrol-2(1H)-yl)-1-(3-(trifluoromethyl)phenyl)ethanol;
rac-1-(3-methoxyphenyl)-2-{5-phenyl-octahydrocyclopenta[c]pyrrol-2-yl}ethan-1-ol;
(3aR,5r,6aS)-5-benzyl-N-(3-chlorophenyl)-5-hydroxyhexahydrocyclopenta[c]pyrrole-2(1H)-carboxamide;
(3aR,5r,6aS)-5-benzyl-5-hydroxy-N-(3-methoxyphenyl)hexahydrocyclopenta[c]pyrrole-2(1H)-carboxamide;
(3aR,5r,6aS)-5-benzyl-N-(4-chloro-3-(trifluoromethyl)phenyl)-5-hydroxyhexahydrocyclopenta[c]pyrrole-2(1H)-carboxamide;
(3aR,5r,6aS)-5-benzyl-N-(2,4-dimethylphenyl)-5-hydroxyhexahydrocyclopenta[c]pyrrole-2(1H)-carboxamide;
(3aR,5r,6aS)-5-benzyl-5-hydroxy-N-phenylhexahydrocyclopenta[c]pyrrole-2(1H)-carboxamide;
(3aR,5r,6aS)-5-benzyl-N-(3-cyanophenyl)-5-hydroxyhexahydrocyclopenta[c]pyrrole-2(1H)-carboxamide;
(3aR,5r,6aS)-5-benzyl-5-hydroxy-N-(2-methoxy-5-methylphenyl)hexahydrocyclopenta[c]pyrrole-2(1H)-carboxamide;
(3aR,5r,6aS)-5-benzyl-5-hydroxy-N-(p-tolyl)hexahydrocyclopenta[c]pyrrole-2(1H)-carboxamide
(3aR,5r,6aS)-5-benzyl-5-hydroxy-N-(4-methoxyphenyl)hexahydrocyclopenta[c]pyrrole-2(1H)-carboxamide;
(3aR,5r,6aS)-5-benzyl-5-hydroxy-N-(2-(trifluoromethyl)phenyl)hexahydrocyclopenta[c]pyrrole-2(1H)-carboxamide;
(3aR,5r,6aS)-5-benzyl-5-hydroxy-N-(2-methoxyphenyl)hexahydrocyclopenta[c]pyrrole-2(1H)-carboxamide;
(3aR,5r,6aS)-5-benzyl-5-hydroxy-N-(m-tolyl)hexahydrocyclopenta[c]pyrrole-2(1H)-carboxamide;
2-((3aR,5r,6aS)-5-benzyl-5-hydroxyhexahydrocyclopenta[c]pyrrol-2(1H)-yl)-1-(4-hydroxyphenyl)ethanone;
rac-(3aR,5r,6aS)-5-benzyl-2-(2-hydroxy-2-(4-hydroxyphenyl)ethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(4-methoxyphenyl)ethanone;
3-((3aR,5r,6aS)-5-benzyl-5-hydroxyhexahydrocyclopenta[c]pyrrol-2(1H)-yl)-1-(4-hydroxyphenyl)propan-1-one;
2-((3aR,5r,6aS)-5-(4-fluorobenzyl)-5-hydroxyhexahydrocyclopenta[c]pyrrol-2(1H)-yl)-1-(4-hydroxyphenyl)ethanone;
rac-(3aR,5r,6aS)-5-(4-fluorobenzyl)-2-(2-hydroxy-2-(4-hydroxyphenyl)ethyl)octahydrocyclopenta[c]pyrrol-5-ol;
(3aR,5R,6aS)-5-benzyl-2-((R)-2-hydroxy-2-(4-hydroxyphenyl)ethyl)octahydrocyclopenta[c]pyrrol-5-ol;
(3aR,5S,6aS)-5-benzyl-2-((S)-2-hydroxy-2-(4-hydroxyphenyl)ethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(4-(2-hydroxypropan-2-yl)phenyl)ethanone;
rac-(3aR,5r,6aS)-5-benzyl-2-(2-hydroxy-2-(4-(2-hydroxypropan-2-yl)phenyl)ethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(5-hydroxypyridin-2-yl)ethanone;
N-(4-(2-((3aR,5r,6aS)-5-benzyl-5-hydroxyhexahydrocyclopenta[c]pyrrol-2(1H)-yl)acetyl)phenyl)acetamide;
(3aR,5R,6aS)-5-benzyl-2-((R)-2-hydroxy-2-(4-hydroxyphenyl)ethyl)octahydrocyclopenta[c]pyrrol-5-ol;
(3aR,5S,6aS)-5-benzyl-2-((S)-2-hydroxy-2-(4-hydroxyphenyl)ethyl)octahydrocyclopenta[c]pyrrol-5-ol;
rac-(3aR,5r,6aS)-5-benzyl-2-(2-hydroxy-2-(5-hydroxypyridin-2-yl)ethyl)octahydrocyclopenta[c]pyrrol-5-ol;
1-((3aR,5r,6aS)-5-benzyl-5-hydroxyhexahydrocyclopenta[c]pyrrol-2(1H)-yl)-3-(4-hydroxyphenyl)propan-2-one;
N-(4-(2-((3aR,5r,6aS)-5-benzyl-5-hydroxyhexahydrocyclopenta[c]pyrrol-2(1H)-yl)acetyl)phenyl)methanesulfonamide;
5-(2-((3aR,5r,6aS)-5-benzyl-5-hydroxyhexahydrocyclopenta[c]pyrrol-2(1H)-yl)acetyl)indolin-2-one;
6-(2-((3aR,5r,6aS)-5-benzyl-5-hydroxyhexahydrocyclopenta[c]pyrrol-2(1H)-yl)acetyl)-3,4-dihydroquinolin-2(1H)-one;
rac-N-(4-(2-((3aR,5r,6aS)-5-benzyl-5-hydroxyhexahydrocyclopenta[c]pyrrol-2(1H)-yl)-1-hydroxyethyl)phenyl)acetamide;
rac-N-(4-(2-((3aR,5r,6aS)-5-benzyl-5-hydroxyhexahydrocyclopenta[c]pyrrol-2(1H)-yl)-1-hydroxyethyl)phenyl)methanesulfonamide;
2-((3aR,5r,6aS)-5-benzyl-5-hydroxyhexahydrocyclopenta[c]pyrrol-2(1H)-yl)-1-(3-fluoro-4-hydroxyphenyl)ethanone;
rac-5-(2-((3aR,5r,6aS)-5-benzyl-5-hydroxyhexahydrocyclopenta[c]pyrrol-2(1H)-yl)-1-hydroxyethyl)indolin-2-one;
rac-6-(2-((3aR,5r,6aS)-5-benzyl-5-hydroxyhexahydrocyclopenta[c]pyrrol-2(1H)-yl)-1-hydroxyethyl)-3,4-dihydroquinolin-2(1H)-one;
rac-6-(2-((3aR,5r,6aS)-5-benzyl-5-hydroxyhexahydrocyclopenta[c]pyrrol-2(1H)-yl)-1-hydroxyethyl)benzo[d]oxazol-2(3H)-one;
2-((3aR,5r,6aS)-5-benzyl-5-hydroxyhexahydrocyclopenta[c]pyrrol-2(1H)-yl)-1-(6-chloropyridin-3-yl)ethanone;
(3aR,5S,6aS)-5-benzyl-2-((S)-2-(3-fluoro-4-hydroxyphenyl)-2-hydroxyethyl)octahydrocyclopenta[c]pyrrol-5-ol;
6-(2-((3aR,5r,6aS)-5-benzyl-5-hydroxyhexahydrocyclopenta[c]pyrrol-2(1H)-yl)acetyl)pyridazin-3(2H)-one;
rac-6-(2-((3aR,5r,6aS)-5-benzyl-5-hydroxyhexahydrocyclopenta[c]pyrrol-2(1H)-yl)-1-hydroxyethyl)pyridazin-3(2H)-one;
2-((3aR,5r,6aS)-5-benzyl-5-hydroxyhexahydrocyclopenta[c]pyrrol-2(1H)-yl)-1-(3,5-difluoro-4-hydroxyphenyl)ethanone;
rac-(3aR,5r,6aS)-5-benzyl-2-(2-(3,5-difluoro-4-hydroxyphenyl)-2-hydroxyethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(6-methoxypyridin-3-yl)ethanone;
2-((3aR,5r,6aS)-5-benzyl-5-hydroxyhexahydrocyclopenta[c]pyrrol-2(1H)-yl)-1-(5-(benzyloxy)pyrazin-2-yl)ethanone;
rac-(3aR,5r,6aS)-5-benzyl-2-(2-(5-(benzyloxy)pyrazin-2-yl)-2-hydroxyethyl)octahydrocyclopenta[c]pyrrol-5-ol;
(3aR,5S,6aS)-5-benzyl-2-((S)-2-hydroxy-2-(5-hydroxypyridin-2-yl)ethyl)octahydrocyclopenta[c]pyrrol-5-ol;
(3aR,5R,6aS)-5-benzyl-2-((R)-2-hydroxy-2-(5-hydroxypyridin-2-yl)ethyl)octahydrocyclopenta[c]pyrrol-5-ol;

2-((3aR,5r,6aS)-5-(4-fluorobenzyl)-5-hydroxyhexahydro-cyclopenta[c]pyrrol-2(1H)-yl)-1-(5-hydroxypyridin-2-yl)ethanone;
2-[(3aR,5R,6aS)-5-benzyl-5-hydroxy-octahydrocyclopenta[c]pyrrol-2-yl]-1-(1H-1,2,3-benzotriazol-5-yl)ethan-1-one;
rac-(3aR,5r,6aS)-5-(4-fluorobenzyl)-2-(2-hydroxy-2-(5-hydroxypyridin-2-yl)ethyl)octahydrocyclopenta[c]pyrrol-5-ol;
1-(3-fluoro-4-hydroxyphenyl)-2-((3aR,5r,6aS)-5-(4-fluorobenzyl)-5-hydroxyhexahydrocyclopenta[c]pyrrol-2(1H)-yl)ethanone;
2-((3aR,5r,6aS)-5-benzyl-5-methoxyhexahydrocyclopenta[c]pyrrol-2(1H)-yl)-1-(3-fluoro-4-hydroxyphenyl)ethanone;
rac-(3aR,5r,6aS)-2-(2-(3-fluoro-4-hydroxyphenyl)-2-hydroxyethyl)-5-(4-fluorobenzyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(3-fluoro-4-(2-(3-fluoro-4-hydroxyphenyl)-2-oxoethoxy)phenyl)ethanone;
2-(2-fluoro-4-(2-((3aR,5r,6aS)-5-(4-fluorobenzyl)-5-hydroxyhexahydrocyclopenta[c]pyrrol-2(1H)-yl)acetyl)phenoxy)-1-(3-fluoro-4-hydroxyphenyl)ethanone;
2-((3aR,5r,6aS)-5-benzyl-5-methoxyhexahydrocyclopenta[c]pyrrol-2(1H)-yl)-1-(4-hydroxyphenyl)ethanone;
rac-4-(2-((3aR,5r,6aS)-5-benzyl-5-methoxyhexahydrocyclopenta[c]pyrrol-2(1H)-yl)-1-hydroxyethyl)-2-fluoro-phenol;
rac-4-(2-((3aR,5r,6aS)-5-benzyl-5-methoxyhexahydrocyclopenta[c]pyrrol-2(1H)-yl)-1-hydroxyethyl)phenol;
rac-6-(2-((3aR,5r,6aS)-5-benzyl-5-methoxyhexahydrocyclopenta[c]pyrrol-2(1H)-yl)-1-hydroxyethyl)pyridin-3-ol;
2-[(3aR,5R,6aS)-5-benzyl-5-hydroxy-octahydrocyclopenta[c]pyrrol-2-yl]-1-(6-hydroxypyridin-3-yl)ethan-1-one;
2-((3aR,5r,6aS)-5-hydroxy-5-(4-methylbenzyl)hexahydrocyclopenta[c]pyrrol-2(1H)-yl)-1-(4-hydroxyphenyl)ethanone;
(3aR,5R,6aS)-5-benzyl-2-((R)-2-(3-fluoro-4-hydroxyphenyl)-2-hydroxyethyl)octahydrocyclopenta[c]pyrrol-5-ol;
(3aR,5S,6aS)-5-benzyl-2-((S)-2-(3-fluoro-4-hydroxyphenyl)-2-hydroxyethyl)octahydrocyclopenta[c]pyrrol-5-ol;
rac-5-{2-[(3aR,5R,6aS)-5-benzyl-5-hydroxy-octahydrocyclopenta[c]pyrrol-2-yl]-1-hydroxyethyl}pyridin-2-ol;
rac-(3aR,5R,6aS)-2-[2-hydroxy-2-(4-hydroxyphenyl)ethyl]-5-[(4-methylphenyl)methyl]-octahydrocyclopenta[c]pyrrol-5-ol;
2-((3aR,5r,6aS)-5-hydroxy-5-(2-methylbenzyl)hexahydrocyclopenta[c]pyrrol-2(1H)-yl)-1-(4-hydroxyphenyl)ethanone;
2-[(3aR,5R,6aS)-5-hydroxy-5-[(4-methoxyphenyl)methyl]-octahydrocyclopenta[c]pyrrol-2-yl]-1-(4-hydroxyphenyl)ethan-1-one;
rac-(3aR,5r,6aS)-2-(2-hydroxy-2-(4-hydroxyphenyl)ethyl)-5-(2-methylbenzyl)octahydrocyclopenta[c]pyrrol-5-ol;
rac-(3aR,5R,6aS)-2-[2-(1H-1,2,3-benzotriazol-5-yl)-2-hydroxyethyl]-5-benzyl-octahydrocyclopenta[c]pyrrol-5-ol;
2-((3aR,5r,6aS)-5-benzyl-5-hydroxyhexahydrocyclopenta[c]pyrrol-2(1H)-yl)-1-(5-hydroxypyrazin-2-yl)ethanone;
rac-(3aR,5r,6aS)-5-benzyl-2-(2-hydroxy-2-(5-hydroxypyrazin-2-yl)ethyl)octahydrocyclopenta[c]pyrrol-5-ol;
rac-(3aR,5r,6aS)-2-(2-hydroxy-2-(4-hydroxyphenyl)ethyl)-5-(4-methoxybenzyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(6-fluoro-5-hydroxypyridin-2-yl)ethanone;
rac-(3aR,5r,6aS)-5-benzyl-2-(2-(6-fluoro-5-hydroxypyridin-2-yl)-2-hydroxyethyl)octahydrocyclopenta[c]pyrrol-5-ol;
2-[(3aR,5R,6aS)-5-hydroxy-5-[(4-methoxyphenyl)methyl]-octahydrocyclopenta[c]pyrrol-2-yl]-1-(5-hydroxypyridin-2-yl)ethan-1-one;
2-((3aR,5r,6aS)-5-hydroxy-5-(3-methoxybenzyl)hexahydrocyclopenta[c]pyrrol-2(1H)-yl)-1-(5-hydroxypyridin-2-yl)ethanone;
2-((3aR,5r,6aS)-5-hydroxy-5-(3-methoxybenzyl)hexahydrocyclopenta[c]pyrrol-2(1H)-yl)-1-(4-hydroxyphenyl)ethanone;
rac-(3aR,5r,6aS)-2-(2-hydroxy-2-(4-hydroxyphenyl)ethyl)-5-(3-methoxybenzyl)octahydrocyclopenta[c]pyrrol-5-ol;
rac-((3aR,5r,6aS)-2-(2-hydroxy-2-(5-hydroxypyridin-2-yl)ethyl)-5-(3-methoxybenzyl)octahydrocyclopenta[c]pyrrol-5-ol;
2-((3aR,5r,6aS)-5-benzyl-5-methoxyhexahydrocyclopenta[c]pyrrol-2(1H)-yl)-1-(6-fluoro-5-hydroxypyridin-2-yl)ethanone;
rac-6-(2-((3aR,5r,6aS)-5-benzyl-5-methoxyhexahydrocyclopenta[c]pyrrol-2(1H)-yl)-1-hydroxyethyl)-2-fluoro-pyridin-3-ol;
rac-6-{2-[(3aR,5R,6aS)-5-hydroxy-5-[(4-methoxyphenyl)methyl]-octahydrocyclopenta[c]pyrrol-2-yl]-1-hydroxyethyl}pyridin-3-ol;
1-(6-fluoro-5-hydroxypyridin-2-yl)-2-((3aR,5r,6aS)-5-hydroxy-5-(3-methoxybenzyl)hexahydrocyclopenta[c]pyrrol-2(1H)-yl)ethanone;
rac-(3aR,5r,6aS)-2-(2-(6-fluoro-5-hydroxypyridin-2-yl)-2-hydroxyethyl)-5-(3-methoxybenzyl)octahydrocyclopenta[c]pyrrol-5-ol;
2-[(3aR,5R,6aS)-5-benzyl-5-hydroxy-octahydrocyclopenta[c]pyrrol-2-yl]-1-(5-hydroxypyrimidin-2-yl)ethan-1-one;
rac-2-{2-[(3aR,5R,6aS)-5-benzyl-5-hydroxy-octahydrocyclopenta[c]pyrrol-2-yl]-1-hydroxyethyl}pyrimidin-5-ol;
rac-(3aR,5r,6aS)-2-(2-hydroxy-2-(4-hydroxyphenyl)ethyl)-5-(thiophen-2-ylmethyl)octahydrocyclopenta[c]pyrrol-5-ol;
2-[(3aR,5R,6aS)-5-(cyclohexylmethyl)-5-hydroxy-octahydrocyclopenta[c]pyrrol-2-yl]-1-(4-hydroxyphenyl)ethan-1-one;
2-[(3aR,5R,6aS)-5-(cyclohexylmethyl)-5-hydroxy-octahydrocyclopenta[c]pyrrol-2-yl]-1-(5-hydroxypyridin-2-yl)ethan-1-one;
2-((3aR,5r,6aS)-5-(cyclopropylmethyl)-5-hydroxyhexahydrocyclopenta[c]pyrrol-2(1H)-yl)-1-(5-hydroxypyridin-2-yl)ethanone;
rac-6-{2-[(3aR,5R,6aS)-5-[(3,5-dimethylphenyl)methyl]-5-hydroxy-octahydrocyclopenta[c]pyrrol-2-yl]-1-hydroxyethyl}pyridin-3-ol-3-ol;
rac-(3aR,5R,6aS)-5-(cyclohexylmethyl)-2-[2-hydroxy-2-(4-hydroxyphenyl)ethyl]-octahydrocyclopenta[c]pyrrol-5-ol;
2-((3aR,5r,6aS)-5-(cyclopropylmethyl)-5-hydroxyhexahydrocyclopenta[c]pyrrol-2(1H)-yl)-1-(4-hydroxyphenyl)ethanone;
rac-(3aR,5r,6aS)-5-(cyclopropylmethyl)-2-(2-hydroxy-2-(4-hydroxyphenyl)ethyl)octahydrocyclopenta[c]pyrrol-5-ol;
2-[(3aR,5R,6aS)-5-[(3,5-dimethylphenyl)methyl]-5-hydroxy-octahydrocyclopenta[c]pyrrol-2-yl]-1-(4-hydroxyphenyl)ethan-1-one;
rac-(3aR,5R,6aS)-5-[(3,5-dimethylphenyl)methyl]-2-[2-hydroxy-2-(4-hydroxyphenyl)ethyl]-octahydrocyclopenta[c]pyrrol-5-ol;

rac-6-{2-[(3aR,5R,6aS)-5-(cyclohexylmethyl)-5-hydroxy-octahydrocyclopenta[c]pyrrol-2-yl]-1-hydroxyethyl}pyridin-3-ol;

rac-2-(2-hydroxy-2-(5-hydroxypyridin-2-yl)ethyl)-5-(thiophen-2-ylmethyl)octahydrocyclopenta[c]pyrrol-5-ol;

2-[(3aR,5R,6aS)-5-hydroxy-5-{[4-(trifluoromethyl)phenyl]methyl}-octahydrocyclopenta[c]pyrrol-2-yl]-1-(5-hydroxypyridin-2-yl)ethan-1-one;

rac-6-{2-[(3aR,5R,6aS)-5-hydroxy-5-{[4-(trifluoromethyl)phenyl]methyl}-octahydrocyclopenta[c]pyrrol-2-yl]-1-hydroxyethyl}pyridin-3-ol;

2-((3aR,5r,6aS)-5-(4-chlorobenzyl)-5-hydroxyhexahydrocyclopenta[c]pyrrol-2(1H)-yl)-1-(5-hydroxypyridin-2-yl)ethanone;

2-[(3aR,5R,6aS)-5-hydroxy-5-{[4-(trifluoromethyl)phenyl]methyl}-octahydrocyclopenta[c]pyrrol-2-yl]-1-(4-hydroxyphenyl)ethan-1-one;

1-(3-fluoro-4-hydroxyphenyl)-2-(5-hydroxy-5-(thiophen-2-ylmethyl)hexahydrocyclopenta[c]pyrrol-2(1H)-yl)ethanone;

2-(5-(2-fluorobenzyl)-5-hydroxyhexahydrocyclopenta[c]pyrrol-2(1H)-yl)-1-(5-hydroxypyridin-2-yl)ethanone;

rac-2-(2-(3-fluoro-4-hydroxyphenyl)-2-hydroxyethyl)-5-(thiophen-2-ylmethyl)octahydrocyclopenta[c]pyrrol-5-ol;

rac-(3aR,5r,6aS)-5-(4-chlorobenzyl)-2-(2-hydroxy-2-(5-hydroxypyridin-2-yl)ethyl)octahydrocyclopenta[c]pyrrol-5-ol;

rac-(3aR,5R,6aS)-2-[2-hydroxy-2-(4-hydroxyphenyl)ethyl]-5-{[4-(trifluoromethyl)phenyl]methyl}-octahydrocyclopenta[c]pyrrol-5-ol;

2-((3aR,5r,6aS)-5-(2-fluorobenzyl)-5-hydroxyhexahydrocyclopenta[c]pyrrol-2(1H)-yl)-1-(4-hydroxyphenyl)ethanone;

2-((3aR,5r,6aS)-5-hydroxy-5-(pyridin-4-ylmethyl)hexahydrocyclopenta[c]pyrrol-2(1H)-yl)-1-(4-hydroxyphenyl)ethanone;

rac-(3aR,5r,6aS)-2-(2-hydroxy-2-(4-hydroxyphenyl)ethyl)-5-(pyridin-4-ylmethyl)octahydrocyclopenta[c]pyrrol-5-ol;

rac-5-(2-fluorobenzyl)-2-(2-hydroxy-2-(5-hydroxypyridin-2-yl)ethyl)octahydrocyclopenta[c]pyrrol-5-olyl)ethanone;

rac-(3aR,5r,6aS)-5-(2-fluorobenzyl)-2-(2-hydroxy-2-(4-hydroxyphenyl)ethyl)octahydrocyclopenta[c]pyrrol-5-ol;

2-((3aR,5r,6aS)-5-(2,4-difluorobenzyl)-5-hydroxyhexahydrocyclopenta[c]pyrrol-2(1H)-yl)-1-(5-hydroxypyridin-2-yl)ethanone;

2-((3aR,5r,6aS)-5-hydroxy-5-(pyridin-2-ylmethyl)hexahydrocyclopenta[c]pyrrol-2(1H)-yl)-1-(4-hydroxyphenyl)ethanone;

rac-(3aR,5r,6aS)-2-(2-hydroxy-2-(4-hydroxyphenyl)ethyl)-5-(pyridin-2-ylmethyl)octahydrocyclopenta[c]pyrrol-5-ol;

rac-(3aR,5r,6aS)-5-(2,4-difluorobenzyl)-2-(2-hydroxy-2-(5-hydroxypyridin-2-yl)ethyl)octahydrocyclopenta[c]pyrrol-5-ol 2-((3aR,5r,6aS)-5-(2-chlorobenzyl)-5-hydroxyhexahydrocyclopenta[c]pyrrol-2(1H)-yl)-1-(5-hydroxypyridin-2-yl)ethanone;

N-(6-(2-((3aR,5r,6aS)-5-benzyl-5-hydroxyhexahydrocyclopenta[c]pyrrol-2(1H)-yl)acetyl)pyridin-3-yl)methanesulfonamide rac-N-(6-(2-((3aR,5r,6aS)-5-benzyl-5-hydroxyhexahydrocyclopenta[c]pyrrol-2(1H)-yl)-1-hydroxyethyl)pyridin-3-yl)methanesulfonamide;

2-[(3aR,5R,6aS)-5-[(2,6-difluorophenyl)methyl]-5-hydroxy-octahydrocyclopenta[c]pyrrol-2-yl]-1-(5-hydroxypyridin-2-yl)ethan-1-one;

2-(5-(2,4-difluorobenzyl)-5-hydroxyhexahydrocyclopenta[c]pyrrol-2(1H)-yl)-1-(4-hydroxyphenyl)ethanone;

2-((3aR,5r,6aS)-5-(3,4-difluorobenzyl)-5-hydroxyhexahydrocyclopenta[c]pyrrol-2(1H)-yl)-1-(5-hydroxypyridin-2-yl)ethanone;

rac-6-{2-[(3aR,5R,6aS)-5-[(2,6-difluorophenyl)methyl]-5-hydroxy-octahydrocyclopenta[c]pyrrol-2-yl]-1-hydroxyethyl}pyridin-3-ol 2-[(3aR,5R,6aS)-5-[(2,6-difluorophenyl)methyl]-5-hydroxy-octahydrocyclopenta[c]pyrrol-2-yl]-1-(4-hydroxyphenyl)ethan-1-one;

2-((3aR,5r,6aS)-5-(4-fluoro-2-methylbenzyl)-5-hydroxyhexahydrocyclopenta[c]pyrrol-2(1H)-yl)-1-(5-hydroxypyridin-2-yl)ethanone;

rac-(3aR,5r,6aS)-5-(4-fluoro-2-methylbenzyl)-2-(2-hydroxy-2-(5-hydroxypyridin-2-yl)ethyl)octahydrocyclopenta[c]pyrrol-5-ol;

2-((3aR,6aS)-5-(2-fluoropyridin-3-yl)-5-hydroxyhexahydrocyclopenta[c]pyrrol-2(1H)-yl)-1-(5-hydroxypyridin-2-yl)ethanone;

rac-5-(2,4-difluorobenzyl)-2-(2-hydroxy-2-(4-hydroxyphenyl)ethyl)octahydrocyclopenta[c]pyrrol-5-ol;

rac-(3aR,5r,6aS)-5-(2-chlorobenzyl)-2-(2-hydroxy-2-(5-hydroxypyridin-2-yl)ethyl)octahydrocyclopenta[c]pyrrol-5-ol;

2-((3aR,5r,6aS)-5-(2,3-difluorobenzyl)-5-hydroxyhexahydrocyclopenta[c]pyrrol-2(1H)-yl)-1-(5-hydroxypyridin-2-yl)ethanone;

rac-(3aR,5r,6aS)-5-(2,3-difluorobenzyl)-2-(2-hydroxy-2-(5-hydroxypyridin-2-yl)ethyl)octahydrocyclopenta[c]pyrrol-5-ol 2-((3aR,5r,6aS)-5-(2,3-difluorobenzyl)-5-hydroxyhexahydrocyclopenta[c]pyrrol-2(1H)-yl)-1-(4-hydroxyphenyl)ethanone;

2-((3aR,5r,6aS)-5-(4-fluoro-2-methylbenzyl)-5-hydroxyhexahydrocyclopenta[c]pyrrol-2(1H)-yl)-1-(4-hydroxyphenyl)ethanone;

rac-(3aR,6aS)-5-(2-fluoropyridin-3-yl)-2-(2-hydroxy-2-(5-hydroxypyridin-2-yl)ethyl)octahydrocyclopenta[c]pyrrol-5-ol;

2-((3aR,5r,6aS)-5-(3,4-difluorobenzyl)-5-hydroxyhexahydrocyclopenta[c]pyrrol-2(1H)-yl)-1-(4-hydroxyphenyl)ethanone;

rac-(3aR,5r,6aS)-5-(3,4-difluorobenzyl)-2-(2-hydroxy-2-(4-hydroxyphenyl)ethyl)octahydrocyclopenta[c]pyrrol-5-ol;

rac-(3aR,5r,6aS)-5-(4-fluoro-2-methylbenzyl)-2-(2-hydroxy-2-(4-hydroxyphenyl)ethyl)octahydrocyclopenta[c]pyrrol-5-ol;

(3aR,5S,6aS)-5-(4-fluorobenzyl)-2-((S)-2-hydroxy-2-(5-hydroxypyridin-2-yl)ethyl)octahydrocyclopenta[c]pyrrol-5-ol;

(3aR,5R,6aS)-5-(4-fluorobenzyl)-2-((R)-2-hydroxy-2-(5-hydroxypyridin-2-yl)ethyl)octahydrocyclopenta[c]pyrrol-5-ol;

2-((3aR,5r,6aS)-5-benzyl-5-hydroxyhexahydrocyclopenta[c]pyrrol-2(1H)-yl)-1-(4'-hydroxy-[1,1'-biphenyl]-4-yl)ethanone;

1-([1,1'-biphenyl]-4-yl)-2-((3aR,5r,6aS)-5-benzyl-5-hydroxyhexahydrocyclopenta[c]pyrrol-2(1H)-yl)ethanone;

2-((3aR,5r,6aS)-5-benzyl-5-hydroxyhexahydrocyclopenta[c]pyrrol-2(1H)-yl)-1-(4'-methoxy-[1,1'-biphenyl]-4-yl)ethanone;

2-((3aR,5r,6aS)-5-benzyl-5-hydroxyhexahydrocyclopenta [c]pyrrol-2(1H)-yl)-1-(2'-methyl-[1,1'-biphenyl]-4-yl) ethanone;
2-((3aR,5r,6aS)-5-benzyl-5-hydroxyhexahydrocyclopenta [c]pyrrol-2(1H)-yl)-1-(3'-fluoro-[1,1'-biphenyl]-4-yl) ethanone;
2-((3aR,5r,6aS)-5-benzyl-5-hydroxyhexahydrocyclopenta [c]pyrrol-2(1H)-yl)-1-(4'-fluoro-[1,1'-biphenyl]-4-yl) ethanone;
2-((3aR,5r,6aS)-5-benzyl-5-hydroxyhexahydrocyclopenta [c]pyrrol-2(1H)-yl)-1-(4'-methoxy-[1,1'-biphenyl]-3-yl) ethanone;
2-((3aR,5r,6aS)-5-benzyl-5-hydroxyhexahydrocyclopenta [c]pyrrol-2(1H)-yl)-1-(3'-methyl-[1,1'-biphenyl]-4-yl) ethanone;
2-((3aR,5r,6aS)-5-benzyl-5-hydroxyhexahydrocyclopenta [c]pyrrol-2(1H)-yl)-1-(3'-methoxy-[1,1'-biphenyl]-4-yl) ethanone;
2-((3aR,5r,6aS)-5-benzyl-5-hydroxyhexahydrocyclopenta [c]pyrrol-2(1H)-yl)-1-(4-(pyridin-2-yl)phenyl)ethanone;
2-((3aR,5r,6aS)-5-benzyl-5-hydroxyhexahydrocyclopenta [c]pyrrol-2(1H)-yl)-1-(4-(pyridin-3-yl)phenyl)ethanone;
1-([1,1'-biphenyl]-3-yl)-2-((3aR,5r,6aS)-5-benzyl-5-hydroxyhexahydrocyclopenta[c]pyrrol-2(1H)-yl)ethanone;
2-[5-hydroxy-5-(2-phenylethyl)-octahydrocyclopenta[c]pyrrol-2-yl]-1-(4-phenylphenyl)ethan-1-one;
1-[4-(3-fluorophenyl)phenyl]-2-[5-hydroxy-5-(2-phenylethyl)-octahydrocyclopenta[c]pyrrol-2-yl]ethan-1-one;
2-((3aR,5r,6aS)-5-benzyl-5-hydroxyhexahydrocyclopenta [c]pyrrol-2(1H)-yl)-1-(3'-fluoro-[1,1'-biphenyl]-3-yl) ethanone;
2-((3aR,5r,6aS)-5-benzyl-5-hydroxyhexahydrocyclopenta [c]pyrrol-2(1H)-yl)-1-(3-(pyridin-3-yl)phenyl)ethanone;
2-((3aR,5r,6aS)-5-benzyl-5-hydroxyhexahydrocyclopenta [c]pyrrol-2(1H)-yl)-1-(3'-methoxy-[1,1'-biphenyl]-3-yl) ethanone;
2-((3aR,5r,6aS)-5-benzyl-5-hydroxyhexahydrocyclopenta [c]pyrrol-2(1H)-yl)-1-(4'-fluoro-[1,1'-biphenyl]-3-yl) ethanone;
2-((3aR,5r,6aS)-5-benzyl-5-hydroxyhexahydrocyclopenta [c]pyrrol-2(1H)-yl)-1-(4'-hydroxy-[1,1'-biphenyl]-3-yl) ethanone;
2-((3aR,5r,6aS)-5-benzyl-5-hydroxyhexahydrocyclopenta [c]pyrrol-2(1H)-yl)-1-(3'-methyl-[1,1'-biphenyl]-3-yl) ethanone;
2-[5-hydroxy-5-(2-phenylethyl)-octahydrocyclopenta[c] pyrrol-2-yl]-1-[4-(3-methylphenyl)phenyl]ethan-1-one;
2-((3aR,5r,6aS)-5-benzyl-5-hydroxyhexahydrocyclopenta [c]pyrrol-2(1H)-yl)-1-(2'-methyl-[1,1'-biphenyl]-3-yl) ethanone;
2-((3aR,5r,6aS)-5-benzyl-5-hydroxyhexahydrocyclopenta [c]pyrrol-2(1H)-yl)-1-(4-(2-methoxypyrimidin-5-yl)phenyl)ethanone;
rac-(3aR,5R,6aS)-5-benzyl-2-[2-hydroxy-2-(4-hydroxyphenyl)propyl]-octahydrocyclopenta[c]pyrrol-5-ol;
deuterated rac-(3aR,6aS)-5-benzyl-2-((S)-2-hydroxy-2-(4-hydroxyphenyl)ethyl)octahydrocyclopenta[c]pyrrol-5-ol;
N-(5-(2-((3aR,5r,6aS)-5-benzyl-5-hydroxyhexahydrocyclopenta[c]pyrrol-2(1H)-yl)acetyl)pyridin-2-yl)acetamide;
rac-N-(5-(2-((3aR,5r,6aS)-5-benzyl-5-hydroxyhexahydrocyclopenta[c]pyrrol-2(1H)-yl)-1-hydroxyethyl)pyridin-2-yl)acetamide;
tert-butyl(5-(2-(5-benzyl-5-hydroxyhexahydrocyclopenta [c]pyrrol-2(1H)-yl)acetyl)pyridin-2-yl)carbamate;
N-(5-(2-(5-benzyl-5-hydroxyhexahydrocyclopenta[c]pyrrol-2(1H)-yl)acetyl)pyridin-2-yl)pivalamide;
rac-N-(5-(2-(5-benzyl-5-hydroxyhexahydrocyclopenta[c] pyrrol-2(1H)-yl)-1-hydroxyethyl)pyridin-2-yl)pivalamide;
rac-(3aR,5r,6aS)-5-benzyl-2-(2-(2,4-dichlorophenyl)-2-hydroxyethyl)octahydrocyclopenta[c]pyrrol-5-ol;
rac-(3aR,5r,6aS)-5-benzyl-2-(2-hydroxy-2-(3-(trifluoromethyl)phenyl)ethyl)octahydrocyclopenta[c]pyrrol-5-ol;
rac-(3aR,5r,6aS)-5-benzyl-2-(2-(4-fluorophenyl)-2-hydroxyethyl)octahydrocyclopenta[c]pyrrol-5-ol;
2-((3aR,5r,6aS)-5-benzyl-5-hydroxyhexahydrocyclopenta [c]pyrrol-2(1H)-yl)-1-(4-hydroxyphenyl)ethanone;
(3aR,5R,6aS)-5-benzyl-2-((R)-2-hydroxy-2-(4-hydroxyphenyl)ethyl)octahydrocyclopenta[c]pyrrol-5-ol;
(3aR,5S,6aS)-5-benzyl-2-((S)-2-hydroxy-2-(4-hydroxyphenyl)ethyl)octahydrocyclopenta[c]pyrrol-5-ol;
rac-2-((3aR,5r,6aS)-5-benzyl-5-hydroxyhexahydrocyclopenta[c]pyrrol-2(1H)-yl)-1-(4-hydroxyphenyl)propan-1-one;
(3aR,6aS)-5-benzyl-N-(3-methoxyphenyl)hexahydrocyclopenta[c]pyrrole-2(1H)-carboxamide;
2-((3aR,6aS)-5-benzylhexahydrocyclopenta[c]pyrrol-2 (1H)-yl)-1-(4-hydroxyphenyl)ethanone;
rac-2-((3aR,6aS)-5-benzylhexahydrocyclopenta[c]pyrrol-2 (1H)-yl)-1-(4-hydroxyphenyl)propan-1-one;
2-{5-benzyl-octahydrocyclopenta[c]pyrrol-2-yl}-1-(5-hydroxypyridin-2-yl)ethan-1-one;
rac-6-(2-{5-benzyl-octahydrocyclopenta[c]pyrrol-2-yl}-1-hydroxyethyl)pyridin-3-ol;
2-{5-benzyl-octahydrocyclopenta[c]pyrrol-2-yl}-1-(3-fluoro-4-hydroxyphenyl)ethan-1-one;
rac-4-(2-((3aR,6aS)-5-benzylhexahydrocyclopenta[c]pyrrol-2(1H)-yl)-1-hydroxyethyl)phenol;
rac-4-{2-[(3aR,5S,6aS)-5-benzyl-octahydrocyclopenta[c] pyrrol-2-yl]-1-hydroxyethyl}-2-fluorophenol;
rac-4-{2-[(3aR,5R,6aS)-5-benzyl-octahydrocyclopenta[c] pyrrol-2-yl]-1-hydroxyethyl}-2-fluorophenol;
2-[(3aR,5S,6aS)-5-benzyl-octahydrocyclopenta[c]pyrrol-2-yl]-1-(4-hydroxyphenyl)ethan-1-onefluorophenol;
rac-4-{2-[(3aR,5S,6aS)-5-benzyl-octahydrocyclopenta[c] pyrrol-2-yl]-1-hydroxyethyl}phenol;
2-[(3aR,5R,6aS)-5-benzyl-octahydrocyclopenta[c]pyrrol-2-yl]-1-(4-hydroxyphenyl)ethan-1-one;
rac-4-{2-[(3aR,5R,6aS)-5-benzyl-octahydrocyclopenta[c] pyrrol-2-yl]-1-hydroxyethyl}phenol;
2-[(3aR,5S,6aS)-5-benzyl-octahydrocyclopenta[c]pyrrol-2-yl]-1-(3-fluoro-4-hydroxyphenyl)ethan-1-one;
2-[(3aR,5R,6aS)-5-benzyl-octahydrocyclopenta[c]pyrrol-2-yl]-1-(3-fluoro-4-hydroxyphenyl)ethan-1-one;
rac-2-((3aR,6aS)-5-benzylhexahydrocyclopenta[c]pyrrol-2 (1H)-yl)-1-(3-(trifluoromethyl)phenyl)ethanol;
2-((3aR,5s,6aS)-5-benzyl-5-fluorohexahydrocyclopenta[c] pyrrol-2(1H)-yl)-1-(4-hydroxyphenyl)ethanone;
rac-4-(2-((3aR,5s,6aS)-5-benzyl-5-fluorohexahydrocyclopenta[c]pyrrol-2(1H)-yl)-1-hydroxyethyl)phenol;
4-(2-((3aR,5s,6aS)-5-benzyl-5-fluorohexahydrocyclopenta [c]pyrrol-2(1H)-yl)-1-hydroxyethyl)phenol;
rac-4-(2-((3aR,5r,6aS)-5-benzyl-5-fluorohexahydrocyclopenta[c]pyrrol-2(1H)-yl)-1-hydroxyethyl)phenol;
4-((R)-2-((3aR,5S,6aS)-5-benzyl-5-fluorohexahydrocyclopenta[c]pyrrol-2(1H)-yl)-1-hydroxyethyl)phenol;
4-((S)-2-((3aR,5R,6aS)-5-benzyl-5-fluorohexahydrocyclopenta[c]pyrrol-2(1H)-yl)-1-hydroxyethyl)phenol;
rac-4-(2-((3aR,5s,6aS)-5-benzyl-5-fluorohexahydrocyclopenta[c]pyrrol-2(1H)-yl)-1-hydroxyethyl)-2-fluorophenol;
rac-2-((3aR,5s,6aS)-5-benzyl-5-fluorohexahydrocyclopenta[c]pyrrol-2(1H)-yl)-1-(4-hydroxyphenyl)propan-1-one;

rac-4-(2-((3aR,5s,6aS)-5-benzyl-5-fluorohexahydrocyclopenta[c]pyrrol-2(1H)-yl)-1-hydroxypropyl)phenol;

rac-2-(5-hydroxy-5-phenethylhexahydrocyclopenta[c]pyrrol-2(1H)-yl)-1-(4-hydroxyphenyl)propan-1-one;

rac-2-(1-hydroxy-1-(4-hydroxyphenyl)propan-2-yl)-5-phenethyloctahydrocyclopenta[c]pyrrol-5-ol;

rac-2-(2-hydroxy-2-(4-hydroxyphenyl)ethyl)-5-phenethyl-octahydrocyclopenta[c]pyrrol-5-ol;

rac-1-(4-hydroxyphenyl)-2-[(5R)-5-(2-phenylethyl)-octahydrocyclopenta[c]pyrrol-2-yl]propan-1-one;

1-(4-hydroxyphenyl)-2-(5-phenethylhexahydrocyclopenta[c]pyrrol-2(1H)-yl)ethanone;

1-(4-hydroxyphenyl)-2-((3aR,5r,6aS)-5-phenethylhexahydrocyclopenta[c]pyrrol-2(1H)-yl)ethanone; or 1-(4-hydroxyphenyl)-2-((3aR,5r,6aS)-5-phenethylhexahydrocyclopenta[c]pyrrol-2(1H)-yl)propan-1-one.

In another aspect, compounds of Formula II are described:

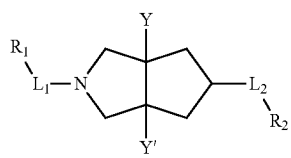

(II)

and pharmaceutically acceptable salts, prodrugs, solvates, hydrates, tautomers, or stereoisomers thereof
wherein $R_1$, $L_1$, Y, Y', $L_2$, and $R_2$ are as described above for Formula II.

In another embodiment, compounds of Formula (IIa) are disclosed:

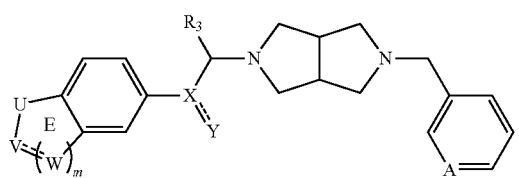

(IIa)

and pharmaceutically acceptable salts, prodrugs, solvates, hydrates, tautomers, or stereoisomers thereof;
wherein:
A is independently N or $CR_x$;
U is O, S, $NR_y$, C=O, or $C(R_x)_m$;
V is O, S, N, $NR_y$, C=O, or $C(R_x)_m$;
each W is independently selected from O, S, C=O, N, $NR_y$, or $C(R_x)_m$;
------- is an optional double bond which allows the E ring to be partially or fully saturated;
X is CH or C;
Y is OH or O;
$R_3$ is H;
each m is independently 1, or 2;
R is H, OH, or $CH_3$;
$R_x$ is H, $C_{1-6}$ alkyl, halogen, —OH, or —$OC_{1-6}$ alkyl; and
$R_y$ is H, or $C_{1-6}$ alkyl.

In another embodiment, compounds of Formula (IIb) are disclosed:

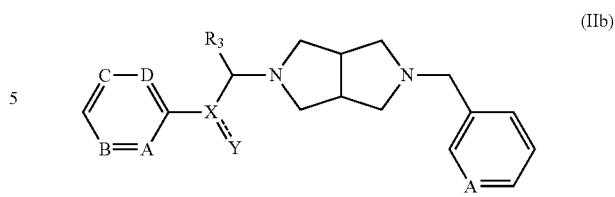

(IIb)

wherein:
A, B, C, and D are independently N or $CR_x$;
X is CH or C;
Y is OH or O;
$R_3$ is H; and
$R_x$ is H, $C_{1-6}$ alkyl, halogen, —OH, or —$OC_{1-6}$ alkyl.

In another embodiment of Formula II $L_1$ is —C(O)—, —C(O)—$C_1$-$C_3$alkylenyl-, —S(O)$_2$—, —S(O)$_2$NH—, —CONH—, —CON($R_{10}$)—, or a bond.

In another embodiment of the compounds of Formula II, $L_1$ is $C_1$-$C_2$ alkyl or $C_1$-$C_2$ branched alkyl substituted with OH.

In another embodiment of the compounds of Formula II, $L_1$ is —C(O)—$C_1$-$C_3$alkylenyl-.

In yet another embodiment of the compounds of Formula II, $L_2$ is a bond, $(CH_2)_n$ or $(CHR_{11})_n$ and n is 1.

In another embodiment of the compounds of Formula II, Y and Y' are H.

In another embodiment of the compounds of Formula II, Y and Y' are methyl.

In other embodiments, illustrative compounds of Formula II include:

2-(5-benzylhexahydropyrrolo[3,4-c]pyrrol-2(1H)-yl)-1-(4-hydroxyphenyl)ethanone;

rac-4-(2-(5-benzylhexahydropyrrolo[3,4-c]pyrrol-2(1H)-yl)-1-hydroxyethyl)phenol;

2-(5-benzylhexahydropyrrolo[3,4-c]pyrrol-2(1H)-yl)-1-(5-hydroxypyridin-2-yl)ethanone;

rac-6-(2-(5-benzylhexahydropyrrolo[3,4-c]pyrrol-2(1H)-yl)-1-hydroxyethyl)pyridin-3-ol;

2-(5-benzylhexahydropyrrolo[3,4-c]pyrrol-2(1H)-yl)-1-(3-fluoro-4-hydroxyphenyl)ethanone; or rac-4-(2-(5-benzylhexahydropyrrolo[3,4-c]pyrrol-2(1H)-yl)-1-hydroxyethyl)-2-fluorophenol.

In another aspect, compounds of Formula III are described:

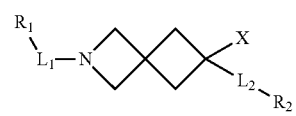

(III)

and pharmaceutically acceptable salts, prodrugs, solvates, hydrates, tautomers, or stereoisomers thereof
wherein $R_1$, $L_1$, X, $L_2$, and $R_2$ are as described above for Formula III:

In another embodiment, compounds of Formula (IIIa) are disclosed:

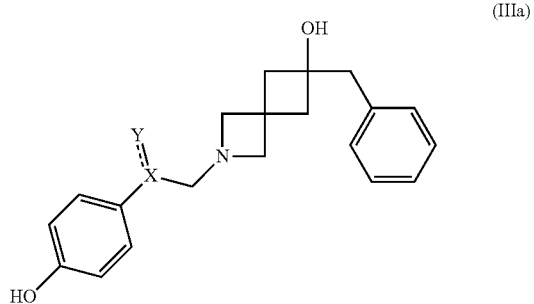

(IIIa)

wherein:

X is CH or C;

Y is OH or O; Other embodiments of this invention relate to compounds of Formula III where $L_1$ is straight or branched $C_1$-$C_5$ alkyl substituted with OH.

In other embodiments of the compounds of Formula III, $L_1$ is —C(O)—$C_1$-$C_3$alkylenyl-.

In other embodiments of the compounds of Formula III, $L_1$ is —C(O)O—.

In other embodiments of the compounds of Formula III, $L_2$ is $(CH_2)_n$ or $(CHR_{11})_n$ and n is 0.

In yet other embodiments of the compounds of Formula III, $L_2$ is $(CH_2)_n$ or $(CHR_{11})_n$ and n is 1.

In other embodiments of the compounds of Formula III, $L_2$ is $(CH_2)_n$ or $(CHR_{11})_n$ and n is 2.

In another embodiment of the compounds of Formula III, $R_2$ is phenyl. In another embodiment of the compounds of Formula III, $R_2$ is phenyl substituted with OH, $OR_{10}$, or CN.

In another embodiment of the compounds of Formula III, $R_1$ is $C_1$-$C_6$ alkyl or cycloalkyl.

In another embodiment of the compounds of Formula III, $R_1$ is $C_1$-$C_6$ alkyl.

In another embodiment of the compounds of Formula III, $R_1$ is aryl substituted with OH.

In another embodiment of the compounds of Formula III, $R_1$ is phenyl substituted with OH.

In another embodiment of the compounds of Formula III, $R_1$ is heteroaryl substituted with OH.

In other embodiments of the invention, suitable compounds of Formula III include:

2-(6-benzyl-6-hydroxy-2-azaspiro[3.3]heptan-2-yl)-1-(4-hydroxyphenyl)ethanone; or rac-6-benzyl-2-(2-hydroxy-2-(4-hydroxyphenyl)ethyl)-2-azaspiro[3.3]heptan-6-ol.

In an embodiment, the present disclosure includes Formula I, Formula II and Formula III compounds where any hydrogen atom may be replaced with a deuterium atom.

In another embodiment, tautomers of Formula I, Formula II, and Formula III are also described.

Methods of Using the Disclosed Compounds

In an embodiment, the present disclosure pertains to compounds that selectively modulate the activity of NMDA receptors that contain an NR2B subunit, which encompasses receptors containing two NR2B subunits or one NR2B subunit in combination with one other NR2 subunit (i.e., NR2A/NR2B, NR2B/NR2C, or NR2B/NR2D receptors). The present disclosure also relates to the therapeutic uses of such compounds.

One therapeutic use of a compound of the present invention that modulates the activity of NR2B-containing NMDA receptors is to treat patients suffering from Major Depressive Disorder (MDD, or depression). Depression is the prolonged experience of sadness, hopelessness, or worthlessness to a degree that significantly impairs quality of life and the ability to function Major Depressive Disorder is now commonly treated with Selective Serotonin Reuptake Inhibitors (SSRIs) such as Prozac, Zoloft and newer variants, but these agents are of limited effectiveness. Of additional concern is that even when these drugs are effective, the onset of action is may be delayed 4-6 weeks or more, during which time patients are at increased risk of suicide. Consequently, the Food and Drug Administration has inserted a black-box warning on all antidepressants concerning suicide risk. There is a need for new agents with greater antidepressant efficacy and faster onset of action.

Another therapeutic use for compounds of the present invention is in the treatment of schizophrenia. Schizophrenia is a debilitating mental disorder encompassing three symptom domains: positive (hallucination, delusions), negative (withdrawal), and cognitive (pervasive reduction in cognitive ability). Schizophrenia typically strikes in early adulthood with the emergence of positive symptoms; however, it is the chronic cognitive deficits that prevent patients from resuming normal activities after the initial onset of symptoms and largely accounts for a lifetime disability.

Given the fundamental role of NR2B containing NMDA receptors in brain function (vide supra), there are many other therapeutic uses for compounds of the present invention that modulate the activity of NR2B-containing NMDA receptors. Compounds of the present invention may improve cognitive function in individuals suffering from cognitive deficits in addition to schizophrenia, including but not limited to those suffering from Alzheimer's disease. Such compounds may also be used in the treatment of post-traumatic stress syndrome. Compounds of the present invention may be used to treat individuals suffering from neurological dysfunction, including but not limited to those suffering from Parkinson's disease, Huntington's disease, amyotrophic lateral sclerosis, multiple sclerosis, and seizure disorders. Compounds of the present invention may be used to treat individuals suffering from emotional disorders in addition to depression, including but not limited to those suffering from bipolar disorder, obsessive-compulsive disorder and other anxiety disorders. Compounds of the present invention may be used to treat individuals that experience dysfunction caused by abnormal brain development, including but not limited to those suffering from autism and autism spectrum disorders, Fragile X syndrome, tuberous sclerosis, Down's syndrome and other forms of mental retardation. Such compounds may also be used to treat abnormal brain function that results from infections of the central nervous system, exposure to toxic agents or other xenobiotics or naturally occurring toxins.

The disclosed compound can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as *acacia*, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, Disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

In many examples and intermediates, there is a plane of symmetry present in the molecules presented resulting in an achiral, meso compound. There is, however, relative stereochemistry between groups which is described. For example, 2-((3aR,5r,6aS)-5-benzyl-5-hydroxyhexahydrocyclopenta[c]pyrrol-2(1H)-yl)-1-(4-methoxyphenyl)ethanone has a core structure that is designated with absolute configuration designations. This nomenclature is used to describe the relative configurations of the benzyl group with respect to the bridgehead hydrogens. In this example, the benzyl substituent is exo with respect to the larger pyrrolidine ring of the bicyclic system as drawn. It is understood that when multiple stereoisomers may exist, all are included within the scope of the invention. In cases where any substituent also contains a stereogenic center, the compound becomes chiral and we use the designator "rac" to denote the synthesis of racemic mixtures of these examples. It is understood that the single enantiomers can be separated from this mixture and are included within the scope of the invention.

Example 1

Preparation of 5-hydroxy-N-(4-methoxyphenyl)-5-phenylhexahydrocyclopenta[c]pyrrole-2(1H)-carboxamide

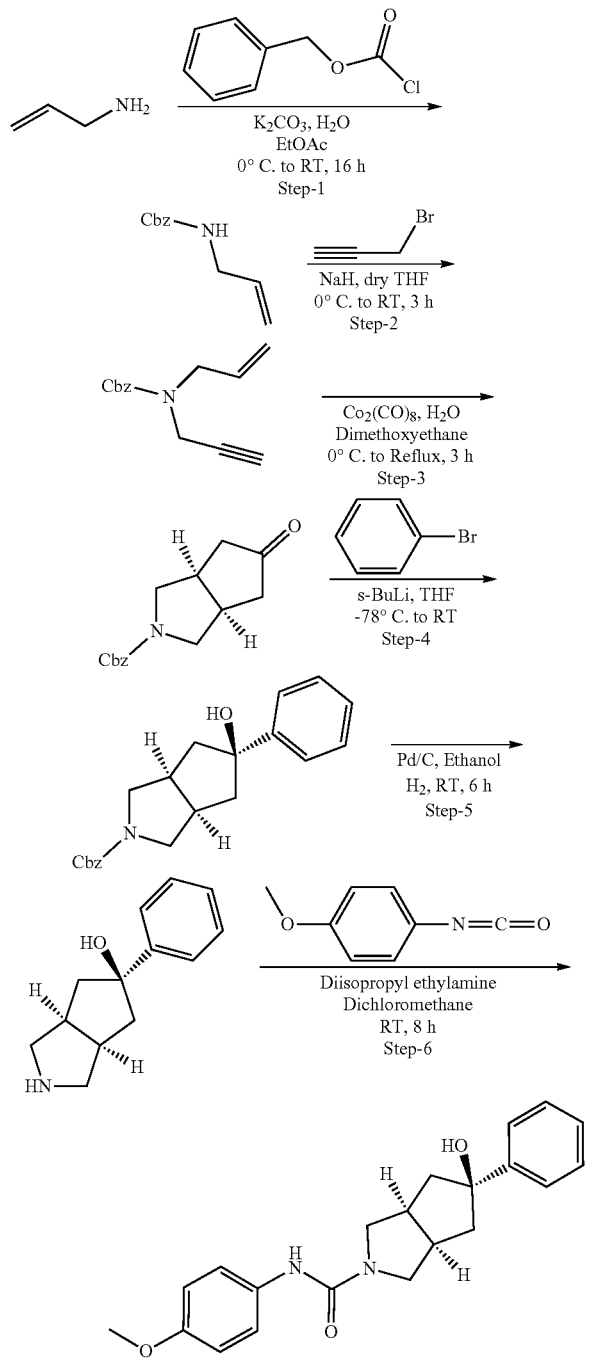

Step-1: Preparation of benzyl allylcarbamate

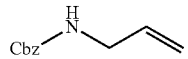

To a stirred suspension of K$_2$CO$_3$ (121 g, 2.0 eq, 876.4 mmol) in ethyl acetate (600 mL) and water (600 mL) was added prop-2-en-1-amine (20.0 g, 350.5 mmol) at room temperature. The reaction mixture was cooled to 0° C. Benzyl carbonochloridate (71.76 g, 420.6 mmol) was added drop wise to the above reaction mixture at 0° C. The reaction mixture was allowed to cool to room temperature and stirred for 16 h. After completion of the reaction (monitored by TLC), the organic layer was washed with sodium bicarbonate solution (200 mL×2), water (200 ml×2), brine (100 mL), dried over sodium sulfate, filtered and evaporated to afford the crude product, which was purified by silica gel column chromatography (10% ethyl acetate/hexane) to obtain the title compound benzyl allylcarbamate (65 g, 97% yield) as colorless liquid. Calculated (M+H): 192.09. Found (M+1): 192.2.

Step-2: Preparation of benzyl allyl(prop-2-yn-1-yl)carbamate

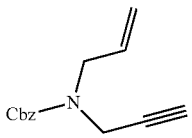 [SMILES: C#CCN(CC=C)C(=O)OCc1ccccc1]

To a stirred suspension of sodium hydride (95%) (19.57 g, 815.8 mmol) in dry tetrahydrofuran (800 mL) was added benzyl allylcarbamate (78 g, 177.0 mmol) slowly at 0° C., the reaction mixture was allowed to warm to room temperature and stirred for 30 min. After 30 min, the reaction mixture was cooled to 0° C., propargyl bromide solution (80 wt. % in toluene) (159 mL, 0.62 mmol) was added slowly to the reaction mixture, and allowed to warm to room temperature and stirred for 3 h. After completion of reaction (monitored by TLC), the reaction mixture was quenched with cold water, extracted with ethyl acetate (500 mL×3). The combined organic layer was washed with water (200 mL×2), brine (200 mL), dried over sodium sulfate, filtered and concentrated under vacuum to afford the crude product, which was purified by silica gel column chromatography (8% ethyl acetate/hexane) to obtain the title compound benzyl allyl(prop-2-yn-1-yl)carbamate (74 g, 79% yield) as a yellow liquid. Calculated (M+H): 230.11. Found (M+1): 230.2.

Step-3: Preparation of benzyl 5-oxohexahydrocyclopenta[c]pyrrole-2(1H)-carboxylate

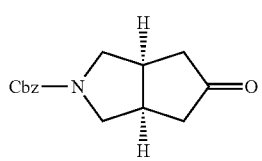 [SMILES: O=C1C[C@@H]2CN(C(=O)OCc3ccccc3)C[C@@H]2C1]

To a stirred solution of benzyl allyl(prop-2-yn-1-yl)carbamate (40 g, 174.4 mmol) in a mixture of water and dimethoxyethane (65 mL: 400 mL) was added dicobalt octacarbonyl [moistened with hexane (hexane 1-10%), ≥90% (Co)] (72 g, 191.9 mmol) at 0° C. The reaction mixture was allowed to warm to room temperature slowly and heated to 100° C. and stirred for 3 h. After completion of reaction (monitored by TLC), the reaction mixture was concentrated to afford crude product which was purified by silica gel column chromatography (50% ethylacetate/hexane) to obtain the title compound benzyl 5-oxohexahydrocyclopenta[c]pyrrole-2(1H)-carboxylate (33 g, 73% yield) as a brown solid. Calculated (M+H): 260.12. Found (M+H): 260.2.

Step-4: Preparation of benzyl 5-hydroxy-5-phenylhexahydrocyclopenta[c]pyrrole-2(1H)-carboxylate

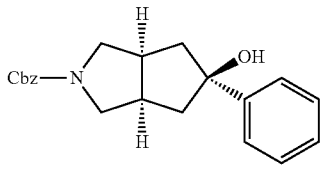 [SMILES: O=C(OCc1ccccc1)N1C[C@@H]2C[C@@](O)(c3ccccc3)C[C@@H]2C1]

To a stirred solution of bromobenzene (6.0 g, 38.21 mmol) in dry tetrahydrofuran (120 mL) was added sec-BuLi (1.3 M in hexane) (43.5 mL, 57.32 mmol) at −78° C. slowly under N₂. The reaction mixture was stirred for 15 min at −78° C., then allowed to warm to −40° C. and stirred for 30 min. The reaction mixture was cooled to −78° C., a solution of benzyl 5-oxohexahydrocyclopenta[c]pyrrole-2(1H)-carboxylate (6.9 g, 26.75 mmol) in dry tetrahydrofuran was added drop wise at −78° C., stirred for 1 h at −78° C. and gradually warmed to room temperature in 2 h. After completion of reaction (monitored by TLC), quenched with saturated solution of ammonium chloride (100 mL) and the mixture extracted with ethyl acetate (250 mL×3). The combined organic layer was concentrated to afford the crude product which was purified by silica gel column chromatography (35% ethylacetate/hexane) to obtain the title compound benzyl 5-hydroxy-5-phenylhexahydrocyclopenta[c]pyrrole-2(1H)-carboxylate (2.95 g, 33% yield) as a pale yellow solid. Calculated (M+H): 338.17. Found [(M+H)−H2O]: 320.2.

Step-5: Preparation of 5-phenyloctahydrocyclopenta[c]pyrrol-5-ol

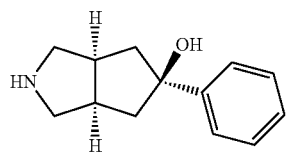 [SMILES: O[C@@]1(c2ccccc2)C[C@H]2CNC[C@H]2C1]

To a stirred solution of benzyl 5-hydroxy-5-phenylhexahydrocyclopenta[c]pyrrole-2(1H)-carboxylate (7.2 g, 0.02 mmol) in ethanol (100 mL), was added 10% Pd/C (1.4 g) under N₂ atmosphere. The reaction subjected to hydrogenation in balloon and stirred for 6 h. After completion of reaction (monitored by TLC), the reaction mixture was filtered through celite bed, washed with methanol. The filtrate was concentrated under vacuum to obtain the title compound 5-phenyloctahydrocyclopenta[c]pyrrol-5-ol (4.0 g (crude), 97% yield) as a pale yellow liquid. Calculated (M+H): 204.13. Found (M+H): 204.0.

Step-6: Preparation of 5-hydroxy-N-(4-methoxyphenyl)-5-phenylhexahydrocyclopenta[c]pyrrole-2(1H)-carboxamide

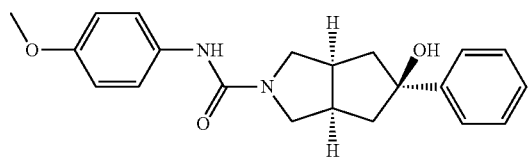 [SMILES: COc1ccc(NC(=O)N2C[C@@H]3C[C@@](O)(c4ccccc4)C[C@@H]3C2)cc1]

To a stirred solution of 5-phenyloctahydrocyclopenta[c]pyrrol-5-ol (0.05 g, 0.25 mmol) in dichloromethane (5 mL), was added diisopropyl ethylamine (0.08 mL, 0.49 mmol) and 1-isocyanato-4-methoxybenzene (0.04 g, 0.27 mmol) at 0° C., the reaction mixture was allowed to warm to room temperature and stirred for 8 h. After completion of reaction (monitored by TLC) the reaction mixture was quenched with saturated sodium bicarbonate solution (10 mL) and extracted with dichloromethane (25 mL×2). The combined organic layer was washed with water (10 mL), brine (10 mL), dried over anhydrous sodium sulfate and concentrated under reduced pressure to afford the crude compound which was purified by silica gel column chromatography (3% methanol/dichloromethane) to obtain the title compound 5-hydroxy-N-(4-methoxyphenyl)-5-phenylhexahydrocyclopenta[c]pyrrole-2(1H)-carboxamide (0.056 g, 69% yield) as a white solid. Calculated (M+H): 353.18. Found (M+H): 353.4.

Example 2

Preparation of (3aR,6aS)-benzyl 5-oxohexahydrocyclopenta[c]pyrrole-2(1H)-carboxylate Scheme 2

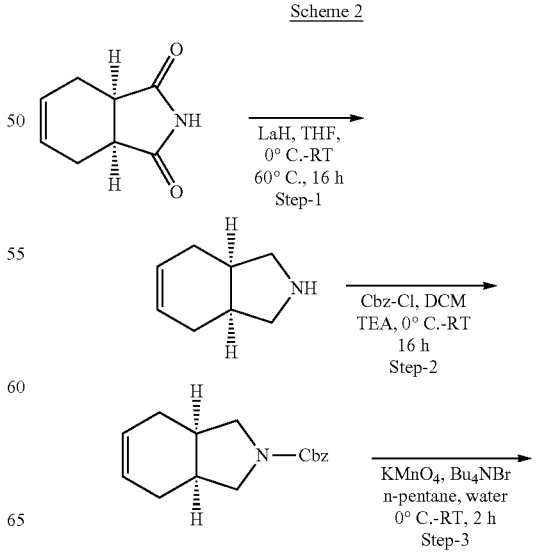

-continued

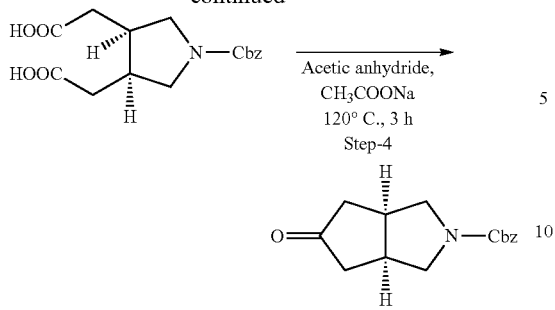

Step-1: Preparation of 2,3,3a,4,7,7a-hexahydro-1H-isoindole

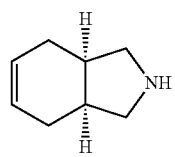

Lithium aluminium hydride (197 g, 5.19 mol) powder was added to tetrahydrofuran (6500 mL) at 0° C. and stirred for 30 minutes. Then a solution of 3a,4,7,7a-tetrahydro-1H-isoindole-1,3(2H)-dione (314 g, 2.077 mol) in tetrahydrofuran (700 mL) was added slowly drop wise to the above suspension over a period of 2 h. The reaction mass was then allowed to warm up to room temperature and stirred at 60° C. for 16 h. After completion of reaction (monitored by TLC), reaction mass was cooled to 0° C. and quenched with water (200 mL) followed by the addition of 15% aqueous potassium hydroxide solution. The resulting suspension was filtered through celite and the bed was thoroughly washed with dichloromethane (2000 mL). The combined filtrate was concentrated under vacuum to get the title compound 2,3,3a,4,7,7a-hexahydro-1H-isoindole (270 g, crude) as a brownish liquid which was used for next step without further purification. Calculated M+H: 124.10. Found M+H: 124.12.

Step-2: Preparation of benzyl 1,3,3a,4,7,7a-hexahydro-2H-isoindole-2-carboxylate

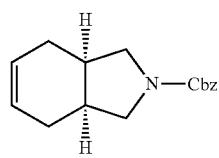 [SMILES: O=C(OCc1ccccc1)N1C[C@H]2CC=CC[C@H]2C1]

To a stirred solution of 2,3,3a,4,7,7a-hexahydro-1H-isoindole (270 g, 2.19 mol) in dry dichloromethane (5.5 liter) at 0° C. were added triethylamine (607 mL, 4.35 mol) and benzyl chloroformate (311.6 mL, 2.19 mol) under inert atmosphere. The reaction mass was warmed to room temperature and stirred for 16 h. After completion of reaction (monitored by TLC), reaction mass was diluted with dichloromethane (2000 mL) followed by addition of water (5000 mL). The organic layer was separated, dried over anhydrous sodium sulfate and evaporated under vacuum to get crude product which was purified by column chromatography using 100-200 mesh silica gel and 5% ethyl acetate/hexane as eluent to afford the title compound benzyl 1,3,3a,4,7,7a-hexahydro-2H-isoindole-2-carboxylate (303 g, 53.7%) as a brownish liquid. Calculated M+H: 258.14. Found M+H: 258.18.

Step-3: Preparation of 2,2'-(1-((benzyloxy)carbonyl)pyrrolidine-3,4-diyl)diacetic acid

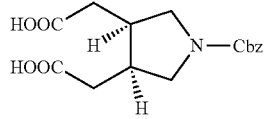 [SMILES: O=C(O)C[C@@H]1CN(C(=O)OCc2ccccc2)C[C@@H]1CC(=O)O]

To a stirred solution of benzyl 1,3,3a,4,7,7a-hexahydro-2H-isoindole-2-carboxylate (303 g, 1.177 mol) in pentane (1200 mL) was added a solution of potassium permanganate (558 g, 3.53 mol) and tetrabutyl ammonium bromide (56.9 g, 0.177 mol) in water (7500 mL) at 0° C. and the reaction mixture was warmed to room temperature. The resulting suspension was stirred at room temperature for 2 h. After completion of reaction (monitored by TLC), reaction mass was filtered through a celite bed and the bed was washed with water (4000 mL). The combined filtrate was washed with ethyl acetate (2000 mL) and the organic layer was separated. The aqueous layer was acidified with 1M hydrochloric acid solution to pH=1 and extracted with ethyl acetate (10000 mL×3). The Combined organic layer was dried over anhydrous sodium sulfate and evaporated in vacuum to get crude title compound 2,2'-(1-((benzyloxy)carbonyl)pyrrolidine-3,4-diyl)diacetic acid (313 g, crude) as yellowish semisolid which was used for next step without further purification. Calculated M+H: 322.33. Found M+H: 322.20.

Step-4: Preparation of benzyl (3aR,6aS)-5-oxohexahydrocyclopenta[c]pyrrole-2(1H)-carboxylate

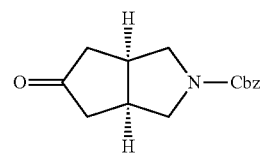 [SMILES: O=C1C[C@@H]2CN(C(=O)OCc3ccccc3)C[C@@H]2C1]

To a stirred solution of 2,2'-(1-((benzyloxy)carbonyl)pyrrolidine-3,4-diyl)diacetic acid (313 g, 0.975 mol) in acetic anhydride (1700 mL) was added sodium acetate (79.9 g, 0.975 mol) under inert atmosphere and resulting suspension was stirred at 120° C. for 3 h. After completion of reaction (monitored by TLC), the reaction mass was cooled to room temperature, filtered and washed with ethyl acetate (1000 mL). The combined filtrate was evaporated in vacuum to get crude product which was purified by column chromatography using 100-200 mesh silica gel and 30% ethyl acetate/hexane as eluent to afford the title compound benzyl (3aR,6aS)-5-oxohexahydrocyclopenta[c]pyrrole-2(1H)-carboxylate (180 g, 71.2% yield) as a white solid. Calculated M+H: 260.12. Found M+H: 260.30.

Example 3

Preparation of 5-(o-tolyl)octahydrocyclopenta[c]pyrrol-5-ol

Scheme 3

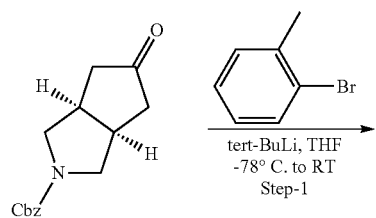

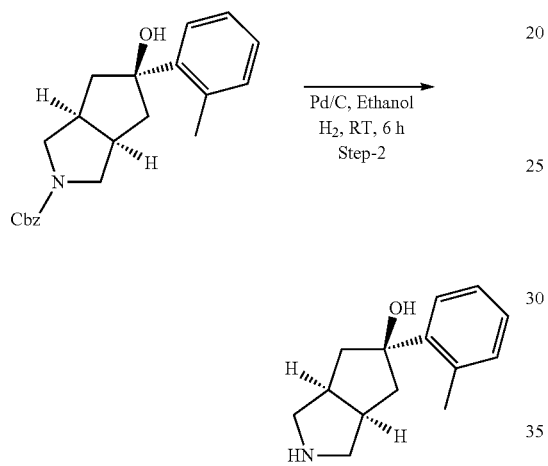

Step-1: Preparation of benzyl 5-hydroxy-5-(o-tolyl)hexahydrocyclopenta[c]pyrrole-2(1H)-carboxylate To a stirred solution of 1-bromo-2-methylbenzene (6.0 g, 35.08 mmol) in dry tetrahydrofuran (100 mL) was added tert-BuLi (1.2 M in hexane, 32 mL, 47.36 mmol) at −78° C. slowly under $N_2$. The reaction mixture was stirred for 15 min at −78° C., then allowed to warm to −40° C. and stirred for 30 min. The reaction mixture was cooled to −78° C., a solution of benzyl 5-oxohexahydrocyclopenta[c]pyrrole-2(1H)-carboxylate (6.3 g, 24.55 mmol) in dry tetrahydrofuran was added drop wise at −78° C., stirred for 1 h at −78° C. and gradually allowed to warm to room temperature in 2 h. After completion of reaction (monitored by TLC), the reaction mixture was quenched with saturated solution of ammonium chloride (100 mL) and the mixture extracted with ethyl acetate (250 mL×2), dried over anhydrous sodium sulfate, concentrated to afford crude product which was purified by silica gel column chromatography (35% ethylacetate/hexane) to obtain the title compound benzyl 5-hydroxy-5-(o-tolyl)hexahydrocyclopenta[c]pyrrole-2(1H)-carboxylate (4.2 g, 49% yield) as a colorless semi solid. Calculated (M+H): 352.18. Found [(M+H)−H2O]: 334.2.

Step-2: Preparation of 5-(o-tolyl)octahydrocyclopenta[c]pyrrol-5-ol

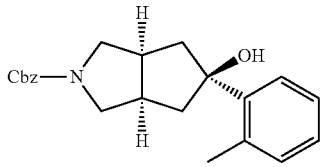 [SMILES: Cc1ccccc1[C@]1(O)C[C@H]2CN(C(=O)OCc3ccccc3)C[C@H]2C1]

To a stirred solution of benzyl 5-hydroxy-5-(o-tolyl)hexahydrocyclopenta[c]pyrrole-2(1H)-carboxylate (7.5 g, 21.10 mmol) in ethanol (100 mL), was added 10% Pd/C (1.4 g) under $N_2$ atmosphere. The reaction was subjected to hydrogenation in balloon and stirred for 6 h. After completion of reaction (monitored by TLC), the mixture was filtered through celite bed, washed with methanol. The filtrate was concentrated under vacuum to obtain the title compound 5-(o-tolyl)octahydrocyclopenta[c]pyrrol-5-ol (4.0 g (crude), 85% yield) as a pale yellow liquid. Calculated (M+H): 218.15. Found (M+H): 218.2.

Example 4

Preparation of 5-(3-methoxyphenyl)octahydrocyclopenta[c]pyrrol-5-ol

Scheme 4

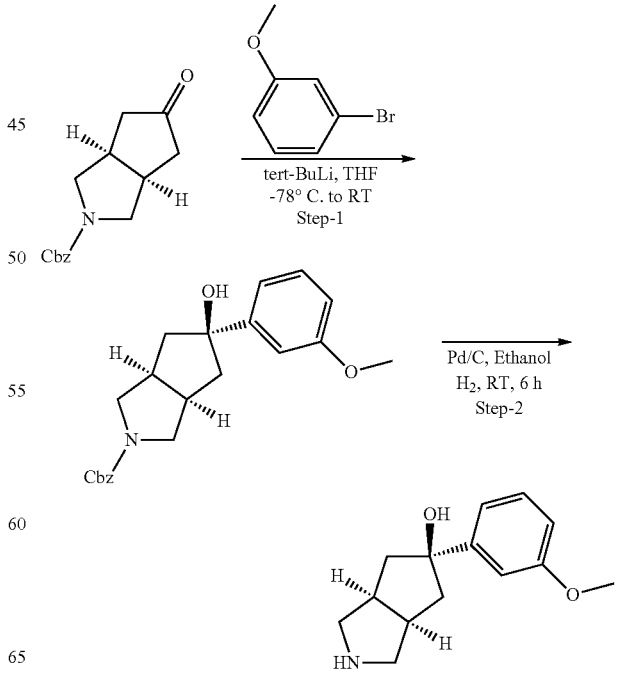

Step-1: Preparation of benzyl 5-hydroxy-5-(3-methoxyphenyl)hexahydrocyclopenta[c]pyrrole-2(1H)-carboxylate

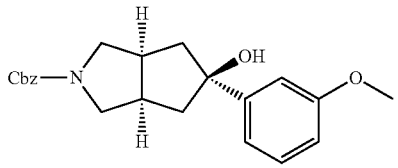 [SMILES: COc1cccc([C@]2(O)C[C@H]3CN(C(=O)OCc4ccccc4)C[C@H]3C2)c1]

To a stirred solution of 1-bromo-3-methoxybenzene (10.0 g, 53.46 mmol) in dry tetrahydrofuran (100 mL) was added tert-BuLi (1.5M in hexane, 50 mL, 74.80 mmol) at −78° C. slowly under $N_2$. The reaction mixture was stirred for 15 min at −78° C., then allowed to warm to −40° C. and stirred for 30 min. The reaction mixture was cooled to −78° C., a solution of benzyl 5-oxohexahydrocyclopenta[c]pyrrole-2(1H)-carboxylate (10.39 g, 40.10 mmol) in dry tetrahydrofuran was added drop wise at −78° C., stirred for 1 h at −78° C. and gradually warmed to room temperature in 2 h. After completion of reaction (monitored by TLC), the mixture was quenched with saturated solution of ammonium chloride (150 mL) and the mixture extracted with ethyl acetate (250 mL×3), dried over anhydrous sodium sulfate, concentrated to afford the crude product which was purified by silica gel column chromatography (60% ethylacetate/hexane) to obtain the title compound benzyl 5-hydroxy-5-(3-methoxyphenyl)hexahydrocyclopenta[c]pyrrole-2(1H)-carboxylate (3.3 g, 22.41% yield) as a colorless semi solid. Calculated (M+H): 368.18. Found (M+H): 368.2.

Step-2: Preparation of 5-(3-methoxyphenyl)octahydrocyclopenta[c]pyrrol-5-ol

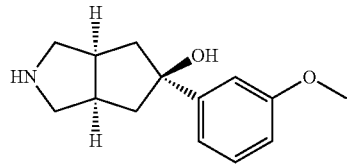 [SMILES: COc1cccc([C@]2(O)C[C@H]3CNC[C@H]3C2)c1]

To a stirred solution of benzyl 5-hydroxy-5-(3-methoxyphenyl)hexahydrocyclopenta[c]pyrrole-2(1H)-carboxylate (3.3 g, 367.43 mmol) in ethanol (50 mL), was added 10% Pd/C (0.7 g) under $N_2$ atmosphere. The reaction subjected to hydrogenation in balloon and stirred for 16 h. After completion of reaction, the reaction mixture was filtered through celite bed, washed with methanol. The filtrate was concentrated under vacuum to obtain the title compound 5-(3-methoxyphenyl)octahydrocyclopenta[c]pyrrol-5-ol (2.0 g, crude) as a white solid. Calculated (M+H): 234.14. Found (M+H): 234.0.

Example 5

Preparation of 5-(4-(tert-butyl)phenyl)octahydrocyclopenta[c]pyrrol-5-ol

Scheme 5

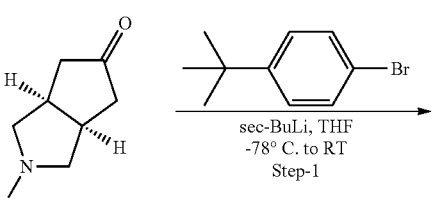

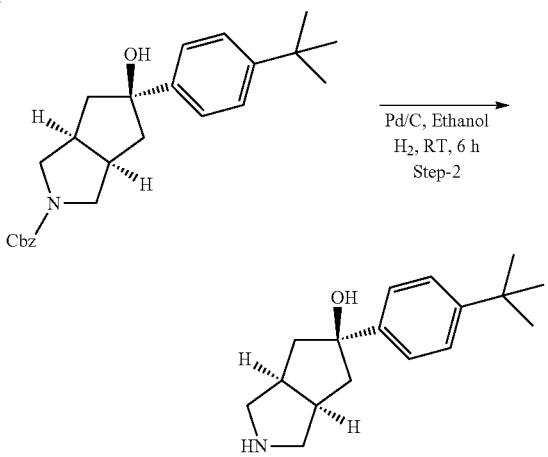

Step-1: Preparation of benzyl 5-(4-(tert-butyl)phenyl)-5-hydroxyhexahydrocyclopenta[c]pyrrole-2(1H)-carboxylate

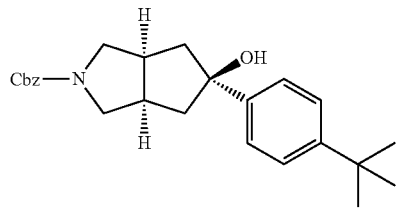 [SMILES: CC(C)(C)c1ccc([C@]2(O)C[C@H]3CN(C(=O)OCc4ccccc4)C[C@H]3C2)cc1]

To a stirred solution of 1-bromo-4-(tert-butyl)benzene (10.0 g, 46.92 mmol) in dry tetrahydrofuran (100 mL) was added sec-BuLi (1.2M in hexane, 47 mL, 56.3 mmol) at −78° C. slowly under $N_2$ atmosphere. The reaction mixture was stirred for 15 min at −78° C., then allowed to warm to −40° C. and stirred for 30 min. The reaction mixture was again cooled to −78° C., a solution of benzyl 5-oxohexahydrocyclopenta[c]pyrrole-2(1H)-carboxylate (12.15 g, 46.92 mmol) in dry tetrahydrofuran was added drop wise at −78° C., stirred for 1 h at −78° C. and gradually allowed to warm to room temperature in 2 h. After completion of reaction (monitored by TLC), the reaction mixture was quenched with saturated solution of ammonium chloride (150 mL) and extracted with ethyl acetate (250 mL×3), dried over anhydrous sodium sulfate, concentrated to afford crude product which was purified by silica gel column chromatography (35% ethylacetate/hexane) to obtain the title compound benzyl 5-(4-(tert-butyl)phenyl)-5-hydroxyhexahydrocyclopenta[c]pyrrole-2(1H)-carboxylate (5.05 g, 27% yield) as off-white solid. Calculated (M+H): 394.23. Found [(M+H)−H2O]: 376.3.

Step-2: Preparation of 5-(4-(tert-butyl)phenyl)octahydrocyclopenta[c]pyrrol-5-ol

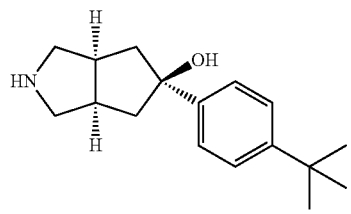 [SMILES: CC(C)(C)c1ccc([C@]2(O)C[C@H]3CNC[C@H]3C2)cc1]

To a stirred solution of benzyl 5-(4-(tert-butyl)phenyl)-5-hydroxyhexahydrocyclopenta[c]pyrrole-2(1H)-carboxylate (5.05 g, 12.8 mmol) in ethanol (500 mL), was added 10% Pd/C (1.0 g) under $N_2$ atmosphere. The reaction subjected to hydrogenation in balloon and stirred for 6 h. After completion of reaction, the mixture was filtered through celite bed, washed with methanol. The filtrate was concentrated under vacuum to obtain the title compound 5-(4-(tert-butyl)phenyl)octahydrocyclopenta[c]pyrrol-5-ol (3.2 g (crude), 97% yield) as off white solid. Calculated (M+H): 260.19. Found (M+H): 260.3.

TABLE 1

The following compounds were prepared by the method described above.

| Structure | IUPAC Name | Calculated M + H | Found M + H |
|---|---|---|---|
| 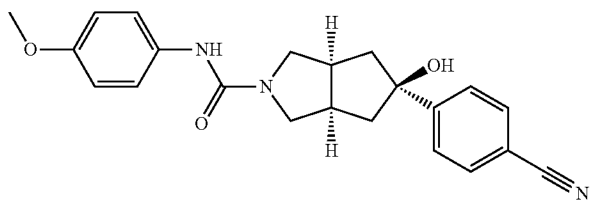 [SMILES: COc1ccc(NC(=O)N2C[C@@H]3C[C@@](O)(c4ccc(C#N)cc4)C[C@@H]3C2)cc1] | 5-(4-cyanophenyl)-5-hydroxy-N-(4-methoxyphenyl)-octahydrocyclopenta[c]pyrrole-2-carboxamide | 378.17 | 378.2 |
| 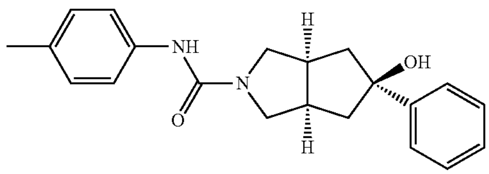 [SMILES: Cc1ccc(NC(=O)N2C[C@@H]3C[C@@](O)(c4ccccc4)C[C@@H]3C2)cc1] | 5-hydroxy-N-(4-methylphenyl)-5-phenyl-octahydrocyclopenta[c]pyrrole-2-carboxamide | 337.18 | 337.4 |
| 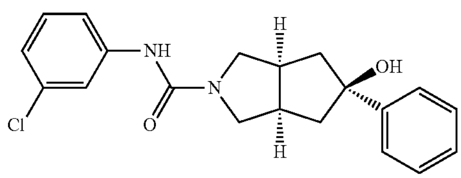 [SMILES: O=C(Nc1cccc(Cl)c1)N1C[C@@H]2C[C@@](O)(c3ccccc3)C[C@@H]2C1] | N-(3-chlorophenyl)-5-hydroxy-5-phenyl-octahydrocyclopenta[c]pyrrole-2-carboxamide | 357.13 | 357.3 |
| 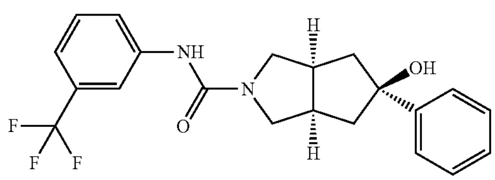 [SMILES: O=C(Nc1cccc(C(F)(F)F)c1)N1C[C@@H]2C[C@@](O)(c3ccccc3)C[C@@H]2C1] | 5-hydroxy-5-phenyl-N-[3-(trifluoromethyl)phenyl]-octahydrocyclopenta[c]pyrrole-2-carboxamide | 389.16 (M − H) | 389.2 (M − H) |
| 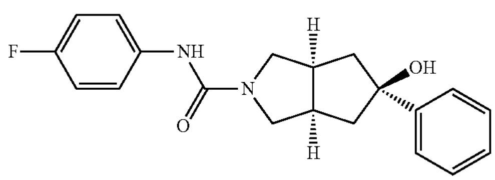 | N-(4-fluorophenyl)-5-hydroxy-5-phenyl-octahydrocyclopenta[c]pyrrole-2-carboxamide | 341.16 | 341.2 |
| 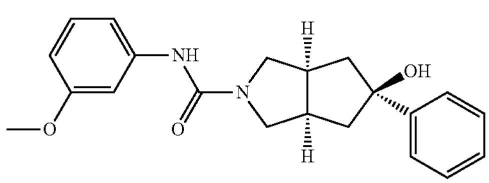 [SMILES: COc1cccc(NC(=O)N2C[C@@H]3C[C@@](O)(c4ccccc4)C[C@@H]3C2)c1] | 5-hydroxy-N-(3-methoxyphenyl)-5-phenyl-octahydrocyclopenta[c]pyrrole-2-carboxamide | 353.18 | 353.2 |

TABLE 1-continued

The following compounds were prepared by the method described above.

| Structure | IUPAC Name | Calculated M + H | Found M + H |
|---|---|---|---|
| 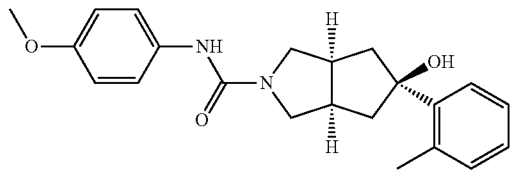 [SMILES: COc1ccc(NC(=O)N2C[C@@H]3C[C@@](O)(c4ccccc4C)C[C@@H]3C2)cc1] | 5-hydroxy-N-(4-methoxyphenyl)-5-(2-methylphenyl)-octahydrocyclopenta[c]pyrrole-2-carboxamide | 367.19 | 367.2 |
| 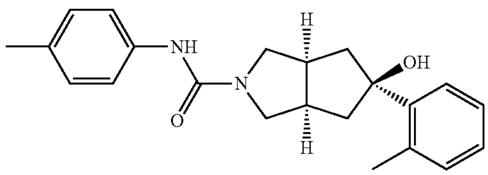 [SMILES: Cc1ccc(NC(=O)N2C[C@@H]3C[C@@](O)(c4ccccc4C)C[C@@H]3C2)cc1] | 5-hydroxy-5-(2-methylphenyl)-N-(4-methylphenyl)-octahydrocyclopenta[c]pyrrole-2-carboxamide | 351.20 | 351.3 |
| 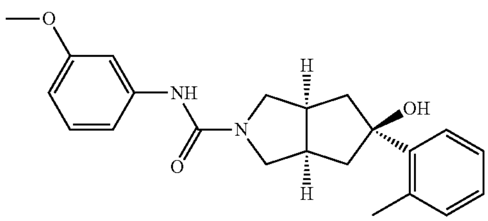 [SMILES: COc1cccc(NC(=O)N2C[C@@H]3C[C@@](O)(c4ccccc4C)C[C@@H]3C2)c1] | 5-hydroxy-N-(3-methoxyphenyl)-5-(2-methylphenyl)-octahydrocyclopenta[c]pyrrole-2-carboxamide | 367.19 | 367.3 |
| 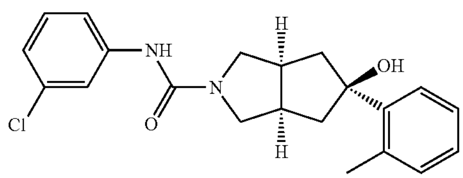 [SMILES: Cc1ccccc1[C@]1(O)C[C@H]2CN(C(=O)Nc3cccc(Cl)c3)C[C@H]2C1] | N-(3-chlorophenyl)-5-hydroxy-5-(2-methylphenyl)-octahydrocyclopenta[c]pyrrole-2-carboxamide | 369.14 (M − H) | 369.2 (M − H) |
| 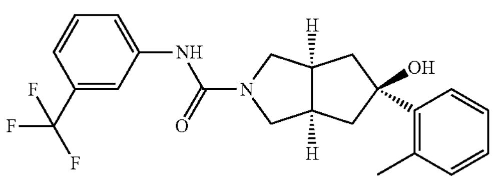 [SMILES: Cc1ccccc1[C@]1(O)C[C@H]2CN(C(=O)Nc3cccc(C(F)(F)F)c3)C[C@H]2C1] | 5-hydroxy-5-(2-methylphenyl)-N-[3-(trifluoromethyl)phenyl]-octahydrocyclopenta[c]pyrrole-2-carboxamide | 403.17 (M − H) | 403.4 (M − H) |
| 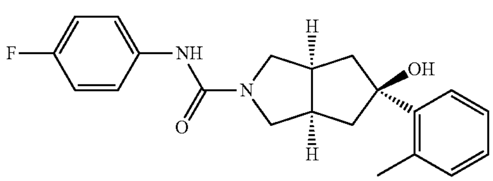 [SMILES: Cc1ccccc1[C@]1(O)C[C@H]2CN(C(=O)Nc3ccc(F)cc3)C[C@H]2C1] | N-(4-fluorophenyl)-5-hydroxy-5-(2-methylphenyl)-octahydrocyclopenta[c]pyrrole-2-carboxamide | 355.17 | 355.2 |
| 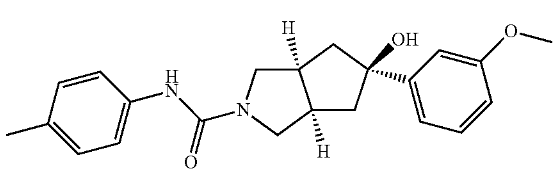 | 5-hydroxy-5-(3-methoxyphenyl)-N-(4-methylphenyl)-octahydrocyclopenta[c]pyrrole-2-carboxamide | 367.19 | 367.2 |

TABLE 1-continued

The following compounds were prepared by the method described above.

| Structure | IUPAC Name | Calculated M + H | Found M + H |
|---|---|---|---|
| 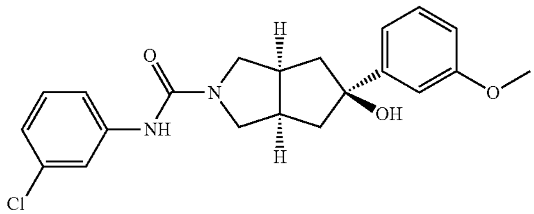 [SMILES: COc1cccc([C@]2(O)C[C@H]3CN(C(=O)Nc4cccc(Cl)c4)C[C@H]3C2)c1] | N-(3-chlorophenyl)-5-hydroxy-5-(3-methoxyphenyl)-octahydrocyclopenta[c]pyrrole-2-carboxamide | 385.14 (M − H) | 385.2 (M − H) |
| 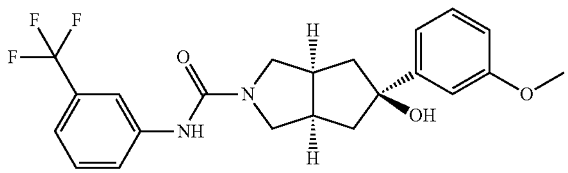 [SMILES: COc1cccc([C@]2(O)C[C@H]3CN(C(=O)Nc4cccc(C(F)(F)F)c4)C[C@H]3C2)c1] | 5-hydroxy-5-(3-methoxyphenyl)-N-[3-(trifluoromethyl)phenyl]-octahydrocyclopenta[c]pyrrole-2-carboxamide | 419.17 (M − H) | 419.4 (M − H) |
| 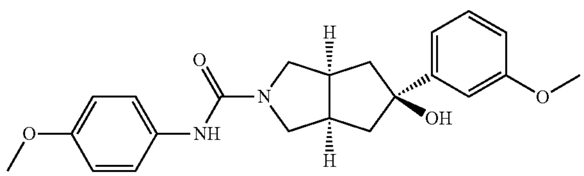 | 5-hydroxy-5-(3-methoxyphenyl)-N-(4-methoxyphenyl)-octahydrocyclopenta[c]pyrrole-2-carboxamide | 383.19 | 383.2 |
| 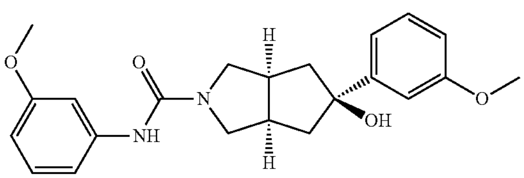 [SMILES: COc1cccc(NC(=O)N2C[C@@H]3C[C@@](O)(c4cccc(OC)c4)C[C@@H]3C2)c1] | 5-hydroxy-N,5-bis(3-methoxyphenyl)-octahydrocyclopenta[c]pyrrole-2-carboxamide | 381.19 (M − H) | 381.3 (M − H) |
| 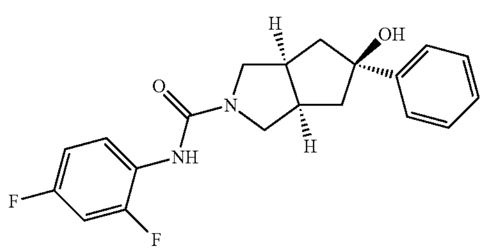 [SMILES: O=C(Nc1ccc(F)cc1F)N1C[C@@H]2C[C@@](O)(c3ccccc3)C[C@@H]2C1] | N-(2,4-difluorophenyl)-5-hydroxy-5-phenyl-octahydrocyclopenta[c]pyrrole-2-carboxamide | 359.15 | 359.2 |
| 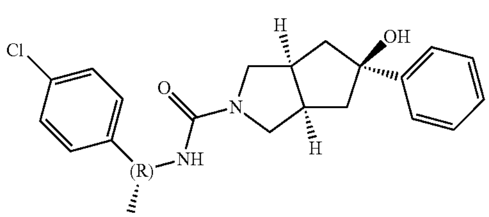 | N-[(1R)-1-(4-chlorophenyl)ethyl]-5-hydroxy-5-phenyl-octahydrocyclopenta[c]pyrrole-2-carboxamide | 385.16 | 385.2 |
| 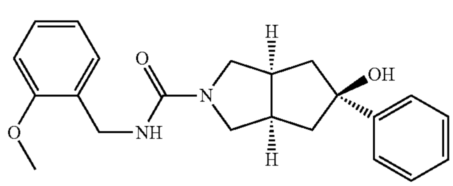 [SMILES: COc1ccccc1CNC(=O)N1C[C@@H]2C[C@@](O)(c3ccccc3)C[C@@H]2C1] | 5-hydroxy-N-[(2-methoxyphenyl)methyl]-5-phenyl-octahydrocyclopenta[c]pyrrole-2-carboxamide | 367.19 | 367.3 |

Example 6

Preparation of methyl 4-(5-hydroxy-5-(o-tolyl)octahydrocyclopenta[c]pyrrole-2-carboxamido)benzoate Scheme 6

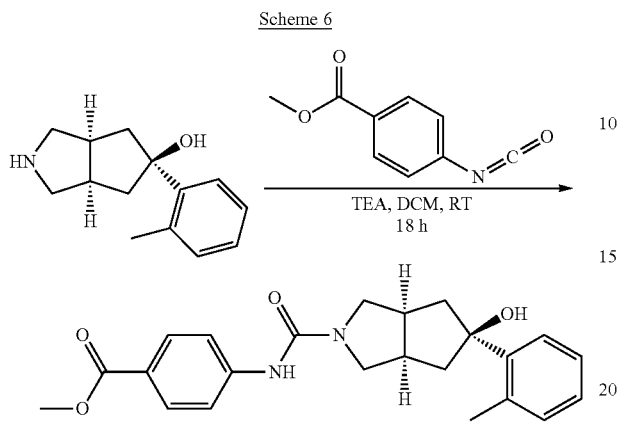

To a solution of 5-phenyloctahydrocyclopenta[c]pyrrol-5-ol (0.040 g, 0.19 mmol) in dichloromethane (2 mL) was added methyl 4-isocyanatobenzoate (0.04 g, 0.22 mmol) and triethylamine (0.036 mL) and resulting suspension was stirred at room temperature for 18 h. After completion of the reaction (monitored by TLC), the reaction mixture was diluted with water (2 mL), extracted with dichloromethane (10 mL×2), dried over sodium sulfate and concentrated to afford the crude material which was purified by prep HPLC (column: XSelect CSH C-18 Prep (19×250 mm, 5 um), mobile phase: A—5 mM ammonium acetate, B—acetonitrile, flow mode: gradient, flow: 15 ml/min, gradient T/% B: 0/30, 0.5/30, 15/90, 21/90, 21.5/30, 26/30).

TABLE 2

The following compounds were prepared by the method described above

| Structure | IUPAC Name | Calculated M + H | Found M + H |
|---|---|---|---|
| 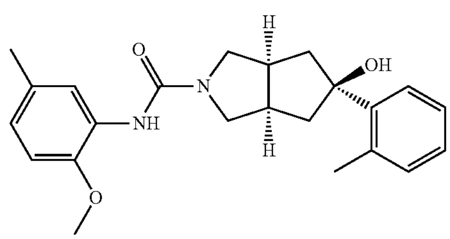 [SMILES: COc1ccc(C)cc1NC(=O)N1C[C@@H]2C[C@@](O)(c3ccccc3C)C[C@@H]2C1] | 5-hydroxy-N-(2-methoxy-5-methylphenyl)-5-(2-methylphenyl)-octahydrocyclopenta[c]pyrrole-2-carboxamide | 381.21 | 381.37 |
| 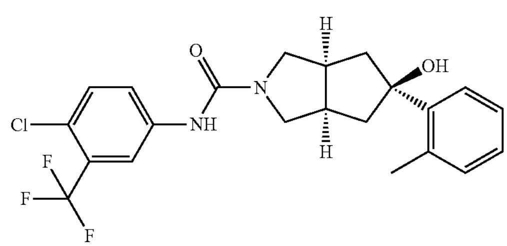 [SMILES: Cc1ccccc1[C@]1(O)C[C@H]2CN(C(=O)Nc3ccc(Cl)c(C(F)(F)F)c3)C[C@H]2C1] | N-[4-chloro-3-(trifluoromethyl)phenyl]-5-hydroxy-5-(2-methylphenyl)-octahydrocyclopenta[c]pyrrole-2-carboxamide | 437.13 (M − H) | 437.31 (M − H) |
| 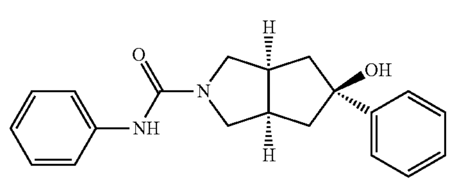 | 5-hydroxy-N,5-diphenyl-octahydrocyclopenta[c]pyrrole-2-carboxamide | 321.17 (M − H) | 321.33 (M − H) |
| 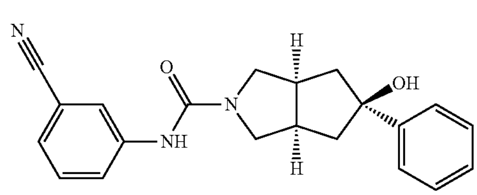 [SMILES: N#Cc1cccc(NC(=O)N2C[C@@H]3C[C@@](O)(c4ccccc4)C[C@@H]3C2)c1] | N-(3-cyanophenyl)-5-hydroxy-5-phenyl-octahydrocyclopenta[c]pyrrole-2-carboxamide | 346.16 (M − H) | 346.32 (M − H) |

TABLE 2-continued

The following compounds were prepared by the method described above

| Structure | IUPAC Name | Calculated M + H | Found M + H |
|---|---|---|---|
| 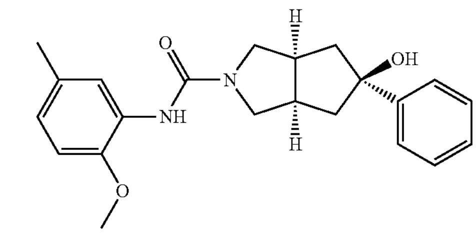 | 5-hydroxy-N-(2-methoxy-5-methylphenyl)-5-phenyl-octahydrocyclopenta[c]pyrrole-2-carboxamide | 367.19 | 367.34 |
| 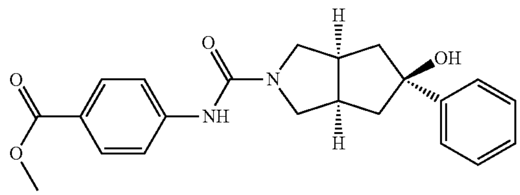 [SMILES: COC(=O)c1ccc(NC(=O)N2C[C@@H]3C[C@@](O)(c4ccccc4)C[C@@H]3C2)cc1] | methyl 4-[({5-hydroxy-5-phenyl-octahydrocyclopenta[c]pyrrol-2-yl}carbonyl)amino]benzoate | 379.17 (M − H) | 379.38 (M − H) |
| 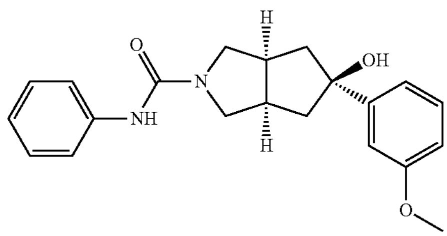 [SMILES: COc1cccc([C@]2(O)C[C@H]3CN(C(=O)Nc4ccccc4)C[C@H]3C2)c1] | 5-hydroxy-5-(3-methoxyphenyl)-N-phenyl-octahydrocyclopenta[c]pyrrole-2-carboxamide | 353.18 (M − H) | 351.32 (M − H) |
| 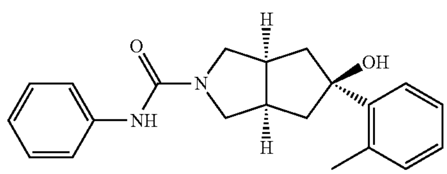 [SMILES: Cc1ccccc1[C@]1(O)C[C@H]2CN(C(=O)Nc3ccccc3)C[C@H]2C1] | 5-hydroxy-5-(2-methylphenyl)-N-phenyl-octahydrocyclopenta[c]pyrrole-2-carboxamide | 337.18 (M − H) | 335.33 (M − H) |
| 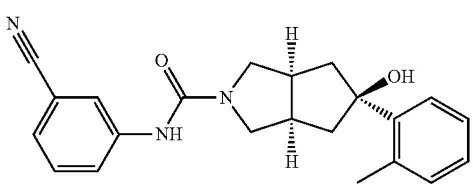 [SMILES: Cc1ccccc1[C@]1(O)C[C@H]2CN(C(=O)Nc3cccc(C#N)c3)C[C@H]2C1] | N-(3-cyanophenyl)-5-hydroxy-5-(2-methylphenyl)-octahydrocyclopenta[c]pyrrole-2-carboxamide | 360.18 (M − H) | 360.33 (M − H) |
| 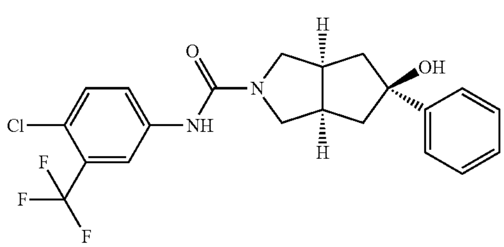 [SMILES: O=C(Nc1ccc(Cl)c(C(F)(F)F)c1)N1C[C@@H]2C[C@@](O)(c3ccccc3)C[C@@H]2C1] | N-[4-chloro-3-(trifluoromethyl)phenyl]-5-hydroxy-5-phenyl-octahydrocyclopenta[c]pyrrole-2-carboxamide | 423.12 | 423.28 |
| 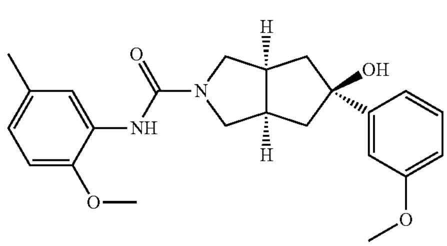 [SMILES: COc1cccc([C@]2(O)C[C@H]3CN(C(=O)Nc4cc(C)ccc4OC)C[C@H]3C2)c1] | 5-hydroxy-N-(2-methoxy-5-methylphenyl)-5-(3-methoxyphenyl)-octahydrocyclopenta[c]pyrrole-2-carboxamide | 397.20 | 397.44 |

TABLE 2-continued

The following compounds were prepared by the method described above

| Structure | IUPAC Name | Calculated M + H | Found M + H |
|---|---|---|---|
| 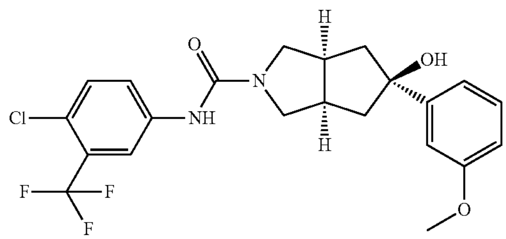 [SMILES: COc1cccc([C@]2(O)C[C@H]3CN(C(=O)Nc4ccc(Cl)c(C(F)(F)F)c4)C[C@H]3C2)c1] | N-[4-chloro-3-(trifluoromethyl)phenyl]-5-hydroxy-5-(3-methoxyphenyl)-octahydrocyclopenta[c]pyrrole-2-carboxamide | 453.13 (M − H) | 453.33 (M − H) |
| 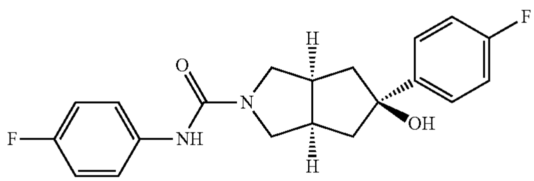 [SMILES: O=C(Nc1ccc(F)cc1)N1C[C@@H]2C[C@@](O)(c3ccc(F)cc3)C[C@@H]2C1] | N,5-bis(4-fluorophenyl)-5-hydroxy-octahydrocyclopenta[c]pyrrole-2-carboxamide | 357.15 (M − H) | 357.34 (M − H) |
| 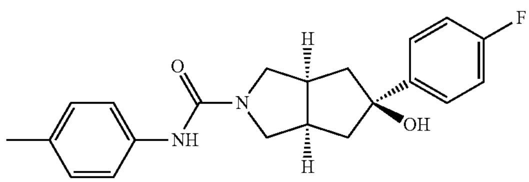 [SMILES: Cc1ccc(NC(=O)N2C[C@@H]3C[C@@](O)(c4ccc(F)cc4)C[C@@H]3C2)cc1] | 5-(4-fluorophenyl)-5-hydroxy-N-(4-methylphenyl)-octahydrocyclopenta[c]pyrrole-2-carboxamide | 353.17 (M − H) | 353.37 (M − H) |
| 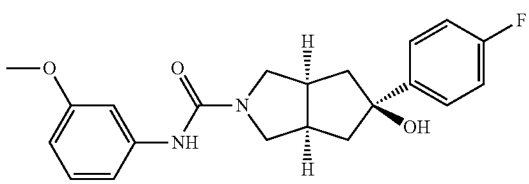 [SMILES: COc1cccc(NC(=O)N2C[C@@H]3C[C@@](O)(c4ccc(F)cc4)C[C@@H]3C2)c1] | 5-(4-fluorophenyl)-5-hydroxy-N-(3-methoxyphenyl)-octahydrocyclopenta[c]pyrrole-2-carboxamide | 371.17 | 371.37 |
| 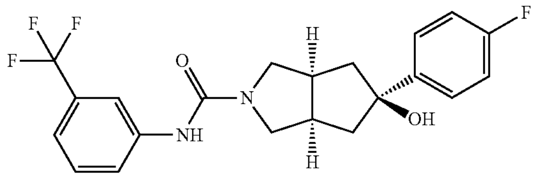 [SMILES: O=C(Nc1cccc(C(F)(F)F)c1)N1C[C@@H]2C[C@@](O)(c3ccc(F)cc3)C[C@@H]2C1] | 5-(4-fluorophenyl)-5-hydroxy-N-[3-(trifluoromethyl)phenyl]-octahydrocyclopenta[c]pyrrole-2-carboxamide | 407.15 (M − H) | 407.37 (M − H) |
| 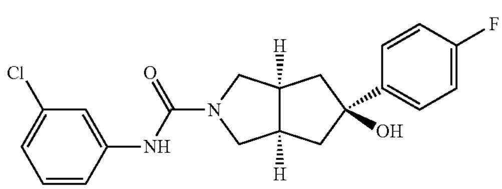 [SMILES: O=C(Nc1cccc(Cl)c1)N1C[C@@H]2C[C@@](O)(c3ccc(F)cc3)C[C@@H]2C1] | N-(3-chlorophenyl)-5-(4-fluorophenyl)-5-hydroxy-octahydrocyclopenta[c]pyrrole-2-carboxamide | 373.12 (M − H) | 373.33 (M − H) |
| 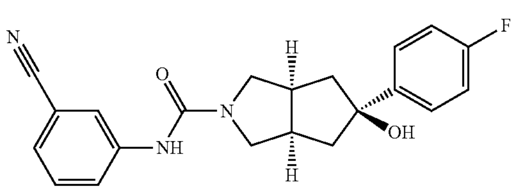 [SMILES: N#Cc1cccc(NC(=O)N2C[C@@H]3C[C@@](O)(c4ccc(F)cc4)C[C@@H]3C2)c1] | N-(3-cyanophenyl)-5-(4-fluorophenyl)-5-hydroxy-octahydrocyclopenta[c]pyrrole-2-carboxamide | 334.15 (M − H) | 364.37 (M − H) |
| 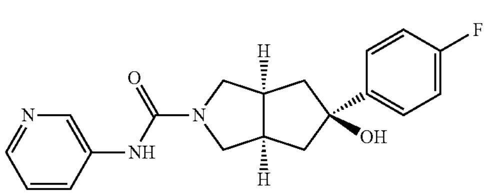 [SMILES: O=C(Nc1cccnc1)N1C[C@@H]2C[C@@](O)(c3ccc(F)cc3)C[C@@H]2C1] | 5-(4-fluorophenyl)-5-hydroxy-N-(pyridin-3-yl)-octahydrocyclopenta[c]pyrrole-2-carboxamide | 342.15 | 342.33 |

TABLE 2-continued

The following compounds were prepared by the method described above

| Structure | IUPAC Name | Calculated M + H | Found M + H |
|---|---|---|---|
| 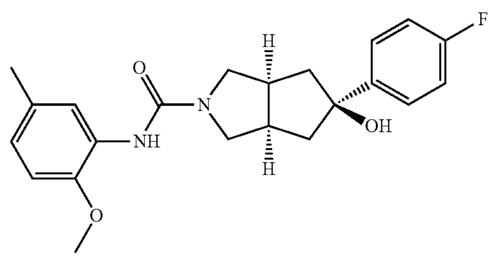 [SMILES: COc1ccc(C)cc1NC(=O)N1C[C@@H]2C[C@@](O)(c3ccc(F)cc3)C[C@@H]2C1] | 5-(4-fluorophenyl)-5-hydroxy-N-(2-methoxy-5-methylphenyl)-octahydrocyclopenta[c]pyrrole-2-carboxamide | 383.18 (M − H) | 383.37 (M − H) |
| 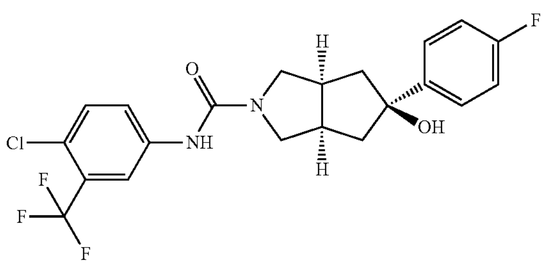 [SMILES: O=C(Nc1ccc(Cl)c(C(F)(F)F)c1)N1C[C@@H]2C[C@@](O)(c3ccc(F)cc3)C[C@@H]2C1] | N-[4-chloro-3-(trifluoromethyl)phenyl]-5-(4-fluorophenyl)-5-hydroxy-octahydrocyclopenta[c]pyrrole-2-carboxamide | 441.11 (M − H) | 441.33 (M − H) |
| 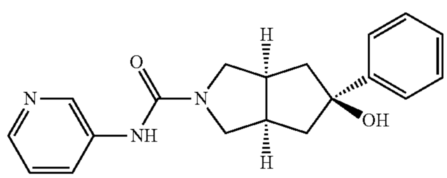 [SMILES: O=C(Nc1cccnc1)N1C[C@@H]2C[C@@](O)(c3ccccc3)C[C@@H]2C1] | 5-hydroxy-5-phenyl-N-(pyridin-3-yl)-octahydrocyclopenta[c]pyrrole-2-carboxamide | 324.16 | 324.35 |
| 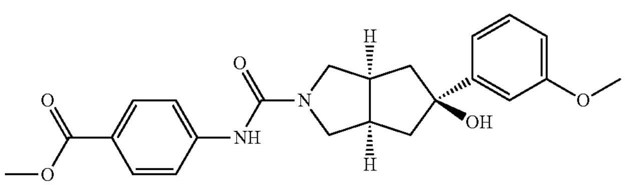 | methyl 4-({[5-hydroxy-5-(3-methoxyphenyl)-octahydrocyclopenta[c]pyrrol-2-yl]carbonyl}amino)benzoate | 411.18 | 411.35 |
| 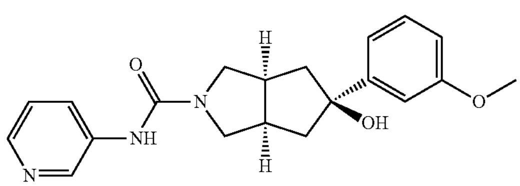 [SMILES: COc1cccc([C@]2(O)C[C@H]3CN(C(=O)Nc4cccnc4)C[C@H]3C2)c1] | 5-hydroxy-5-(3-methoxyphenyl)-N-(pyridin-3-yl)-octahydrocyclopenta[c]pyrrole-2-carboxamide | 354.17 | 354.37 |
| 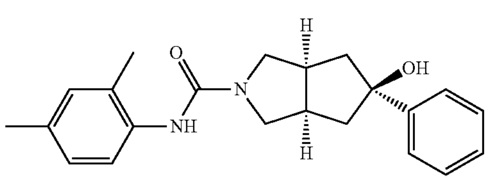 [SMILES: Cc1ccc(NC(=O)N2C[C@@H]3C[C@@](O)(c4ccccc4)C[C@@H]3C2)c(C)c1] | N-(2,4-dimethylphenyl)-5-hydroxy-5-phenyl-octahydrocyclopenta[c]pyrrole-2-carboxamide | 351.2 | 351.38 |
| 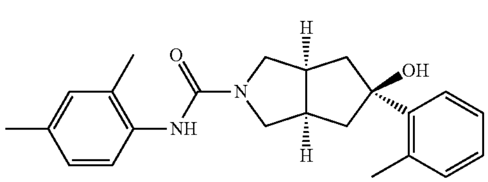 [SMILES: Cc1ccc(NC(=O)N2C[C@@H]3C[C@@](O)(c4ccccc4C)C[C@@H]3C2)c(C)c1] | N-(2,4-dimethylphenyl)-5-hydroxy-5-(2-methylphenyl)-octahydrocyclopenta[c]pyrrole-2-carboxamide | 365.22 | 365.41 |

TABLE 2-continued

The following compounds were prepared by the method described above

| Structure | IUPAC Name | Calculated M + H | Found M + H |
|---|---|---|---|
| 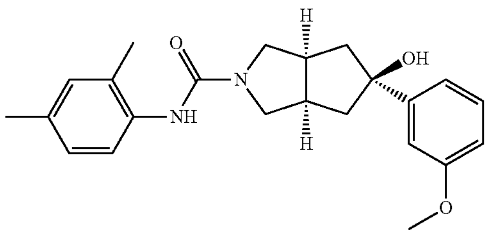 [SMILES: COc1cccc([C@]2(O)C[C@H]3CN(C(=O)Nc4ccc(C)cc4C)C[C@H]3C2)c1] | N-(2,4-dimethylphenyl)-5-hydroxy-5-(3-methoxyphenyl)-octahydrocyclopenta[c]pyrrole-2-carboxamide | 381.21 | 381.41 |
| 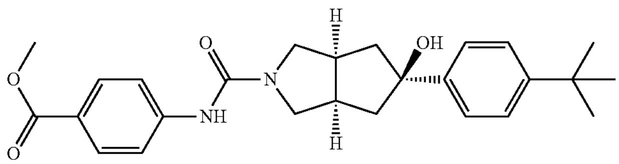 [SMILES: COC(=O)c1ccc(NC(=O)N2C[C@@H]3C[C@@](O)(c4ccc(C(C)(C)C)cc4)C[C@@H]3C2)cc1] | methyl 4-({[5-(4-tert-butylphenyl)-5-hydroxy-octahydrocyclopenta[c]pyrrol-2-yl]carbonyl}amino)benzoate | 435.24 (M − H) | 435.5 (M − H) |
| 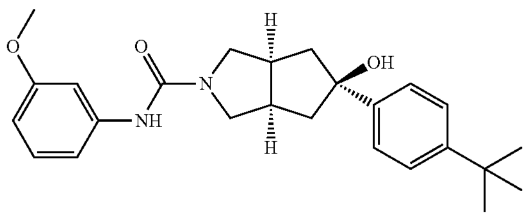 [SMILES: COc1cccc(NC(=O)N2C[C@@H]3C[C@@](O)(c4ccc(C(C)(C)C)cc4)C[C@@H]3C2)c1] | 5-(4-tert-butylphenyl)-5-hydroxy-N-(3-methoxyphenyl)-octahydrocyclopenta[c]pyrrole-2-carboxamide | 409.24 | 409.47 |
| 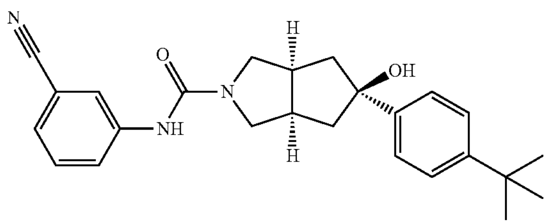 [SMILES: CC(C)(C)c1ccc([C@]2(O)C[C@H]3CN(C(=O)Nc4cccc(C#N)c4)C[C@H]3C2)cc1] | 5-(4-tert-butylphenyl)-N-(3-cyanophenyl)-5-hydroxy-octahydrocyclopenta[c]pyrrole-2-carboxamide | 402.23 (M − H) | 402.5 (M − H) |
| 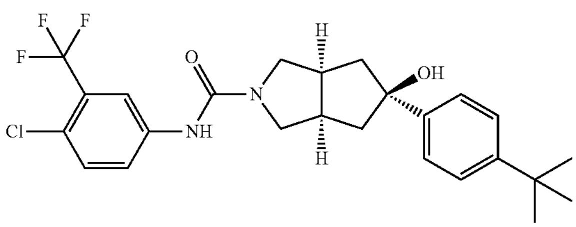 [SMILES: CC(C)(C)c1ccc([C@]2(O)C[C@H]3CN(C(=O)Nc4ccc(Cl)c(C(F)(F)F)c4)C[C@H]3C2)cc1] | 5-(4-tert-butylphenyl)-N-[4-chloro-3-(trifluoromethyl)phenyl]-5-hydroxy-octahydrocyclopenta[c]pyrrole-2-carboxamide | 479.18 (M − H) | 479.47 (M − H) |
| 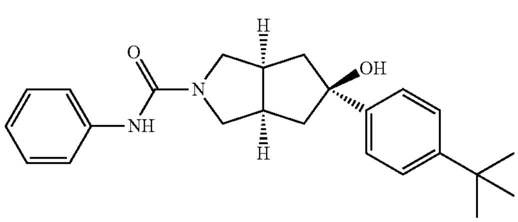 [SMILES: CC(C)(C)c1ccc([C@]2(O)C[C@H]3CN(C(=O)Nc4ccccc4)C[C@H]3C2)cc1] | 5-(4-tert-butylphenyl)-5-hydroxy-N-phenyl-octahydrocyclopenta[c]pyrrole-2-carboxamide | 379.23 | 379.47 |
| 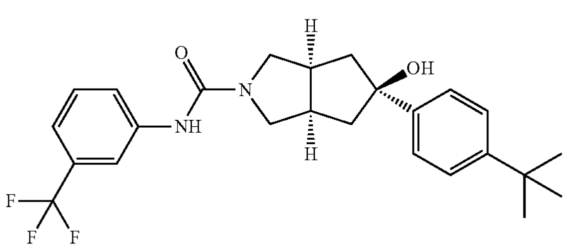 [SMILES: CC(C)(C)c1ccc([C@]2(O)C[C@H]3CN(C(=O)Nc4cccc(C(F)(F)F)c4)C[C@H]3C2)cc1] | 5-(4-tert-butylphenyl)-5-hydroxy-N-[3-(trifluoromethyl)phenyl]-octahydrocyclopenta[c]pyrrole-2-carboxamide | 445.22 (M − H) | 445.47 (M − H) |

TABLE 2-continued

The following compounds were prepared by the method described above

| Structure | IUPAC Name | Calculated M + H | Found M + H |
|---|---|---|---|
| 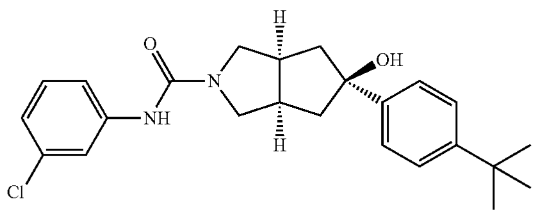 [SMILES: CC(C)(C)c1ccc([C@]2(O)C[C@H]3CN(C(=O)Nc4cccc(Cl)c4)C[C@H]3C2)cc1] | 5-(4-tert-butylphenyl)-N-(3-chlorophenyl)-5-hydroxy-octahydrocyclopenta[c]pyrrole-2-carboxamide | 411.19 (M − H) | 411.24 (M − H) |

Example 7

Preparation of rac-2-(2-hydroxy-2-phenylethyl)-5-phenyloctahydrocyclopenta[c]pyrrol-5-ol Scheme 7

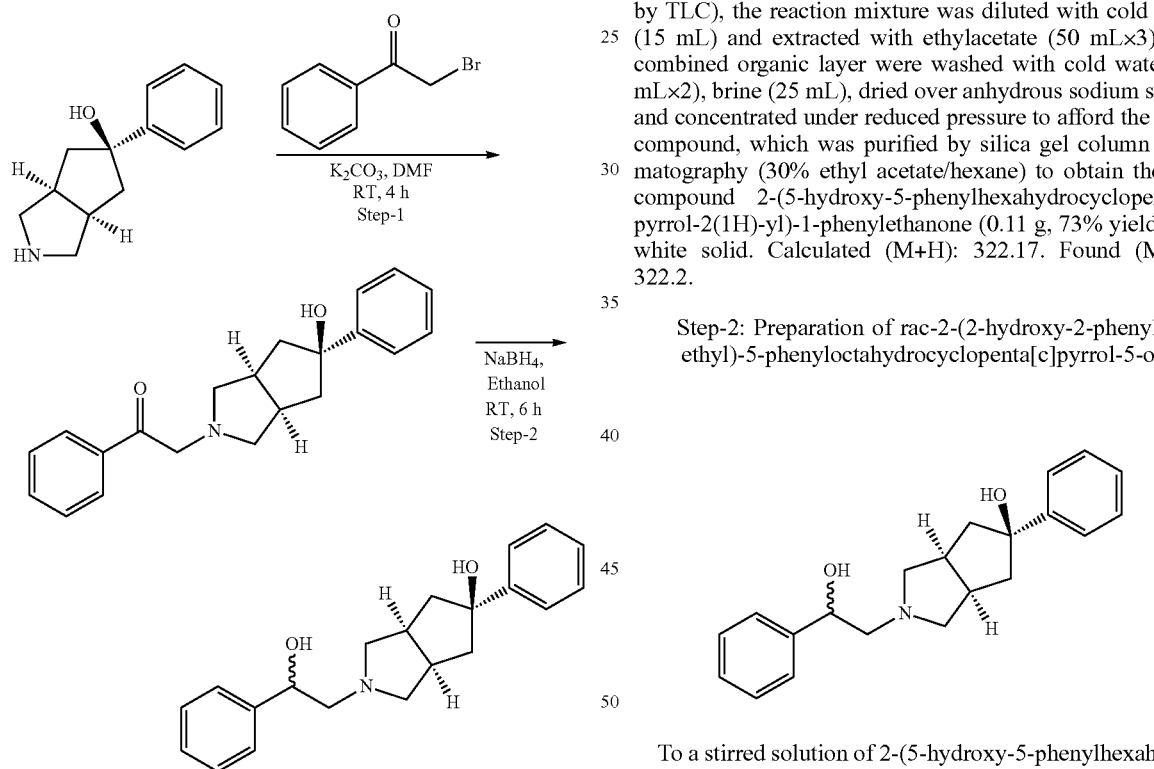

Step-1: 2-(5-hydroxy-5-phenylhexahydrocyclopenta[c]pyrrol-2(1H)-yl)-1-phenylethanone

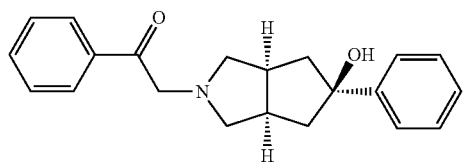 [SMILES: O=C(CN1C[C@@H]2C[C@@](O)(c3ccccc3)C[C@@H]2C1)c1ccccc1]

To a stirred solution of 5-phenyloctahydrocyclopenta[c]pyrrol-5-ol (0.1 g, 0.46 mmol) in dimethylformamide (5 mL) was added potassium carbonate (0.13 g, 0.98 mmol) and 2-bromo-1-phenylethanone (0.1 g, 0.54 mmol) at room temperature. The reaction mixture was stirred at room temperature for 4 h. After completion of reaction (monitored by TLC), the reaction mixture was diluted with cold water (15 mL) and extracted with ethylacetate (50 mL×3). The combined organic layer were washed with cold water (25 mL×2), brine (25 mL), dried over anhydrous sodium sulfate and concentrated under reduced pressure to afford the crude compound, which was purified by silica gel column chromatography (30% ethyl acetate/hexane) to obtain the title compound 2-(5-hydroxy-5-phenylhexahydrocyclopenta[c]pyrrol-2(1H)-yl)-1-phenylethanone (0.11 g, 73% yield) as a white solid. Calculated (M+H): 322.17. Found (M+H): 322.2.

Step-2: Preparation of rac-2-(2-hydroxy-2-phenylethyl)-5-phenyloctahydrocyclopenta[c]pyrrol-5-ol To a stirred solution of 2-(5-hydroxy-5-phenylhexahydrocyclopenta[c]pyrrol-2(1H)-yl)-1-phenylethanone (0.05 g, 0.16 mmol) in ethanol (15 mL) was added sodium borohydride (0.059 g, 1.55 mmol) at room temperature and stirred for 6 h. After completion of reaction (monitored by TLC), the solvent was removed under reduced pressure. The residue was diluted with water (10 mL) and extracted with ethyl acetate (25 mL×3). The combined organic layer was washed with water (10 mL×2), brine (10 mL), dried over anhydrous sodium sulfate and concentrated under reduced pressure to afford the crude compound, which was purified by silica gel column chromatography (3% methanol/dichloromethane) to obtain the title compound 2-(2-hydroxy-2-phenylethyl)-5-phenyloctahydrocyclopenta[c]pyrrol-5-ol (0.02 g, 40% yield) as off-white solid. Calculated (M+H): 324.19. Found (M+H): 324.4.

TABLE 3

The following compounds were prepared by the method described above.

| Structure | IUPAC Name | Calculated M + H | Found M + H |
|---|---|---|---|
| 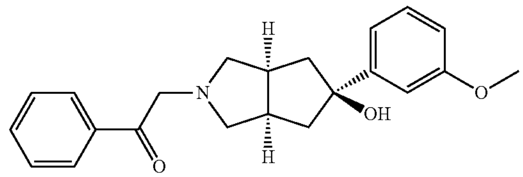 [SMILES: COc1cccc([C@]2(O)C[C@H]3CN(CC(=O)c4ccccc4)C[C@H]3C2)c1] | 2-[5-hydroxy-5-(3-methoxyphenyl)-octahydrocyclopenta[c]pyrrol-2-yl]-1-phenylethan-1-one | 352.18 | 352.3 |
| 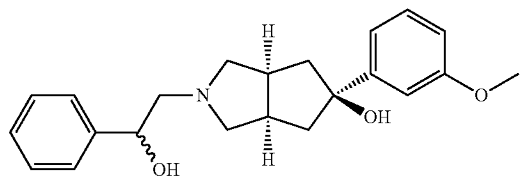 [SMILES: COc1cccc([C@]2(O)C[C@H]3CN(CC(O)c4ccccc4)C[C@H]3C2)c1] | rac-2-(2-hydroxy-2-phenylethyl)-5-(3-methoxyphenyl)-octahydrocyclopenta[c]pyrrol-5-ol | 354.20 | 354.4 |
| 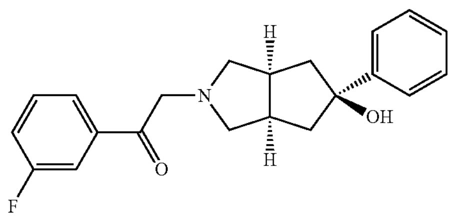 [SMILES: O=C(CN1C[C@@H]2C[C@@](O)(c3ccccc3)C[C@@H]2C1)c1cccc(F)c1] | 1-(3-fluorophenyl)-2-{5-hydroxy-5-phenyl-octahydrocyclopenta[c]pyrrol-2-yl}ethan-1-one | 340.16 | 340.2 |
| 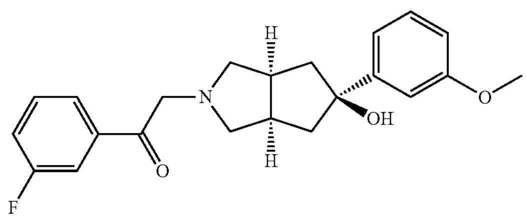 | 1-(3-fluorophenyl)-2-[5-hydroxy-5-(3-methoxyphenyl)-octahydrocyclopenta[c]pyrrol-2-yl]ethan-1-one | 370.17 | 370.2 |
| 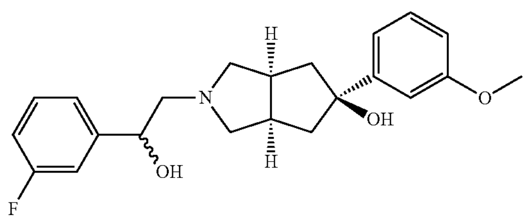 | rac-2-[2-(3-fluorophenyl)-2-hydroxyethyl]-5-(3-methoxyphenyl)-octahydrocyclopenta[c]pyrrol-5-ol | 372.19 | 372.2 |
| 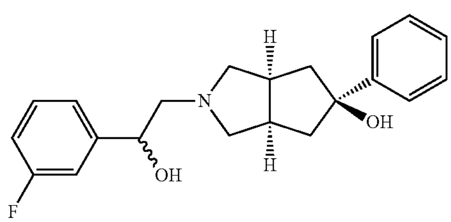 [SMILES: OC(CN1C[C@@H]2C[C@@](O)(c3ccccc3)C[C@@H]2C1)c1cccc(F)c1] | rac-2-[2-(3-fluorophenyl)-2-hydroxyethyl]-5-phenyl-octahydrocyclopenta[c]pyrrol-5-ol | 342.18 | 342.4 |
| 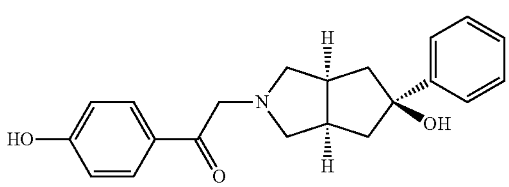 [SMILES: O=C(CN1C[C@@H]2C[C@@](O)(c3ccccc3)C[C@@H]2C1)c1ccc(O)cc1] | 2-{5-hydroxy-5-phenyl-octahydrocyclopenta[c]pyrrol-2-yl}-1-(4-hydroxyphenyl)ethan-1-one | 338.17 | 338.3 |

TABLE 3-continued

The following compounds were prepared by the method described above.

| Structure | IUPAC Name | Calculated M + H | Found M + H |
|---|---|---|---|
| 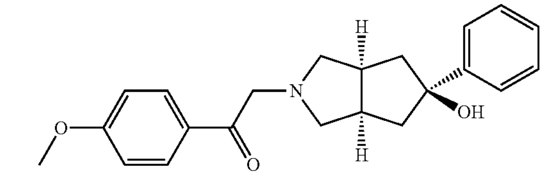 [SMILES: COc1ccc(C(=O)CN2C[C@@H]3C[C@@](O)(c4ccccc4)C[C@@H]3C2)cc1] | 2-{5-hydroxy-5-phenyl-octahydrocyclopenta[c]pyrrol-2-yl}-1-(4-methoxyphenyl)ethan-1-one | 352.18 | 352.2 |
| 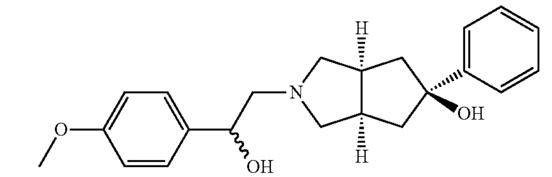 | rac-2-[2-hydroxy-2-(4-methoxyphenyl)ethyl]-5-phenyl-octahydrocyclopenta[c]pyrrol-5-ol | 354.20 | 354.2 |
| 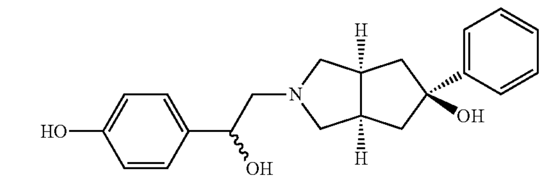 [SMILES: Oc1ccc(C(O)CN2C[C@@H]3C[C@@](O)(c4ccccc4)C[C@@H]3C2)cc1] | rac-2-[2-hydroxy-2-(4-hydroxyphenyl)ethyl]-5-phenyl-octahydrocyclopenta[c]pyrrol-5-ol | 340.18 | 340.2 |
| 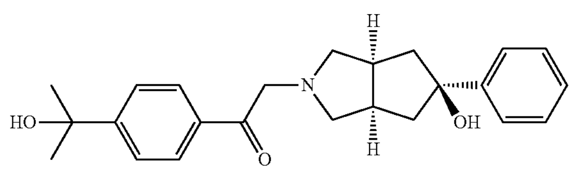 [SMILES: CC(C)(O)c1ccc(C(=O)CN2C[C@@H]3C[C@@](O)(c4ccccc4)C[C@@H]3C2)cc1] | 2-(5-hydroxy-5-phenylhexahydrocyclopenta[c]pyrrol-2(1H)-yl)-1-(4-(2-hydroxypropan-2-yl)phenyl)ethanone | 380.49 | 380.5 |
| 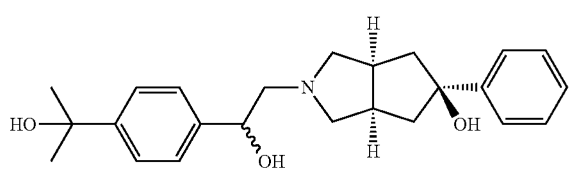 | rac-2-(2-hydroxy-2-(4-(2-hydroxypropan-2-yl)phenyl)ethyl)-5-phenyloctahydrocyclopenta[c]pyrrol-5-ol | 382.50 | 382.5 |

Example 8

Preparation of rac-5-(4-(tert-butyl)phenyl)-2-(2-hydroxy-2-(3-(trifluoromethyl)phenyl)ethyl)octahydrocyclonenta[c]pyrrol-5-ol Scheme 8

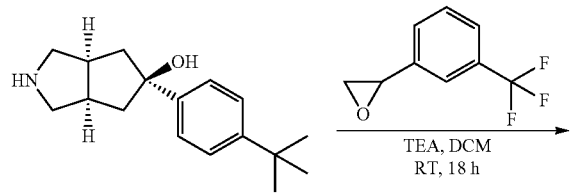

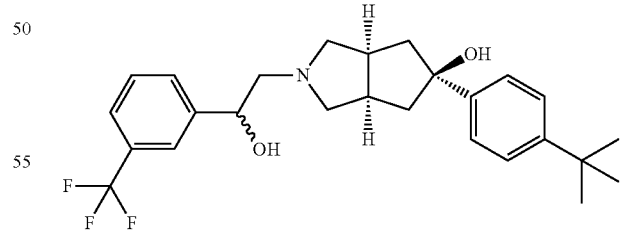

To a solution of 5-(4-(tert-butyl)phenyl)octahydrocyclopenta[c]pyrrol-5-ol (0.040 g, 0.15 mmol) in dichloromethane (2 mL) was added 2-(2,4-dichlorophenyl)oxirane (0.031 g, 0.17 mmol) and triethylamine (0.041 mL, 0.295 mmol) and resulting solution was stirred at room temperature for 18 h. After completion of reaction (monitored by TLC), the reaction mixture was diluted with water (2 mL) and extracted with dichloromethane (5 mL×2), washed with water (10 mL), brine (10 mL), dried over sodium sulfate and concentrated under vacuum to afford the crude -5-(4-(tert-butyl)phenyl)-2-(2-hydroxy-2-(3-(trifluoromethyl)phenyl)ethyl) octahydrocyclopenta[c]pyrrol-5-ol which was purified by prep HPLC (Method: Column: XSelect CSH C-18 Prep (19×250 mm, 5 um), Mobile phase: A—5 mM ammonium acetate, B—Acetonitrile, Flow mode: Gradient, Flow: 15 ml/min, T/% B: 0.0/30, 0.5/30, 15.0/90, 21.0/90, 21.5/30, 26.0/30).

TABLE 5

The following compounds were prepared by the method described above.

| Structure | IUPAC Name | Calculated M + H | Found M + H |
|---|---|---|---|
| 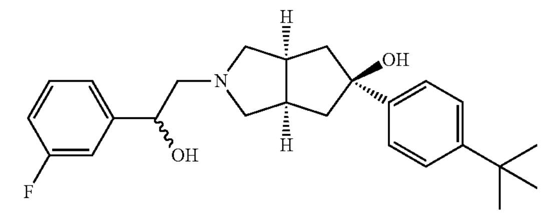 [SMILES: CC(C)(C)c1ccc([C@]2(O)C[C@H]3CN(CC(O)c4cccc(F)c4)C[C@H]3C2)cc1] | rac-5-(4-tert-butylphenyl)-2-[2-(3-fluorophenyl)-2-hydroxyethyl]-octahydrocyclopenta[c]pyrrol-5-ol | 398.24 | 398.51 |
| 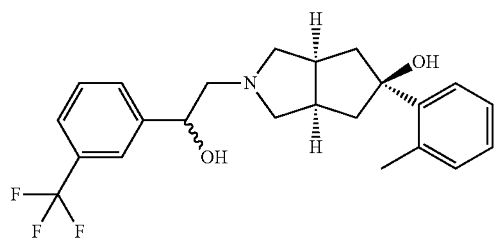 [SMILES: Cc1ccccc1[C@]1(O)C[C@H]2CN(CC(O)c3cccc(C(F)(F)F)c3)C[C@H]2C1] | rac-2-{2-hydroxy-2-[3-(trifluoromethyl)phenyl]ethyl}-5-(2-methylphenyl)-octahydrocyclopenta[c]pyrrol-5-ol | 406.19 | 406.44 |
| 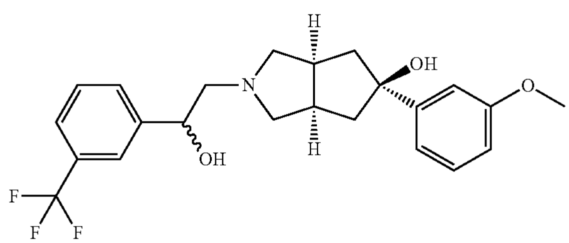 [SMILES: COc1cccc([C@]2(O)C[C@H]3CN(CC(O)c4cccc(C(F)(F)F)c4)C[C@H]3C2)c1] | rac-2-{2-hydroxy-2-[3-(trifluoromethyl)phenyl]ethyl}-5-(3-methoxyphenyl)-octahydrocyclopenta[c]pyrrol-5-ol | 422.19 | 422.43 |
| 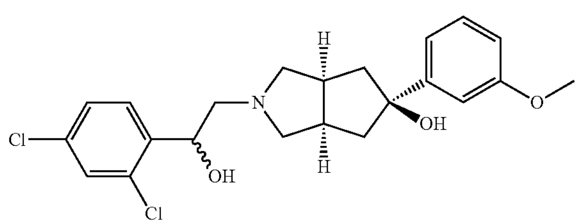 [SMILES: COc1cccc([C@]2(O)C[C@H]3CN(CC(O)c4ccc(Cl)cc4Cl)C[C@H]3C2)c1] | rac-2-[2-(2,4-dichlorophenyl)-2-hydroxyethyl]-5-(3-methoxyphenyl)-octahydrocyclopenta[c]pyrrol-5-ol | 422.12 | 422.37 |
| 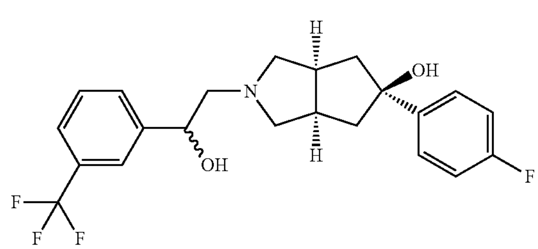 [SMILES: OC(CN1C[C@@H]2C[C@@](O)(c3ccc(F)cc3)C[C@@H]2C1)c1cccc(C(F)(F)F)c1] | rac-5-(4-fluorophenyl)-2-{2-hydroxy-2-[3-(trifluoromethyl)phenyl]ethyl}-octahydrocyclopenta[c]pyrrol-5-ol | 410.17 | 410.41 |
| 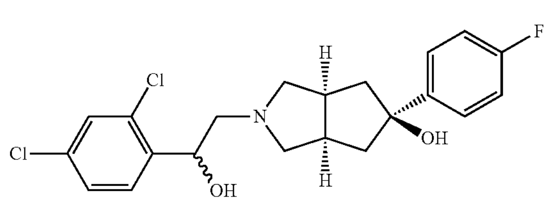 [SMILES: OC(CN1C[C@@H]2C[C@@](O)(c3ccc(F)cc3)C[C@@H]2C1)c1ccc(Cl)cc1Cl] | rac-2-[2-(2,4-dichlorophenyl)-2-hydroxyethyl]-5-(4-fluorophenyl)-octahydrocyclopenta[c]pyrrol-5-ol | 410.10 | 410.3 |

TABLE 5-continued

The following compounds were prepared by the method described above.

| Structure | IUPAC Name | Calculated M + H | Found M + H |
|---|---|---|---|
| 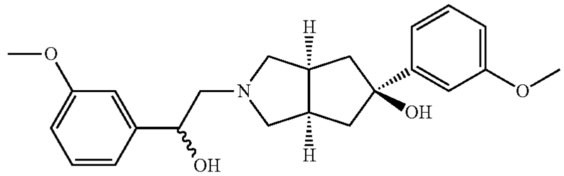 | rac-2-[2-hydroxy-2-(3-methoxyphenyl)ethyl]-5-(3-methoxyphenyl)-octahydrocyclopenta[c]pyrrol-5-ol | 384.21 | 384.41 |
| 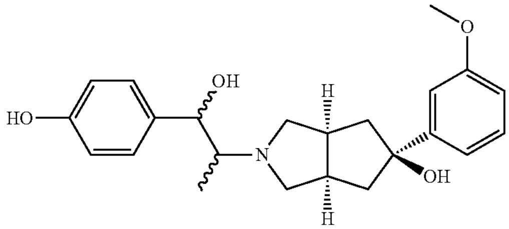 [SMILES: COc1cccc([C@]2(O)C[C@H]3CN(C(C)C(O)c4ccc(O)cc4)C[C@H]3C2)c1] | rac-2-(1-hydroxy-1-(4-hydroxyphenyl)propan-2-yl)-5-(3-methoxyphenyl)octahydrocyclopenta[c]pyrrol-5-ol | 384.21 | 384.3 |

Example 9

Preparation of 5-phenyl-2-(pyridin-2-yl)octahydrocyclopenta[c]pyrrol-5-ol

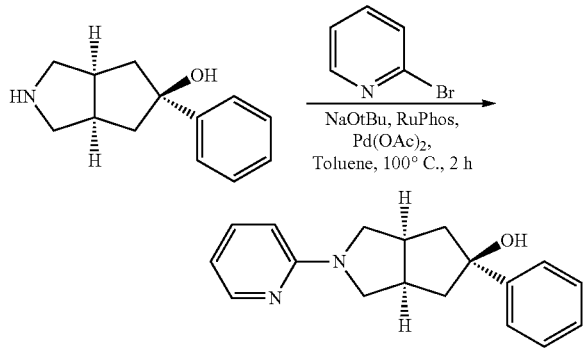

Scheme 9

To a stirred solution of 5-phenyloctahydrocyclopenta[c]pyrrol-5-ol (0.15 g, 0.74 mmol) in toluene (10 ml) was added 2-bromopyridine (0.11 g, 0.74 mmol). The reaction mixture was purged with argon for 20 min. Then $Pd(OAc)_2$ (0.015 g, 0.074 mmol) and RuPhos (0.034 g, 0.074 mmol) were added under argon atmosphere, followed by the addition of Sodium tert-butoxide. The reaction mixture was heated to 100° C. and stirred for 2 h. After completion of reaction (monitored by TLC), the reaction mixture was allowed to cool to room temperature, filtered through celite bed and washed thoroughly with ethyl acetate. The filtrate was concentrated under vacuum. The residue was dissolved in ethyl acetate, the organic layer was washed with water (15 mL×2), brine (15 mL), dried over anhydrous sodium sulfate, concentrated under vacuum to obtain crude compound, which was purified by silica gel column chromatography (4% methanol/dichloromethane) to obtain the title compound 5-phenyl-2-(pyridin-2-yl)octahydrocyclopenta[c]pyrrol-5-ol (0.12 g, 92% yield) as a white solid. Calculated (M+H): 281.36. Found (M+H): 281.2.

TABLE 6

The following compounds were prepared by the method described above

| Structure | IUPAC Name | Calculated M + H | Found M + H |
|---|---|---|---|
| 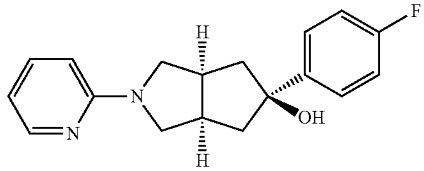 [SMILES: O[C@@]1(c2ccc(F)cc2)C[C@H]2CN(c3ccccn3)C[C@H]2C1] | 5-(4-fluorophenyl)-2-(pyridin-2-yl)-octahydrocyclopenta[c]pyrrol-5-ol | 299.15 | 299.3 |

TABLE 6-continued

The following compounds were prepared by the method described above

| Structure | IUPAC Name | Calculated M + H | Found M + H |
|---|---|---|---|
| 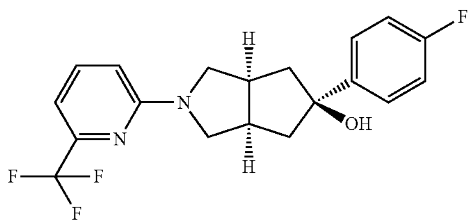 [SMILES: O[C@@]1(c2ccc(F)cc2)C[C@H]2CN(c3cccc(C(F)(F)F)n3)C[C@H]2C1] | 5-(4-fluorophenyl)-2-[6-(trifluoromethyl)pyridin-2-yl]-octahydrocyclopenta[c]pyrrol-5-ol | 367.14 | 367.2 |
| 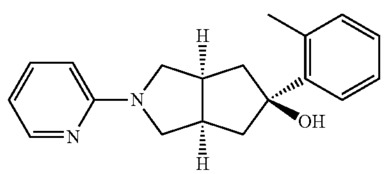 [SMILES: Cc1ccccc1[C@]1(O)C[C@H]2CN(c3ccccn3)C[C@H]2C1] | 5-(2-methylphenyl)-2-(pyridin-2-yl)-octahydrocyclopenta[c]pyrrol-5-ol | 295.17 | 295.2 |
| 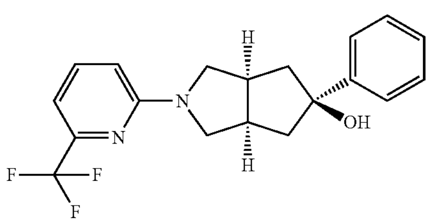 | 5-phenyl-2-[6-(trifluoromethyl)pyridin-2-yl]-octahydrocyclopenta[c]pyrrol-5-ol | 349.14 | 349.2 |
| 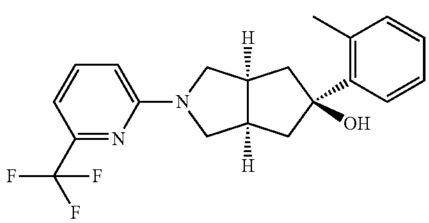 [SMILES: Cc1ccccc1[C@]1(O)C[C@H]2CN(c3cccc(C(F)(F)F)n3)C[C@H]2C1] | 5-(2-methylphenyl)-2-[6-(trifluoromethyl)pyridin-2-yl]-octahydrocyclopenta[c]pyrrol-5-ol | 363.16 | 363.2 |
| 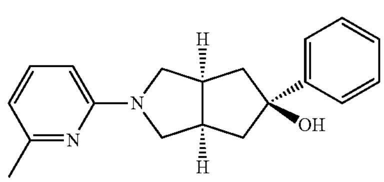 [SMILES: Cc1cccc(N2C[C@@H]3C[C@@](O)(c4ccccc4)C[C@@H]3C2)n1] | 2-(6-methylpyridin-2-yl)-5-phenyl-octahydrocyclopenta[c]pyrrol-5-ol | 295.17 | 295.2 |
| 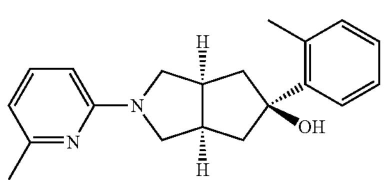 [SMILES: Cc1cccc(N2C[C@@H]3C[C@@](O)(c4ccccc4C)C[C@@H]3C2)n1] | 5-(2-methylphenyl)-2-(6-methylpyridin-2-yl)-octahydrocyclopenta[c]pyrrol-5-ol | 309.19 | 309.2 |
| 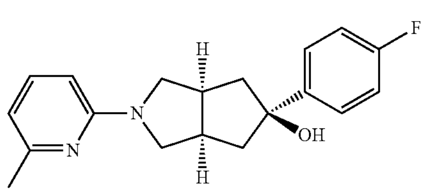 [SMILES: Cc1cccc(N2C[C@@H]3C[C@@](O)(c4ccc(F)cc4)C[C@@H]3C2)n1] | 5-(4-fluorophenyl)-2-(6-methylpyridin-2-yl)-octahydrocyclopenta[c]pyrrol-5-ol | 313.16 | 313.2 |

TABLE 6-continued

The following compounds were prepared by the method described above

| Structure | IUPAC Name | Calculated M + H | Found M + H |
|---|---|---|---|
| 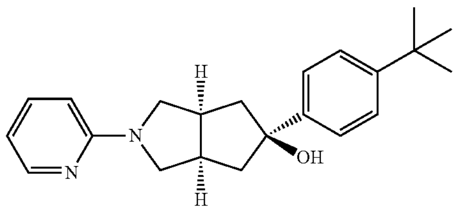 [SMILES: CC(C)(C)c1ccc([C@]2(O)C[C@H]3CN(c4ccccn4)C[C@H]3C2)cc1] | 5-(4-tert-butylphenyl)-2-(pyridin-2-yl)-octahydrocyclopenta[c]pyrrol-5-ol | 337.22 | 337.3 |
| 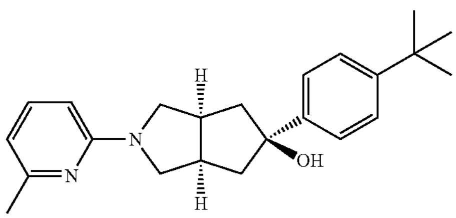 [SMILES: Cc1cccc(N2C[C@@H]3C[C@@](O)(c4ccc(C(C)(C)C)cc4)C[C@@H]3C2)n1] | 5-(4-tert-butylphenyl)-2-(6-methylpyridin-2-yl)-octahydrocyclopenta[c]pyrrol-5-ol | 351.24 | 351.3 |

Example 10

Preparation of rac-2-(1-hydroxy-1-(4-hydroxyphenyl)propan-2-yl)-5-phenyloctahydrocyclopenta[c]pyrrol-5-ol Scheme 10

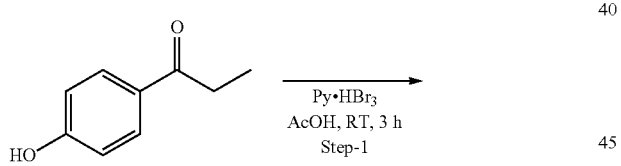

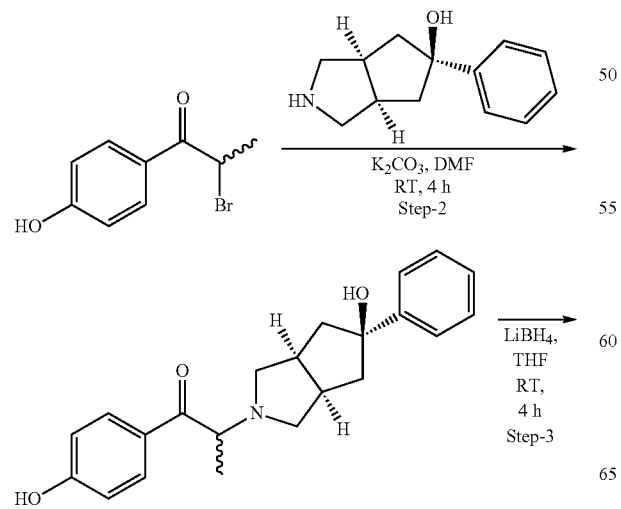

Step-1: Preparation of 2-bromo-1-(4-hydroxyphenyl)propan-1-one

To stirred solution of 2-bromo-1-(4-hydroxyphenyl)propan-1-one (1.0 g, 6.67 mmol) in acetic acid (2.5 mL) was added pyridinium tribromide (2.3 g, 7.33 mmol) at room temperature and stirred for 3 h. After completion of reaction (monitored by TLC), the reaction mixture was diluted with cold water (100 mL) and stirred for 30 min, product get precipitated. The solid was filtered, washed thoroughly with water, dried to afford the title compound 2-bromo-1-(4-hydroxyphenyl)propan-1-one (1.0 g, 66% yield) as a white solid and taken for next step without purification. Calculated (M+H): 228.98. Found (M+2H): 231.0.

Step-2: Preparation of rac-2-((3aR,5r,6aS)-5-hydroxy-5-phenylhexahydrocyclopenta[c]pyrrol-2(1H)-yl)-1-(4-hydroxyphenyl)propan-1-one

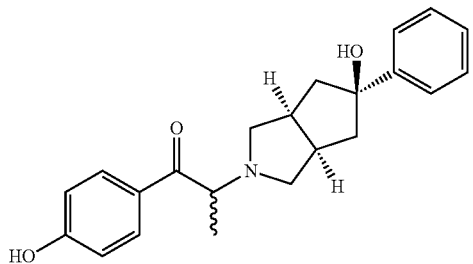 [SMILES: CC(C(=O)c1ccc(O)cc1)N1C[C@@H]2C[C@@](O)(c3ccccc3)C[C@@H]2C1]

To a stirred solution of 5-phenyloctahydrocyclopenta[c]pyrrol-5-ol (0.15 g, 0.74 mmol) in dimethylformamide (5 mL) was added potassium carbonate (0.13 g, 2.22 mmol) and 2-bromo-1-(4-hydroxyphenyl)propan-1-one (0.18 g, 0.81 mmol) at room temperature. The reaction mixture was stirred at room temperature for 4 h. After completion of reaction (monitored by TLC), the reaction mixture was diluted with cold water (20 mL) and extracted with ethylacetate (50 mL×3). The combined organic layer was washed with cold water (15 mL×3), brine (10 mL) dried over anhydrous sodium sulfate and concentrated under vacuum to afford the crude compound which was purified by silica gel column chromatography (4% methanol/dichloromethane) to obtain the title compound 5-(4-(tert-butyl)phenyl)-2-(2-hydroxy-2-(3-(trifluoromethyl)phenyl)ethyl)octahydrocyclopenta[c]pyrrol-5-ol (0.02 g, 7% yield) as a white solid. Calculated (M+H): 352.18. Found (M+H): 352.2.

Step-3: Preparation of rac-2-(1-hydroxy-1-(4-hydroxyphenyl)propan-2-yl)-5-phenyloctahydrocyclopenta[c]pyrrol-5-ol

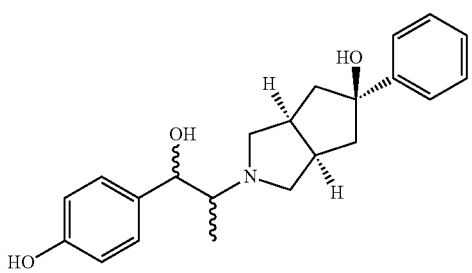 [SMILES: CC(C(O)c1ccc(O)cc1)N1C[C@@H]2C[C@@](O)(c3ccccc3)C[C@@H]2C1]

To a mixture of lithium borohydride (0.043 g, 1.99 mmol), in tetrahydrofuran (10 mL) was added 2-(5-hydroxy-5-phenyloctahydropentalen-2-yl)-1-(4-hydroxyphenyl)propan-1-one (0.07 g, 0.12 mmol) at room temperature and stirred for 4 h. After completion of reaction (monitored by TLC), the mixture was quenched with ice water (15 mL) and extracted with ethyl acetate (50 ml×3), the combined organic layer was washed with water (15 mL), brine (10 mL), dried over anhydrous sodium sulfate, filtered and concentrated to afford the crude compound, which was purified by silica gel column chromatography (4% methanol/dichloromethane) to obtain the title compound 2-(1-hydroxy-1-(4-hydroxyphenyl)propan-2-yl)-5-phenyloctahydrocyclopenta[c]pyrrol-5-ol (0.015 g, 21% yield) as off-white solid. Calculated (M+H): 354.20. Found (M+H): 354.3.

TABLE 7

The following compounds were prepared by the method described above.

| Structure | IUPAC Name | Calculated M + H | Found M + H |
|---|---|---|---|
| 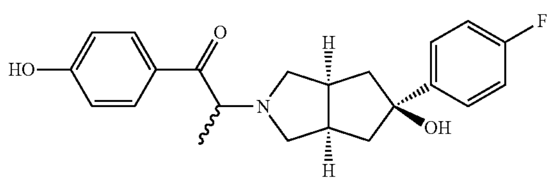 [SMILES: CC(C(=O)c1ccc(O)cc1)N1C[C@@H]2C[C@@](O)(c3ccc(F)cc3)C[C@@H]2C1] | rac-2-[5-(4-fluorophenyl)-5-hydroxy-octahydrocyclopenta[c]pyrrol-2-yl]-1-(4-hydroxyphenyl)propan-1-one | 370.17 | 370.2 |
| 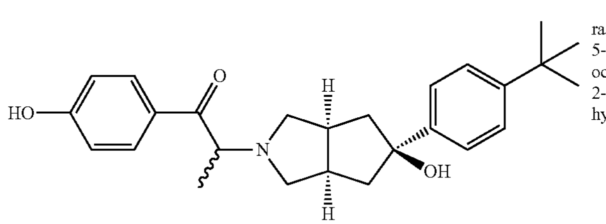 | rac-2-[5-(4-tert-butylphenyl)-5-hydroxy-octahydrocyclopenta[c]pyrrol-2-yl]-1-(4-hydroxyphenyl)propan-1-one | 406.25 (M − H) | 406.5 (M − H) |
| 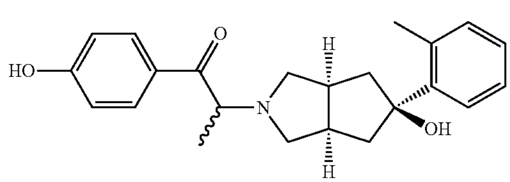 | rac-2-[5-hydroxy-5-(2-methylphenyl)-octahydrocyclopenta[c]pyrrol-2-yl]-1-(4-hydroxyphenyl)propan-1-one | 366.20 | 366.3 |

TABLE 7-continued

The following compounds were prepared by the method described above.

| Structure | IUPAC Name | Calculated M + H | Found M + H |
|---|---|---|---|
| 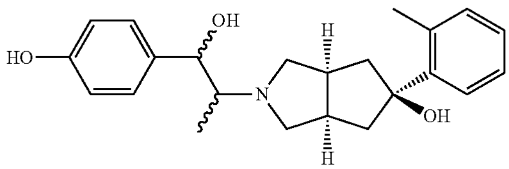 | rac-2-[1-hydroxy-1-(4-hydroxyphenyl)propan-2-yl]-5-(2-methylphenyl)-octahydrocyclopenta[c]pyrrol-5-ol | 368.21 | 368.3 |
| 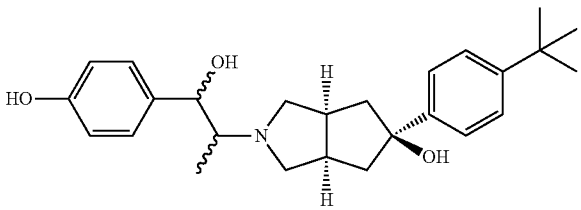 [SMILES: CC(C(=O)c1ccc(O)cc1)N1C[C@@H]2C[C@@](O)(c3ccc(C(C)(C)C)cc3)C[C@@H]2C1] | rac-5-(4-tert-butylphenyl)-2-[1-hydroxy-1-(4-hydroxyphenyl)propan-2-yl]-octahydrocyclopenta[c]pyrrol-5-ol | 410.26 | 410.3 |

Example 11

Preparation of 2-(3-hydroxy-3-(4-hydroxyphenyl)propyl)-5-phenyloctahydrocyclopenta[c]pyrrol-5-ol Scheme 11

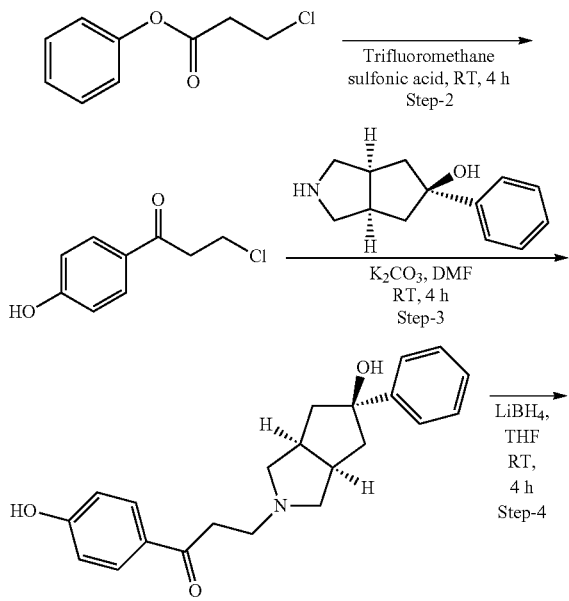

Step-1: Preparation of phenyl 3-chloropropanoate

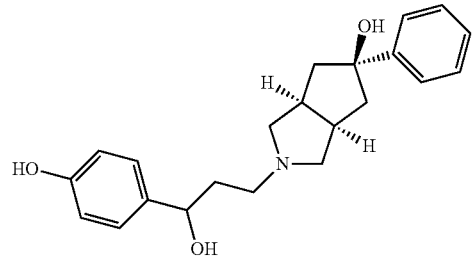

A mixture of phenol (5 g, 53.1 mmol) and 3-chloropropanoyl chloride (8.09 g, 63.7 mmol) were taken in round bottomed flask. The resulting mixture was heated to 100° C. and stirred for 16 h. After completion of reaction (monitored by TLC), the reaction mixture was allowed to cool to room temperature, poured in to ice water (100 mL), extracted with ethyl acetate (100 mL×3). The combined organic layer was washed with 1M sodium hydroxide solution (100 mL×2), water (50 mL×2), brine (50 mL), dried over anhydrous sodium sulfate, filtered and concentrated under vacuum to afford crude compound which was purified by silica gel column chromatography (5% ethyl acetate/hexane) to obtain the title compound phenyl 3-chloropropanoate (2.5 g, 25% yield) as a colorless liquid. $^1$H NMR (400 MHz, CdCl3) δ 7.38 (t, J=7.6 Hz, 2H), 7.24 (t, J=7.6 Hz, 1H), 7.11 (t, J=10.4 Hz, 2H), 3.87 (t, J=6.4 Hz, 2H), 3.05 (t, J=6.8 Hz, 2H).

Step-2: Preparation of 3-chloro-1-(4-hydroxyphenyl)propan-1-one

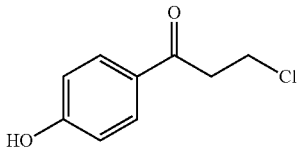 [SMILES: O=C(CCCl)c1ccc(O)cc1]

A mixture of phenyl 3-chloropropanoate (1.0 g, 5.41 mmol) and trifluoromethanesulfonic acid (2.4 g, 27.0 mmol) were taken in round bottomed flask and stirred for 4 h. After completion of reaction (monitored by TLC), the mixture was concentrated under vacuum. The residue was diluted with ethyl acetate (100 mL), washed with 20% sodium bicarbonate solution (20 mL×3), water (25 mL), dried over anhydrous sodium sulfate, filtered and concentrated under vacuum to afford the crude compound, which was purified by silica gel column chromatography (30% ethyl acetate/hexane) to obtain the title compound 3-chloro-1-(4-hydroxyphenyl)propan-1-one (0.53 g, 53% yield) as a white solid. Calculated (M−H): 183.03. Found (M−H): 183.1.

Step-3: Preparation of 3-(5-hydroxy-5-phenylhexahydrocyclopenta[c]pyrrol-2(1H)-yl)-1-(4-hydroxyphenyl)propan-1-one

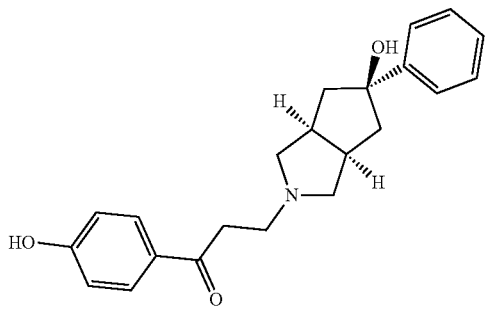 [SMILES: O=C(CCN1C[C@@H]2C[C@@](O)(c3ccccc3)C[C@@H]2C1)c1ccc(O)cc1]

To a stirred solution of 5-phenyloctahydrocyclopenta[c]pyrrol-5-ol (0.2 g, 0.98 mmol) in dimethylformamide (10 mL) was added potassium carbonate (0.34 g, 2.46 mmol) and 3-chloro-1-(4-hydroxyphenyl)propan-1-one (0.19 g, 1.08 mmol) at room temperature. The reaction mixture was stirred at room temperature for 4 h. After completion of reaction (monitored by TLC), the reaction mixture was diluted with cold water (25 mL) and extracted with ethylacetate (50 mL×3). The combined organic layer was washed with cold water (15 mL×3), brine (25 mL), dried over anhydrous sodium sulfate, filtered and concentrated under reduced pressure to afford the crude compound which was purified by silica gel column chromatography (5% methanol/dichloromethane) to obtain the title compound 3-(5-hydroxy-5-phenylhexahydrocyclopenta[c]pyrrol-2(1H)-yl)-1-(4-hydroxyphenyl)propan-1-one (0.15 g, 44% yield) as a white solid. Calculated (M+H): 352.18. Found (M+H): 352.3.

Step-4: Preparation of 2-(3-hydroxy-3-(4-hydroxyphenyl)propyl)-5-phenyloctahydrocyclopenta[c]pyrrol-5-ol

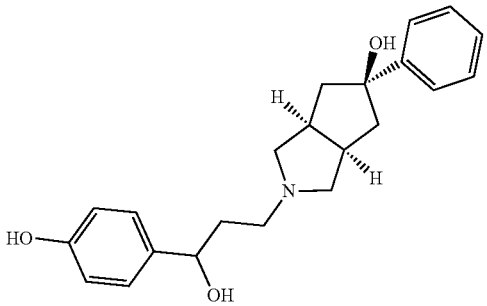 [SMILES: Oc1ccc(C(O)CCN2C[C@@H]3C[C@@](O)(c4ccccc4)C[C@@H]3C2)cc1]

To a stirred slurry of lithium borohydride (0.061 g, 2.85 mmol) in tetrahydrofuran (10 mL) was added 3-(5-hydroxy-5-phenylhexahydrocyclopenta[c]pyrrol-2(1H)-yl)-1-(4-hydroxyphenyl)propan-1-one (0.1 g, 0.28 mmol) at room temperature and stirred for 4 h. After completion of reaction (monitored by TLC), the mixture was quenched with ice water (10 mL) and extracted with ethyl acetate (50 mL×3), the combined organic layer was washed with water (10 mL×2), brine (10 mL), dried over anhydrous sodium sulfate, filtered and concentrated to afford the crude compound, which was purified by silica gel column chromatography (8% methanol/dichloromethane) to obtain the title compound 2-(3-hydroxy-3-(4-hydroxyphenyl)propyl)-5-phenyloctahydrocyclopenta[c]pyrrol-5-ol (0.052 g, 74% yield) as off-white solid. Calculated (M+H): 354.20. Found (M+H): 354.5.

Example 12

Preparation of 2N-(4-methoxyphenyl)-5-phenyl-hexahydrocyclopenta[c]pyrrole-2(1H)-carboxamide Scheme 12

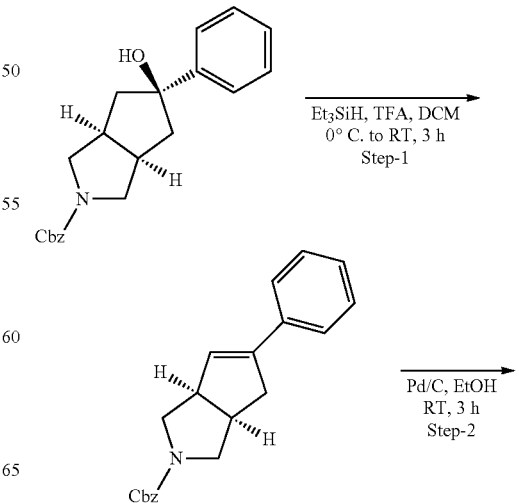

-continued

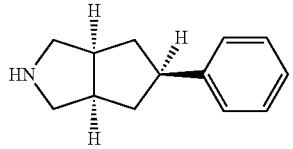

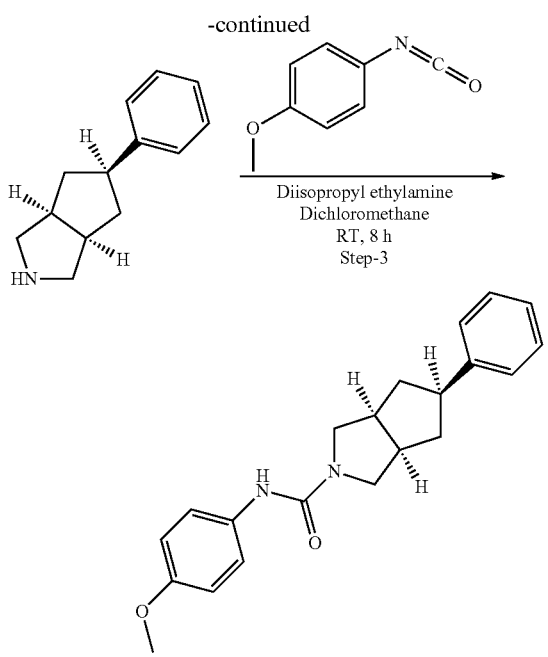

Step-1: Preparation of benzyl 5-phenyl-3,3a,6,6a-tetrahydrocyclopenta[c]pyrrole-2(1H)-carboxylate

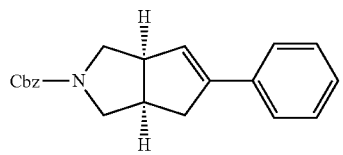 [SMILES: O=C(OCc1ccccc1)N1C[C@@H]2CC(c3ccccc3)=C[C@@H]2C1]

To a stirred solution of benzyl 5-hydroxy-5-phenylhexahydrocyclopenta[c]pyrrole-2(1H)-carboxylate (2.0 g, 5.93 mmol) in dichloromethane (20 ml) was added trifluoroacetic acid (2.26 mL, 29.64 mmol) and triethylsilane (5 ml, 29.64 mmol) at 0° C. under argon atmosphere. The reaction mixture was allowed to room temperature and stirred for 12 h. After completion of reaction (monitored by TLC), the reaction mixture was concentrated under vacuum. The residue was dissolved in ethyl acetate (250 mL), washed with water (50 mL), brine (50 mL), dried over anhydrous sodium sulfate, concentrated under vacuum to obtain crude compound, which was purified by silica gel column chromatography (15% ethyl acetate/hexane) to obtain the title compound benzyl 5-phenyl-3,3a,6,6a-tetrahydrocyclopenta[c]pyrrole-2(1H)-carboxylate (1.82 g, 96% yield) as a pale yellow liquid. Calculated (M+H): 320.16. Found (M+H): 320.2.

Step-2: Preparation of 5-phenyloctahydrocyclopenta[c]pyrrole

To a stirred solution of benzyl 5-phenyl-3,3a,6,6a-tetrahydrocyclopenta[c]pyrrole-2(1H)-carboxylate (1.8 g, 0.56 mmol) in ethanol (20 mL), was added 10% Pd/C (0.5 g) under $N_2$ atmosphere. The reaction was subjected to hydrogenation in balloon and stirred for 6 h at room temperature. After completion of reaction (monitored by TLC), the mixture was filtered through celite bed, washed with methanol. The filtrate was concentrated under vacuum to obtain the title compound 5-phenyloctahydrocyclopenta[c]pyrrole (1.0 g (crude), 95% yield) as a colorless liquid. Calculated (M+H): 188.14. Found (M+H): 188.2.

Step-3: Preparation of N-(4-methoxyphenyl)-5-phenylhexahydrocyclopenta[c]pyrrole-2(1H)-carboxamide

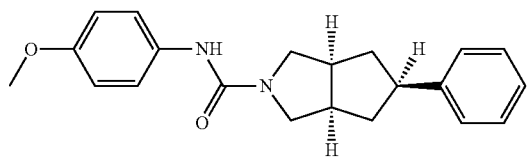 [SMILES: COc1ccc(NC(=O)N2C[C@H]3C[C@@H](c4ccccc4)C[C@H]3C2)cc1]

To a stirred solution of 5-phenyloctahydrocyclopenta[c]pyrrole (0.1 g, 0.53 mmol) in dichloromethane (5 mL), was added diisopopyl ethylamine (0.22 mL, 1.60 mmol) and 1-isocyanato-4-methoxybenzene (0.087 g, 0.59 mmol) at 0° C. The reaction mixture allowed to warm to room temperature and stirred for 8 h. After completion of reaction (monitored by TLC), the reaction mixture was diluted with water (20 mL) and extracted with dichloromethane (30 mL×3). The combined organic layer was washed with brine solution (10 mL), dried over anhydrous sodium sulfate and concentrated under vacuum to afford the crude compound which was purified by silica gel column chromatography (50% ethyl acetate/hexane), the column purified product was re-purified by preparative TLC to obtain the title compound N-(4-methoxyphenyl)-5-phenylhexahydrocyclopenta[c]pyrrole-2(1H)-carboxamide (0.1 g, 58% yield) as off-white solid. Calculated (M+H): 337.18. Found (M+H): 337.2.

TABLE 8

The following compounds were prepared by the method described above.

| Structure | IUPAC Name | Calculated (M + H) | Found (M + H) |
|---|---|---|---|
| 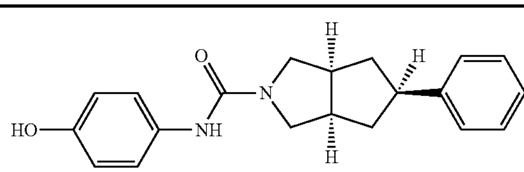 | N-(4-hydroxyphenyl)-5-phenyl-octahydrocyclopenta[c]pyrrole-2-carboxamide | 323.17 | 323.2 |

TABLE 8-continued

The following compounds were prepared by the method described above.

| Structure | IUPAC Name | Calculated (M + H) | Found (M + H) |
|---|---|---|---|
| 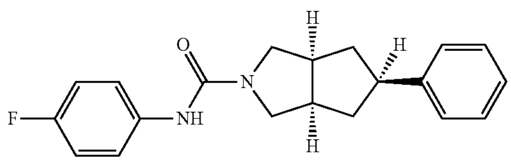 [SMILES: O=C(Nc1ccc(F)cc1)N1C[C@H]2C[C@@H](c3ccccc3)C[C@H]2C1] | N-(4-fluorophenyl)-5-phenyl-octahydrocyclopenta[c]pyrrole-2-carboxamide | 325.16 | 325.2 |
| 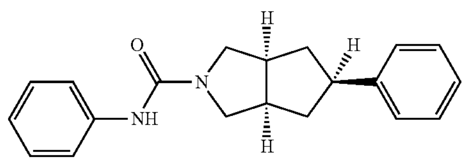 [SMILES: O=C(Nc1ccccc1)N1C[C@H]2C[C@@H](c3ccccc3)C[C@H]2C1] | N,5-diphenyl-octahydrocyclopenta[c]pyrrole-2-carboxamide | 307.17 | 307.33 |
| 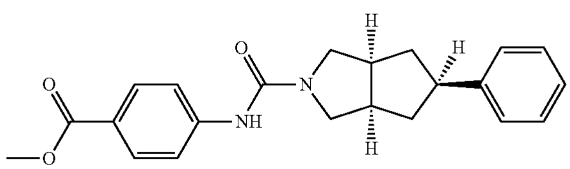 [SMILES: COC(=O)c1ccc(NC(=O)N2C[C@H]3C[C@@H](c4ccccc4)C[C@H]3C2)cc1] | methyl 4-[({5-phenyl-octahydrocyclopenta[c]pyrrol-2-yl}carbonyl)amino]benzoate | 365.18 | 365.36 |
| 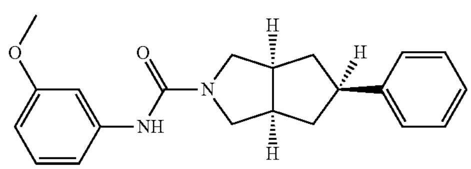 [SMILES: COc1cccc(NC(=O)N2C[C@H]3C[C@@H](c4ccccc4)C[C@H]3C2)c1] | N-(3-methoxyphenyl)-5-phenyl-octahydrocyclopenta[c]pyrrole-2-carboxamide | 337.18 | 337.37 |
| 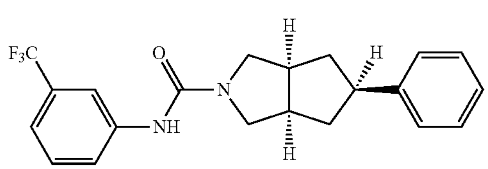 | 5-phenyl-N-[3-(trifluoromethyl)phenyl]-octahydrocyclopenta[c]pyrrole-2-carboxamide | 375.16 | 375.33 |
| 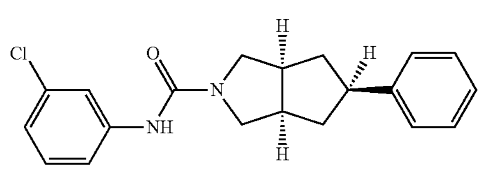 [SMILES: O=C(Nc1cccc(Cl)c1)N1C[C@H]2C[C@@H](c3ccccc3)C[C@H]2C1] | N-(3-chlorophenyl)-5-phenyl-octahydrocyclopenta[c]pyrrole-2-carboxamide | 341.13 | 341.32 |
| 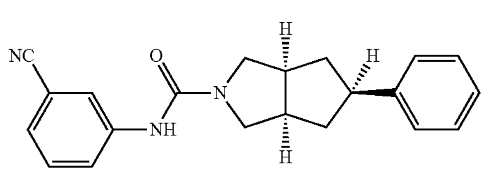 [SMILES: N#Cc1cccc(NC(=O)N2C[C@H]3C[C@@H](c4ccccc4)C[C@H]3C2)c1] | N-(3-cyanophenyl)-5-phenyl-octahydrocyclopenta[c]pyrrole-2-carboxamide | 332.17 | 332.33 |

TABLE 8-continued

The following compounds were prepared by the method described above.

| Structure | IUPAC Name | Calculated (M + H) | Found (M + H) |
|---|---|---|---|
| 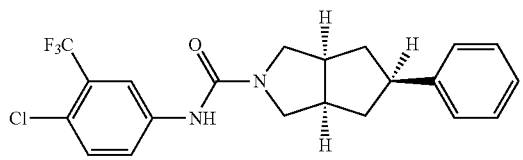 [SMILES: O=C(Nc1ccc(Cl)c(C(F)(F)F)c1)N1C[C@H]2C[C@@H](c3ccccc3)C[C@H]2C1] | N-[4-chloro-3-(trifluoromethyl)phenyl]-5-phenyl-octahydrocyclopenta[c]pyrrole-2-carboxamide | 409.12 | 409.33 |
| 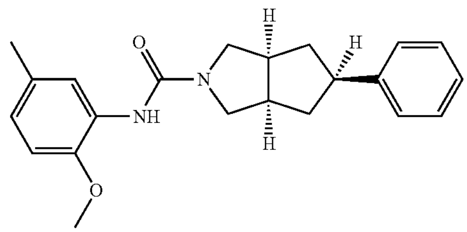 [SMILES: COc1ccc(C)cc1NC(=O)N1C[C@H]2C[C@@H](c3ccccc3)C[C@H]2C1] | N-(2-methoxy-5-methylphenyl)-5-phenyl-octahydrocyclopenta[c]pyrrole-2-carboxamide | 351.20 | 351.38 |
| 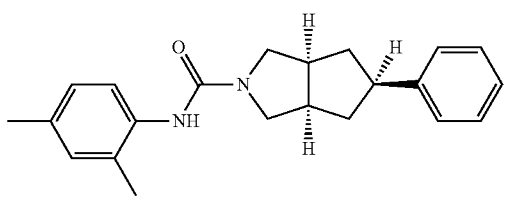 [SMILES: Cc1ccc(NC(=O)N2C[C@H]3C[C@@H](c4ccccc4)C[C@H]3C2)c(C)c1] | N-(2,4-dimethylphenyl)-5-phenyl-octahydrocyclopenta[c]pyrrole-2-carboxamide | 335.20 | 335.39 |
| 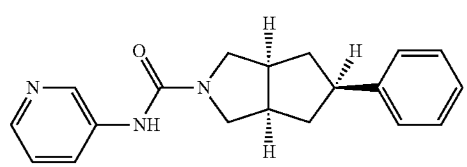 | 5-phenyl-N-(pyridin-3-yl)-octahydrocyclopenta[c]pyrrole-2-carboxamide | 308.17 | 308.36 |
| 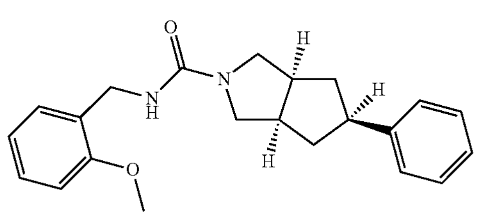 [SMILES: COc1ccccc1CNC(=O)N1C[C@H]2C[C@@H](c3ccccc3)C[C@H]2C1] | N-[(2-methoxyphenyl)methyl]-5-phenyl-octahydrocyclopenta[c]pyrrole-2-carboxamide | 351.20 | 351.3 |
| 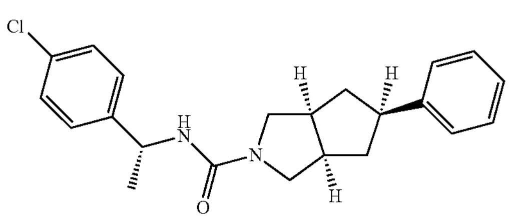 [SMILES: C[C@@H](NC(=O)N1C[C@H]2C[C@@H](c3ccccc3)C[C@H]2C1)c1ccc(Cl)cc1] | N-[(1R)-1-(4-chlorophenyl)ethyl]-5-phenyl-octahydrocyclopenta[c]pyrrole-2-carboxamide | 369.17 | 369.4 |

Example 13

Preparation of rac-4-(1-hydroxy-2-(5-phenylhexahydrocyclopenta[c]pyrrol-2(1H)-yl)ethyl)phenol Scheme 13

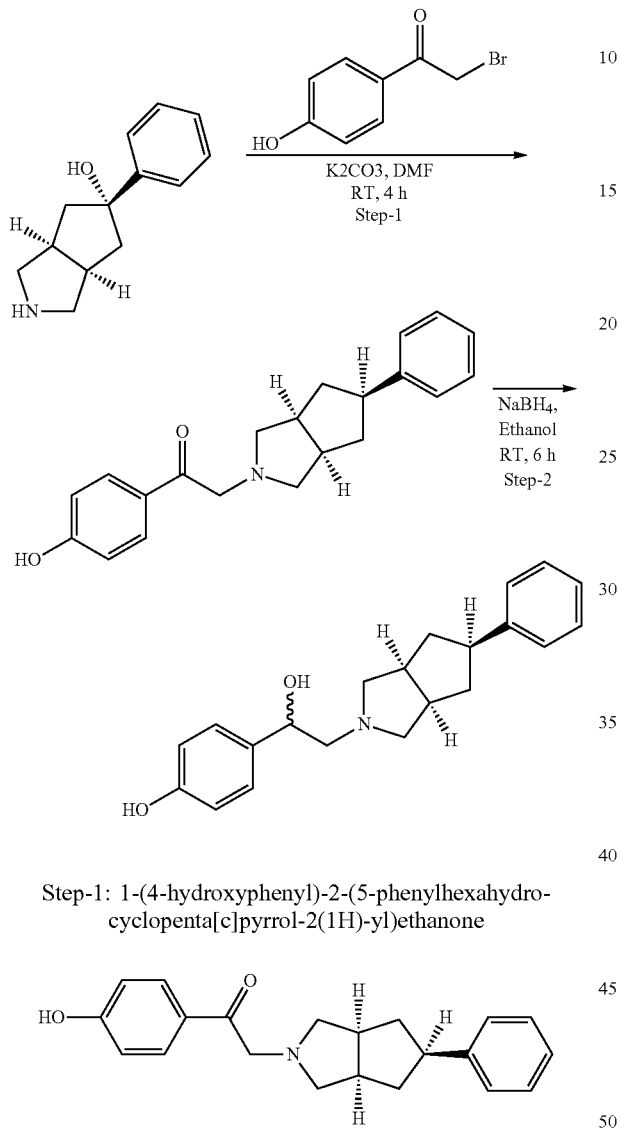

Step-1: 1-(4-hydroxyphenyl)-2-(5-phenylhexahydrocyclopenta[c]pyrrol-2(1H)-yl)ethanone To a stirred solution of 5-phenyloctahydrocyclopenta[c]pyrrole (0.3 g, 1.60 mmol) in dimethylformamide (10 mL) was added potassium carbonate (0.44 g, 3.20 mmol) and 2-bromo-1-(4-hydroxyphenyl)ethanone (0.34 g, 1.60 mmol) at room temperature and the reaction mixture was stirred for 4 h. After completion of reaction (monitored by TLC), the reaction mixture was diluted with cold water (25 mL) and extracted with ethylacetate (50 mL×3). The combined organic layer was washed with cold water (25 ml×3), brine (25 mL) dried over anhydrous sodium sulfate, filtered and concentrated under vacuum to afford the crude compound which was purified by silica gel column chromatography (30% ethyl acetate/hexane) to obtain the title compound 1-(4-hydroxyphenyl)-2-(5-phenylhexahydrocyclopenta[c]pyrrol-2(1H)-yl)ethanone (0.3 g, 63% yield) as a pale yellow solid. Calculated (M+H): 322.27. Found (M+H): 322.2.

Step-2: rac-4-(1-hydroxy-2-(5-phenylhexahydrocyclopenta[c]pyrrol-2(1H)-yl)ethyl)phenol

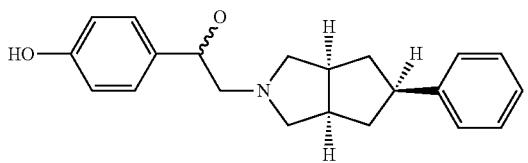

To a stirred solution of 1-(4-hydroxyphenyl)-2-(5-phenylhexahydrocyclopenta[c]pyrrol-2(1H)-yl)ethanone (0.1 g, 0.31 mmol) in ethanol was added sodium borohydride (0.058 g, 1.55 mmol) at room temperature and stirred for 6 h. After completion of reaction (monitored by TLC), the solvent was removed by vacuum and the residue was diluted with water (15 mL) and extracted with ethyl acetate (25 mL×3). The combined organic layer was washed with water (15 mL), brine (15 mL), dried over anhydrous sodium sulfate, filtered and concentrated under reduced pressure to afford the crude compound which was purified by silica gel column chromatography (3% methanol/dichloromethane) to obtain the title compound 4-(1-hydroxy-2-(5-phenylhexahydrocyclopenta[c]pyrrol-2(1H)-yl)ethyl)phenol (0.054 g, 50% yield) as off-white solid. Calculated (M+H): 324.19. Found (M+H): 324.3.

Example 14

Preparation of rac-2-(5-phenylhexahydrocyclopenta[c]pyrrol-2(1H)-yl)-1-(3-(trifluoromethyl)phenyl)ethanol Scheme 14

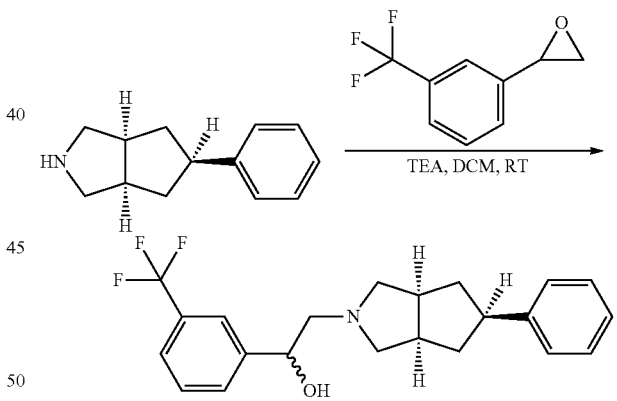

To a solution of 5-phenyloctahydrocyclopenta[c]pyrrole (0.040 g, 0.21 mmol) in dichloromethane (2 mL) was added 2-(3-(trifluoromethoxy)phenyl)oxirane (0.044 g, 0.24 mmol) and triethylamine (0.041 mL, 0.3 mmol) and resulting solution was stirred at room temperature for 18 h. After completion of reaction (monitored by TLC), reaction mixture was diluted with water (2 mL) and extracted with dichloromethane (5 mL×2), washed with brine (10 mL), dried over sodium sulfate and concentrated under vacuum to afford the crude 2-(5-phenylhexahydrocyclopenta[c]pyrrol-2(1H)-yl)-1-(3-(trifluoromethyl)phenyl)ethanol which was purified by prep HPLC (column: XSelect CSH C-18 Prep (19×250 mm, 5 um), mobile phase: A—5 mM ammonium acetate, B—acetonitrile, flow mode: gradient, flow: 15 ml/min, gradient T/% B: 0/30, 0.5/30, 15/90, 21/90, 21.5/30, 26/30).

TABLE 9

The following compound was prepared by the method described above.

| Structure | IUPAC Name | Calculated (M + H) | Found (M + H) |
|---|---|---|---|
| 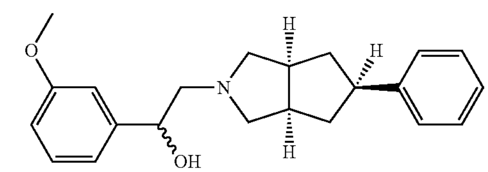 [SMILES: COc1cccc(C(O)CN2C[C@H]3C[C@@H](c4ccccc4)C[C@H]3C2)c1] | rac-1-(3-methoxyphenyl)-2-{5-phenyl-octahydrocyclopenta[c]pyrrol-2-yl}ethan-1-ol | 338.20 | 338.38 |

Example 15

Preparation of (3aR,5r,6aS)-5-benzyl-N-(3-chlorophenyl)-5-hydroxyhexahydrocyclopenta[c]pyrrole-2(1H)-carboxamide Scheme 15

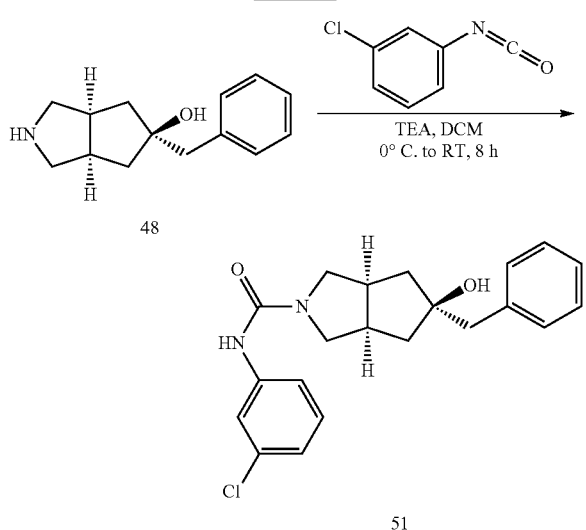

To a stirred solution of (3aR,5r,6aS)-5-benzyloctahydrocyclopenta[c]pyrrol-5-ol (0.05 g, 0.23 mmol) in dichloromethane (5 mL), was added triethylamine (0.97 mL, 0.69 mmol) and 1-chloro-3-isocyanatobenzene (0.038 g, 0.25 mmol) at 0° C. The reaction mixture was allowed to warm to room temperature and stirred for 8 h. After completion of the reaction (monitored by TLC), the reaction mixture was quenched with 50% sodium bicarbonate solution and extracted with dichloromethane. The combined organic layer was washed with water, brine solution, dried over anhydrous sodium sulfate and concentrated under reduced pressure to afford the crude compound which was purified by silica gel column chromatography (3% methanol/dichloromethane) to obtain the title compound (3aR,5r,6aS)-5-benzyl-N-(3-chlorophenyl)-5-hydroxyhexahydrocyclopenta[c]pyrrole-2(1H)-carboxamide (0.056 g, 62% yield) as a white solid. Calculated (M+H): 371.14. Found (M+H): 371.2.

TABLE 10

The following compounds were prepared by the method described above.

| Structure | IUPAC Name | Calculated (M + H) | Found (M + H) |
|---|---|---|---|
| 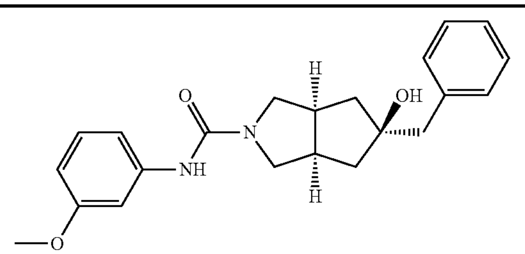 | (3aR,5r,6aS)-5-benzyl-5-hydroxy-N-(3-methoxyphenyl)hexahydro-cyclopenta[c]pyrrole-2(1H)-carboxamide | 367.19 | 367.4 |
| | (3aR,5r,6aS)-5-benzyl-N-(4-chloro-3-(trifluoromethyl)phenyl)-5-hydroxyhexahydrocyclopenta[c]pyrrole-2(1H)-carboxamide | 439.13 | 439.4 |

TABLE 10-continued

The following compounds were prepared by the method described above.

| Structure | IUPAC Name | Calculated (M + H) | Found (M + H) |
|---|---|---|---|
| 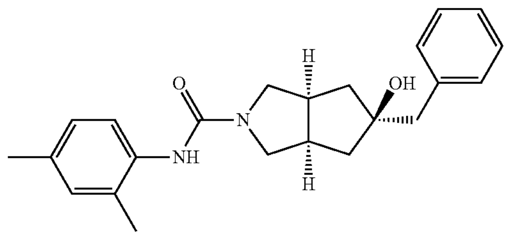 [SMILES: Cc1ccc(NC(=O)N2C[C@@H]3C[C@@](O)(Cc4ccccc4)C[C@@H]3C2)c(C)c1] | (3aR,5r,6aS)-5-benzyl-N-(2,4-dimethylphenyl)-5-hydroxyhexahydrocyclopenta[c]pyrrole-2(1H)-carboxamide | 365.22 | 365.49 |
| 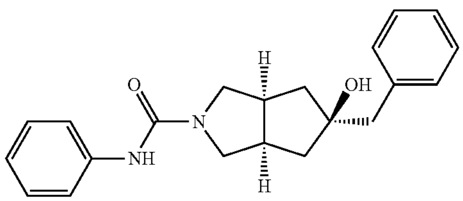 [SMILES: O=C(Nc1ccccc1)N1C[C@@H]2C[C@@](O)(Cc3ccccc3)C[C@@H]2C1] | (3aR,5r,6aS)-5-benzyl-5-hydroxy-N-phenylhexahydrocyclopenta[c]pyrrole-2(1H)-carboxamide | 335.18 (M − H) | 335.19 (M − H) |
| 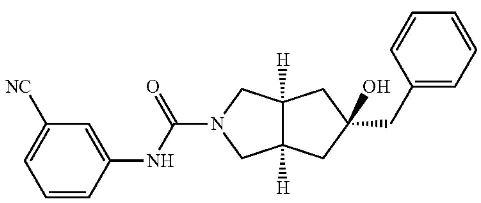 [SMILES: N#Cc1cccc(NC(=O)N2C[C@@H]3C[C@@](O)(Cc4ccccc4)C[C@@H]3C2)c1] | (3aR,5r,6aS)-5-benzyl-N-(3-cyanophenyl)-5-hydroxyhexahydrocyclopenta[c]pyrrole-2(1H)-carboxamide | 360.18 (M − H) | 360.23 (M − H) |
| 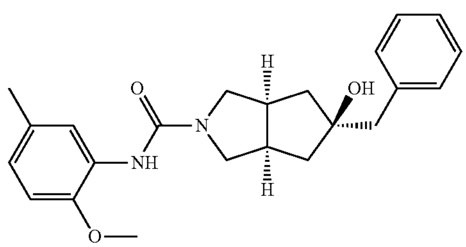 [SMILES: COc1ccc(C)cc1NC(=O)N1C[C@@H]2C[C@@](O)(Cc3ccccc3)C[C@@H]2C1] | (3aR,5r,6aS)-5-benzyl-5-hydroxy-N-(2-methoxy-5-methylphenyl)hexahydrocyclopenta[c]pyrrole-2(1H)-carboxamide | 381.21 | 381.21 |
|  | (3aR,5r,6aS)-5-benzyl-5-hydroxy-N-(p-tolyl)hexahydrocyclopenta[c]pyrrole-2(1H)-carboxamide | 351.2 | 351.4 |
| 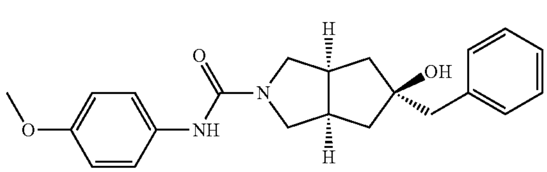 [SMILES: COc1ccc(NC(=O)N2C[C@@H]3C[C@@](O)(Cc4ccccc4)C[C@@H]3C2)cc1] | (3aR,5r,6aS)-5-benzyl-5-hydroxy-N-(4-methoxyphenyl)hexahydrocyclopenta[c]pyrrole-2(1H)-carboxamide | 367.19 | 367.3 |
|  | (3aR,5r,6aS)-5-benzyl-5-hydroxy-N-(2-(trifluoromethyl)phenyl)hexahydrocyclopenta[c]pyrrole-2(1H)-carboxamide | 405.17 | 405.2 |

TABLE 10-continued

The following compounds were prepared by the method described above.

| Structure | IUPAC Name | Calculated (M + H) | Found (M + H) |
|---|---|---|---|
| | (3aR,5r,6aS)-5-benzyl-5-hydroxy-N-(2-methoxyphenyl)hexahydrocyclopenta[c]pyrrole-2(1H)-carboxamide | 367.19 | 367.2 |
| | (3aR,5r,6aS)-5-benzyl-5-hydroxy-N-(m-tolyl)hexahydrocyclopenta[c]pyrrole-2(1H)-carboxamide | 351.2 | 351.2 |

Example 16

Preparation of rac-(3aR,5r,6aS)-5-benzyl-2-(2-hydroxy-2-(4-hydroxyphenyl)ethyl)octahydrocyclopenta[c]pyrrol-5-ol Scheme 16

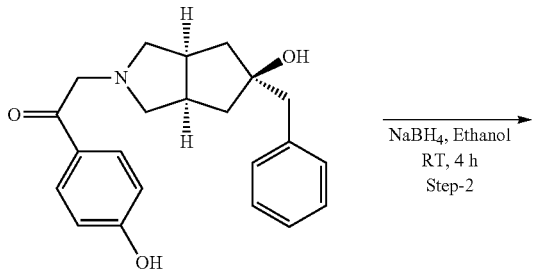

Step 1: Preparation of 2-((3aR,5r,6aS)-5-benzyl-5-hydroxyhexahydrocyclopenta[c]pyrrol-2(1H)-yl)-1-(4-hydroxyphenyl)ethanone

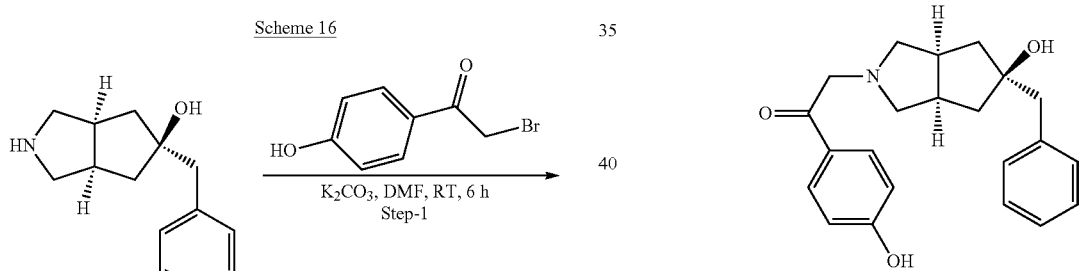

To a stirred solution of (3aR,5r,6aS)-5-benzyloctahydrocyclopenta[c]pyrrol-5-ol (0.3 g, 1.38 mmol) in dimethylformamide (10 mL), was added potassium carbonate (0.572 g, 4.14 mmol) and 2-bromo-1-(4-hydroxyphenyl)ethanone (0.326 g, 1.51 mmol) at room temperature and stirred for 6 h. After completion of the reaction (monitored by TLC), the reaction mixture was quenched with cold water (50 mL) and extracted with ethyl acetate (100 mL×3). The combined organic layer was washed with cold water (50 mL), brine (50 mL), dried over anhydrous sodium sulfate, filtered and concentrated under vacuum to afford the crude compound which was purified by silica gel column chromatography (35% ethyl acetate/hexane) to obtain the title compound 2-((3aR,5r,6aS)-5-benzyl-5-hydroxyhexahydrocyclopenta[c]pyrrol-2(1H)-yl)-1-(4-hydroxyphenyl)ethanone (0.1 g, 20% yield) as off white solid. Calculated M+H: 352.18. Found M+H: 352.3.

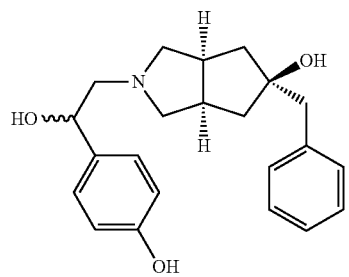

Step 2: Preparation of rac-(3aR,5r,6aS)-5-benzyl-2-(2-hydroxy-2-(4-hydroxyphenyl)ethyl)octahydrocyclopenta[c]pyrrol-5-ol

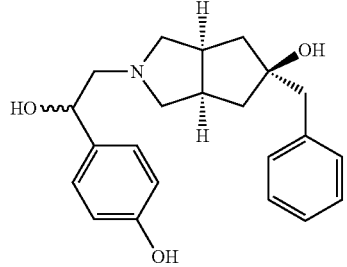 [SMILES: Oc1ccc(C(O)CN2C[C@@H]3C[C@@](O)(Cc4ccccc4)C[C@@H]3C2)cc1]

To a stirred solution of 2-((3aR,5r,6aS)-5-benzyl-5-hydroxyhexahydrocyclopenta[c]pyrrol-2(1H)-yl)-1-(4-hydroxyphenyl)ethanone (0.080 g, 0.23 mmol) in ethanol (20 mL), was added sodium borohydride (0.043 g, 1.14 mmol) at room temperature and stirred for 2 h. After completion of the reaction (monitored by TLC), the reaction mixture was concentrated under vacuum and the residue was diluted with water (10 mL) and extracted with ethyl acetate (30 mL×3), The combined organic layer was washed with water (10 mL×3), brine (15 mL), dried over anhydrous sodium sulfate and concentrated under vacuum to afford the crude compound which was purified by silica gel column chromatography (10% methanol/dichloromethane) to obtain the title compound (3aR,5r,6aS)-5-benzyl-2-(2-hydroxy-2-(4-hydroxyphenyl)ethyl)octahydrocyclopenta[c]pyrrol-5-ol (0.020 g, 25% yield) as off-white solid. Calculated M+H: 354.20. Found M+H: 354.3.

Example 17

Preparation of 2-bromo-1-(5-hydroxypyridin-2-yl)ethanone

Scheme 17

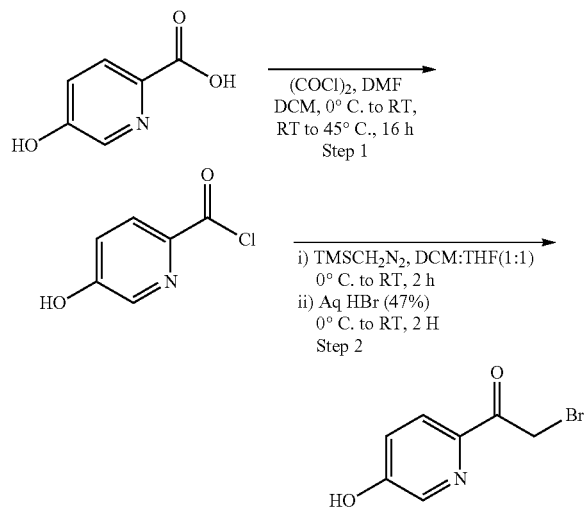

Step 1: Preparation of 5-hydroxypicolinoyl chloride

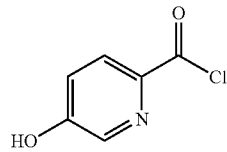

To a suspension of 5-hydroxypicolinic acid (1.0 g, 7.18 mmol) in dichloromethane (70 mL) and catalytic amount of N,N-dimethyl formamide (0.2 mL), was added oxalyl chloride (1.25 mL, 14.37 mmol) slowly at 0° C., the resulting suspension was allowed to warm to room temperature and refluxed for 16 h. The mixture was allowed to cool to room temperature and concentrated under vacuum to afford the title compound 5-hydroxypicolinoyl chloride (1.1 g, crude) which was as such taken for next step without further purification.

Step 2: Preparation of 2-bromo-1-(5-hydroxypyridin-2-yl)ethanone

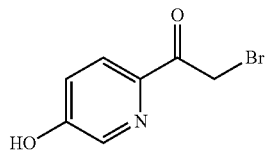 [SMILES: O=C(CBr)c1ccc(O)cn1]

To a suspension of 5-hydroxypicolinoyl chloride (1.1 g, 7.18 mmol, crude) in dichloromethane:tetrahydrofuran mixture (1:1, 50 mL) was added trimethyl silyl diazomethane (9.5 mL, 19.04 mmol, 2M in hexane) slowly at 0° C. and the reaction mixture was stirred at room temperature for 2 h. The reaction mixture was cooled to 0° C. and aqueous hydrobromic acid (47%, 3 mL, 19.04 mmol) was added. The reaction mixture was allowed to room temperature and stirred for 2 h. The solid formed was filtered, the washed with dichloromethane, diethyl ether and dried to obtain the title compound 2-bromo-1-(5-hydroxypyridin-2-yl)ethanone (0.6 g, crude) as pale brown solid. Calculated M+H: 215.96. Found M+H: 216.0.

Example 18

Preparation of 2-bromo-1-(4-(2-hydroxypropan-2-yl)phenyl)ethanone

Scheme 18

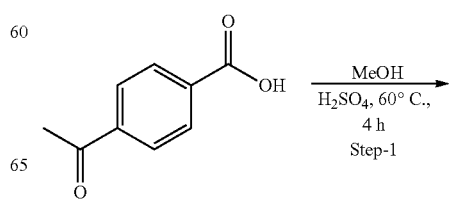

-continued

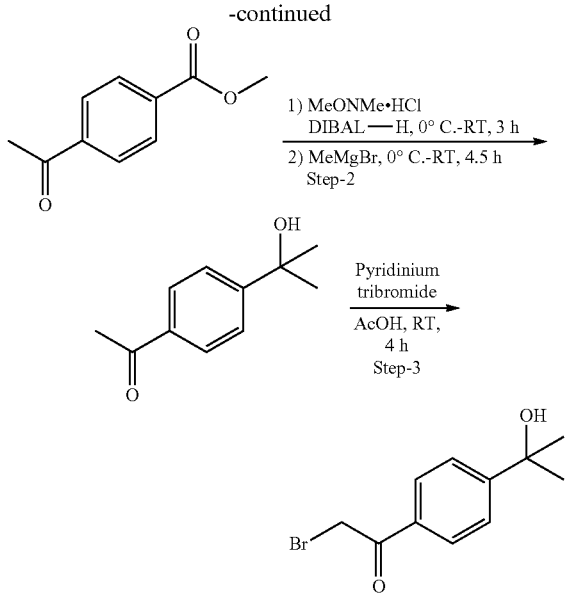

Step 1: Preparation of methyl 4-acetylbenzoate

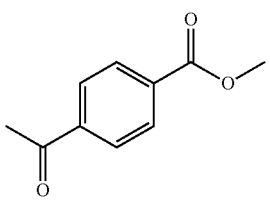

To a solution of 4-acetylbenzoic acid (10 g, 60.91 mmol) in methanol (60 mL) was added sulphuric acid (10 mL). The reaction mixture was heated at 60° C. for 4 h. After completion of the reaction (as monitored by TLC), the solution was concentrated, the residue was dissolved in ethyl acetate (600 mL) and washed with saturated sodium bicarbonate solution (200 mL). The organic layer was dried over anhydrous sodium sulfate, filtered and concentrated. The crude was purified by silica gel column chromatography using 10% ethyl acetate in hexane to afford the title compound methyl 4-acetylbenzoate (9 g, 82% yield) as yellow solid. $^1$H NMR (400 MHz, DMSO-$d_6$) δ 8.061 (s, 4H), 3.877 (s, 3H), 2.165 (s, 3H).

Step 2: Preparation of 1-(4-(2-hydroxypropan-2-yl)phenyl)ethanone

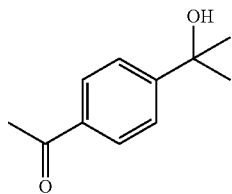

A solution of diisobutylaluminium hydride (5.26 mL, 0.926 mmol, 25% in toluene) was added to a suspension of N,O-dimethylhydroxylamine hydrochloride (0.82 g, 8.418 mmol) in diethyl ether/tetrahydrofuran mixture (1:1, 200 mL) at 0° C. under nitrogen atmosphere. The mixture was stirred for 1 h allowing the temperature slowly to warm to room temperature. This solution was added to a 0° C. solution of methyl 4-acetylbenzoate (1.5 g, 8.418 mmol) in diethyl ether (200 mL) and stirred at room temperature for 2 h. Then methyl magnesium bromide in diethyl ether (10 mL) was added at 0° C. and stirred at room temperature for 1 h. Additional methyl magnesium bromide (18 mL, 84.18 mmol) in diethyl ether was added and the reaction mixture was stirred at room temperature for 3.5 h. The reaction was quenched with saturated aqueous ammonium chloride solution and extracted with ethyl acetate (100 mL×2). The combined organic layer was washed with brine (50 mL), dried over anhydrous sodium sulfate, filtered and concentrated. The crude was purified by silica gel column chromatography using 14% ethyl acetate in hexane to afford the title 1-(4-(2-hydroxypropan-2-yl)phenyl)ethanone (0.4 g, 26% yield) as colorless liquid. $^1$H NMR (400 MHz, DMSO-$d_6$) δ 7.884-7.863 (d, J=8.4 Hz, 2H), 7.593-7.572 (d, J=8.4 Hz, 2H), 5.133 (s, 1H). 2.538 (s, 3H), 1.421 (s, 6H).

Step 3: Preparation of 2-bromo-1-(4-(2-hydroxypropan-2-yl)phenyl)ethanone

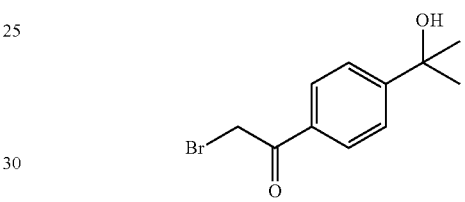

To a solution of 1-(4-(2-hydroxypropan-2-yl)phenyl)ethanone (0.4 g, 2.24 mmol) in acetic acid (5 mL) was added pyridinium tribromide (0.78 g, 2.46 mmol). The reaction mixture was stirred at room temperature for 4 h. The solution was concentrated, diluted with water (30 mL) and extract with ethyl acetate (100 mL×3). The combined organic layer was dried over anhydrous sodium sulfate, filtered and concentrated. The crude was purified by silica gel column chromatography using 15% ethyl acetate in hexane to afford the title compound 2-bromo-1-(4-(2-hydroxypropan-2-yl) phenyl)ethanone (0.05 g, 8.6% yield) as a yellow solid. $^1$H NMR (400 MHz, DMSO-$d_6$) δ 7.934-7.913 (d, J=8.4 Hz, 2H), 7.619-7.559 (d, J=24 Hz, 2H), 5.222 (s, 1H), 4.873 (s, 2H), 1.424 (s, 6H).

Example 19

Preparation of 1-bromo-3-(4-hydroxyphenyl)propan-2-one

Scheme 19

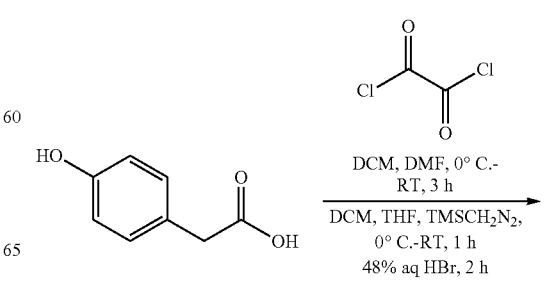

-continued

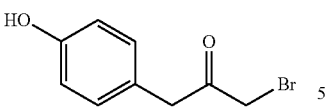

To a stirred solution of 2-(4-hydroxyphenyl)acetic acid (1.5 g, 9.86 mmol) in a mixture of dichloromethane (75 mL) and N,N-dimethylformaldehyde (0.1 mL), oxalyl chloride (2.11 mL, 24.65 mmol) was added at 0° C. and stirred at room temperature for 3 h under nitrogen atmosphere. The reaction mixture was evaporated under vacuum to get solid which was dissolved in a mixture of tetrahydrofuran:dichloromethane (150 mL, 1:1). Then (trimethylsilyl)diazomethane (67.1 mL, 49.3 mmol) was added at 0° C. and stirred at room temperature for 1 h. 48% aqueous hydrogen bromide was added at 0° C. and the reaction mixture was stirred at room temperature for 2 h. The organic layer was separated, dried over anhydrous sodium sulfate and evaporated under vacuum to get crude which was purified by silica gel flash column chromatography using 20% ethyl acetate in hexane to afford the title compound 1-bromo-3-(4-hydroxyphenyl)propan-2-one (0.549 g, crude) as a brownish solid. The crude was as such taken for next step without further purification.

Example 20

Preparation of 2-bromo-1-(3-fluoro-4-hydroxyphenyl)ethanone

Scheme 20

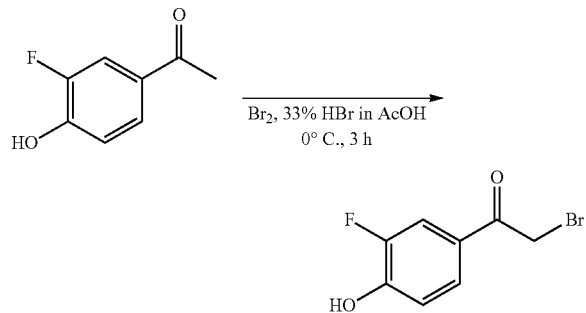

To a suspension of 1-(3-fluoro-4-hydroxyphenyl)ethanone (2.0 g, 12.98 mmol) in 33% hydrobromic acid in acetic acid (200 mL), was added a solution of bromine (0.53 mL, 10.389 mmol) in 20 mL of 33% hydrobromic acid in acetic acid at 0° C. and stirred at the same temperature for 3 h. The reaction mixture was diluted with ice water (100 mL) and extract with ethyl acetate (100 mL×3). The combined organic layer was dried over anhydrous sodium sulfate, filtered and concentrated. The crude was purified by silica gel column chromatography using 3% ethyl acetate in hexane to afford the title compound 2-bromo-1-(3-fluoro-4-hydroxyphenyl)ethanone (1.5 g, 49.66% yield) as a white solid. Calculated M+H: 232.95. Found M+H: 233.0.

Example 21

Preparation of 2-bromo-1-(6-chloropyridin-3-yl)ethanone

Scheme 21

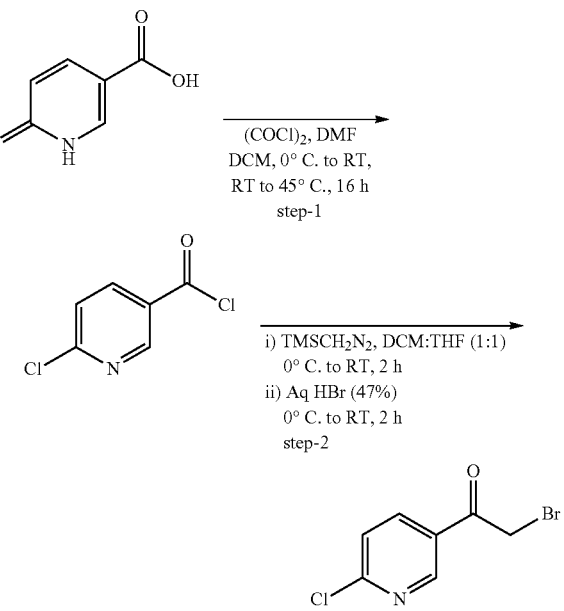

Step-1: Preparation of 6-chloronicotinoyl chloride

To a suspension of 6-oxo-1,6-dihydropyridine-3-carboxylic acid (1.0 g, 7.18 mmol) in dichloromethane (150 mL) and catalytical amount of DMF (0.5 mL), was added oxalyl chloride (1.25 mL, 14.37 mmol) slowly at 0° C., the resulting suspension was allowed to warm to room temperature and refluxed for 16 h. The mixture was allowed to cool to room temperature and the volatiles were removed by vacuum to afford 6-chloronicotinoyl chloride (crude) which was taken to next step without purification.

Step-2: Preparation of 2-bromo-1-(6-chloropyridin-3-yl)ethanone

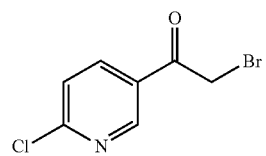 [SMILES: O=C(CBr)c1ccc(Cl)nc1]

To a suspension of 6-chloronicotinoyl chloride (1.0 g, crude) in dichloromethane:tetrahydrofuran mixture (30 mL, 1:1) was added trimethylsilyl diazomethane (2M in hexane, 9.5 mL, 25.38 mmol) slowly at 0° C. The mixture was slowly allowed to warm to room temperature and stirred for 2 h. The solution was cooled to 0° C. and aqueous hydrobromic acid (47% in water, 3 mL, 19.04 mmol) was added slowly. The reaction mixture was allowed to warm to room temperature and stirred for 2 h. The mixture was diluted with dichloromethane (50 mL), washed with 20% sodium bicarbonate solution (30 mL), water (30 mL), dried over anhydrous sodium sulfate, filtered and concentrated. The crude product was purified by silica gel column chromatography using 15% ethyl acetate in hexane to obtain title compound 2-bromo-1-(6-chloropyridin-3-yl)ethanone (0.98 g, 65% yield) as a white solid. Calculated M+H: 233.92. Found M+H: 234.1.

Example 22

Preparation of 6-(2-bromoacetyl)pyridazin-3(2H)-one

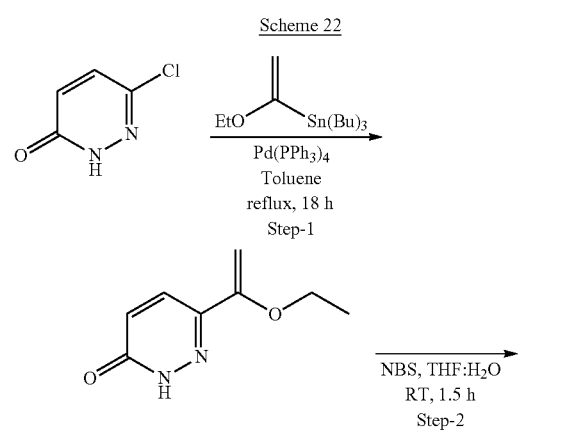

Step-1: Preparation of 6-(1-ethoxyvinyl)pyridazin-3(2H)-one

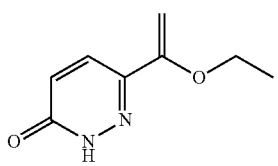

To a solution of 6-chloropyridazin-3(2H)-one (0.5 g, 3.83 mmol) and tributyl(1-ethoxyvinyl)stannane (1.42 mL, 4.21 mmol) in toluene (30 mL) argon was purged for 5 minutes. Tetrakis(triphenylphosphine)palladium(0) (0.22 g, 0.19 mmol) was added and the reaction mixture was heated at 100° C. for 18 h. The solution was filtered through celite and filtrate was concentrated to afford the title compound 6-(1-ethoxyvinyl)pyridazin-3(2H)-one (0.63 g, crude) as a brownish gum. Calculated (M+H): 167.07. Found (M+1): 167.3.

Step-2: Preparation of 6-(2-bromoacetyl)pyridazin-3(2H)-one

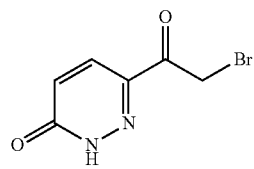 [SMILES: O=C(CBr)c1ccc(=O)[nH]n1]

To a solution of 6-(1-ethoxyvinyl)pyridazin-3(2H)-one (0.63 g, 3.79 mmol) in tetrahydrofuran:water mixture (20 ml: 4 mL) was added N-bromosuccinimide (1.0 g, 5.69 mmol) and the reaction mixture was stirred at room temperature for 1.5 h. The reaction mixture was diluted with water (20 mL) and extracted with ethyl acetate (30 mL×2). The combined organic layer was dried over anhydrous sodium sulfate, filtered and concentrated to afford the crude product which was purified by silica gel column chromatography (30% ethyl acetate/hexane) to obtain the title compound 6-(2-bromoacetyl)pyridazin-3(2H)-one (0.41 g, 50% yield) as a brownish solid. Calculated (M+H): 216.95. Found (M+1): 217.1.

Example 23

Preparation of 2-bromo-1-(3,5-difluoro-4-hydroxyphenyl)ethanone

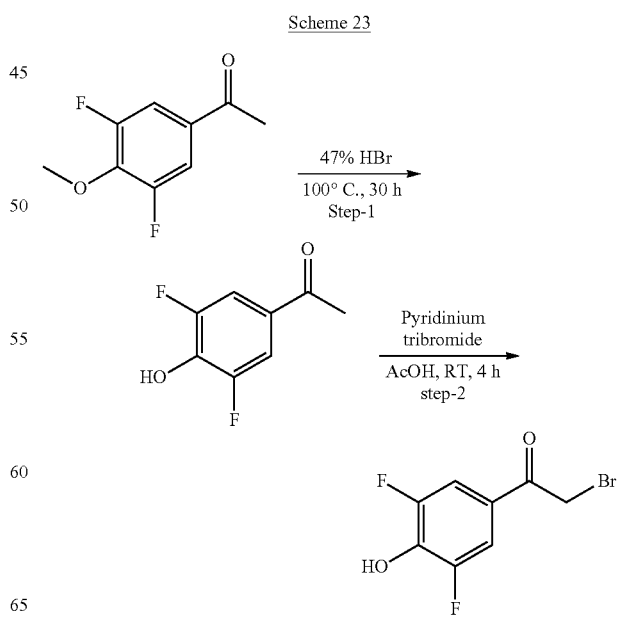

Step 1: Preparation of 1-(3,5-difluoro-4-hydroxyphenyl)ethanone

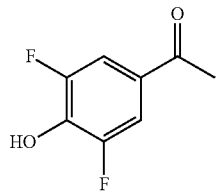

A solution of 1-(3,5-difluoro-4-methoxyphenyl)ethanone (0.1 g, 0.53 mmol) in 47% hydrobromic acid (3 mL) was heated at 100° C. for 30 h. The reaction mixture was cooled to room temperature, diluted with water (30 mL) and extracted with dichloromethane (50 mL×3). The combined organic layer was dried over anhydrous sodium sulfate, filtered and concentrated. The crude was purified by silica gel column chromatography using 20% ethyl acetate in hexane to afford the title compound 1-(3,5-difluoro-4-hydroxyphenyl)ethanone (0.08 g, 86% yield) as a white solid. Calculated M−H: 171.03. Found M−H: 171.1.

Step 2: Preparation of 2-bromo-1-(3,5-difluoro-4-hydroxyphenyl)ethanone

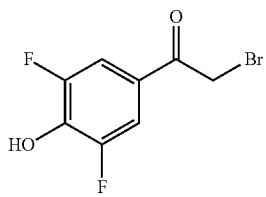 [SMILES: O=C(CBr)c1cc(F)c(O)c(F)c1]

To a solution of 1-(3,5-difluoro-4-hydroxyphenyl)ethanone (0.08 g, 0.465 mmol) in acetic acid (5 mL) was added pyridinium tribromide (0.163 g, 0.511 mmol). The reaction mixture was stirred at room temperature for 4 h. The solution was concentrated, diluted with water (20 mL) and extracted with ethyl acetate (50 mL×3). The combined organic layer was dried over anhydrous sodium sulfate, filtered and concentrated. The crude was purified by silica gel column chromatography using 80% dichloromethane in hexane to afford the title compound 2-bromo-1-(3,5-difluoro-4-hydroxyphenyl)ethanone (0.07 g, 60% yield) as a white solid. Calculated M+H: 250.94. Found M+H: 251.0.

Example 24

Preparation of 1-(5-(benzyloxy)pyrazin-2-yl)-2-bromoethanone

Scheme 24

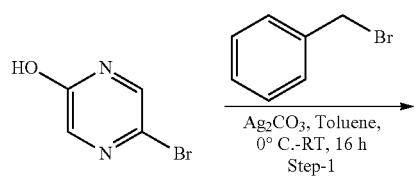

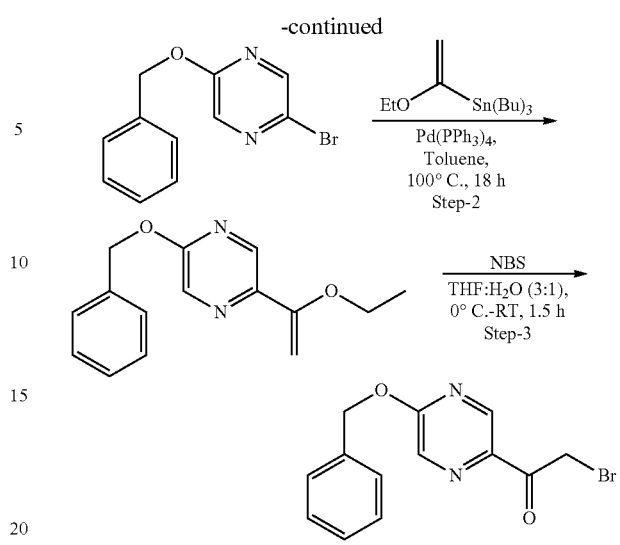

Step 1: Preparation of 2-(benzyloxy)-5-bromopyrazine

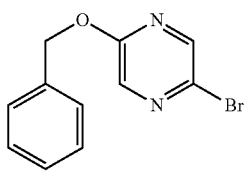 [SMILES: Brc1cnc(OCc2ccccc2)cn1]

To a solution 5-bromopyrazin-2-ol (0.5 g, 2.857 mmol) in toluene (20 mL) was added silver carbonate (1.574 g, 5.714 mmol) and stirred at room temperature for 5 minutes. Then benzyl bromide (0.47 ml, 3.428 mmol) was added drop wise and the reaction mixture was stirred at room temperature for 16 h. The suspension was filtered through celite, the filtrate was diluted with ethyl acetate (200 mL) and washed with water (50 mL). The organic layer was dried over anhydrous sodium sulfate, filtered and concentrated. The crude was purified by silica gel column chromatography using 3% ethyl acetate in hexane to afford the title compound 2-(benzyloxy)-5-bromopyrazine (0.3 g, 40% yield) as a white solid. Calculated M+H: 264.99. Found M+H: 265.0.

Step 2: Preparation of 2-(benzyloxy)-5-(1-ethoxyvinyl)pyrazine

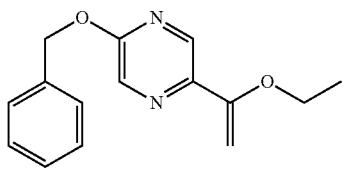 [SMILES: C=C(OCC)c1cnc(OCc2ccccc2)cn1]

To a solution 2-(benzyloxy)-5-bromopyrazine (0.3 g, 1.13 mmol) in toluene (15 mL) was added tributyl(1-ethoxyvinyl) stannane (0.382 g, 1.131 mmol) and purged with argon for 20 minutes. Then tetrakis(triphenyphosphine)palladium(0) (0.065 g, 0.056 mmol) was added and reaction mixture was stirred at 100° C. for 18 h. The suspension was filtered through celite and the filtrate was concentrated to afford the title compound 2-(benzyloxy)-5-(1-ethoxyvinyl)pyrazine (0.3 g, crude) as brownish gum. The crude was as such taken for next step without purification. Calculated M+H: 257.12. Found M+H: 257.1.

Step 3: Preparation of 1-(5-(benzyloxy)pyrazin-2-yl)-2-bromoethanone

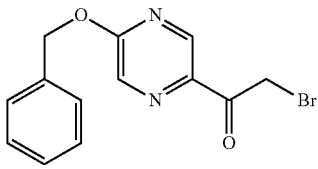 [SMILES: O=C(CBr)c1cnc(OCc2ccccc2)cn1]

To a solution of 2-(benzyloxy)-5-(1-ethoxyvinyl)pyrazine (0.3 g, 1.17 mmol) in tetrahydrofuran:water mixture (7.5 mL: 2.5 mL) at 0° C. was added N-bromo succinimide (0.312 g, 1.755 mmol)) and the reaction mixture was stirred at room temperature for 1.5 h. The solution was diluted with water (30 mL) and extracted with diethyl ether (80 mL×3). The combined organic layer was dried over anhydrous sodium sulphate, filtered and concentrated. The crude was purified by silica gel column chromatography using 2.7% ethyl acetate in hexane to afford the title compound 1-(5-(benzyloxy)pyrazin-2-yl)-2-bromoethanone (0.12 g, 33% yield) as a white solid. Calculated M+H: 307. Found M+H: 307.0.

Example 25

Preparation of 1-(1H-benzo[d][1,2,3]triazol-5-yl)-2-bromoethanone

Scheme 25

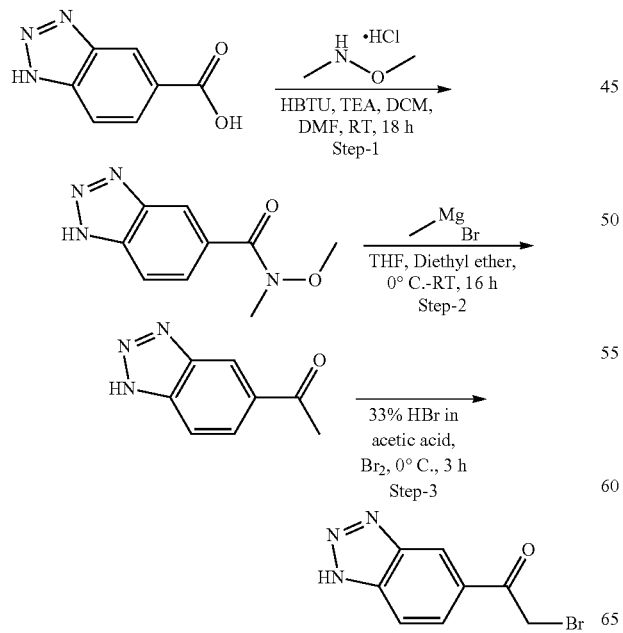

Step-1: Preparation of N-methoxy-N-methyl-1H-benzo[d][1,2,3]triazole-5-carboxamide

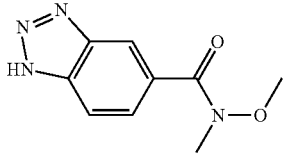

To a mixture of 1H-benzo[d][1,2,3]triazole-5-carboxylic acid (0.5 g, 3.1 mmol), N,O-dimethylhydroxylamine hydrochloride (0.3 g, 3.1 mmol) in dichloromethane (40 mL), HBTU (1.4 g, 3.7 mmol), triethylamine (0.94 g, 9.3 mmol) and N,N-dimethylformaldehyde (5 mL) were added and the reaction mixture was stirred at room temperature for 18 h under nitrogen atmosphere. The reaction mixture was diluted with dichloromethane (100 mL) and washed with ice cold water (25 mL). The organic layer was dried over anhydrous sodium sulfate, filtered and evaporated under vacuum to get crude which was purified by silica gel flash column chromatography using 5% methanol in dichloromethane to afford the title compound N-methoxy-N-methyl-1H-benzo[d][1,2,3]triazole-5-carboxamide (0.61 g, 95%) as yellowish gum. Calculated (M+H): 207.2. Found (M+1): 207.1.

Step-2: Preparation of 1-(1H-benzo[d][1,2,3]triazol-5-yl)ethanone

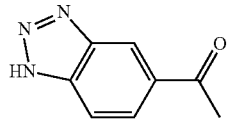

To a solution of N-methoxy-N-methyl-1H-benzo[d][1,2,3]triazole-5-carboxamide (0.6 g, 2.91 mmol) in a mixture of tetrahydrofuran (5 mL):diethyl ether (20 mL), 3M methyl magnesium bromide in diethyl ether (1.45 mL, 4.36 mmol) was added at 0° C. and the reaction mixture was stirred at room temperature for 16 h under nitrogen atmosphere. The reaction mixture was quenched with saturated ammonium chloride solution (10 mL) and extracted with ethyl acetate (300 mL×2). Then combined organic layer was dried over anhydrous sodium sulfate, filtered and evaporated under vacuum to get crude which was purified by silica gel flash column chromatography using 5% methanol in dichloromethane to afford the title compound 1-(1H-benzo[d][1,2,3]triazol-5-yl)ethanone (0.251 g, 53.5%) as off-white solid. Calculated (M+H): 162.16. Found (M+1): 162.1.

Step-3: Preparation of 1-(1H-benzo[d][1,2,3]triazol-5-yl)-2-bromoethanone

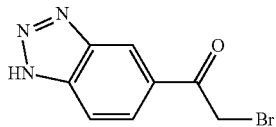 [SMILES: O=C(CBr)c1ccc2[nH]nnc2c1]

A mixture of 1-(1H-benzo[d][1,2,3]triazol-5-yl)ethanone (0.15 g, 0.93 mmol) and 33% hydrogen bromide in acetic acid (10 mL) was cooled to 0° C. A solution of bromine (0.05 mL, 0.93 mmol) in 5 ml, of 33% hydrogen bromide in acetic acid was added at 0° C. and the reaction mixture was stirred at 0° C. for 3 h. The solution was quenched with ice cold water (30 mL) and extracted with ethyl acetate (100 mL×2). The combined organic layer was washed with saturated sodium bicarbonate solution (30 mL), dried over anhydrous sodium sulfate and evaporated under vacuum to get crude which was purified by silica gel flash column chromatography using 2% methanol in dichloromethane to afford the title compound 1-(1H-benzo[d][1,2,3]triazol-5-yl)-2-bromoethanone (0.075 g, 33%) as off-white solid. Calculated (M+H): 239.97. Found (M+1): 240.0.

Example 26

Preparation of (3aR,5r,6aS)-5-benzyl-5-methoxyoctahydrocyclopenta[c]pyrrole

Scheme 26

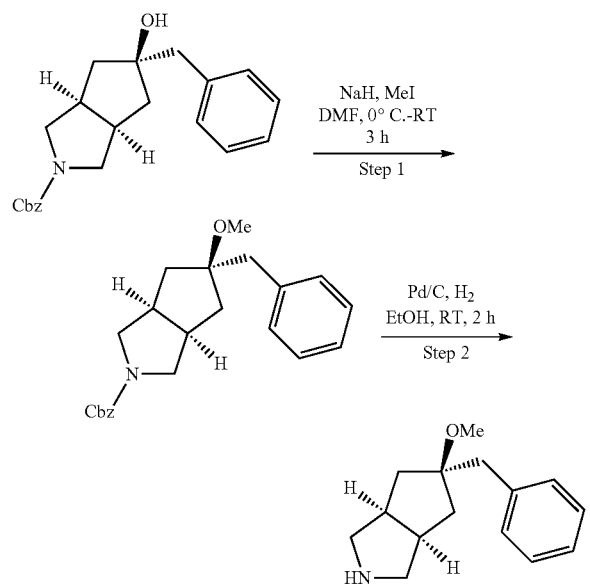

Step 1: Preparation of (3aR,5r,6aS)-benzyl 5-benzyl-5-methoxyhexahydrocyclopenta[c]pyrrole-2(1H)-carboxylate

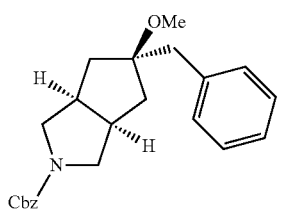 [SMILES: CO[C@@]1(Cc2ccccc2)C[C@H]2CN(C(=O)OCc3ccccc3)C[C@H]2C1]

Sodium hydride (0.273 g, 60%, 6.82 mmol) was added to a solution of (3aR,5r,6aS)-benzyl 5-benzyl-5-hydroxyhexahydrocyclopenta[c]pyrrole-2(1H)-carboxylate (1.2 g, 3.41 mmol) in N,N-dimethylformamide (15 mL) at 0° C. and the reaction mixture was stirred at room temperature for 30 minutes. The suspension was cooled to 0° C., added methyl iodide (0.425 mL, 6.82 mmol) and stirred at room temperature for 3 h. The reaction mixture was diluted with ice-water (25 mL) and extracted with ethyl acetate (30 mL×2). The combined organic extract was washed with water (30 mL), brine (30 mL), dried over anhydrous sodium sulfate and evaporated. The crude material was purified by combiflash purifier using 15% ethyl acetate in hexane to afford (3aR,5r,6aS)-benzyl 5-benzyl-5-methoxyhexahydrocyclopenta[c] pyrrole-2(1H)-carboxylate as a yellow liquid (1.0 g, 80% yield). Calculated M+H: 366.2. Found M+H: 366.2.

Step 2: Preparation of (3aR,5r,6aS)-5-benzyl-5-methoxyoctahydrocyclopenta[c]pyrrole

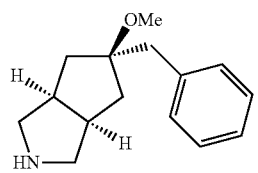

To a solution of (3aR,5r,6aS)-benzyl 5-benzyl-5-methoxyhexahydrocyclopenta[c]pyrrole-2(1H)-carboxylate (1.0 g, 2.73 mmol) in ethanol (25 mL) was added 10% Pd/C (0.1 g, 50% wet). The reaction mixture was degassed and hydrogenated under hydrogen bladder pressure for 2 h. The reaction mixture was filtered through celite and the filtrate was evaporated to afford the title compound (3aR,5r,6aS)-5-benzyl-5-methoxyoctahydrocyclopenta[c]pyrrole (0.6 g, crude) as yellow gum. Calculated M+H: 232.16. Found M+H: 232.2.

Example 27

Preparation of 2-bromo-1-(6-hydroxypyridin-3-yl)ethanone

Scheme 27

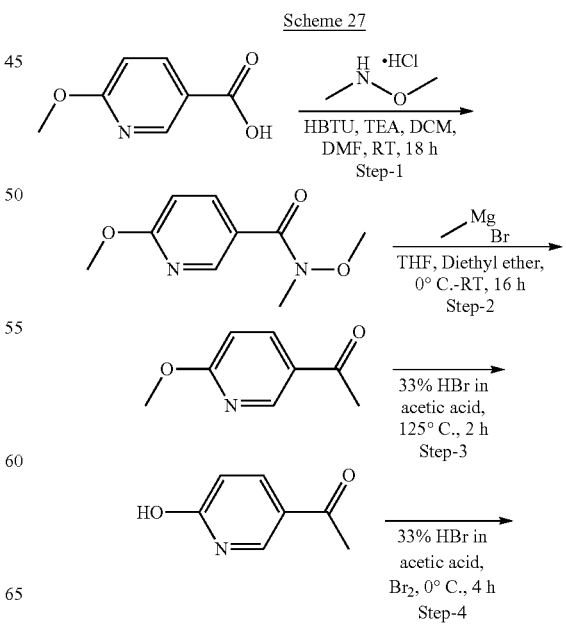

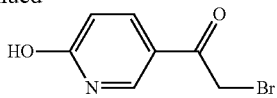

Step-1: Preparation of N,6-dimethoxy-N-methylnicotinamide

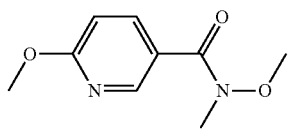

To a mixture of 6-methoxynicotinic acid (2.0 g, 13.06 mmol) and N,O-dimethylhydroxylamine hydrochloride (1.42 g, 14.58 mmol) in dichloromethane (20 mL), HBTU (6.6 g, 17.5 mmol), triethylamine (6 mL, 43.7 mmol) and N,N-dimethylformaldehyde (5 mL) were added and the reaction mixture was stirred at room temperature for 18 h under nitrogen atmosphere. The reaction mixture was diluted with dichloromethane (50 mL) and washed with ice cold water (25 mL). The organic layer was dried over anhydrous sodium sulfate, filtered and evaporated under vacuum to get crude which was purified by silica gel flash column chromatography using 5% methanol in dichloromethane to afford the title compound N,6-dimethoxy-N-methylnicotinamide (1.2 g, 42%) as off-white solid. Calculated (M+H): 197.2. Found (M+1): 197.1.

Step-2: Preparation of 1-(6-methoxypyridin-3-yl)ethanone

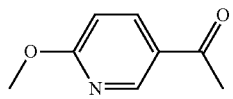

To a solution of N,4-dimethoxy-N-methylbenzamide (1.4 g, 7.14 mmol) in a mixture of tetrahydrofuran (5 mL):diethyl ether (100 mL), 3M methyl magnesium bromide in diethyl ether (4.75 mL, 4.27 mmol) was added at 0° C. and the reaction mixture was stirred at room temperature for 16 h under nitrogen atmosphere. The solution was quenched with saturated ammonium chloride solution (20 mL) and extracted with ethyl acetate (100 mL×2). The combined organic layer was dried over anhydrous sodium sulfate and evaporated under vacuum to get crude which was purified by silica gel flash column chromatography using 12% ethyl acetate in hexane to afford the title compound 1-(6-methoxypyridin-3-yl)ethanone (0.825 g, 77.1%) as off-white solid. Calculated (M+H): 152.16. Found (M+1): 152.1.

Step-3: Preparation of 1-(6-hydroxypyridin-3-yl)ethanone

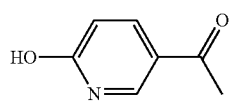

A solution of 1-(6-methoxypyridin-3-yl)ethanone (0.65 g, 4.30 mmol) in 33% hydrogen bromide in acetic acid (20 mL) was heated at 125° C. for 2 h. The reaction mixture was quenched with ice cold water (50 mL) and extracted with ethyl acetate (100 mL×2). The combined organic layer was dried over anhydrous sodium sulfate, filtered and evaporated under vacuum to get the title compound 1-(6-hydroxypyridin-3-yl)ethanone (0.66 g, 77.8%) as off-white solid. $^1$H NMR (400 MHz, DMSO-$d_6$) δ 12.078 (s, 1H), 8.172 (d, 1H, J=2 Hz), 7.817 (dd, 1H, J=9.6 Hz, J=2.8 Hz), 6.335 (d, 1H, J=10 Hz), 2.368 (s, 3H).

Step-4: Preparation of 2-bromo-1-(6-hydroxypyridin-3-yl)ethanone

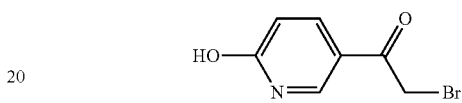

A solution of 1-(6-hydroxypyridin-3-yl)ethanone (0.2 g, 1.46 mmol) in 33% hydrogen bromide in acetic acid (15 mL) was cooled at 0° C., a solution of bromine (0.075 mL, 1.46 mmol) in 5 mL of 33% hydrogen bromide in acetic acid was added drop wise and stirred at 0° C. for 4 h. The reaction mixture was quenched with ice cold water (30 mL) and extracted with ethyl acetate (100 mL×3). The combined organic layer was washed with saturated sodium bicarbonate solution (30 mL), dried over anhydrous sodium sulfate and evaporated under vacuum to get crude which was purified by silica gel flash column chromatography using 3% methanol in dichloromethane to afford the title compound 2-bromo-1-(6-hydroxypyridin-3-yl)ethanone (0.175 g, 55.6%) as off-white solid. Calculated (M+H): 217.03. Found (M+1): 217.9.

Example 28

Preparation of 2-bromo-1-(5-hydroxypyrazin-2-yl)ethanone

Scheme 28

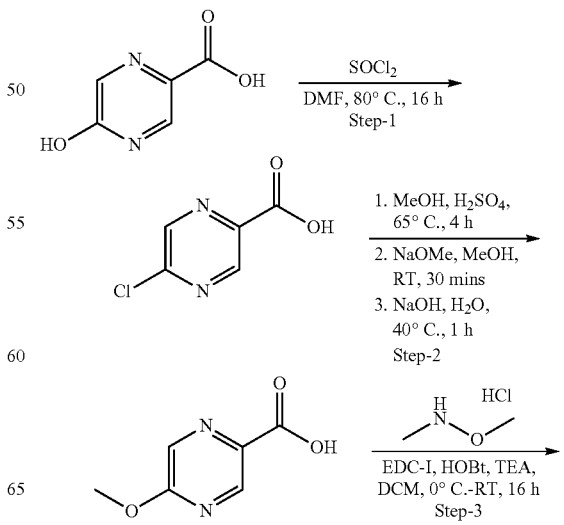

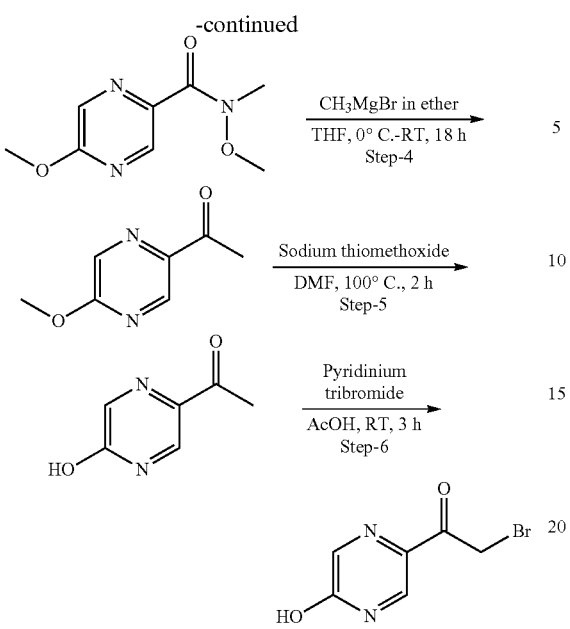

Step 1: Preparation of
5-chloropyrazine-2-carboxylic acid

To a solution 5-hydroxypyrazine-2-carboxylic acid (10 g, 71.42 mmol) in thionyl chloride (100 mL) was added N,N-dimethyl formamide (1 mL) and the reaction mixture was stirred at 80° C. for 16 h. Thionyl chloride was distilled off, the residue was diluted with ice water and extracted ethyl acetate (600 mL×3). The combined organic layer was dried over anhydrous sodium sulfate, filtered and concentrated. The crude was triturated with diethyl ether to afford the title compound 5-chloropyrazine-2-carboxylic acid (10.53 g, 93% yield) as a brown solid. Calculated M+H: 158.99. Found M+H: 159.0.

Step 2: Preparation of
5-methoxypyrazine-2-carboxylic acid

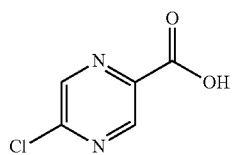

To a solution 5-chloropyrazine-2-carboxylic acid (7 g, 44.15 mmol) in methanol (55 mL) was added concentrated sulphuric acid (0.4 mL) and heated at 65° C. for 4 h. The reaction mixture was cooled to room temperature and diluted with methanol (15 mL). Then a solution of sodium methoxide in methanol (8.58 g, 158.94 mmol, 35 mL) was added and the reaction mixture was stirred at room temperature for 30 minutes. Sodium hydroxide (2.825 g, 70.643 mmol) in 30 ml water was added into the reaction mixture followed by addition of 40 mL water. Then the reaction mixture was heated at 40° C. for 1 h and concentrated to remove methanol. The residue was diluted with water, acidified with 38% aqueous hydrochloric acid solution (pH 2-3) and extracted ethyl acetate (600 mL×3). The combined organic layer was dried over anhydrous sodium sulfate, filtered and concentrated to afford the title compound 5-methoxypyrazine-2-carboxylic acid (6.43 g, 94% yield) as an orange solid. Calculated M+H: 155.04. Found M+H: 155.1.

Step 3: Preparation of
N,5-dimethoxy-N-methylpyrazine-2-carboxamide

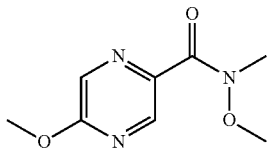

To a solution of 5-methoxypyrazine-2-carboxylic acid (7.1 g, 46.09 mmol) and triethylamine (19.27, 138.28 mmol) in dichloromethane (250 mL) were added 1-ethyl-3-(3-dimethylaminopropyl)carbodiimide (13.48 g, 69.141 mmol) and 1-hydroxybenzotriazole (7.472 g, 55.312 mmol) at 0° C. The reaction mixture was stirred at 0° C. for 30 minutes. Then N,O-dimethylhydroxylamine hydrochloride (13.488 g, 138.284 mmol) was added and the reaction mixture was stirred at room temperature for 16 h. The solution was diluted with dichloromethane (200 mL), washed with water (200 mL), dried over anhydrous sodium sulphate, filtered and concentrated. The crude was purified by silica gel column chromatography using 16% ethyl acetate in hexane to afford the title compound N,5-dimethoxy-N-methylpyrazine-2-carboxamide (4.93 g, 54%) as a white solid. Calculated M+H: 198.08. Found M+H: 198.1.

Step 4: Preparation of
1-(5-methoxypyrazin-2-yl)ethanone

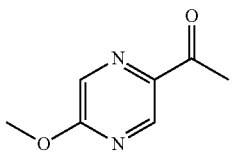

To a solution N,5-dimethoxy-N-methylpyrazine-2-carboxamide (4.93 g, 25.01 mmol) in tetrahydrofuran (25 mL) and diethyl ether (100 ml) at 0° C. was added 3M methyl magnesium bromide in ether (12.49 ml, 37.5 mmol) drop wise. The reaction mixture was stirred at room temperature for 18 h, quenched with saturated ammonium chloride solution and extracted with ethyl acetate (300 mL×3). The combined organic layer was dried over anhydrous sodium sulfate, filtered and concentrated to afford the title compound 1-(5-methoxypyrazin-2-yl)ethanone (3.61 g, 94% yield) as a yellow solid. Calculated M+H: 153.06. Found M+H: 153.1.

Step 5: Preparation of 1-(5-hydroxypyrazin-2-yl)ethanone

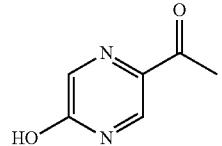

A mixture of 1-(5-methoxypyrazin-2-yl)ethanone (0.1 g, 0.65 mmol) and sodium thiomethoxide (0.184 g, 2.628 mmol) in N, N-dimethyl formamide (4 mL) was heated at 100° C. for 2 h. The reaction mixture was cooled to room temperature, diluted with water (15 mL), acidified with 1.5 M aqueous hydrochloric acid solution (pH 2-3) and extracted with ethyl acetate (60 mL×3). The combined organic layer was dried over anhydrous sodium sulfate, filtered and concentrated to afford 1-(5-hydroxypyrazin-2-yl)ethanone (0.085 g, 94%) as a brownish solid. Calculated M+H: 139.04. Found M+H: 139.1.

Step 6: Preparation of 2-bromo-1-(5-hydroxypyrazin-2-yl)ethanone

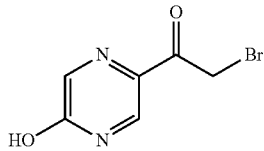 [SMILES: O=C(CBr)c1cnc(O)cn1]

To a solution of 1-(5-hydroxypyrazin-2-yl)ethanone (0.7 g, 5.06 mmol) in acetic acid (30 mL) was added pyridinium tribromide (1.782 g, 5.574 mmol). The reaction mixture was stirred at room temperature for 3 h and concentrated. The residue was diluted with water (50 mL) and extracted with ethyl acetate (150 ml×3). The combined organic layer was dried over anhydrous sodium sulfate, filtered and concentrated. The crude was purified by silica gel column chromatography using 2% methanol in dichloromethane to afford the title compound 2-bromo-1-(5-hydroxypyrazin-2-yl)ethanone (0.25 g, 22% yield) as a yellow solid. Calculated M+H: 216.95. Found M+H: 216.9.

Example 29

Preparation of 2-bromo-1-(6-fluoro-5-hydroxypyridin-2-yl)ethanone

Scheme 29

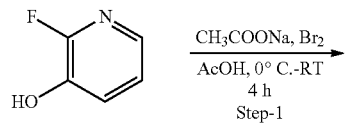

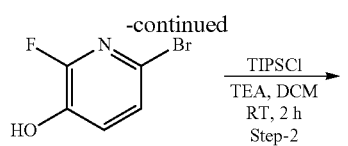

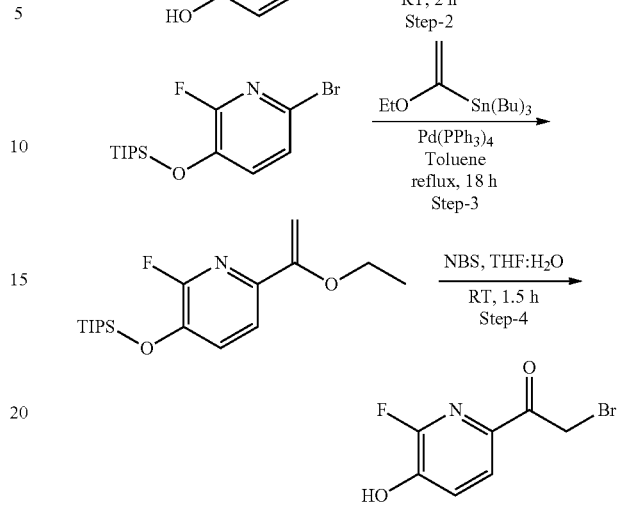

Step-1: Preparation of 6-bromo-2-fluoropyridin-3-ol

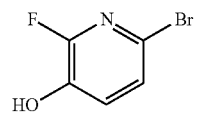

To a solution of 2-fluoropyridin-3-ol (1 g, 8.842 mmol) and sodium acetate (0.72 g, 8.842 mmol) in acetic acid (10 mL) was added bromine (0.23 mL, 8.842 mmol) at 0° C. and the reaction mixture was stirred at room temperature for 4 h. The solution was poured into ice, pH was adjusted to 6 using 2N sodium hydroxide solution and extracted with ethyl acetate (50 mL×2). The combined organic layer was dried over anhydrous sodium sulfate, filtered and concentrated to afford the crude product, which was purified by silica gel column chromatography (10% ethyl acetate/hexane) to obtain the title compound 6-bromo-2-fluoropyridin-3-ol (0.5 g, 30% yield) as a colorless liquid. Calculated (M+H): 193. Found (M+1): 193.9.

Step-2: Preparation of 6-bromo-2-fluoro-3-((triisopropylsilyl)oxy)pyridine

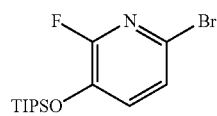

To a solution of 6-bromo-2-fluoropyridin-3-ol (0.5 g, 2.604 mmol) in tetrahydrofuran (20 mL) was added triethylamine (0.54 mL, 3.906 mmol) and the reaction mixture was cooled to 0° C. Chlorotriisopropylsilane (0.73 mL, 3.385 mmol) was added drop wise and the solution was stirred at room temperature for 2 h. The reaction mixture was diluted with water (30 mL) and extracted with ethyl acetate (50 ml×2). The combined organic layer was dried over anhydrous sodium sulfate, filtered and concentrated to afford the crude product, which was purified by silica gel column chromatography (5% ethyl acetate/hexane) to obtain the title compound 6-bromo-2-fluoro-3-((triisopropylsilyl)oxy)pyridine (0.8 g, 87% yield) as a colorless liquid. Calculated (M+H): 348.07. Found (M+1): 348.1.

Step-3: Preparation of 6-(1-ethoxyvinyl)-2-fluoro-3-((triisopropylsilyl)oxy)pyridine

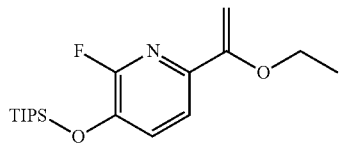

To a solution of 6-bromo-2-fluoro-3-((triisopropylsilyl)oxy)pyridine (0.4 g, 1.148 mmol) and tributyl(1-ethoxyvinyl)stannane (0.43 mL, 1.263 mmol) in toluene argon was purged for 10 minutes. Tetrakis(triphenylphosphine)palladium(0) was added and the reaction mixture was heated at 100° C. for 18 h. The solution was filtered through celite and filtrate was concentrated to afford the title compound 6-(1-ethoxyvinyl)-2-fluoro-3-((triisopropylsilyl)oxy)pyridine (0.36 g, crude) as brownish gum. Calculated (M+H): 340.5. Found (M+1): 340.2.

Step-4: Preparation of 2-bromo-1-(6-fluoro-5-hydroxypyridin-2-yl)ethanone

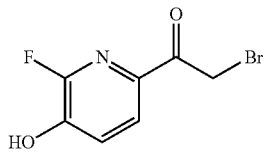

To a solution of 6-(1-ethoxyvinyl)-2-fluoro-3-((triisopropylsilyl)oxy)pyridine (8.46 g, 24.93 mmol) in tetrahydrofuran:water (280 ml, 3:1) mixture was added N-bromosuccinimide and the reaction mixture was stirred at room temperature for 1.5 h. The reaction mixture was diluted with water (150 mL) and extracted with ethyl acetate (300 ml×2). The combined organic layer was dried over anhydrous sodium sulfate, filtered and concentrated to afford the crude product, which was purified by silica gel column chromatography (40% ethyl acetate/hexane) to obtain the title compound 2-bromo-1-(6-fluoro-5-hydroxypyridin-2-yl)ethanone (5.5 g, 95% yield) as brownish gum. Calculated (M+H): 235.02. Found (M+1): 235.9.

Example 30

Preparation of 2-bromo-1-(6-chloropyridin-3-yl)ethanone

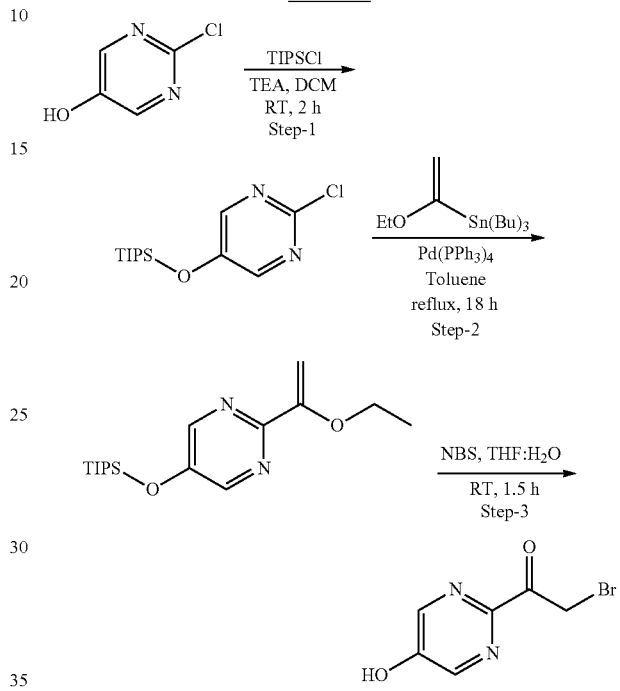

Step-1: Preparation of 2-chloro-5-((triisopropylsilyl)oxy)pyrimidine

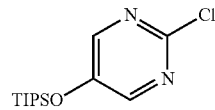

To a solution of 2-chloropyrimidin-5-ol (1.0 g, 7.67 mmol) in tetrahydrofuran (20 mL) was added triethylamine (2.15 mL, 15.34 mmol) and the reaction mixture was cooled to 0° C. Chlorotriisopropylsilane (2.46 mL, 11.50 mmol) was added drop wise and the solution was stirred at room temperature for 2 h. The reaction mixture was diluted with water (50 mL) and extracted with ethyl acetate (100 ml×2). The combined organic layer was dried over anhydrous sodium sulfate, filtered and concentrated to afford the crude product, which was purified by silica gel column chromatography using 5% ethyl acetate in hexane to obtain the title compound 2-chloro-5-((triisopropylsilyl)oxy)pyrimidine (1.9 g, 86% yield) as a colorless liquid. Calculated (M+H): 287.13. Found (M+1): 287.1.

Step-2: Preparation of 2-(1-ethoxyvinyl)-5-((triisopropylsilyl)oxy)pyrimidine

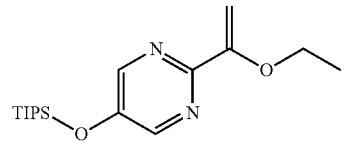

To a solution of 2-chloro-5-((triisopropylsilyl)oxy)pyrimidine (0.45 g, 1.56 mmol) and tributyl(1-ethoxyvinyl)stannane (0.62 mL, 1.72 mmol) in toluene, argon was purged for 10 minutes. Tetrakis(triphenylphosphine)palladium(0) (0.09 g, 0.078 mmol) was added and the reaction mixture was heated at 100° C. for 18 h. The solution was filtered through celite and filtrate was concentrated to afford the title compound 2-(1-ethoxyvinyl)-5-((triisopropylsilyl)oxy)pyrimidine (0.36 g, crude) as a brownish gum. Calculated (M+H): 323.21. Found (M+1): 323.3.

Step-3: Preparation of 2-bromo-1-(5-hydroxypyrimidin-2-yl)ethanone

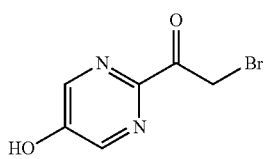

To a solution of 2-(1-ethoxyvinyl)-5-((triisopropylsilyl)oxy)pyrimidine (0.5 g, 1.55 mmol) in tetrahydrofuran:water (10 ml, 3:1) mixture was added N-bromosuccinimide (0.41 g, 2.32 mmol) and the reaction mixture was stirred at room temperature for 1.5 h. The reaction mixture was diluted with water (15 mL) and extracted with ethyl acetate (30 ml×2). The combined organic layer was dried over anhydrous sodium sulfate, filtered and concentrated to afford the crude product which was purified by silica gel column chromatography using 6% methanol in dichloromethane to obtain the title compound 2-bromo-1-(5-hydroxypyrimidin-2-yl)ethanone (0.18 g) as brownish solid. Calculated (M+H): 216.95. Found (M+1): 217.1.

Example 31

Preparation of (3aR,5r,6aS)-benzyl 5-(2-fluorobenzyl)-5-hydroxyhexahydrocyclopenta[c]pyrrole-2(1H)-carboxylate Scheme 31

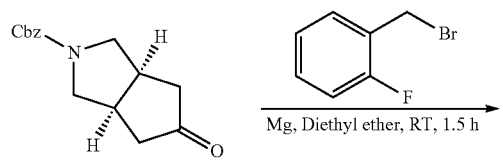

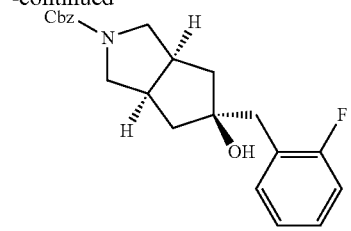

To a suspension of activated magnesium turnings (0.598 g, 24.7 mmol) in dry diethyl ether (25 mL) was added 2-fluorobenzyl bromide (4.3 g, 23.0 mmol) and 1,2-dibromoethane (4 drops). The resulting mixture was stirred at room temperature until all magnesium turnings goes into the solution. To the above mixture was added a solution of benzyl (3aR,6aS)-5-oxohexahydrocyclopenta[c]pyrrole-2(1H)-carboxylate (1.0 g, 3.8 mmol) in diethyl ether (5 mL) at 0° C. and resulting suspension was stirred at room temperature for 20 minutes. After completion of reaction (as monitored by TLC) the reaction mixture was quenched with saturated ammonium chloride solution (10 mL), extracted with ethyl acetate (100 mL×3), washed with brine (100 mL), dried over $Na_2SO_4$ and concentrated under vacuum to get the crude material which was purified by column chromatography using 100-200 mesh silica gel with 40% ethyl acetate in hexane as eluent affording the title compound (3aR,5r,6aS)-benzyl 5-(2-fluorobenzyl)-5-hydroxyhexahydrocyclopenta[c]pyrrole-2(1H)-carboxylate (0.800 g, 57% yield) as a white solid. Calculated M+H: 370.17. Found M+H: 370.33.

Example 32

Preparation of (3aR,5r,6aS)-benzyl 5-(cyclohexylmethyl)-5-hydroxyhexahydrocyclopenta[c]pyrrole-2(1H)-carboxylate Scheme 32

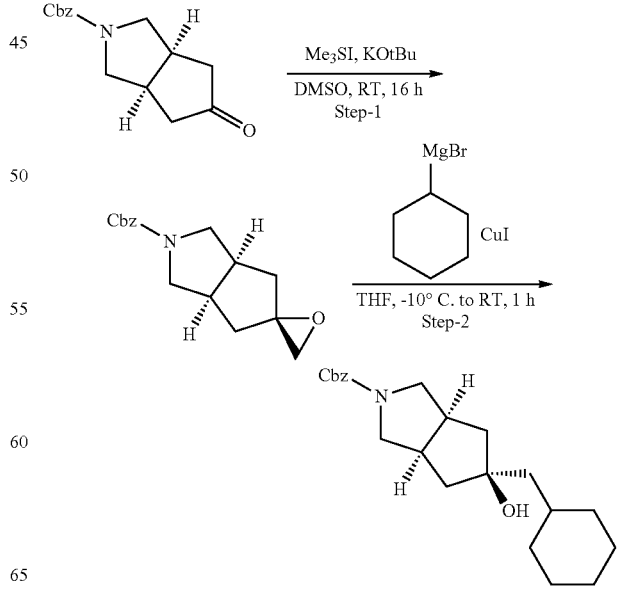

Step-1: Preparation of (2's,3aR,6aS)-benzyl tetrahydro-1H-spiro[cyclopenta[c]pyrrole-5,2'-oxirane]-2(3H)-carboxylate

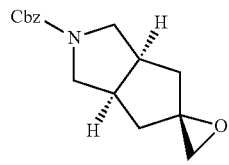 [SMILES: O=C(OCc1ccccc1)N1C[C@@H]2C[C@]3(CO3)C[C@@H]2C1]

To a solution of benzyl (3aR,6aS)-5-oxohexahydrocyclopenta[c]pyrrole-2(1H)-carboxylate (2.0 g, 7.7 mmol) and trimethylsulphonium iodide (2.6 g, 13.1 mmol) in dimethylsulfoxide (22 mL) was added a solution of potassium tertiary butoxide (1.37 g, 12.3 mmol) in dimethylsulfoxide (26 mL) drop wise at room temperature and the resulting mixture was stirred at room temperature for 16 h. After completion of reaction (as monitored by TLC), the reaction mixture was poured into ice-cold water (200 mL) and extracted with ether (150 mL×3). The combined ether layer was washed with water (150 mL), brine (100 mL), dried over anhydrous sodium sulfate, filtered and evaporated to obtain the title compound (2's,3aR,6aS)-benzyl tetrahydro-1H-spiro[cyclopenta[c]pyrrole-5,2'-oxirane]-2(3H)-carboxylate (2.1 g, 77% yield) as light brown oil which was used for next step without purification. Calculated M+H: 274.14. Found M+H: 274.18.

Step-2: Preparation of (3aR,5r,6aS)-benzyl 5-(cyclohexylmethyl)-5-hydroxyhexahydrocyclopenta[c]pyrrole-2(1H)-carboxylate

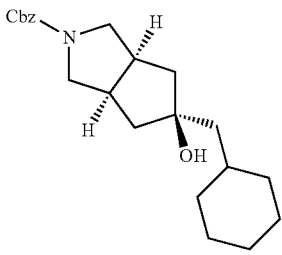 [SMILES: O=C(OCc1ccccc1)N1C[C@@H]2C[C@@](O)(CC3CCCCC3)C[C@@H]2C1]

To a suspension of copper iodide (0.695 g, 3.6 mmol) in tetrahydrofuran (35 mL) was added cyclohexylmagnesium bromide (4.5 mL, 2M in tetrahydrofuran) at −10° C. and resulting suspension was stirred for 10 min at same temperature. To the mixture was then added (2's,3aR,6aS)-benzyl tetrahydro-1H-spiro[cyclopenta[c]pyrrole-5,2'-oxirane]-2(3H)-carboxylate (1 g, 3.6 mmol) in tetrahydrofuran (10 mL) via syringe and the resulting solution was stirred at 0° C. for 1 h. After completion of reaction (as monitored by TLC), the reaction mixture was quenched with saturated ammonium chloride solution (30 mL) and extracted with ethyl acetate (100 mL×3). The combined ethyl acetate layer was washed with brine (100 mL), dried over sodium sulfate and evaporated under vacuum to obtain crude product which was purified by column chromatography on silica gel using 25% ethyl acetate in hexane as eluent to obtain title compound (3aR,5r,6aS)-benzyl 5-(cyclohexylmethyl)-5-hydroxyhexahydrocyclopenta[c]pyrrole-2(1H)-carboxylate (0.900 g, 69%) as light yellow oil. Calculated M+H: 358.23. Found M+H: 358.0.

Example 33

Preparation of (3aR,5r,6aS)-5-(thiophen-2-ylmethyl)octahydrocyclopenta[c]pyrrol-5-ol Scheme 33

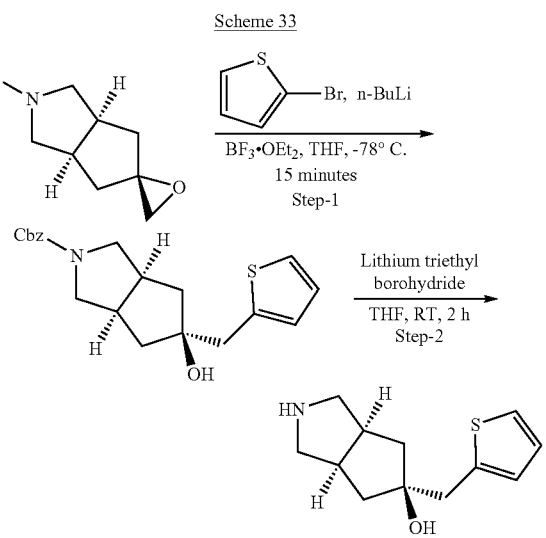

Step-1: Preparation of benzyl (3aR,5r,6aS)-5-hydroxy-5-(thiophen-2-ylmethyl)hexahydrocyclopenta[c]pyrrole-2(1H)-carboxylate

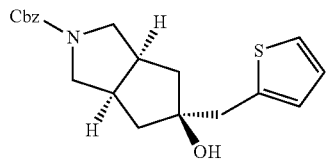 [SMILES: O=C(OCc1ccccc1)N1C[C@@H]2C[C@@](O)(Cc3cccs3)C[C@@H]2C1]

To a solution of 2-bromothiophene (0.567 g, 3.5 mmol) in dry THF (20 mL.) was added n-butyl lithium (2.5M in hexane, 1.4 mL, 3.5 mmol) at −78° C. (slowly drop wise) and resulting solution was stirred at −78° C. for 20 minutes. Then boron trifluoride etherate (0.30 mL, 2.9 mmol) was added. After 5 minutes a solution of benzyl (3aR,5S,6aS)-tetrahydro-1H-spiro[cyclopenta[c]pyrrole-5,2'-oxirane]-2(3H)-carboxylate (0.800 g, 2.9 mmol) in tetrahydrofuran (5.0 mL) was added and stirred at −78° C. for 15 minutes. The reaction mixture was then quenched with saturated ammonium chloride solution (10 mL), extracted with ethyl acetate (100 mL×3) washed with brine (100 mL), dried over sodium sulfate and concentrated to get the crude material which was purified by column chromatography using 100-200 mesh silica with 20% ethyl acetate in hexane as eluent to obtain title compound benzyl (3aR,5r,6aS)-5-hydroxy-5-(thiophen-2-ylmethyl)hexahydrocyclopenta[c]pyrrole-2(1H)-carboxylate (0.125 g, 12%) as off white solid. Calculated M+H: 358.14. Found M+H: 358.24.

Step 2: Preparation of 5-(thiophen-2-ylmethyl) octahydrocyclopenta[c]pyrrol-5-ol

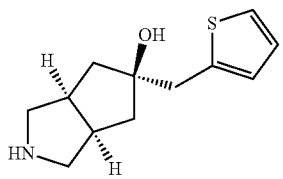 [SMILES: O[C@@]1(Cc2cccs2)C[C@H]2CNC[C@H]2C1]

To a solution of benzyl 5-hydroxy-5-(thiophen-2-ylmethyl)hexahydrocyclopenta[c]pyrrole-2(1H)-carboxylate (0.34 g, 0.952 mmol) in tetrahydrofuran (15 mL) was added lithium triethylborohydride (4.7 mL, 4.76 mmol) at 0° C. and allowed the reaction mixture to stir at room temperature for 2 h. The solution was quenched with saturated ammonium chloride solution and extracted with ethyl acetate (50 mL×2). The combined organic layer was dried over anhydrous sodium sulfate, filtered and concentrated to afford the title compound 5-(thiophen-2-ylmethyl) octahydro cyclopenta[c]pyrrol-5-ol (0.18 g, 85.71% yield) as colorless liquid. Calculated M+H: 224.1. Found M+H: 224.2.

Example 34

Preparation of (3aR,5r,6aS)-benzyl 5-hydroxy-5-(pyridin-4-ylmethyl)hexahydrocyclopenta[c]pyrrole-2(1H)-carboxylate Scheme 34

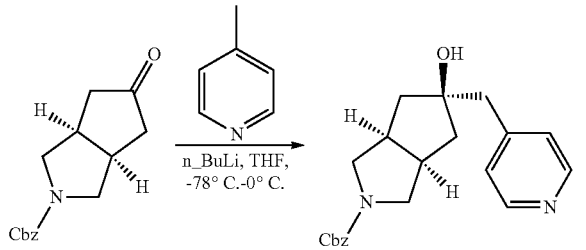

n-Butyl lithium (3.86 mL, 5.79 mmol, 1.5 M in hexane) was added drop wise to a solution of 4-methylpyridine (0.27 g, 2.89 mmol) in tetrahydrofuran (15 mL) at −78° C. and the reaction mixture was stirred at 0° C. for 1 h. Then the reaction mixture was cooled to −78° C. and added a solution of (3aR,6aS)-benzyl 5-oxohexahydrocyclopenta[c]pyrrole-2 (1H)-carboxylate (0.5 g, 1.93 mmol) in tetrahydrofuran (10 mL). The solution was stirred at same temperature for one hour, warmed to room temperature, quenched with saturated ammonium chloride solution and extracted with ethyl acetate (50 mL×2). The combined organic extract was washed with water (35 mL), brine (35 mL), dried over anhydrous sodium sulphate and evaporated. The crude material was purified by combiflash purifier using 3% methanol in dichloromethane to afford the title compound (3aR,5r,6aS)-benzyl 5-hydroxy-5-(pyridin-4-ylmethyl)hexahydrocyclopenta[c]pyrrole-2(1H)-carboxylate (0.3 g, 44% yield) as a colorless gum. Calculated M+H: 353.23. Found M+H: 353.2.

Example 35

Preparation of (3aR,5r,6aS)-benzyl 5-(2-fluoropyridin-3-yl)-5-hydroxyhexahydrocyclopenta[c]pyrrole-2(1H)-carboxylate Scheme 35

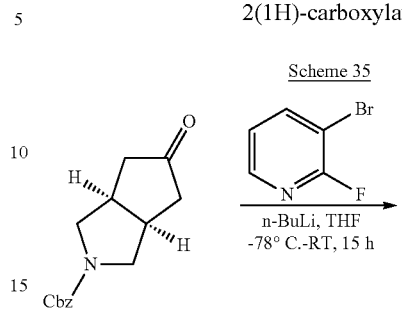

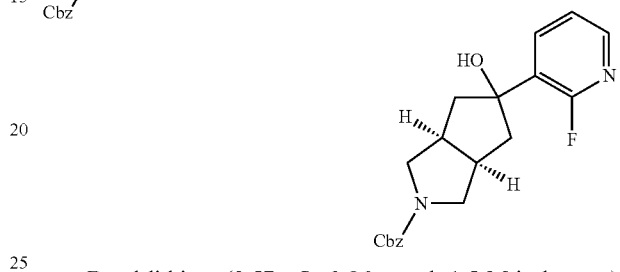

n-Butyl lithium (2.57 mL, 3.86 mmol, 1.5 M in hexane) was added drop wise to a solution of 3-bromo-2-fluoropyridine (0.5 g, 2.89 mmol) in tetrahydrofuran (15 mL) at −78° C. and the reaction mixture was stirred at same temperature for 30 minutes. Then added a solution of (3aR,6aS)-benzyl 5-oxohexahydrocyclopenta[c]pyrrole-2(1H)-carboxylate (0.5 g, 1.93 mmol) in tetrahydrofuran (5 mL), stirred at same temperature for one hour, warmed to room temperature and was stirred for 15 h. Then the reaction mixture was quenched with saturated ammonium chloride solution (30 mL) and extracted with ethyl acetate (50 mL×3). The combined organic extract was washed with water (50 mL), brine (50 mL), dried over anhydrous sodium sulfate and evaporated. The crude material was purified by combiflash purifier using 60% ethyl acetate in hexane to afford the title compound (3aR,5r,6aS)-benzyl 5-(2-fluoropyridin-3-yl)-5-hydroxyhexahydrocyclopenta[c]pyrrole-2(1H)-carboxylate (0.2 g, 30% yield) as a yellow gum. Calculated M+H: 357.39. Found M+H: 357.2.

Example 36

Preparation of N-(6-(2-bromoacetyl)pyridin-3-yl)methanesulfonamide

Scheme 36

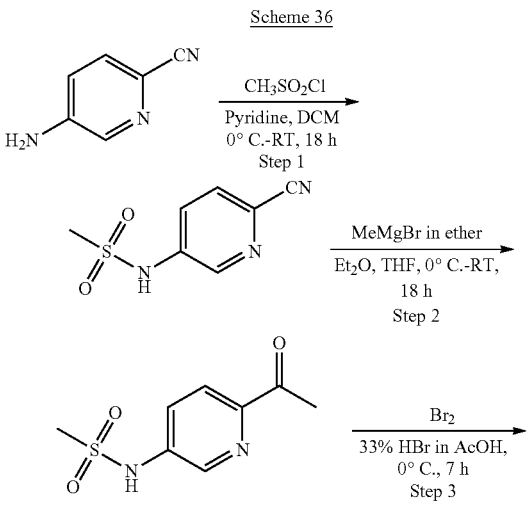

-continued

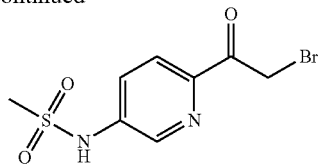

Step 1: Preparation of
N-(6-cyanopyridin-3-yl)methanesulfonamide

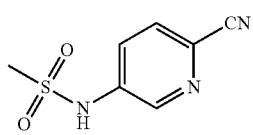

To a solution of 5-aminopicolinonitrile (0.5 g, 4.19 mmol) in dichloromethane (40 mL) was added pyridine (1.0 mL, 12.57 mmol) and the solution was cooled to 0° C. Methanesulfonyl chloride (0.32 mL, 4.19 mmol) was added drop wise and the reaction mixture was stirred at room temperature for 18 h. The solution was diluted with dichloromethane (100 mL), washed sequentially with 1.5M hydrochloric acid solution (30 mL) and brine solution (40 mL). The organic layer was dried over anhydrous sodium sulfate, filtered and concentrated. The crude was purified by combiflash column chromatography using 30% ethyl acetate in hexane to afford the title compound N-(6-cyanopyridin-3-yl)methanesulfonamide (0.18 g, 21% yield) as a brownish solid. Calculated M+H: 198.03. Found M+H: 198.

Step 2: Preparation of
N-(6-acetylpyridin-3-yl)methanesulfonamide

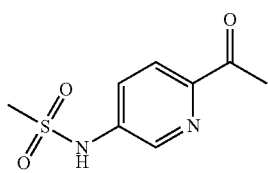

To a solution N-(6-cyanopyridin-3-yl)methanesulfonamide (0.5 g, 2.537 mmol) in tetrahydrofuran:diethyl ether mixture (20 ml, 1:3) cooled at 0° C. was added 3M methyl magnesium bromide in ether (4.22 ml, 12.688 mmol) and the reaction mixture was stirred at room temperature for 18 h. The solution was quenched with saturated ammonium chloride solution and extracted with ethyl acetate (300 mL×3). The combined organic layer was dried over anhydrous sodium sulfate, filtered and concentrated. The crude was purified by column chromatography using 40% ethyl acetate in hexane to afford the title compound N-(6-acetylpyridin-3-yl)methanesulfonamide (0.4 g, 73% yield) as a yellow solid. Calculated M+H: 215.04. Found M+H: 215.0.

Step 3: Preparation of N-(6-(2-bromoacetyl)pyridin-3-yl)methanesulfonamide

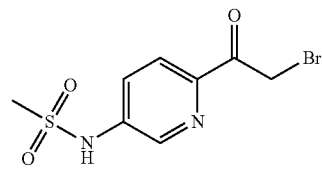

To a solution of N-(6-acetylpyridin-3-yl)methanesulfonamide (1.5 g, 7.008 mmol) in 33% hydrobromic acid in acetic acid (50 mL) was added bromine (0.35 mL, 7.008 mmol) dissolved in 33% hydrobromic acid in acetic acid (20 mL) drop wise at 0° C. and the reaction mixture was stirred at room temperature for 7 h. The reaction mixture was diluted with diethyl ether, the solid formed was separated, dissolved in dichloromethane and washed with saturated sodium bicarbonate solution. The organic layer was dried over anhydrous sodium sulfate, filtered and concentrated. The crude was purified by column chromatography using 30% ethyl acetate in hexane to afford the title compound N-(6-(2-bromoacetyl)pyridin-3-yl)methanesulfonamide (0.51 g, 25% yield) as a yellow solid. Calculated M+H: 292.95. Found M+H: 292.9.

TABLE 11

The following compounds were prepared by the methods described above using intermediates made by the methods described above.

| Structure | IUPAC Name | Calculated (M + H) | Found (M + H) |
|---|---|---|---|
| 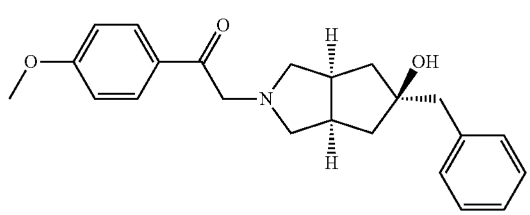 [SMILES: COc1ccc(C(=O)CN2C[C@@H]3C[C@@](O)(Cc4ccccc4)C[C@@H]3C2)cc1] | 2-((3aR,5r,6aS)-5-benzyl-5-hydroxyhexahydrocyclopenta[c]pyrrol-2(1H)-yl)-1-(4-methoxyphenyl)ethanone | 366.20 | 366.3 |

TABLE 11-continued

The following compounds were prepared by the methods described above using intermediates made by the methods described above.

| Structure | IUPAC Name | Calculated (M + H) | Found (M + H) |
|---|---|---|---|
|  | 3-((3aR,5r,6aS)-5-benzyl-5-hydroxyhexahydrocyclopenta[c]pyrrol-2(1H)-yl)-1-(4-hydroxyphenyl)propan-1-one | 366.20 | 366.3 |
|  | 2-((3aR,5r,6aS)-5-(4-fluorobenzyl)-5-hydroxyhexahydrocyclopenta[c]pyrrol-2(1H)-yl)-1-(4-hydroxyphenyl)ethanone | 370.17 | 370.4 |
| 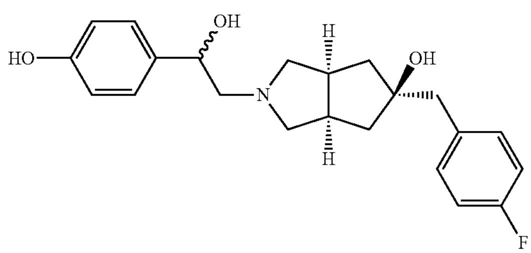 | rac-(3aR,5r,6aS)-5-(4-fluorobenzyl)-2-(2-hydroxy-2-(4-hydroxyphenyl)ethyl)-octahydrocyclopenta[c]-pyrrol-5-ol | 372.19 | 372.5 |
| 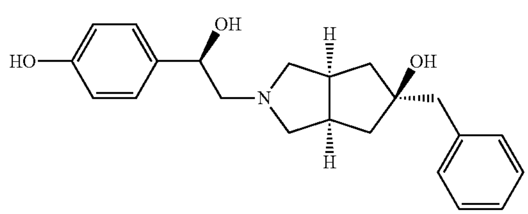 [SMILES: Oc1ccc([C@@H](O)CN2C[C@@H]3C[C@@](O)(Cc4ccccc4)C[C@@H]3C2)cc1] | (3aR,5R,6aS)-5-benzyl-2-((R)-2-hydroxy-2-(4-hydroxyphenyl)ethyl)-octahydrocyclopenta[c]-pyrrol-5-ol | 354.2 | 354.5 |
| 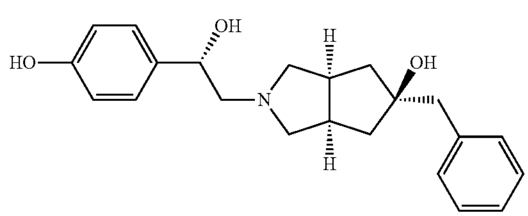 [SMILES: Oc1ccc([C@H](O)CN2C[C@@H]3C[C@@](O)(Cc4ccccc4)C[C@@H]3C2)cc1] | (3aR,5S,6aS)-5-benzyl-2-((S)-2-hydroxy-2-(4-hydroxyphenyl)ethyl)-octahydrocyclopenta[c]-pyrrol-5-ol | 354.2 | 354.5 |
|  | 2-((3aR,5r,6aS)-5-benzyl-5-hydroxyhexahydrocyclopenta[c]pyrrol-2(1H)-yl)-1-(4-(2-hydroxypropan-2-yl)phenyl)ethanone | 394.23 | 394.3 |

TABLE 11-continued

The following compounds were prepared by the methods described above using intermediates made by the methods described above.

| Structure | IUPAC Name | Calculated (M + H) | Found (M + H) |
|---|---|---|---|
| | rac-(3aR,5r,6aS)-5-benzyl-2-(2-hydroxy-2-(4-(2-hydroxypropan-2-afryl)phenyl)ethyl)octahydrocyclopenta[c]pyrrol-5-ol | 396.25 | 396.6 |
| | 2-((3aR,5r,6aS)-5-benzyl-5-hydroxyhexahydrocyclopenta[c]pyrrol-2(1H)-yl)-1-(5-hydroxypyridin-2-yl)ethanone | 353.18 | 353.2 |
| | N-(4-(2-((3aR,5r,6aS)-5-benzyl-5-hydroxyhexahydrocyclopenta[c]pyrrol-2(1H)-yl)acetyl)phenyl)acetamide | 393.21 | 393.5 |
| | (3aR,5R,6aS)-5-benzyl-2-((R)-2-hydroxy-2-(4-hydroxyphenyl)ethyl)-octahydrocyclopenta[c]-pyrrol-5-ol | 354.20 | 354.5 |
| | (3aR,5S,6aS)-5-benzyl-2-((S)-2-hydroxy-2-(4-hydroxyphenyl)ethyl)octahydrocyclopenta[c]pyrrol-5-ol | 354.20 | 354.5 |
| | rac-(3aR,5r,6aS)-5-benzyl-2-(2-hydroxy-2-(5-hydroxypyridin-2-yl)ethyl)octahydrocyclopenta[c]pyrrol-5-ol | 355.19 | 355.2 |
| | 1-((3aR,5r,6aS)-5-benzyl-5-hydroxyhexahydrocyclopenta[c]pyrrol-2(1H)-yl)-3-(4-hydroxyphenyl)propan-2-one | 366.47 | 366.5 |

TABLE 11-continued

The following compounds were prepared by the methods described above using intermediates made by the methods described above.

| Structure | IUPAC Name | Calculated (M + H) | Found (M + H) |
|---|---|---|---|
| | N-(4-(2-((3aR,5r,6aS)-5-benzyl-5-hydroxyhexahydrocyclopenta[c]pyrrol-2(1H)-yl)acetyl)phenyl)methanesulfonamide | 429.54 | 429.5 |
| | 5-(2-((3aR,5r,6aS)-5-benzyl-5-hydroxyhexahydrocyclopenta[c]pyrrol-2(1H)-yl)acetyl)indolin-2-one | 391.42 | 391.5 |
| | 6-(2-((3aR,5r,6aS)-5-benzyl-5-hydroxyhexahydrocyclopenta[c]pyrrol-2(1H)-yl)acetyl)-3,4-dihydroquinolin-2(1H)-one | 405.5 | 405.2 |
| | rac-N-(4-(2-((3aR,5r,6aS)-5-benzyl-5-hydroxyhexahydrocyclopenta[c]pyrrol-2(1H)-yl)-1-hydroxyethyl)phenyl)acetamide | 395.23 | 395.6 |
| | rac-N-(4-(2-((3aR,5r,6aS)-5-benzyl-5-hydroxyhexahydrocyclopenta[c]pyrrol-2(1H)-yl)-1-hydroxyethyl)phenyl)methanesulfonamide | 431.56 | 431.5 |

TABLE 11-continued

The following compounds were prepared by the methods described above using intermediates made by the methods described above.

| Structure | IUPAC Name | Calculated (M + H) | Found (M + H) |
|---|---|---|---|
| 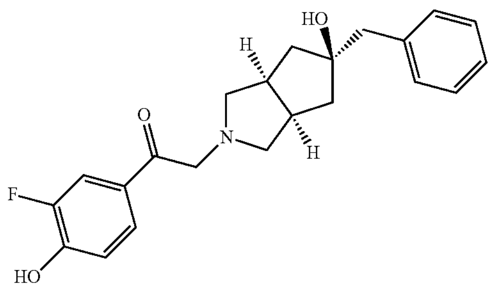 [SMILES: O=C(CN1C[C@@H]2C[C@@](O)(Cc3ccccc3)C[C@@H]2C1)c1ccc(O)c(F)c1] | 2-((3aR,5r,6aS)-5-benzyl-5-hydroxyhexahydrocyclopenta[c]pyrrol-2(1H)-yl)-1-(3-fluoro-4-hydroxyphenyl)ethanone | 370.43 | 370.5 |
| 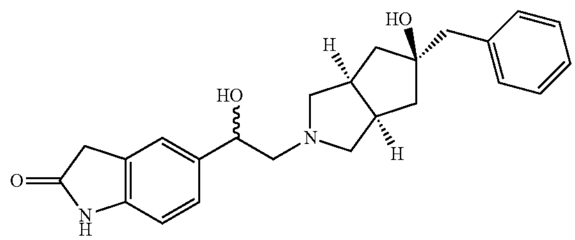 [SMILES: O=C1Cc2cc(C(O)CN3C[C@@H]4C[C@@](O)(Cc5ccccc5)C[C@@H]4C3)ccc2N1] | rac-5-(2-((3aR,5r,6aS)-5-benzyl-5-hydroxyhexahydrocyclopenta[c]pyrrol-2(1H)-yl)-1-hydroxyethyl)indolin-2-one | 393.49 | 393.3 |
| 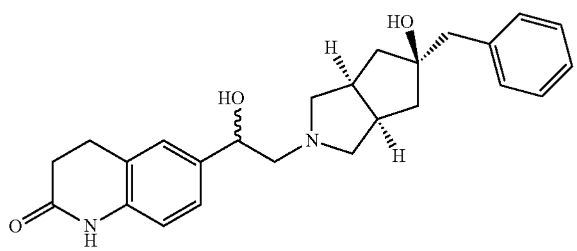 [SMILES: O=C1CCc2cc(C(O)CN3C[C@@H]4C[C@@](O)(Cc5ccccc5)C[C@@H]4C3)ccc2N1] | rac-6-(2-((3aR,5r,6aS)-5-benzyl-5-hydroxyhexahydrocyclopenta[c]pyrrol-2(1H)-yl)-1-hydroxyethyl)-3,4-dihydroquinolin-2(1H)-one | 407.52 | 407.5 |
|  | rac-6-(2-((3aR,5r,6aS)-5-benzyl-5-hydroxyhexahydrocyclopenta[c]pyrrol-2(1H)-yl)-1-hydroxyethyl)benzo[d]oxazol-2(3H)-one | 395.19 | 395.5 |
| 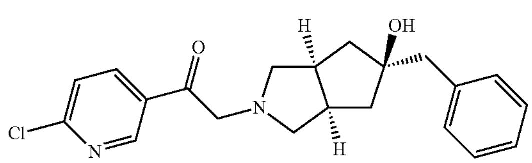 [SMILES: O=C(CN1C[C@@H]2C[C@@](O)(Cc3ccccc3)C[C@@H]2C1)c1ccc(Cl)nc1] | 2-((3aR,5r,6aS)-5-benzyl-5-hydroxyhexahydrocyclopenta[c]pyrrol-2(1H)-yl)-1-(6-chloropyridin-3-yl)ethanone | 369.4 (M − H) | 369.4 (M − H) |
| 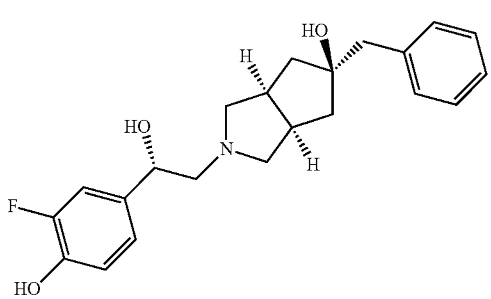 [SMILES: Oc1ccc([C@H](O)CN2C[C@@H]3C[C@@](O)(Cc4ccccc4)C[C@@H]3C2)cc1F] | rac-(3aR,5S,6aS)-5-benzyl-2-((S)-2-(3-fluoro-4-hydroxyphenyl)-2-hydroxyethyl)octahydrocyclopenta[c]pyrrol-5-ol | 372.45 | 372.5 |

TABLE 11-continued

The following compounds were prepared by the methods described above using intermediates made by the methods described above.

| Structure | IUPAC Name | Calculated (M + H) | Found (M + H) |
|---|---|---|---|
| 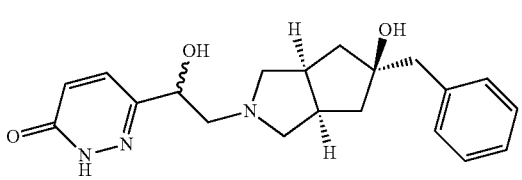 [SMILES: O=c1ccc(C(O)CN2C[C@@H]3C[C@@](O)(Cc4ccccc4)C[C@@H]3C2)n[nH]1] | 6-(2-((3aR,5r,6aS)-5-benzyl-5-hydroxyhexahydrocyclopenta[c]pyrrol-2(1H)-yl)acetyl)pyridazin-3(2H)-one | 354.17 | 354.5 |
| 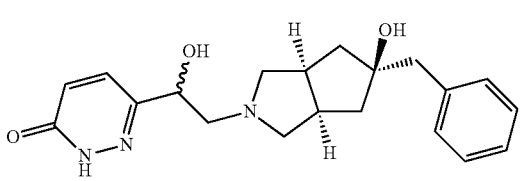 [SMILES: O=c1ccc(C(O)CN2C[C@@H]3C[C@@](O)(Cc4ccccc4)C[C@@H]3C2)n[nH]1] | rac-6-(2-((3aR,5r,6aS)-5-benzyl-5-hydroxyhexahydrocyclopenta[c]pyrrol-2(1H)-yl)-1-hydroxyethyl)pyridazin-3(2H)-one | 356.19 | 356.5 |
| 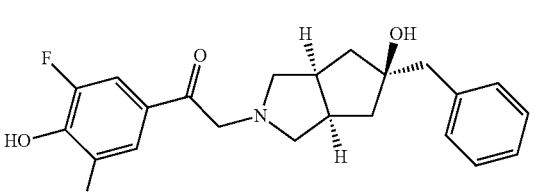 | 2-((3aR,5r,6aS)-5-benzyl-5-hydroxyhexahydrocyclopenta[c]pyrrol-2(1H)-yl)-1-(3,5-difluoro-4-hydroxyphenyl)ethanone | 388.42 | 388.4 |
| 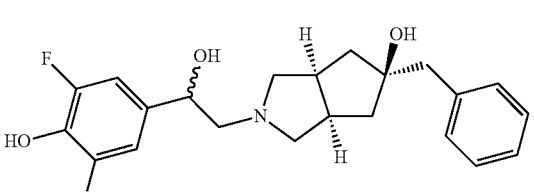 | rac-(3aR,5r,6aS)-5-benzyl-2-(2-(3,5-difluoro-4-hydroxyphenyl)-2-hydroxyethyl)octahydrocyclopenta[c]pyrrol-5-ol | 390.44 | 390.44 |
| 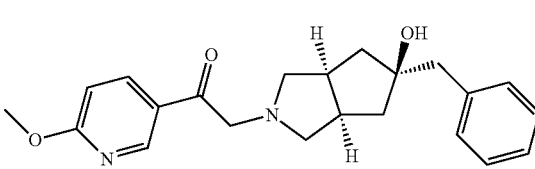 | 2-((3aR,5r,6aS)-5-benzyl-5-hydroxyhexahydrocyclopenta[c]pyrrol-2(1H)-yl)-1-(6-methoxypyridin-3-yl)ethanone | 367.19 | 367.2 |
| 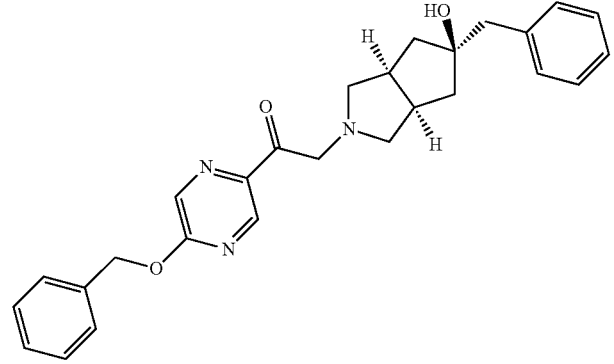 [SMILES: O=C(CN1C[C@@H]2C[C@@](O)(Cc3ccccc3)C[C@@H]2C1)c1cnc(OCc2ccccc2)cn1] | 2-((3aR,5r,6aS)-5-benzyl-5-hydroxyhexahydrocyclopenta[c]pyrrol-2(1H)-yl)-1-(5-(benzyloxy)pyrazin-2-yl)ethanone | 444.54 | 444.2 |

TABLE 11-continued

The following compounds were prepared by the methods described above using intermediates made by the methods described above.

| Structure | IUPAC Name | Calculated (M + H) | Found (M + H) |
|---|---|---|---|
| | rac-(3aR,5r,6aS)-5-benzyl-2-(2-(5-(benzyloxy)pyrazin-2-yl)-2-hydroxyethyl)octahydrocyclopenta[c]pyrrol-5-ol | 446.55 | 446 |
| | (3aR,5S,6aS)-5-benzyl-2-((S)-2-hydroxy-2-(5-hydroxypyridin-2-yl)ethyl)octahydrocyclopenta[c]pyrrol-5-ol | 355.19 | 355.2 |
| | (3aR,5R,6aS)-5-benzyl-2-((R)-2-hydroxy-2-(5-hydroxypyridin-2-yl)ethyl)octahydrocyclopenta[c]pyrrol-5-ol | 355.19 | 355.2 |
| | 2-((3aR,5r,6aS)-5-(4-fluorobenzyl)-5-hydroxyhexahydrocyclopenta[c]pyrrol-2(1H)-yl)-1-(5-hydroxypyridin-2-yl)ethanone | 371.41 | 371.2 |
| | 2-[(3aR,5R,6aS)-5-benzyl-5-hydroxy-octahydrocyclopenta[c]-pyrrol-2-yl]-1-(1H-1,2,3-benzotriazol-5-yl)ethan-1-one | 377.45 | 377.5 |
| | rac-(3aR,5r,6aS)-5-(4-fluorobenzyl)-2-(2-hydroxy-2-(5-hydroxypyridin-2-yl)ethyl)octahydrocyclopenta[c]pyrrol-5-ol | 373.43 | 373.2 |

TABLE 11-continued

The following compounds were prepared by the methods described above using intermediates made by the methods described above.

| Structure | IUPAC Name | Calculated (M + H) | Found (M + H) |
|---|---|---|---|
| | 1-(3-fluoro-4-hydroxyphenyl)-2-((3aR,5r,6aS)-5-(4-fluorobenzyl)-5-hydroxyhexahydrocyclopenta[c]pyrrol-2(1H)-yl)ethanone | 388.42 | 388.2 |
| | 2-((3aR,5r,6aS)-5-benzyl-5-methoxyhexahydrocyclopenta[c]pyrrol-2(1H)-yl)-1-(3-fluoro-4-hydroxyphenyl)ethanone | 384.46 | 384.2 |
| | rac-(3aR,5r,6aS)-2-(2-(3-fluoro-4-hydroxyphenyl)-2-hydroxyethyl)-5-(4-fluorobenzyl)octahydrocyclopenta[c]pyrrol-5-ol | 390.44 | 390.5 |
| | 2-((3aR,5r,6aS)-5-benzyl-5-hydroxyhexahydrocyclopenta[c]pyrrol-2(1H)-yl)-1-(3-fluoro-4-(2-(3-fluoro-4-hydroxyphenyl)-2-oxoethoxy)phenyl)-ethanone | 522.55 | 522.5 |
| | 2-(2-fluoro-4-(2-((3aR,5r,6aS)-5-(4-fluorobenzyl)-5-hydroxyhexahydrocyclopenta[c]pyrrol-2(1H)-yl)acetyl)phenoxy)-1-(3-fluoro-4-hydroxyphenyl)ethanone | 540.54 | 540.2 |
| | 2-((3aR,5r,6aS)-5-benzyl-5-methoxyhexahydrocyclopenta[c]pyrrol-2(1H)-yl)-1-(4-hydroxyphenyl)ethanone | 366.47 | 366.3 |
| | rac-4-(2-((3aR,5r,6aS)-5-benzyl-5-methoxyhexahydrocyclopenta[c]pyrrol-2(1H)-yl)-1-hydroxyethyl)-2-fluorophenol | 386.47 | 386.2 |

TABLE 11-continued

The following compounds were prepared by the methods described above using intermediates made by the methods described above.

| Structure | IUPAC Name | Calculated (M + H) | Found (M + H) |
|---|---|---|---|
|  | rac-4-(2-((3aR,5r,6aS)-5-benzyl-5-methoxyhexahydrocyclopenta[c]pyrrol-2(1H)-yl)-1-hydroxyethyl)phenol | 368.48 | 368.2 |
|  | rac-6-(2-((3aR,5r,6aS)-5-benzyl-5-methoxyhexahydrocyclopenta[c]pyrrol-2(1H)-yl)-1-hydroxyethyl)pyridin-3-ol | 369.47 | 369.2 |
| 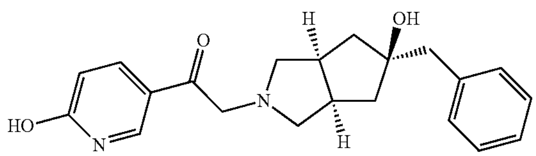 [SMILES: O=C(CN1C[C@@H]2C[C@@](O)(Cc3ccccc3)C[C@@H]2C1)c1ccc(O)nc1] | 2-[(3aR,5R,6aS)-5-benzyl-5-hydroxy-octahydrocyclopenta[c]-pyrrol-2-yl]-1-(6-hydroxypyridin-3-yl)ethan-1-one | 351.43 (M − H) | 351.4 (M − 1) |
|  | 2-((3aR,5r,6aS)-5-hydroxy-5-(4-methylbenzyl)hexahydrocyclopenta[c]pyrrol-2(1H)-yl)-1-(4-hydroxyphenyl)ethanone | 366.47 | 366.23 |
| 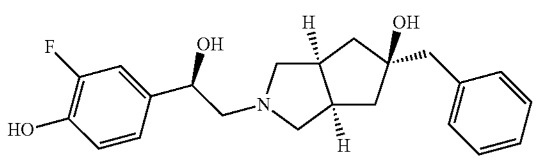 [SMILES: Oc1ccc([C@@H](O)CN2C[C@@H]3C[C@@](O)(Cc4ccccc4)C[C@@H]3C2)cc1F] | (3aR,5R,6aS)-5-benzyl-2-((R)-2-(3-fluoro-4-hydroxyphenyl)-2-hydroxyethyl)octahydro-cyclopenta[c]pyrrol-5-ol | 372.45 | 372.5 |
| 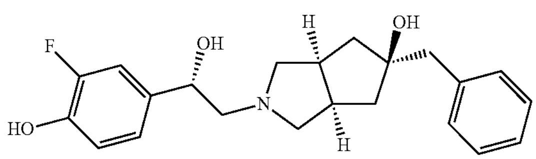 [SMILES: Oc1ccc([C@H](O)CN2C[C@@H]3C[C@@](O)(Cc4ccccc4)C[C@@H]3C2)cc1F] | (3aR,5S,6aS)-5-benzyl-2-((S)-2-(3-fluoro-4-hydroxyphenyl)-2-hydroxyethyl)octahydro-cyclopenta[c]pyrrol-5-ol | 372.45 | 372.5 |
| 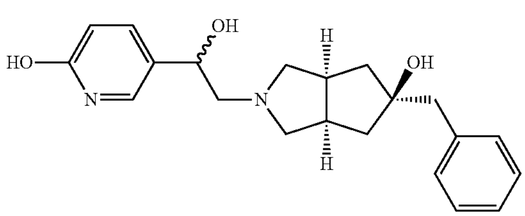 | rac-5-{2-[(3aR,5R,6aS)-5-benzyl-5-hydroxy-octahydrocyclopenta[c]-pyrrol-2-yl]-1-hydroxyethyl}pyridin-2-ol | 355.44 | 355.2 |

TABLE 11-continued

The following compounds were prepared by the methods described above using intermediates made by the methods described above.

| Structure | IUPAC Name | Calculated (M + H) | Found (M + H) |
|---|---|---|---|
| | rac-(3aR,5R,6aS)-2-[2-hydroxy-2-(4-hydroxyphenyl)ethyl]-5-[(4-methylphenyl)methyl]-octahydrocyclopenta[c]pyrrol-5-ol | 368.48 | 368.22 |
| | 2-((3aR,5r,6aS)-5-hydroxy-5-(2-methylbenzyl)hexahydro-cyclopenta[c]pyrrol-2(1H)-yl)-1-(4-hydroxyphenyl)ethanone | 366.47 | 366.21 |
| | 2-[(3aR,5R,6aS)-5-hydroxy-5-[(4-methoxyphenyl)methyl]-octahydrocyclopenta[c]pyrrol-2-yl]-1-(4-hydroxyphenyl)ethan-1-one | 382.19 | 382.10 |
| | rac-(3aR,5r,6aS)-2-(2-hydroxy-2-(4-hydroxyphenyl)ethyl)-5-(2-methylbenzyl)octahydro-cyclopenta[c]pyrrol-5-ol | 368.48 | 368.25 |
| | rac-(3aR,5R,6aS)-2-[2-(1H-1,2,3-benzotriazol-5-yl)-2-hydroxyethyl]-5-benzyl-octahydrocyclopenta[c]pyrrol-5-ol | 379.47 | 379.5 |
| | 2-((3aR,5r,6aS)-5-benzyl-5-hydroxyhexahydrocyclopenta[c]pyrrol-2(1H)-yl)-1-(5-hydroxypyrazin-2-yl)ethanone | 354.41 | 354.2 |

TABLE 11-continued

The following compounds were prepared by the methods described above using intermediates made by the methods described above.

| Structure | IUPAC Name | Calculated (M + H) | Found (M + H) |
|---|---|---|---|
| 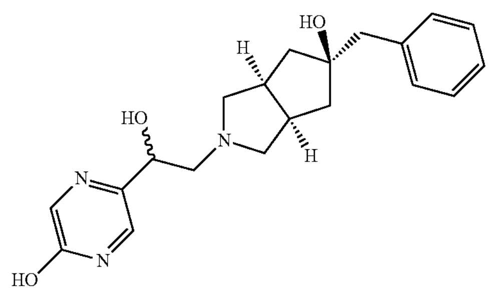 [SMILES: Oc1cnc(C(O)CN2C[C@@H]3C[C@@](O)(Cc4ccccc4)C[C@@H]3C2)cn1] | rac-(3aR,5r,6aS)-5-benzyl-2-(2-hydroxy-2-(5-hydroxypyrazin-2-yl)ethyl)octahydrocyclopenta[c]pyrrol-5-ol | 356.43 | 356.2 |
| 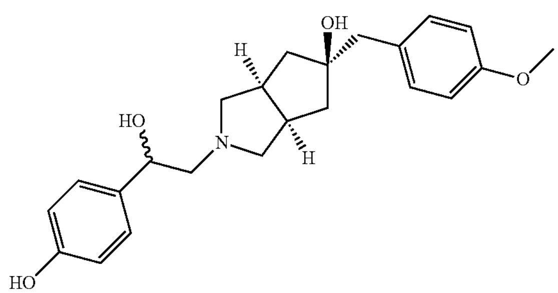 [SMILES: COc1ccc(C[C@]2(O)C[C@H]3CN(CC(O)c4ccc(O)cc4)C[C@H]3C2)cc1] | rac-(3aR,5r,6aS)-2-(2-hydroxy-2-(4-hydroxyphenyl)ethyl)-5-(4-methoxybenzyl)octahydrocyclopenta[c]pyrrol-5-ol | 384.48 | 384.37 |
| 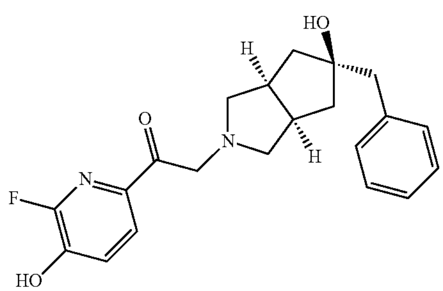 [SMILES: O=C(CN1C[C@@H]2C[C@@](O)(Cc3ccccc3)C[C@@H]2C1)c1ccc(O)c(F)n1] | 2-((3aR,5r,6aS)-5-benzyl-5-hydroxyhexahydrocyclopenta[c]pyrrol-2(1H)-yl)-1-(6-fluoro-5-hydroxypyridin-2-yl)ethanone | 371.42 | 371.2 |
| 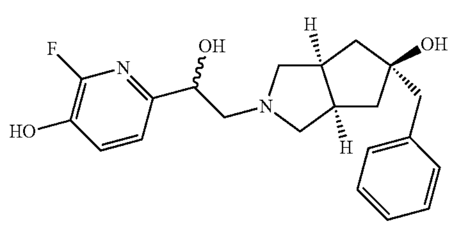 [SMILES: Oc1ccc(C(O)CN2C[C@@H]3C[C@@](O)(Cc4ccccc4)C[C@@H]3C2)nc1F] | rac-(3aR,5r,6aS)-5-benzyl-2-(2-(6-fluoro-5-hydroxypyridin-2-yl)-2-hydroxyethyl)octahydrocyclopenta[c]pyrrol-5-ol | 373.43 | 373.3 |
| 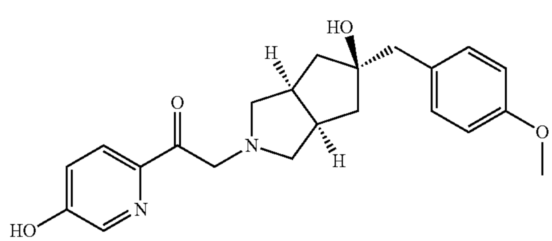 [SMILES: COc1ccc(C[C@]2(O)C[C@H]3CN(CC(=O)c4ccc(O)cn4)C[C@H]3C2)cc1] | 2-[(3aR,5R,6aS)-5-hydroxy-5-[(4-methoxyphenyl)methyl]-octahydrocyclopenta[c]-pyrrol-2-yl]-1-(5-hydroxypyridin-2-yl)ethan-1-one | 383.45 | 383.4 |

TABLE 11-continued

The following compounds were prepared by the methods described above using intermediates made by the methods described above.

| Structure | IUPAC Name | Calculated (M + H) | Found (M + H) |
|---|---|---|---|
| 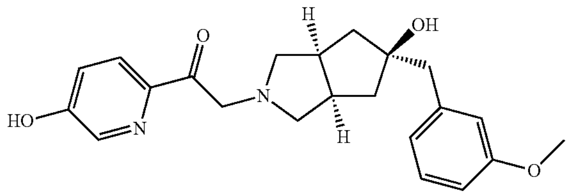 | 2-((3aR,5r,6aS)-5-hydroxy-5-(3-methoxybenzyl)hexahydrocyclopenta[c]pyrrol-2(1H)-yl)-1-(5-hydroxypyridin-2-yl)ethanone | 383.19 | 383.3 |
| 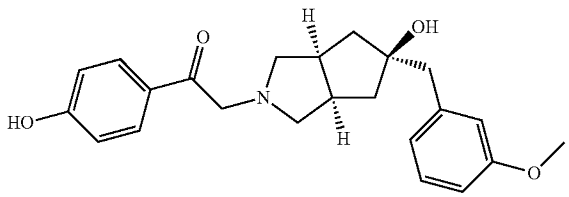 [SMILES: COc1cccc(C[C@]2(O)C[C@H]3CN(CC(=O)c4ccc(O)cc4)C[C@H]3C2)c1] | 2-((3aR,5r,6aS)-5-hydroxy-5-(3-methoxybenzyl)hexahydrocyclopenta[c]pyrrol-2(1H)-yl)-1-(4-hydroxyphenyl)ethanone | 382.19 | 382.2 |
| 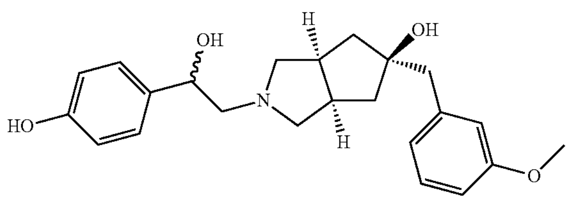 [SMILES: COc1cccc(C[C@]2(O)C[C@H]3CN(CC(O)c4ccc(O)cc4)C[C@H]3C2)c1] | rac-(3aR,5r,6aS)-2-(2-hydroxy-2-(4-hydroxyphenyl)ethyl)-5-(3-methoxybenzyl)octahydrocyclopenta[c]pyrrol-5-ol | 384.21 | 384.4 |
| 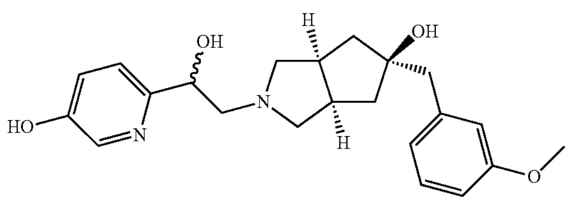 [SMILES: COc1cccc(C[C@]2(O)C[C@H]3CN(CC(O)c4ccc(O)cn4)C[C@H]3C2)c1] | rac-((3aR,5r,6aS)-2-(2-hydroxy-2-(5-hydroxypyridin-2-yl)ethyl)-5-(3-methoxybenzyl)octahydrocyclopenta[c]pyrrol-5-ol | 385.2 | 385.2 |
| 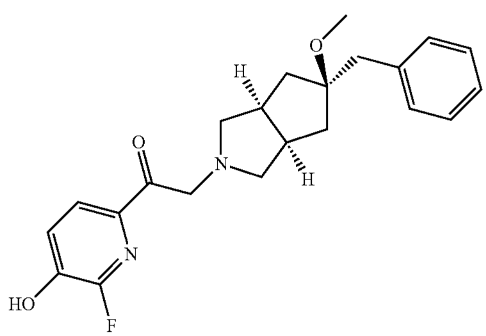 [SMILES: CO[C@@]1(Cc2ccccc2)C[C@H]2CN(CC(=O)c3ccc(O)c(F)n3)C[C@H]2C1] | 2-((3aR,5r,6aS)-5-benzyl-5-methoxyhexahydrocyclopenta[c]pyrrol-2(1H)-yl)-1-(6-fluoro-5-hydroxypyridin-2-yl)ethanone | 385.44 | 385.2 |
| 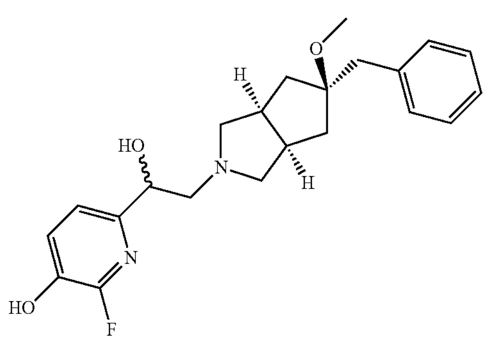 [SMILES: CO[C@@]1(Cc2ccccc2)C[C@H]2CN(CC(O)c3ccc(O)c(F)n3)C[C@H]2C1] | rac-6-(2-((3aR,5r,6aS)-5-benzyl-5-methoxyhexahydrocyclopenta[c]pyrrol-2(1H)-yl)-1-hydroxyethyl)-2-fluoropyridin-3-ol | 387.46 | 387.2 |

TABLE 11-continued

The following compounds were prepared by the methods described above using intermediates made by the methods described above.

| Structure | IUPAC Name | Calculated (M + H) | Found (M + H) |
|---|---|---|---|
| 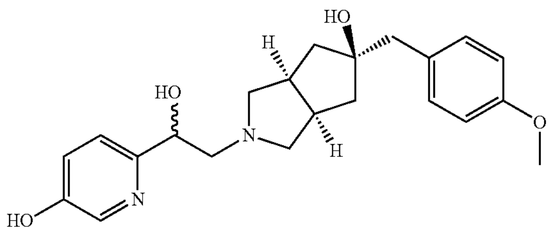 [SMILES: COc1ccc(C[C@]2(O)C[C@H]3CN(CC(O)c4ccc(O)cn4)C[C@H]3C2)cc1] | rac-6-{2-[(3aR,5R,6aS)-5-hydroxy-5-[(4-methoxyphenyl)methyl]-octahydrocyclopenta[c]-pyrrol-2-yl]-1-hydroxyethyl}pyridin-3-ol | 385.47 | 385.5 |
| 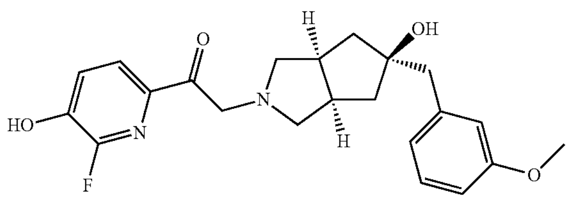 [SMILES: COc1cccc(C[C@]2(O)C[C@H]3CN(CC(=O)c4ccc(O)c(F)n4)C[C@H]3C2)c1] | 1-(6-fluoro-5-hydroxypyridin-2-yl)-2-((3aR,5r,6aS)-5-hydroxy-5-(3-methoxybenzyl)hexa-hydrocyclopenta[c]pyrrol-2(1H)-yl)ethanone | 401.18 | 401.2 |
| 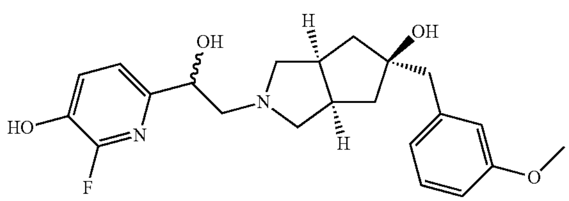 | rac-(3aR,5r,6aS)-2-(2-(6-fluoro-5-hydroxypyridin-2-yl)-2-hydroxyethyl)-5-(3-methoxybenzyl)octa-hydrocyclopenta[c]pyrrol-5-ol | 403.2 | 403.2 |
| 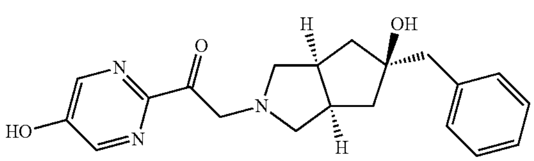 [SMILES: O=C(CN1C[C@@H]2C[C@@](O)(Cc3ccccc3)C[C@@H]2C1)c1ncc(O)cn1] | 2-[(3aR,5R,6aS)-5-benzyl-5-hydroxy-octahydrocyclopenta[c]-pyrrol-2-yl]-1-(5-hydroxypyrimidin-2-yl)ethan-1-one | 354.17 | 354.2 |
| 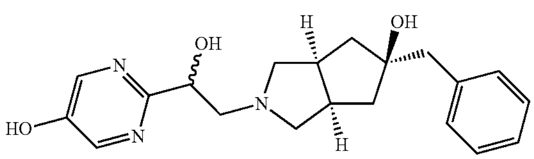 [SMILES: Oc1cnc(C(O)CN2C[C@@H]3C[C@@](O)(Cc4ccccc4)C[C@@H]3C2)nc1] | rac-2-{2-[(3aR,5R,6aS)-5-benzyl-5-hydroxy-octahydrocyclopenta[c]-pyrrol-2-yl]-1-hydroxyethyl}pyrimidin-5-ol | 356.19 | 356.5 |
| 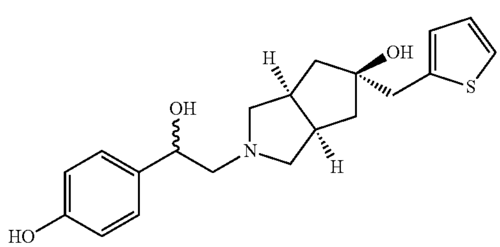 [SMILES: Oc1ccc(C(O)CN2C[C@@H]3C[C@@](O)(Cc4cccs4)C[C@@H]3C2)cc1] | rac-(3aR,5r,6aS)-2-(2-hydroxy-2-(4-hydroxyphenyl)ethyl)-5-(thiophen-2-ylmethyl)octahydro-cyclopenta[c]pyrrol-5-ol | 360.48 | 360.3 |
| 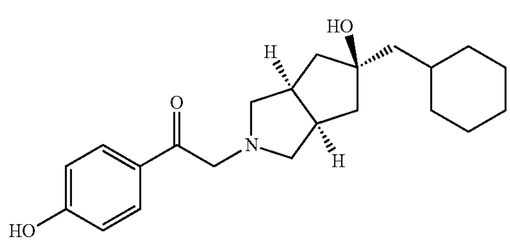 [SMILES: O=C(CN1C[C@@H]2C[C@@](O)(CC3CCCCC3)C[C@@H]2C1)c1ccc(O)cc1] | 2-[(3aR,5R,6aS)-5-(cyclohexylmethyl)-5-hydroxy-octahydrocyclopenta[c]-pyrrol-2-yl]-1-(4-hydroxyphenyl)ethan-1-one | 358.49 | 358.2 |

TABLE 11-continued

The following compounds were prepared by the methods described above using intermediates made by the methods described above.

| Structure | IUPAC Name | Calculated (M + H) | Found (M + H) |
|---|---|---|---|
| 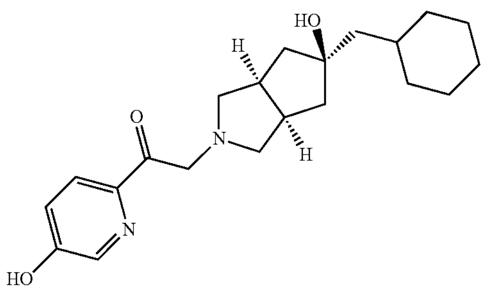 [SMILES: O=C(CN1C[C@@H]2C[C@@](O)(CC3CCCCC3)C[C@@H]2C1)c1ccc(O)cn1] | 2-[(3aR,5R,6aS)-5-(cyclohexylmethyl)-5-hydroxy-octahydrocyclopenta[c]-pyrrol-2-yl]-1-(5-hydroxypyridin-2-yl)ethan-1-one | 359.47 | 359.2 |
| 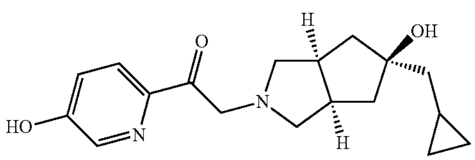 | 2-((3aR,5r,6aS)-5-(cyclopropylmethyl)-5-hydroxyhexahydrocyclo-penta[c]pyrrol-2(1H)-yl)-1-(5-hydroxypyridin-2-yl)ethanone | 317.18 | 317.2 |
| 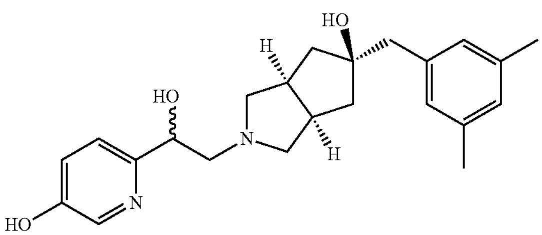 [SMILES: Cc1cc(C)cc(C[C@]2(O)C[C@H]3CN(CC(O)c4ccc(O)cn4)C[C@H]3C2)c1] | rac-6-{2-[(3aR,5R,6aS)-5-[(3,5-dimethylphenyl)methyl]-5-hydroxy-octahydrocyclopenta[c]-pyrrol-2-yl]-1-hydroxyethyl}pyridin-3-ol | 383.5 | 383.5 |
| 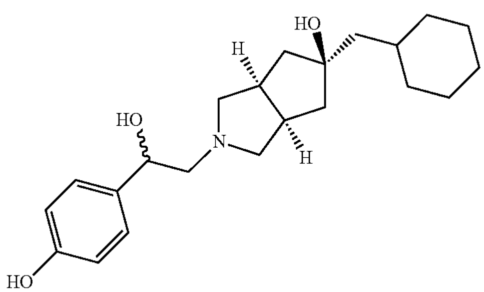 [SMILES: Oc1ccc(C(O)CN2C[C@@H]3C[C@@](O)(CC4CCCCC4)C[C@@H]3C2)cc1] | rac-(3aR,5R,6aS)-5-(cyclohexylmethyl)-2-[2-hydroxy-2-(4-hydroxyphenyl)ethyl]-octahydrocyclopenta[c]-pyrrol-5-ol | 360.5 | 360.5 |
| 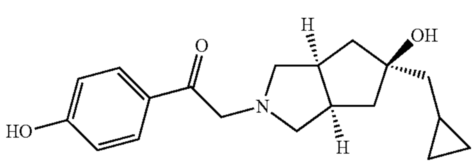 [SMILES: O=C(CN1C[C@@H]2C[C@@](O)(CC3CC3)C[C@@H]2C1)c1ccc(O)cc1] | 2-((3aR,5r,6aS)-5-(cyclopropylmethyl)-5-hydroxyhexahydrocyclo-penta[c]pyrrol-2(1H)-yl)-1-(4-hydroxyphenyl)ethanone | 316.18 | 316.2 |
| 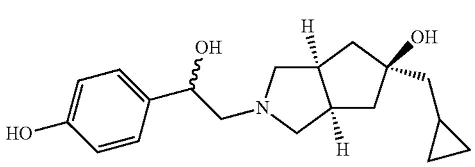 [SMILES: Oc1ccc(C(O)CN2C[C@@H]3C[C@@](O)(CC4CC4)C[C@@H]3C2)cc1] | rac-(3aR,5r,6aS)-5-(cyclopropylmethyl)-2-(2-hydroxy-2-(4-hydroxyphenyl)ethyl)ctahydrocyclopenta[c]-pyrrol-5-ol | 318.2 | 318.3 |

TABLE 11-continued

The following compounds were prepared by the methods described above using intermediates made by the methods described above.

| Structure | IUPAC Name | Calculated (M + H) | Found (M + H) |
|---|---|---|---|
| 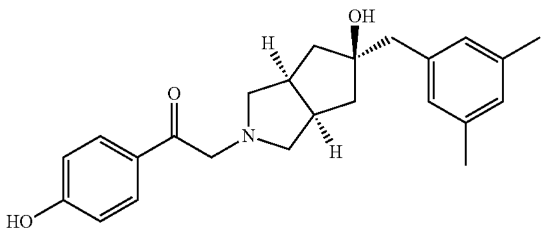 [SMILES: Cc1cc(C)cc(C[C@]2(O)C[C@H]3CN(CC(=O)c4ccc(O)cc4)C[C@H]3C2)c1] | 2-[(3aR,5R,6aS)-5-[(3,5-dimethylphenyl)methyl]-5-hydroxy-octahydrocyclopenta[c]-pyrrol-2-yl]-1-(4-hydroxyphenyl)ethan-1-one | 380.49 | 380.2 |
| 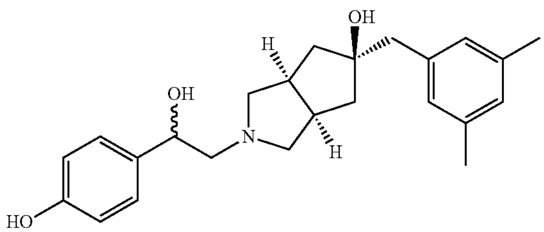 [SMILES: Cc1cc(C)cc(C[C@]2(O)C[C@H]3CN(CC(O)c4ccc(O)cc4)C[C@H]3C2)c1] | rac-(3aR,5R,6aS)-5-[(3,5-dimethylphenyl)methyl]-2-[2-hydroxy-2-(4-hydroxyphenyl)ethyl]-octahydrocyclopenta[c]-pyrrol-5-ol | 382.51 | 382.2 |
| 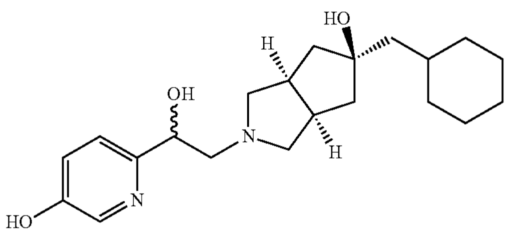 [SMILES: Oc1ccc(C(O)CN2C[C@@H]3C[C@@](O)(CC4CCCCC4)C[C@@H]3C2)nc1] | rac-6-{2-[(3aR,5R,6aS)-5-(cyclohexylmethyl)-5-hydroxy-octahydrocyclopenta[c]pyrrol-2-yl]-1-hydroxyethyl}pyridin-3-ol | 361.49 | 361.2 |
| 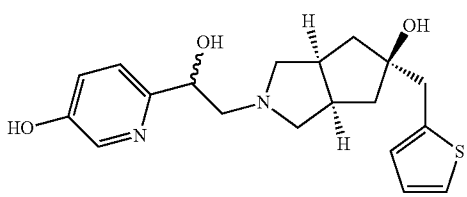 [SMILES: Oc1ccc(C(O)CN2C[C@@H]3C[C@@](O)(Cc4cccs4)C[C@@H]3C2)nc1] | rac-2-(2-hydroxy-2-(5-hydroxypyridin-2-yl)ethyl)-5-(thiophen-2-ylmethyl)octahydro-cyclopenta[c]pyrrol-5-ol | 361.15 | 361.2 |
| 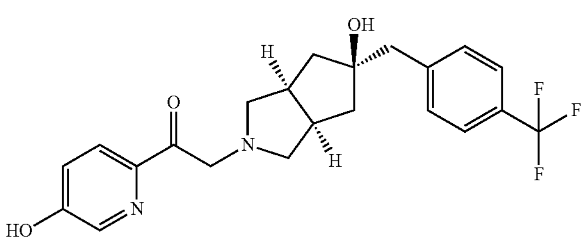 [SMILES: O=C(CN1C[C@@H]2C[C@@](O)(Cc3ccc(C(F)(F)F)cc3)C[C@@H]2C1)c1ccc(O)cn1] | 2-[(3aR,5R,6aS)-5-hydroxy-5-{[4-(trifluoromethyl)phenyl]-methyl}-octahydrocyclopenta[c]-pyrrol-2-yl]-1-(5-hydroxypyridin-2-yl)ethan-1-one | 421.42 | 421.3 |
| 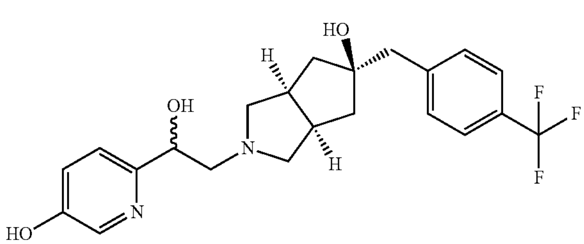 [SMILES: Oc1ccc(C(O)CN2C[C@@H]3C[C@@](O)(Cc4ccc(C(F)(F)F)cc4)C[C@@H]3C2)nc1] | rac-6-{2-[(3aR,5R,6aS)-5-hydroxy-5-{[4-(trifluoromethyl)phenyl]-methyl}-octahydrocyclopenta[c]-pyrrol-2-yl]-1-hydroxyethyl}pyridin-3-ol | 423.44 | 423.3 |

TABLE 11-continued

The following compounds were prepared by the methods described above using intermediates made by the methods described above.

| Structure | IUPAC Name | Calculated (M + H) | Found (M + H) |
|---|---|---|---|
|  | 2-((3aR,5r,6aS)-5-(4-chlorobenzyl)-5-hydroxyhexahydrocyclopenta[c]pyrrol-2(1H)-yl)-1-(5-hydroxypyridin-2-yl)ethanone | 387.14 | 387.1 |
|  | 2-[(3aR,5R,6aS)-5-hydroxy-5-{[4-(trifluoromethyl)phenyl]-methyl}-octahydrocyclopenta[c]-pyrrol-2-yl]-1-(4-hydroxyphenyl)ethan-1-one | 420.44 | 420.2 |
|  | 1-(3-fluoro-4-hydroxyphenyl)-2-(5-hydroxy-5-(thiophen-2-ylmethyl)hexahydrocyclopenta[c]pyrrol-2(1H)-yl)ethanone | 376.13 | 376.3 |
|  | 2-(5-(2-fluorobenzyl)-5-hydroxyhexahydrocyclopenta[c]pyrrol-2(1H)-yl)-1-(5-hydroxypyridin-2-yl)ethanone | 371.17 | 371.5 |
|  | rac-2-(2-(3-fluoro-4-hydroxyphenyl)-2-hydroxyethyl)-5-(thiophen-2-ylmethyl)octahydrocyclopenta[c]pyrrol-5-ol | 378.15 | 378.3 |
|  | rac-(3aR,5r,6aS)-5-(4-chlorobenzyl)-2-(2-hydroxy-2-(5-hydroxypyridin-2-yl)ethyl)octahydrocyclopenta[c]pyrrol-5-ol | 389.16 | 389.2 |

TABLE 11-continued

The following compounds were prepared by the methods described above using intermediates made by the methods described above.

| Structure | IUPAC Name | Calculated (M + H) | Found (M + H) |
|---|---|---|---|
| | rac-(3aR,5R,6aS)-2-[2-hydroxy-2-(4-hydroxyphenyl)ethyl]-5-{[4-(trifluoromethyl)phenyl]methyl}-octahydrocyclopenta[c]pyrrol-5-ol | 422.45 | 422.2 |
| | 2-((3aR,5r,6aS)-5-(2-fluorobenzyl)-5-hydroxyhexahydrocyclopenta[c]pyrrol-2(1H)-yl)-1-(4-hydroxyphenyl)ethanone | 370.43 | 370.2 |
| | 2-((3aR,5r,6aS)-5-hydroxy-5-(pyridin-4-ylmethyl)hexahydrocyclopenta[c]pyrrol-2(1H)-yl)-1-(4-hydroxyphenyl)ethanone | 353.43 | 353.5 |
| | rac-(3aR,5r,6aS)-2-(2-hydroxy-2-(4-hydroxyphenyl)ethyl)-5-(pyridin-4-ylmethyl)octahydrocyclopenta[c]pyrrol-5-ol | 354.44 | 355.5 |
| | rac-5-(2-fluorobenzyl)-2-(2-hydroxy-2-(5-hydroxypyridin-2-yl)ethyl)octahydrocyclopenta[c]pyrrol-5-olyl)ethanone | 373.18 | 373.2 |
| | rac-(3aR,5r,6aS)-5-(2-fluorobenzyl)-2-(2-hydroxy-2-(4-hydroxyphenyl)ethyl)-octahydrocyclopenta[c]pyrrol-5-ol | 372.45 | 372.2 |

TABLE 11-continued

The following compounds were prepared by the methods described above using intermediates made by the methods described above.

| Structure | IUPAC Name | Calculated (M + H) | Found (M + H) |
|---|---|---|---|
| 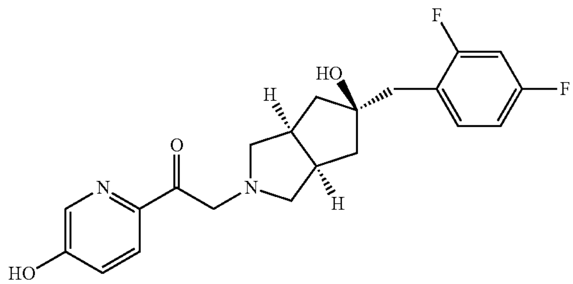 [SMILES: O=C(CN1C[C@@H]2C[C@@](O)(Cc3ccc(F)cc3F)C[C@@H]2C1)c1ccc(O)cn1] | 2-((3aR,5r,6aS)-5-(2,4-difluorobenzyl)-5-hydroxyhexahydrocyclopenta[c]pyrrol-2(1H)-yl)-1-(5-hydroxypyridin-2-yl)ethanone | 389.41 | 389.2 |
| 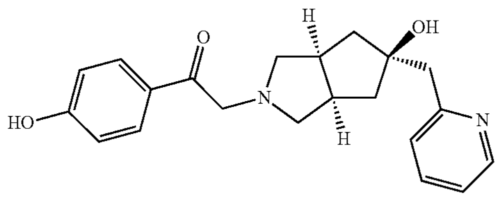 [SMILES: O=C(CN1C[C@@H]2C[C@@](O)(Cc3ccccn3)C[C@@H]2C1)c1ccc(O)cc1] | 2-((3aR,5r,6aS)-5-hydroxy-5-(pyridin-2-ylmethyl)hexahydrocyclopenta[c]pyrrol-2(1H)-yl)-1-(4-hydroxyphenyl)ethanone | 353.43 | 353.5 |
| 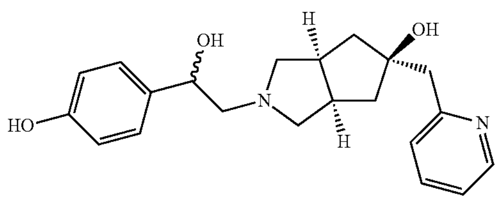 [SMILES: Oc1ccc(C(O)CN2C[C@@H]3C[C@@](O)(Cc4ccccn4)C[C@@H]3C2)cc1] | rac-(3aR,5r,6aS)-2-(2-hydroxy-2-(4-hydroxyphenyl)ethyl)-5-(pyridin-2-ylmethyl)octahydrocyclopenta[c]pyrrol-5-ol | 355.44 | 355.4 |
| 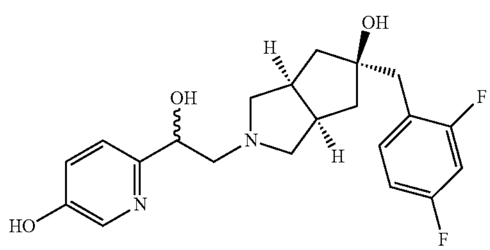 [SMILES: Oc1ccc(C(O)CN2C[C@@H]3C[C@@](O)(Cc4ccc(F)cc4F)C[C@@H]3C2)nc1] | rac-(3aR,5r,6aS)-5-(2,4-difluorobenzyl)-2-(2-hydroxy-2-(5-hydroxypyridin-2-yl)ethyl)octahydrocyclopenta[c]pyrrol-5-ol | 391.42 | 391.2 |
| 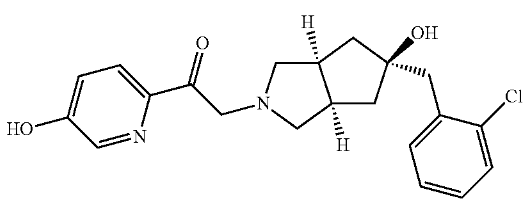 [SMILES: O=C(CN1C[C@@H]2C[C@@](O)(Cc3ccccc3Cl)C[C@@H]2C1)c1ccc(O)cn1] | 2-((3aR,5r,6aS)-5-(2-chlorobenzyl)-5-hydroxyhexahydrocyclopenta[c]pyrrol-2(1H)-yl)-1-(5-hydroxypyridin-2-yl)ethanone | 387.14 | 387.1 |
| 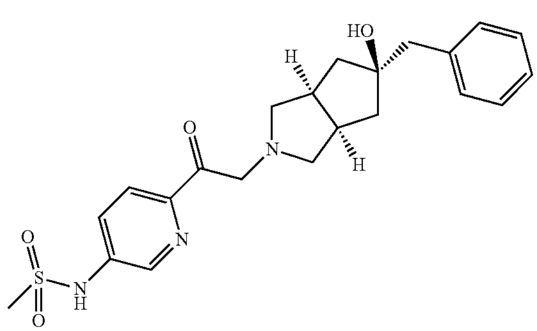 [SMILES: CS(=O)(=O)Nc1ccc(C(=O)CN2C[C@@H]3C[C@@](O)(Cc4ccccc4)C[C@@H]3C2)nc1] | N-(6-(2-((3aR,5r,6aS)-5-benzyl-5-hydroxyhexahydrocyclopenta[c]pyrrol-2(1H)-yl)acetyl)pyridin-3-yl)methanesulfonamide | 430.53 | 430.2 |

TABLE 11-continued

The following compounds were prepared by the methods described above using intermediates made by the methods described above.

| Structure | IUPAC Name | Calculated (M + H) | Found (M + H) |
|---|---|---|---|
| 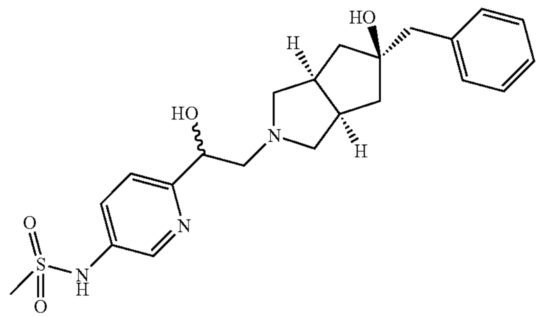 [SMILES: CS(=O)(=O)Nc1ccc(C(O)CN2C[C@@H]3C[C@@](O)(Cc4ccccc4)C[C@@H]3C2)nc1] | rac-N-(6-(2-((3aR,5r,6aS)-5-benzyl-5-hydroxyhexahydrocyclopenta[c]pyrrol-2(1H)-yl)-1-hydroxyethyl)pyridin-3-yl)methanesulfonamide | 432.55 | 432.2 |
| 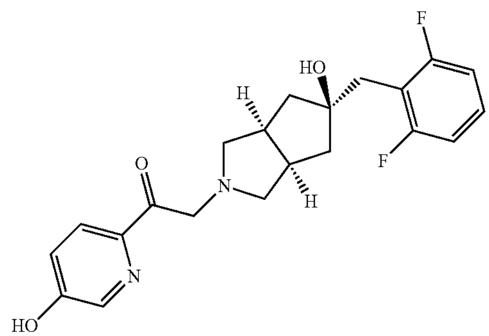 [SMILES: O=C(CN1C[C@@H]2C[C@@](O)(Cc3c(F)cccc3F)C[C@@H]2C1)c1ccc(O)cn1] | 2-[(3aR,5R,6aS)-5-[(2,6-difluorophenyl)methyl]-5-hydroxy-octahydrocyclopenta[c]-pyrrol-2-yl]-1-(5-hydroxypyridin-2-yl)ethan-1-one | 389.41 | 389.2 |
| 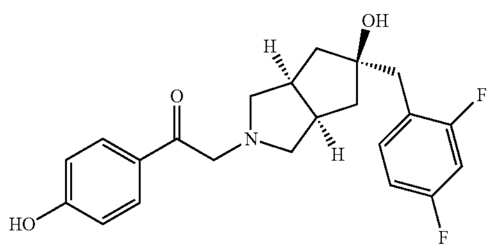 [SMILES: O=C(CN1C[C@@H]2C[C@@](O)(Cc3ccc(F)cc3F)C[C@@H]2C1)c1ccc(O)cc1] | 2-(5-(2,4-difluorobenzyl)-5-hydroxyhexahydrocyclopenta[c]pyrrol-2(1H)-yl)-1-(4-hydroxyphenyl)ethanone | 388.16 | 388.2 |
| 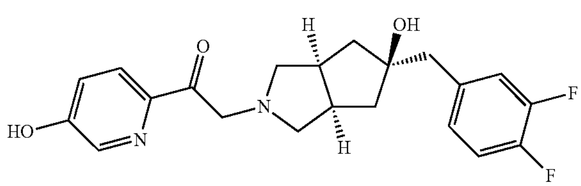 | 2-((3aR,5r,6aS)-5-(3,4-difluorobenzyl)-5-hydroxyhexahydrocyclopenta[c]pyrrol-2(1H)-yl)-1-(5-hydroxypyridin-2-yl)ethanone | 389.41 | 389.1 |
| 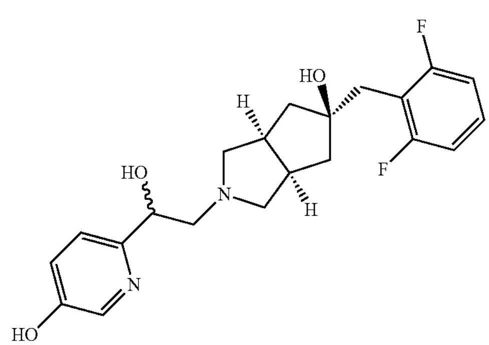 [SMILES: Oc1ccc(C(O)CN2C[C@@H]3C[C@@](O)(Cc4c(F)cccc4F)C[C@@H]3C2)nc1] | rac-6-{2-[(3aR,5R,6aS)-5-[(2,6-difluorophenyl)methyl]-5-hydroxy-octahydrocyclopenta[c]-pyrrol-2-yl]-1-hydroxyethyl}pyridin-3-ol | 391.42 | 391.2 |

TABLE 11-continued

The following compounds were prepared by the methods described above using intermediates made by the methods described above.

| Structure | IUPAC Name | Calculated (M + H) | Found (M + H) |
|---|---|---|---|
| | 2-[(3aR,5R,6aS)-5-[(2,6-difluorophenyl)methyl]-5-hydroxy-octahydrocyclopenta[c]pyrrol-2-yl]-1-(4-hydroxyphenyl)ethan-1-one | 388.42 | 388.1 |
| | 2-((3aR,5r,6aS)-5-(4-fluoro-2-methylbenzyl)-5-hydroxyhexahydrocyclopenta[c]pyrrol-2(1H)-yl)-1-(5-hydroxypyridin-2-yl)ethanone | 385.44 | 385.2 |
| | rac-(3aR,5r,6aS)-5-(4-fluoro-2-methylbenzyl)-2-(2-hydroxy-2-(5-hydroxypyridin-2-yl)ethyl)octahydrocyclopenta[c]pyrrol-5-ol | 387.46 | 387.2 |
| | 2-((3aR,6aS)-5-(2-fluoropyridin-3-yl)-5-hydroxyhexahydrocyclopenta[c]pyrrol-2(1H)-yl)-1-(5-hydroxypyridin-2-yl)ethanone | 358.38 | 358.2 |
| | rac-5-(2,4-difluorobenzyl)-2-(2-hydroxy-2-(4-hydroxyphenyl)ethyl)octahydrocyclopenta[c]pyrrol-5-ol | 390.18 | 390.5 |
| | rac-(3aR,5r,6aS)-5-(2-chlorobenzyl)-2-(2-hydroxy-2-(5-hydroxypyridin-2-yl)ethyl)octahydrocyclopenta[c]pyrrol-5-ol | 389.16 | 389.1 |

TABLE 11-continued

The following compounds were prepared by the methods described above using intermediates made by the methods described above.

| Structure | IUPAC Name | Calculated (M + H) | Found (M + H) |
|---|---|---|---|
| | 2-((3aR,5r,6aS)-5-(2,3-difluorobenzyl)-5-hydroxyhexahydrocyclopenta[c]pyrrol-2(1H)-yl)-1-(5-hydroxypyridin-2-yl)ethanone | 389.16 | 389.2 |
| | rac-(3aR,5r,6aS)-5-(2,3-difluorobenzyl)-2-(2-hydroxy-2-(5-hydroxypyridin-2-yl)ethyl)octahydrocyclopenta[c]pyrrol-5-ol | 391.18 | 391.2 |
| | 2-((3aR,5r,6aS)-5-(2,3-difluorobenzyl)-5-hydroxyhexahydrocyclopenta[c]pyrrol-2(1H)-yl)-1-(4-hydroxyphenyl)ethanone | 388.16 | 388.1 |
| | 2-((3aR,5r,6aS)-5-(4-fluoro-2-methylbenzyl)-5-hydroxyhexahydrocyclopenta[c]pyrrol-2(1H)-yl)-1-(4-hydroxyphenyl)ethanone | 384.46 | 384.2 |
| | rac-(3aR,6aS)-5-(2-fluoropyridin-3-yl)-2-(2-hydroxy-2-(5-hydroxypyridin-2-yl)ethyl)octahydrocyclopenta[c]pyrrol-5-ol | 360.39 | 360.3 |
| | 2-((3aR,5r,6aS)-5-(3,4-difluorobenzyl)-5-hydroxyhexahydrocyclopenta[c]pyrrol-2(1H)-yl)-1-(4-hydroxyphenyl)ethanone | 388.42 | 388.2 |

TABLE 11-continued

The following compounds were prepared by the methods described above using intermediates made by the methods described above.

| Structure | IUPAC Name | Calculated (M + H) | Found (M + H) |
|---|---|---|---|
| 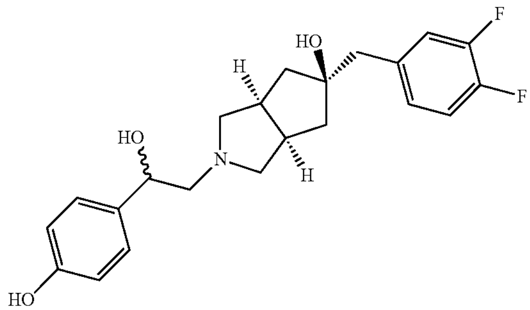 [SMILES: Oc1ccc(C(O)CN2C[C@@H]3C[C@@](O)(Cc4ccc(F)c(F)c4)C[C@@H]3C2)cc1] | rac-(3aR,5r,6aS)-5-(3,4-difluorobenzyl)-2-(2-hydroxy-2-(4-hydroxyphenyl)ethyl)octahydrocyclopenta[c]-pyrrol-5-ol | 390.44 | 390.2 |
| 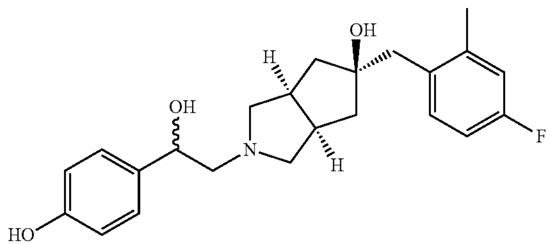 [SMILES: Cc1cc(F)ccc1C[C@]1(O)C[C@H]2CN(CC(O)c3ccc(O)cc3)C[C@H]2C1] | rac-(3aR,5r,6aS)-5-(4-fluoro-2-methylbenzyl)-2-(2-hydroxy-2-(4-hydroxyphenyl)ethyl)octahydrocyclopenta[c]-pyrrol-5-ol | 386.47 | 386.2 |
| | (3aR,5S,6aS)-5-(4-fluorobenzyl)-2-((S)-2-hydroxy-2-(5-hydroxypyridin-2-yl)ethyl)octahydrocyclopenta[c]pyrrol-5-ol | 373.43 | 373.2 |
| | (3aR,5R,6aS)-5-(4-fluorobenzyl)-2-((R)-2-hydroxy-2-(5-hydroxypyridin-2-yl)ethyl)octahydrocyclopenta[c]pyrrol-5-ol | 373.43 | 373.2 |

Example 37

Preparation of 2-((3aR,5r,6aS)-5-benzyl-5-hydroxy-hexahydrocyclopenta[c]pyrrol-2(1H)-yl)-1-(4'-hydroxy-[1,1'-biphenyl]-4-yl)ethanone Scheme 37

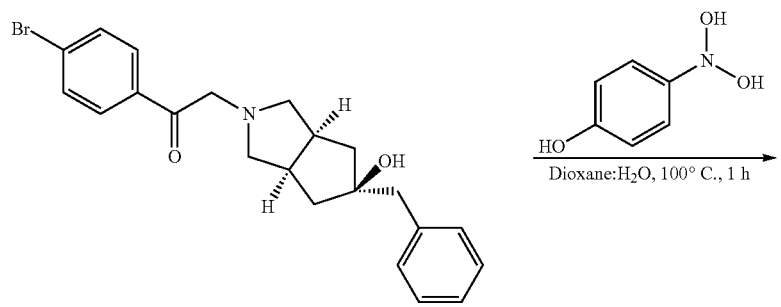

-continued

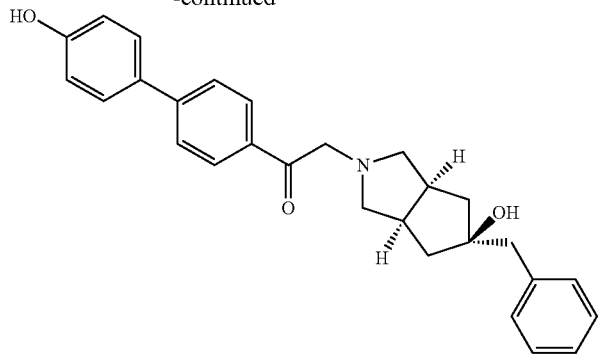

To a solution of 2-((3aR,5r,6aS)-5-benzyl-5-hydroxyhexahydrocyclopenta[c]pyrrol-2(1H)-yl)-1-(4-bromophenyl)ethanone (0.100 g, 0.24 mmol) and (4-hydroxyphenyl)boronic acid (0.040 g, 0.029 mmol) in dioxane:water (3:1, 8 mL) was added potassium carbonate (0.099 g, 0.72 mmol) and resulting mixture was degassed with nitrogen for 5 minutes. To the above mixture was added [1,1'-bis(diphenylphosphino)ferrocene]dichloropalladium(II), complex with dichloromethane (0.008 g, 0.012 mmol) and resulting suspension was heated at 100° C. under microwave irradiation for 30 minutes. After completion of reaction (as monitored by TLC), the reaction mixture was cooled to room temperature and diluted with water (10 mL). The solution was extracted with ethyl acetate (20 mL×2), the combined organic layer was washed with water (50 mL), dried over sodium sulfate and concentrated under vacuum to obtain crude material which was purified by prep HPLC affording the title compound 2-((3aR,5r,6aS)-5-benzyl-5-hydroxyhexahydrocyclopenta[c]pyrrol-2(1H)-yl)-1-(4'-hydroxy-[1,1'-biphenyl]-4-yl)ethanone (5) (0.008 g, 8%) as off white solid. Calculated M+H: 428.21. Found M+H: 428.12.

TABLE 12

The following compounds were prepared by the methods described above using intermediates made by the methods described above.

| Structure | IUPAC Name | Calculated M + H | Found M + H |
|---|---|---|---|
| 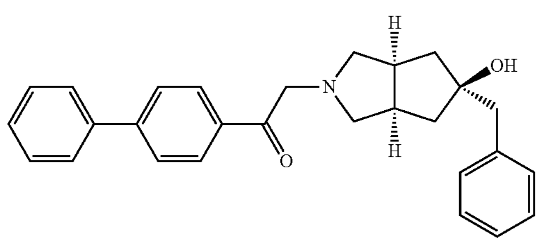 | 1-([1,1'-biphenyl]-4-yl)-2-((3aR,5r,6aS)-5-benzyl-5-hydroxyhexahydrocyclopenta[c]pyrrol-2(1H)-yl)ethanone | 412.54 | 412.36 |
| 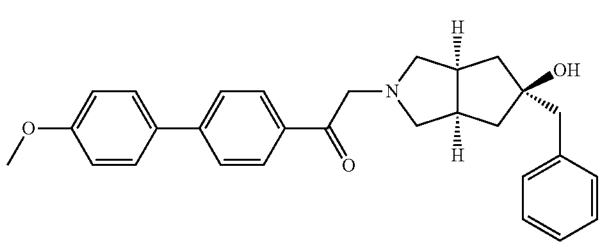 [SMILES: COc1ccc(-c2ccc(C(=O)CN3C[C@@H]4C[C@@](O)(Cc5ccccc5)C[C@@H]4C3)cc2)cc1] | 2-((3aR,5r,6aS)-5-benzyl-5-hydroxyhexahydrocyclopenta[c]pyrrol-2(1H)-yl)-1-(4'-methoxy-[1,1'-biphenyl]-4-yl)ethanone | 442.23 | 442.10 |
| 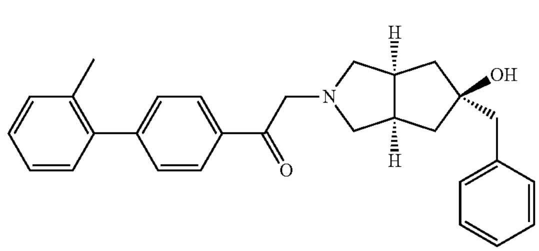 [SMILES: Cc1ccccc1-c1ccc(C(=O)CN2C[C@@H]3C[C@@](O)(Cc4ccccc4)C[C@@H]3C2)cc1] | 2-((3aR,5r,6aS)-5-benzyl-5-hydroxyhexahydrocyclopenta[c]pyrrol-2(1H)-yl)-1-(2'-methyl-[1,1'-biphenyl]-4-yl)ethanone | 426.24 | 426.12 |

TABLE 12-continued

The following compounds were prepared by the methods described above using intermediates made by the methods described above.

| Structure | IUPAC Name | Calculated M + H | Found M + H |
|---|---|---|---|
| 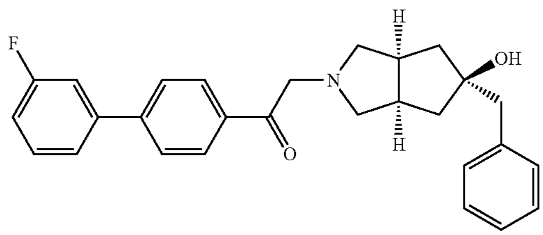 [SMILES: O=C(CN1C[C@@H]2C[C@@](O)(Cc3ccccc3)C[C@@H]2C1)c1ccc(-c2cccc(F)c2)cc1] | 2-((3aR,5r,6aS)-5-benzyl-5-hydroxyhexahydrocyclopenta[c]pyrrol-2(1H)-yl)-1-(3'-fluoro-[1,1'-biphenyl]-4-yl)ethanone | 430.21 | 430.10 |
| 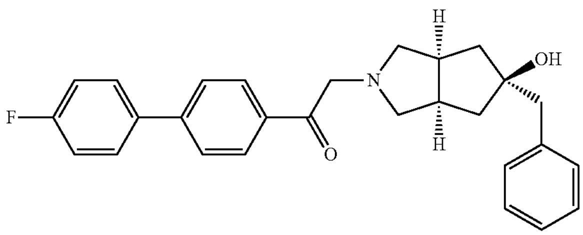 [SMILES: O=C(CN1C[C@@H]2C[C@@](O)(Cc3ccccc3)C[C@@H]2C1)c1ccc(-c2ccc(F)cc2)cc1] | 2-((3aR,5r,6aS)-5-benzyl-5-hydroxyhexahydrocyclopenta[c]pyrrol-2(1H)-yl)-1-(4'-fluoro-[1,1'-biphenyl]-4-yl)ethanone | 430.21 | 430.12 |
| 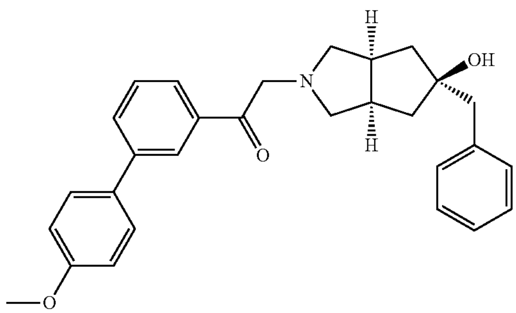 [SMILES: COc1ccc(-c2cccc(C(=O)CN3C[C@@H]4C[C@@](O)(Cc5ccccc5)C[C@@H]4C3)c2)cc1] | 2-((3aR,5r,6aS)-5-benzyl-5-hydroxyhexahydrocyclopenta[c]pyrrol-2(1H)-yl)-1-(4'-methoxy-[1,1'-biphenyl]-3-yl)ethanone | 442.23 | 442.12 |
| 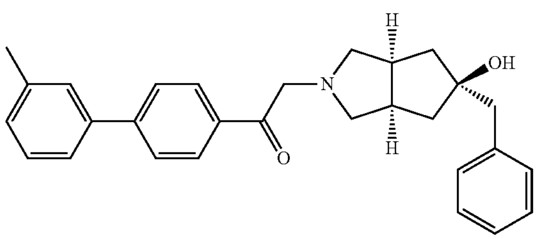 [SMILES: Cc1cccc(-c2ccc(C(=O)CN3C[C@@H]4C[C@@](O)(Cc5ccccc5)C[C@@H]4C3)cc2)c1] | 2-((3aR,5r,6aS)-5-benzyl-5-hydroxyhexahydrocyclopenta[c]pyrrol-2(1H)-yl)-1-(3'-methyl-[1,1'-biphenyl]-4-yl)ethanone | 426.24 | 426.11 |
| 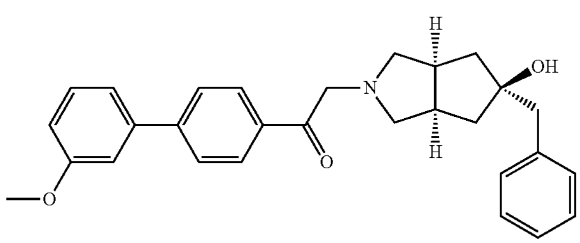 [SMILES: COc1cccc(-c2ccc(C(=O)CN3C[C@@H]4C[C@@](O)(Cc5ccccc5)C[C@@H]4C3)cc2)c1] | 2-((3aR,5r,6aS)-5-benzyl-5-hydroxyhexahydrocyclopenta[c]pyrrol-2(1H)-yl)-1-(3'-methoxy-[1,1'-biphenyl]-4-yl)ethanone | 442.23 | 442.0 |
| 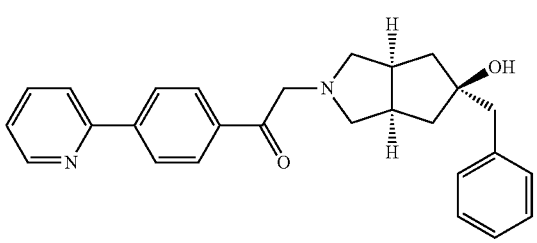 [SMILES: O=C(CN1C[C@@H]2C[C@@](O)(Cc3ccccc3)C[C@@H]2C1)c1ccc(-c2ccccn2)cc1] | 2-((3aR,5r,6aS)-5-benzyl-5-hydroxyhexahydrocyclopenta[c]pyrrol-2(1H)-yl)-1-(4-(pyridin-2-yl)phenyl)ethanone | 413.22 | 413.11 |

TABLE 12-continued

The following compounds were prepared by the methods described above using intermediates made by the methods described above.

| Structure | IUPAC Name | Calculated M + H | Found M + H |
|---|---|---|---|
| 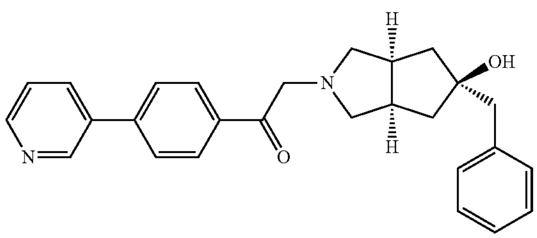 [SMILES: O=C(CN1C[C@@H]2C[C@@](O)(Cc3ccccc3)C[C@@H]2C1)c1ccc(-c2cccnc2)cc1] | 2-((3aR,5r,6aS)-5-benzyl-5-hydroxyhexahydrocyclopenta[c]pyrrol-2(1H)-yl)-1-(4-(pyridin-3-yl)phenyl)ethanone | 413.22 | 413.10 |
| 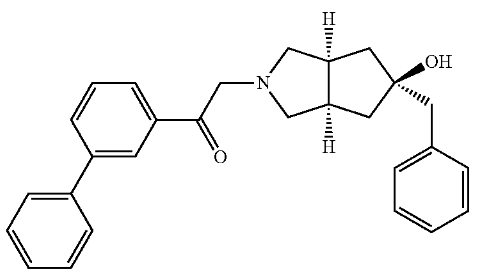 [SMILES: O=C(CN1C[C@@H]2C[C@@](O)(Cc3ccccc3)C[C@@H]2C1)c1cccc(-c2ccccc2)c1] | 1-([1,1'-biphenyl]-3-yl)-2-((3aR,5r,6aS)-5-benzyl-5-hydroxyhexahydrocyclopenta[c]pyrrol-2(1H)-yl)ethanone | 412.22 | 412.11 |
| | 2-[5-hydroxy-5-(2-phenylethyl)-octahydro-cyclopenta[c]pyrrol-2-yl]-1-(4-phenyl-phenyl)ethan-1-one | 426.24 | 426.10 |
| | 1-[4-(3-fluorophenyl)phenyl]-2-[5-hydroxy-5-(2-phenylethyl)-octahydro-cyclopenta[c]pyrrol-2-yl]ethan-1-one | 444.23 | 444.12 |
| 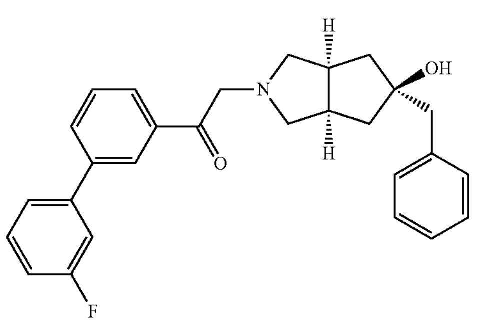 [SMILES: O=C(CN1C[C@@H]2C[C@@](O)(Cc3ccccc3)C[C@@H]2C1)c1cccc(-c2cccc(F)c2)c1] | 2-((3aR,5r,6aS)-5-benzyl-5-hydroxyhexahydrocyclopenta[c]pyrrol-2(1H)-yl)-1-(3'-fluoro-[1,1'-biphenyl]-3-yl)ethanone | 430.21 | 430.10 |

TABLE 12-continued

The following compounds were prepared by the methods described above using intermediates made by the methods described above.

| Structure | IUPAC Name | Calculated M + H | Found M + H |
|---|---|---|---|
| 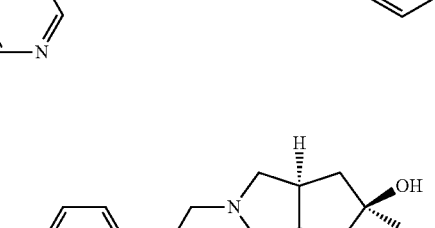 | 2-((3aR,5r,6aS)-5-benzyl-5-hydroxyhexahydrocyclopenta[c]pyrrol-2(1H)-yl)-1-(3-(pyridin-3-yl)phenyl)ethanone | 413.22 | 413.14 |
| 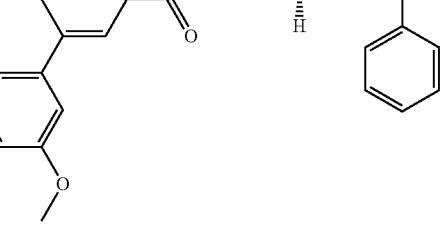 | 2-((3aR,5r,6aS)-5-benzyl-5-hydroxyhexahydrocyclopenta[c]pyrrol-2(1H)-yl)-1-(3'-methoxy-[1,1'-biphenyl]-3-yl)ethanone | 442.23 | 442.0 |
| 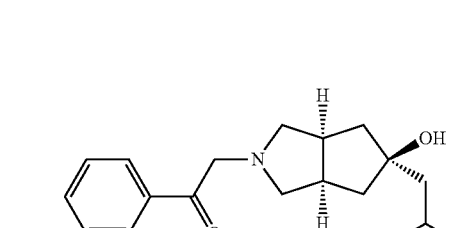 | 2-((3aR,5r,6aS)-5-benzyl-5-hydroxyhexahydrocyclopenta[c]pyrrol-2(1H)-yl)-1-(4'-fluoro-[1,1'-biphenyl]-3-yl)ethanone | 430.21 | 430.0 |
| 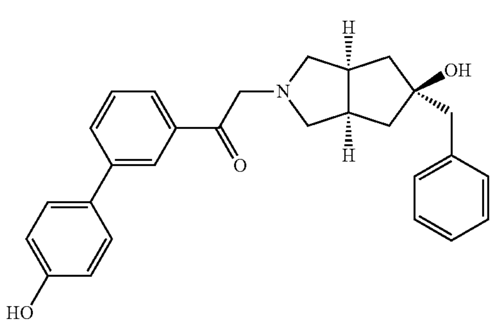 [SMILES: O=C(CN1C[C@@H]2C[C@@](O)(Cc3ccccc3)C[C@@H]2C1)c1cccc(-c2ccc(O)cc2)c1] | 2-((3aR,5r,6aS)-5-benzyl-5-hydroxyhexahydrocyclopenta[c]pyrrol-2(1H)-yl)-1-(4'-hydroxy-[1,1'-biphenyl]-3-yl)ethanone | 428.21 | 428.10 |

TABLE 12-continued

The following compounds were prepared by the methods described above using intermediates made by the methods described above.

| Structure | IUPAC Name | Calculated M + H | Found M + H |
|---|---|---|---|
| 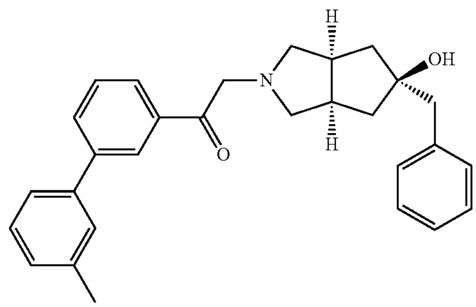 [SMILES: Cc1cccc(-c2cccc(C(=O)CN3C[C@@H]4C[C@@](O)(Cc5ccccc5)C[C@@H]4C3)c2)c1] | 2-((3aR,5r,6aS)-5-benzyl-5-hydroxyhexahydrocyclopenta[c]pyrrol-2(1H)-yl)-1-(3'-methyl-[1,1'-biphenyl]-3-yl)ethanone | 426.24 | 426.12 |
|  | 2-[5-hydroxy-5-(2-phenylethyl)-octahydro-cyclopenta[c]pyrrol-2-yl]-1-[4-(3-methylphenyl)phenyl]ethan-1-one | 440.25 | 44.0 |
| 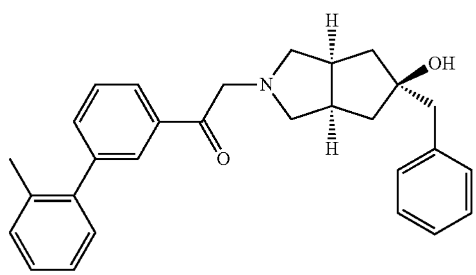 [SMILES: Cc1ccccc1-c1cccc(C(=O)CN2C[C@@H]3C[C@@](O)(Cc4ccccc4)C[C@@H]3C2)c1] | 2-((3aR,5r,6aS)-5-benzyl-5-hydroxyhexahydrocyclopenta[c]pyrrol-2(1H)-yl)-1-(2'-methyl-[1,1'-biphenyl]-3-yl)ethanone | 426.24 | 426.11 |
| 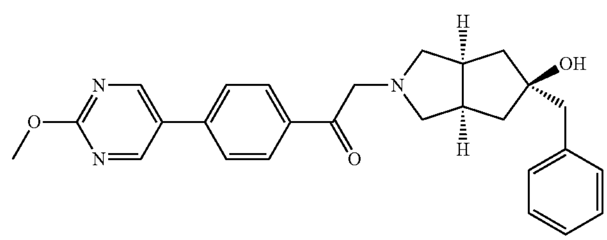 | 2-((3aR,5r,6aS)-5-benzyl-5-hydroxyhexahydrocyclopenta[c]pyrrol-2(1H)-yl)-1-(4-(2-methoxypyrimidin-5-yl)phenyl)ethanone | 444.22 | 444.21 |

Example 38

Preparation of rac-(3aR,5R,6aS)-5-benzyl-2-[2-hydroxy-2-(4-hydroxyphenyl)propyl]-octahydrocyclopenta[c]pyrrol-5-ol Scheme 38

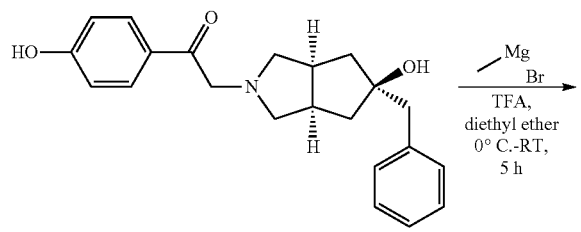
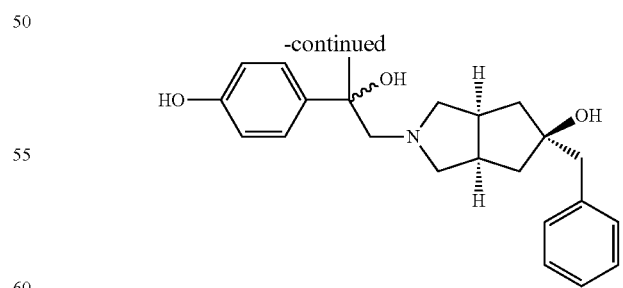

To a solution of 2-(5-benzyl-5-hydroxyhexahydrocyclopenta[c]pyrrol-2(1H)-yl)-1-(4-hydroxyphenyl)ethanone (0.2 g, 0.57 mmol) in tetrahydrofuran (50 mL), 3M methyl magnesium bromide in diethyl ether (0.94 mL, 2.84 mmol) was added at 0° C. and the reaction mixture was stirred at room temperature for 5 h under nitrogen atmosphere. The solution was quenched with saturated ammonium chloride solution (20 mL) and extracted with ethyl acetate (300 mL×2). The combined organic layer was dried over anhydrous sodium sulfate, filtered and evaporated under vacuum to get crude which was purified by silica gel flash column chromatography using 15% methanol in dichloromethane to afford the title compound (3aR,5R,6aS)-5-benzyl-2-[2-hydroxy-2-(4-hydroxyphenyl)propyl]-octahydrocyclopenta[c]pyrrol-5-ol (0.025 g, 11.9%) as a brownish solid. Calculated (M+H): 368.48. Found (M+1): 368.3.

Example 39

Preparation of deuterated rac-(3aR,6aS)-5-benzyl-2-((S)-2-hydroxy-2-(4-hydroxyphenyl)ethyl)octahydrocyclopenta[c]pyrrol-5-ol Scheme 39

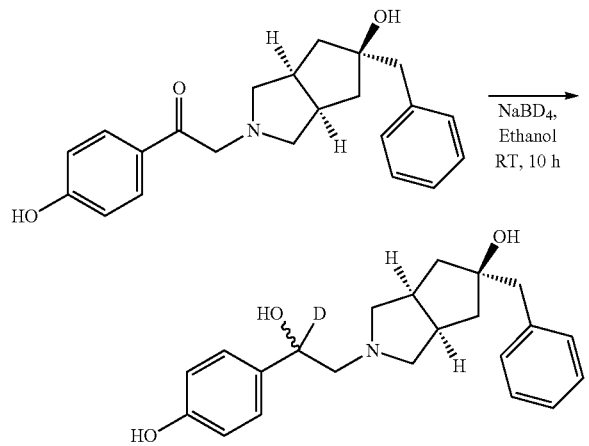

To a stirred solution of 2-((3aR,6aS)-5-benzyl-5-hydroxyhexahydrocyclopenta[c]pyrrol-2(1H)-yl)-1-(4-hydroxyphenyl)ethanone (0.05 g, 0.142 mmol) in ethanol (10 mL), was added sodium borodeuteride (0.059 g, 1.42 mmol) at room temperature and stirred for 10 h. After completion of the reaction (as monitored by TLC), the reaction mixture was concentrated under vacuum. The residue was diluted with water (10 mL) and extracted with ethyl acetate (30 mL×3). The combined organic layer was washed with water (10 mL×2), brine (15 mL), dried over anhydrous sodium sulfate and concentrated under vacuum to afford the crude compound which was triturated with diethyl ether:pentane (1:1) mixture to obtain the title compound deuterated (3aR,6aS)-5-benzyl-2-((S)-2-hydroxy-2-(4-hydroxyphenyl)ethyl)octahydrocyclopenta[c]pyrrol-5-ol (0.010 g, 20% yield) as off-white solid. Calculated M+H: 355.21. Found M+H: 355.5.

Example 40

Preparation of N-(5-(2-((3aR,5r,6aS)-5-benzyl-5-hydroxyhexahydrocyclopenta[c]pyrrol-2(1H)-yl)acetyl)pyridin-2-yl)acetamide Scheme 40

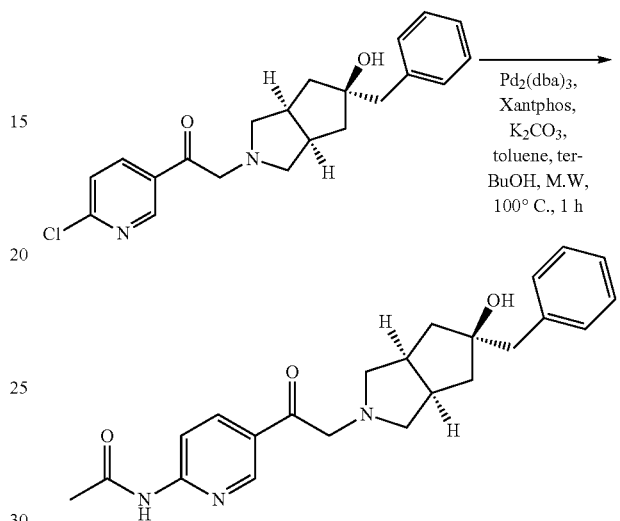

To a solution of 2-(5-benzyl-5-hydroxyhexahydrocyclopenta[c]pyrrol-2(1H)-yl)-1-(6-chloropyridin-3-yl)ethanone (0.1 g, 0.268 mmol) in toluene (2 mL) and tert-butanol (2 mL) mixture was added potassium carbonate (0.11 g, 0.806 mmol) followed by acetamide (0.024 g, 0.403 mmol). The reaction mixture was purged with nitrogen gas for 10 minutes. Finally 4,5-bis (diphenyl phosphino)-9,9-dimethyl xanthene (0.031 g, 0.053 mmol) and tri(dibenzylideneacetone)dipalladium(0) (0.025 g, 0.026) were added. The reaction mixture was heated at 100° C. in CEM microwave for 1 h. The solution was diluted with water (100 mL) and extracted with dichloromethane (100 mL×2). The combined organic layer was dried over anhydrous sodium sulfate, filtered and concentrated. The crude was purified by silica gel flash column chromatography using 80% ethyl acetate in hexane to afford the title compound N-(5-(2-((3aR,5r,6aS)-5-benzyl-5-hydroxyhexahydrocyclopenta[c]pyrrol-2(1H)-yl)acetyl)pyridin-2-yl)acetamide (0.045 g, 21.43% yield) as pale yellow solid. Calculated M+H: 394.48. Found M+H: 394.2.

TABLE 13

The following compounds were prepared by the method described above.

| Structure | IUPAC Name | Calculated (M + H) | Found (M + H) |
|---|---|---|---|
| 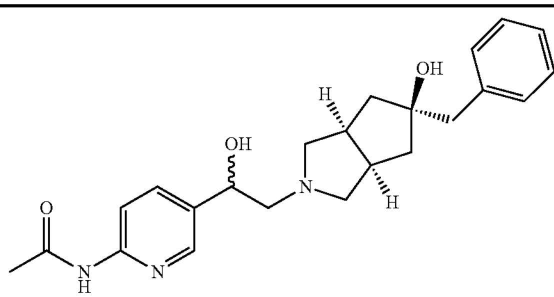 | rac-N-(5-(2-((3aR,5r,6aS)-5-benzyl-5-hydroxyhexahydrocyclopenta[c]pyrrol-2(1H)-yl)-1-hydroxyethyl)pyridin-2-yl)acetamide | 396.49 | 396.2 |

TABLE 13-continued

The following compounds were prepared by the method described above.

| Structure | IUPAC Name | Calculated (M + H) | Found (M + H) |
|---|---|---|---|
| 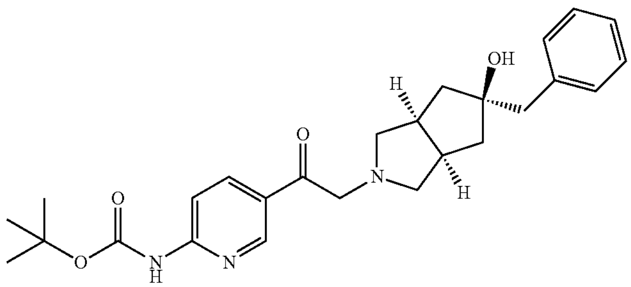 [SMILES: CC(C)(C)OC(=O)Nc1ccc(C(=O)CN2C[C@@H]3C[C@@](O)(Cc4ccccc4)C[C@@H]3C2)cn1] | tert-butyl (5-(2-(5-benzyl-5-hydroxyhexahydrocyclopenta[c]pyrrol-2(1H)-yl)acetyl)pyridin-2-yl)carbamate | 452.25 | 452.3 |
| 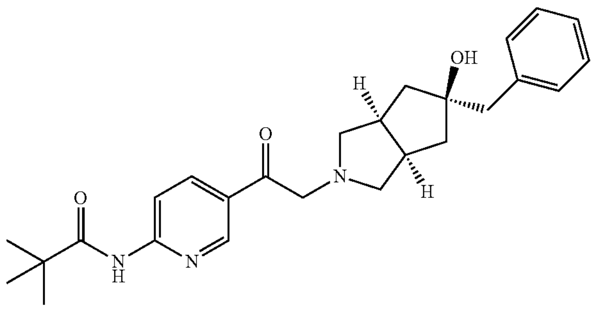 [SMILES: CC(C)(C)C(=O)Nc1ccc(C(=O)CN2C[C@@H]3C[C@@](O)(Cc4ccccc4)C[C@@H]3C2)cn1] | N-(5-(2-(5-benzyl-5-hydroxyhexahydrocyclopenta[c]pyrrol-2(1H)-yl)acetyl)pyridin-2-yl)pivalamide | 461.08 | 461.12 |
| 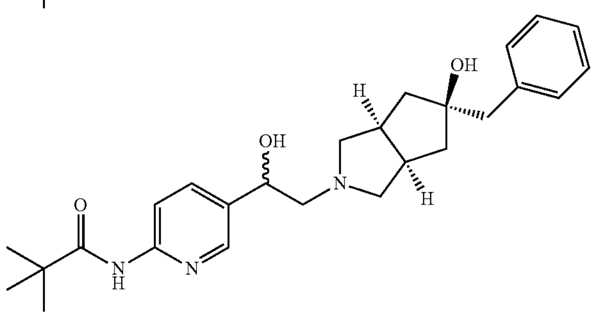 | rac-N-(5-(2-(5-benzyl-5-hydroxyhexahydrocyclopenta[c]pyrrol-2(1H)-yl)-1-hydroxyethyl)pyridin-2-yl)pivalamide | 438.27 | 438.6 |

Example 41

Preparation of rac-(3aR,5r,6aS)-5-benzyl-2-(2-(2,4-dichlorophenyl)-2-hydroxyethyl)octahydrocyclopenta[c]pyrrol-5-ol Scheme 41

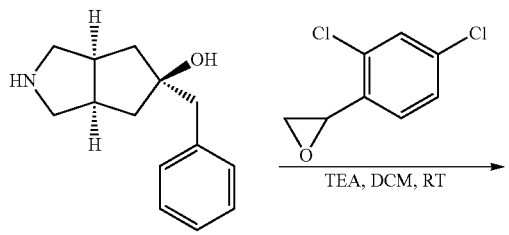

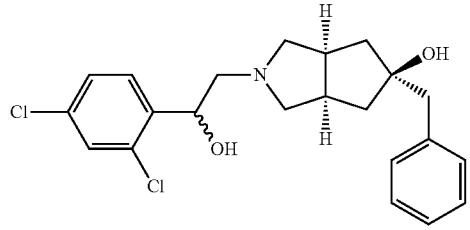

To a solution of (3aR,5r,6aS)-5-benzyloctahydrocyclopenta[c]pyrrol-5-ol (0.040 g, 0.12 mmol) in dichloromethane (2 mL) was added 2-(2,4-dichlorophenyl)oxirane (0.044 g, 0.21 mmol) and triethylamine (0.041 mL, 0.29 mmol) and resulting solution was stirred at room temperature for 18 h. After completion of reaction (monitored by TLC), reaction mixture was diluted with water (2 mL). The organic layer was extracted with dichloromethane (5 mL×2), washed with brine (10 mL), dried over sodium sulfate and concentrated under vacuum to afford the crude (3aR,5r,6aS)-5-benzyl-2-(2-(2,4-dichlorophenyl)-2-hydroxyethyl)octahydrocyclopenta[c]pyrrol-5-ol which was purified by prep HPLC (column: XSelect CSH C-18 Prep (19×250 mm, 5 um), mobile phase: A—5 mM ammonium acetate, B—Acetonitrile, flow mode: gradient, flow: 15 ml/min, gradient T/% B: 0/30, 0.5/30, 15/90, 21/90, 21.5/30, 26/30).

TABLE 14

The following compounds were prepared by the method described above.

| Structure | IUPAC Name | Calculated (M + H) | Found (M + H) |
|---|---|---|---|
| | rac-(3aR,5r,6aS)-5-benzyl-2-(2-hydroxy-2-(3-(trifluoromethyl)phenyl)-ethyl)octahydrocyclopenta[c]pyrrol-5-ol | 406.19 | 406.4 |
| | rac-(3aR,5r,6aS)-5-benzyl-2-(2-(4-fluorophenyl)-2-hydroxyethyl)octahydrocyclopenta[c]pyrrol-5-ol | 356.19 | 356.39 |

Example 42

Preparation of 5-benzyl-2-((R)-2-hydroxy-2-(4-hydroxyphenyl)ethyl)octahydrocyclopenta[c]pyrrol-5-ol Scheme 42

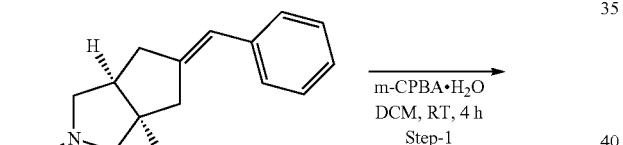
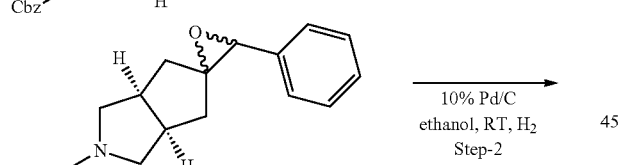
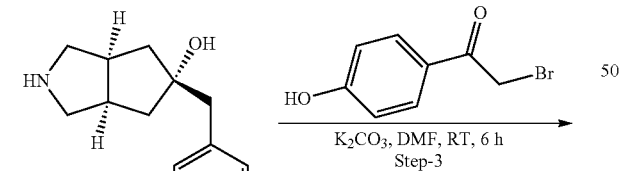
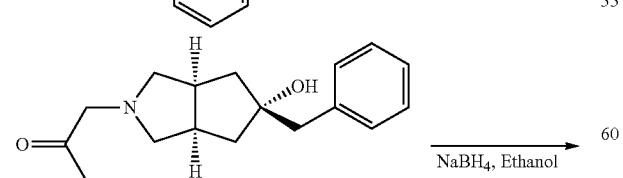

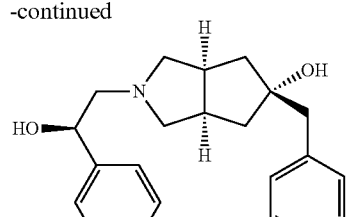

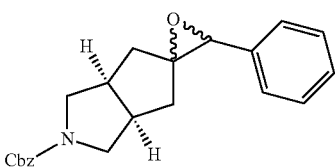

Step 1: Preparation of benzyl (3aR,6aS)-3'-phenyltetrahydro-1H-spiro[cyclopenta[c]pyrrole-5,2'-oxirane]-2(3H)-carboxylate To stirred solution of (3aR,6aS,Z)-benzyl 5-benzylidenehexahydrocyclopenta[c]pyrrole-2(1H)-carboxylate (0.2 g, 0.60 mmol) in dichloromethane (prepared by the method described below), was added meta-Chloroperoxybenzoic acid (mCPBA) (0.41 g, 2.40 mmol) at room temperature and stirred for 4 h. After completion of the reaction (monitored by TLC), the mixture was diluted with ethyl acetate (50 mL). The ethyl acetate layer was washed with 50% sodium bicarbonate solution (15 mL×2), water (15 mL), brine (15 mL), dried over anhydrous sodium sulfate, filtered and concentrated under vacuum to afford the crude compound, which was purified by preparative HPLC (Column: CHIRALPAK IA (250 mm×4.6 mm×5 μm), Mobile phase: n-Hexane:Ethanol (80:20), Flow rate: 1.0 mL/min) separated two isomers to obtain the title compound benzyl (3aR,6aS)-3'-phenyltetrahydro-1H-spiro[cyclopenta[c]pyrrole-5,2'-oxirane]-2(3H)-carboxylate (0.1 g, major isomer, 6.93 retention time, off white semi solid) and 0.065 g of minor isomer, 10.29 retention time, off white semi solid). Calculated M+H: 350.17. Found M+H: 350.2.

Step-2: Preparation of (3aR,5r,6aS)-5-benzyloctahydrocyclopenta[c]pyrrol-5-ol

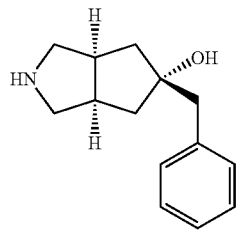

To a solution of benzyl (3aR,6aS)-benzyl 3'-phenyltetrahydro-1H-spiro[cyclopenta[c]pyrrole-5,2'-oxirane]-2(3H)-carboxylate (major isomer from previous step, 6.93 retention time) (0.2 g, 0.57 mmol) in ethanol (10 mL), was added 10% Pd/C (0.05 g) at room temperature. The reaction mixture was subjected to hydrogenation in balloon and stirred for 3 h. After completion of the reaction (monitored by TLC), the mixture was filtered through celite and washed with methanol. The filtrate was concentrated under vacuum to obtain the title compound (3aR,5r,6aS)-5-benzyloctahydrocyclopenta[c]pyrrol-5-ol (0.12 g (crude), 97% yield) as off white liquid. Calculated M+H: 218.15. Found M+H: 218.2.

Step-3: Preparation of 2-((3aR,5r,6aS)-5-benzyl-5-hydroxyhexahydrocyclopenta[c]pyrrol-2(1H)-yl)-1-(4-hydroxyphenyl)ethanone

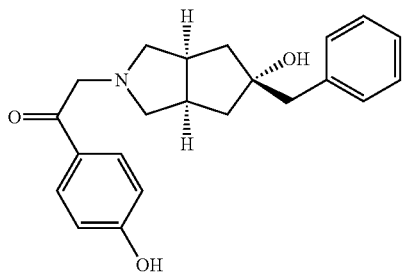 [SMILES: O=C(CN1C[C@@H]2C[C@](O)(Cc3ccccc3)C[C@@H]2C1)c1ccc(O)cc1]

To a stirred solution of (3aR,5r,6aS)-5-benzyloctahydrocyclopenta[c]pyrrol-5-ol (0.11 g, 0.51 mmol) in dimethyl formamide (10 mL), was added potassium carbonate (0.14 g, 1.01 mmol) and 2-bromo-1-(4-hydroxyphenyl)ethanone (0.087 g, 0.40 mmol) at room temperature and stirred for 6 h. After completion of the reaction (monitored by TLC), the reaction mixture was quenched with cold water and extracted with ethyl acetate (50 mL×3). The combined organic layer was washed with cold water (20 mL), brine (20 mL), dried over anhydrous sodium sulfate, filtered and concentrated under vacuum to afford the crude compound which was purified by preparative HPLC (Column: CHIRALPAK IA (250 mm×4.6 mm×5 μm), Mobile phase: nHexane:Ethanol (50:50), Flow rate: 1.0 mL/min) to obtain the title compound 2-((3aR,5r,6aS)-5-benzyl-5-hydroxyhexahydrocyclopenta[c]pyrrol-2(1H)-yl)-1-(4-hydroxyphenyl)ethanone (0.065 g, 36% yield) as a pale yellow solid. Calculated M+H: 352.18. Found M+H: 352.5.

Step 4: Preparation of (3aR,5R,6aS)-5-benzyl-2-((R)-2-hydroxy-2-(4-hydroxyphenyl)ethyl)octahydrocyclopenta[c]pyrrol-5-ol & (3aR,5S,6aS)-5-benzyl-2-((S)-2-hydroxy-2-(4-hydroxyphenyl)ethyl)octahydrocyclopenta[c]pyrrol-5-ol

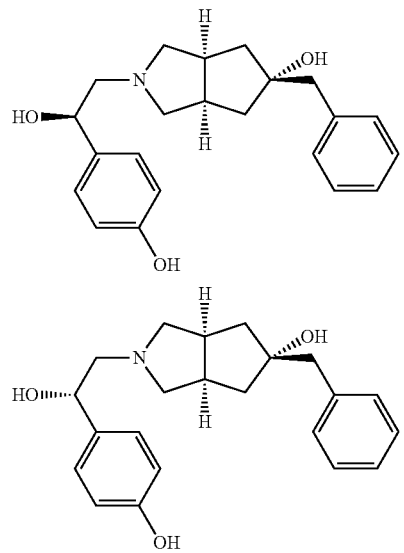

To a stirred solution of 2-((3aR,5r,6aS)-5-benzyl-5-hydroxyhexahydrocyclopenta[c]pyrrol-2(1H)-yl)-1-(4-hydroxyphenyl)ethanone (0.04 g, 0.11 mmol) in ethanol (20 mL), was added sodium borohydride (0.043 g, 1.14 mmol) at room temperature and stirred for 2 h. After completion of the reaction (monitored by TLC), the reaction mixture was concentrated under vacuum and the residue was diluted with water (15 mL) and extracted with ethyl acetate (50 mL×3). The combined organic layer was washed with brine (10 mL), dried over anhydrous sodium sulfate and concentrated under vacuum to afford the crude compound which was purified by preparative HPLC (Column: CHIRALPAK IA (250 mm×4.6 mm×5 μm), Mobile phase: nHexane:Ethanol (50:50), Flow rate: 1.0 mL/min) to obtain the title compound (3aR,5R,6aS)-5-benzyl-2-((R)-2-hydroxy-2-(4-hydroxyphenyl)ethyl)octahydrocyclopenta[c]pyrrol-5-ol (0.0052 g, 13% yield) as off-white solid. Calculated M+H: 354.20. Found M+H: 354.2, and (3aR,5S,6aS)-5-benzyl-2-((S)-2-hydroxy-2-(4-hydroxyphenyl)ethyl)octahydrocyclopenta[c]pyrrol-5-ol (0.0044 g, 11% yield) as off-white solid. Calculated M+H: 354.20. Found M+H: 354.3.

Example 43

Preparation of rac-2-((3aR,5r,6aS)-5-benzyl-5-hydroxyhexahydrocyclopenta[c]pyrrol-2(1H)-yl)-1-(4-hydroxyphenyl)propan-1-one Scheme 43

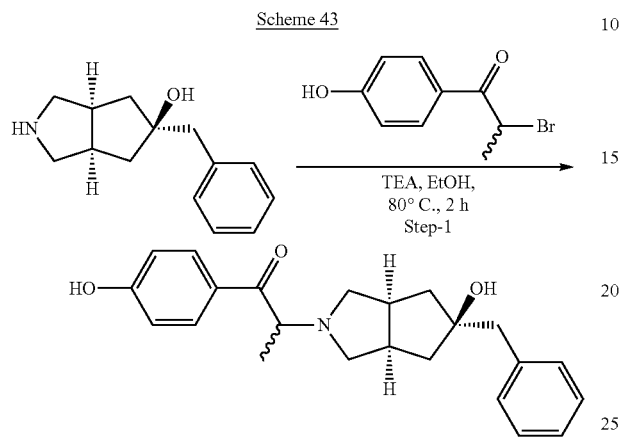

To a stirred solution of (3aR,5r,6aS)-5-benzyloctahydrocyclopenta[c]pyrrol-5-ol (0.15 g, 0.69 mmol) in ethanol (10 mL), was added triethylamine (0.21 g, 2.07 mmol) and 2-bromo-1-(4-hydroxyphenyl)propan-1-one (0.174 g, 0.76 mmol) at room temperature. The reaction mixture was heated to 80° C. and stirred for 2 h. After completion of the reaction (monitored by TLC), the mixture was concentrated under vacuum to afford the crude compound which was purified by preparative TLC using 10% methanol/dichloromethane to obtain the title compound 2-((3aR,5r,6aS)-5-benzyl-5-hydroxyhexahydrocyclopenta[c]pyrrol-2(1H)-yl)-1-(4-hydroxyphenyl)propan-1-one (0.09 g, 35.6% yield) as off white solid. Calculated M+H: 366.20. Found M+H: 366.3.

Example 44

Preparation of (3aR,6aS)-5-benzyl-N-(3-methoxyphenyl)hexahydrocyclopenta[c]pyrrole-2(1H)-carboxamide Scheme 44

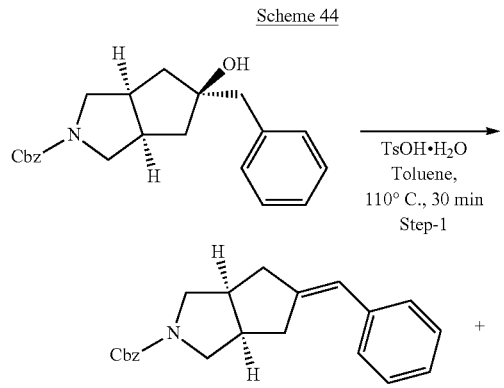

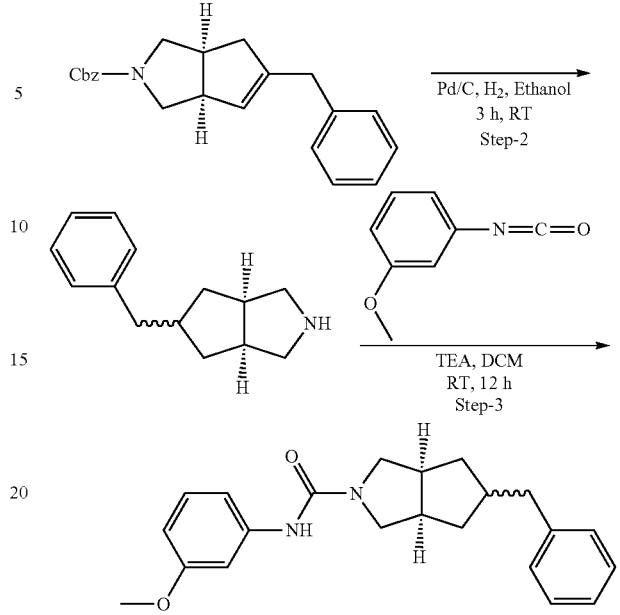

Step 1: Preparation of (3aR,6aS,Z)-benzyl 5-benzylidenehexahydrocyclopenta[c]pyrrole-2(1H)-carboxylate & (3aR,6aS)-benzyl 5-benzyl-3,3a,6,6a-tetrahydrocyclopenta[c]pyrrole-2(1H)-carboxylate

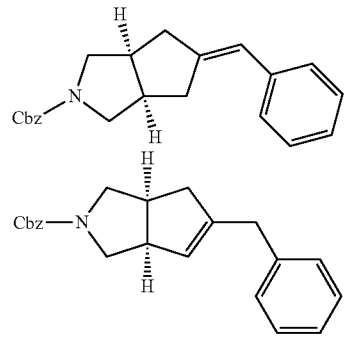

To a stirred solution of (3aR,5r,6aS)-benzyl 5-benzyl-5-hydroxyhexahydrocyclopenta[c]pyrrole-2(1H)-carboxylate (4.48 g, 12.78 mmol) in toluene was added p-Toluenesulfonic acid (2.67 g, 14.06 mmol) at room temperature. The reaction mixture was heated to 110° C. and stirred for 1.5 h. After completion of the reaction (monitored by TLC), the reaction mixture was allowed to cool to room temperature and diluted with ethyl acetate (250 mL). The ethyl acetate layer was washed with 50% sodium bicarbonate solution (50 ml×3), water (50 mL), brine (25 mL), dried over anhydrous sodium sulfate, filtered and concentrated under vacuum to afford the crude compound, which was purified by silica gel column chromatography (20% ethyl acetate/hexane) to obtain the title compound (3aR,6aS,Z)-benzyl 5-benzylidenehexahydrocyclopenta[c]pyrrole-2(1H)-carboxylate and (3aR,6aS)-benzyl 5-benzyl-3,3a,6,6a-tetrahydrocyclopenta[c]pyrrole-2(1H)-carboxylate (2.87 g, 66% yield) as a pale brown liquid (mixture of both the compounds taken for next step). Calculated M+H: 334.17. Found M+H: 334.2.

Step 2: Preparation of (3aR,6aS)-5-benzyloctahydrocyclopenta[c]pyrrole

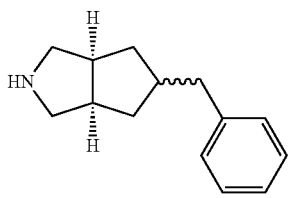 [SMILES: c1ccc(CC2C[C@H]3CNC[C@H]3C2)cc1]

To a solution of (3aR,6aS,Z)-benzyl 5-benzylidenehexahydrocyclopenta[c]pyrrole-2(1H)-carboxylate and (3aR,6aS)-benzyl 5-benzyl-3,3a,6,6a-tetrahydrocyclopenta[c]pyrrole-2(1H)-carboxylate (0.6 g, 1.8 mmol) in ethanol (30 mL), was added 10% Pd/C (0.3 g) at room temperature. The reaction mixture subjected to hydrogenation in balloon and stirred for 3 h. After completion of the reaction (monitored by TLC), the mixture was filtered through celite bed, washed with methanol. The filtrate was concentrated under vacuum to obtain the title compound (3aR,6aS)-5-benzyloctahydrocyclopenta[c]pyrrole (0.336 g, 92.8% yield) as a colorless liquid. Calculated M+H: 202.15. Found M+H: 202.2.

Step 3: Preparation of (3aR,6aS)-5-benzyl-N-(3-methoxyphenyl)hexahydrocyclopenta[c]pyrrole-2(1H)-carboxamide

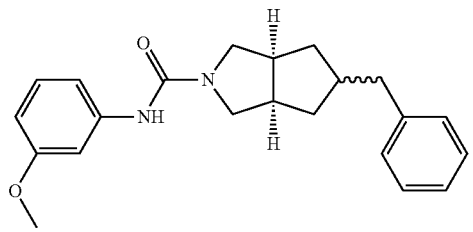 [SMILES: COc1cccc(NC(=O)N2C[C@H]3CC(Cc4ccccc4)C[C@H]3C2)c1]

To a solution of 5-benzyloctahydrocyclopenta[c]pyrrole (0.1 g, 0.49 mmol) and triethylamine (0.151 g, 1.49 mmol) in dichloromethane (10 mL) was added 1-isocyanato-3-methoxybenzene (0.071 g, 0.59 mmol) at 0° C. The reaction mixture was allowed to warm to room temperature and stirred for 12 h. After completion of the reaction (monitored by TLC), the reaction mixture was quenched with saturated sodium bicarbonate solution (15 mL) and extracted with dichloromethane (25 mL×3). The combined organic layer was washed with water (10 mL×3), brine (10 mL), dried over anhydrous sodium sulfate and concentrated under reduced pressure to afford the crude compound which was purified by silica column chromatography (3% methanol/dichloromethane) to obtain the title compound (3aR,6aS)-5-benzyl-N-(3-methoxyphenyl)hexahydrocyclopenta[c]pyrrole-2(1H)-carboxamide (0.11 g, 64.9% yield) as off-white solid. Calculated M+H: 351.20. Found M+H: 351.3.

Example 45

Preparation of rac-2-((3aR,6aS)-5-benzylhexahydrocyclopenta[c]pyrrol-2(1H)-yl)-1-(4-hydroxyphenyl)ethanone Scheme 45

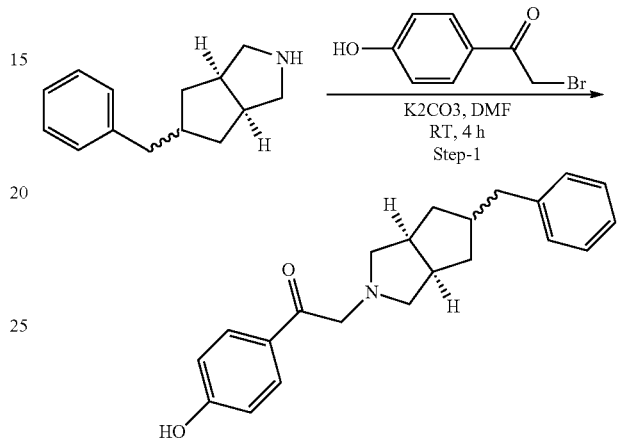

To a stirred solution of (3aR,6aS)-5-benzyloctahydrocyclopenta[c]pyrrole (0.1 g, 0.49 mmol) in dimethyl formamide (5 mL), was added potassium carbonate (0.20 g, 1.49 mmol) and 2-bromo-1-(4-hydroxyphenyl)ethanone (0.13 g, 0.59 mmol) at room temperature and stirred for 6 h. After completion of the reaction (monitored by TLC), the reaction mixture was quenched with cold water and extracted with ethyl acetate (30 mL×3). The combined organic layer were washed with cold water (25 mL×2), brine (20 mL), dried over anhydrous sodium sulfate, filtered and concentrated under vacuum to afford crude 2-((3aR,6aS)-5-benzylhexahydrocyclopenta[c]pyrrol-2(1H)-yl)-1-(4-hydroxyphenyl)ethanone which was purified by preparative HPLC (Method: Zorbax Eclipse Plus C18 RHD (50 mm×2.1 mm×1.8 μm), Mobile phase (A): 0.01% TFA in water, Mobile phase (B): ACN Flow rate: 0.3 mL/min T/% B: 0/10, 2/90, 3.8/90, 4.2/10, 5/10) to obtain the title compound 2-((3aR,6aS)-5-benzylhexahydrocyclopenta[c]pyrrol-2(1H)-yl)-1-(4-hydroxyphenyl)ethan-1-one as a TFA salt (0.013 g, 7.8% yield) as off white solid. Calculated M+H: 336.19. Found M+H: 336.5.

TABLE 15

The following compounds were prepared by the method described above

| Structure | IUPAC Name | Calculated (M + H) | Found (M + H) |
|---|---|---|---|
|  | rac-2-((3aR,6aS)-5-benzylhexahydrocyclopenta[c]pyrrol-2(1H)-yl)-1-(4-hydroxyphenyl)-propan-1-one | 350.20 | 350.3 |

TABLE 15-continued

The following compounds were prepared by the method described above

| Structure | IUPAC Name | Calculated (M + H) | Found (M + H) |
|---|---|---|---|
| | 2-{5-benzyl-octahydrocyclopenta[c]pyrrol-2-yl}-1-(5-hydroxypyridin-2-yl)ethan-1-one | 337.43 | 337.0 |
| | rac-6-(2-{5-benzyl-octahydrocyclopenta[c]pyrrol-2-yl}-1-hydroxyethyl)pyridin-3-ol | 339.44 | 339.2 |
| | 2-{5-benzyl-octahydrocyclopenta[c]pyrrol-2-yl}-1-(3-fluoro-4-hydroxyphenyl)ethan-1-one | 354.43 | 354.5 |
| | rac-4-(2-((3aR,6aS)-5-benzylhexahydrocyclopenta[c]pyrrol-2(1H)-yl)-1-hydroxyethyl)phenol | 338.2 | 338.2 |

Example 46

Preparation of (3aR,5r,6aS)-benzyl 5-benzylhexahydrocyclopenta[c]pyrrole-2(1H)-carboxylate and (3aR,5s,6aS)-benzyl 5-benzylhexahydrocyclopenta[c]pyrrole-2(1H)-carboxylate Scheme 46

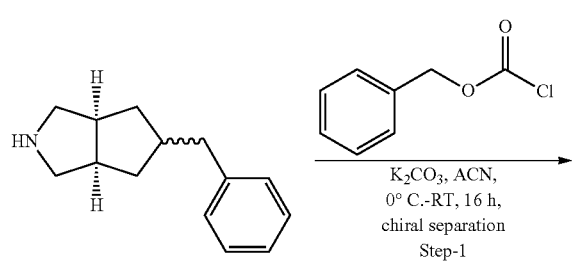

K₂CO₃, ACN,
0° C.-RT, 16 h,
chiral separation
Step-1

-continued

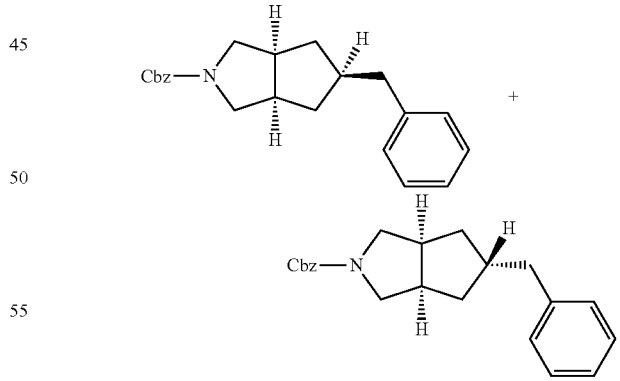

To a stirred solution of (3aR,6aS)-5-benzyloctahydrocyclopenta[c]pyrrole (1.5 g, 7.46 mmol) in acetonitrile (20 ml), potassium carbonate (3.1 g, 22.38 mmol) and benzyl carbonochloridate (1.6 mL, 11.19 mmol) were added at 0° C. The reaction mixture was stirred at room temperature for 16 h. The suspension was diluted with ethyl acetate (25 mL), filtered and washed with 25 mL ethyl acetate. The combined filtrate was dried over anhydrous sodium sulfate, filtered and evaporated in vacuum to afford crude which was purified by chiral HPLC (analytical conditions: column: CHIRALPAK IA (250 mm×4.6 mm×5 μm), mobile phase: 0.01% DEA in IPA, flow rate: 0.5 mL/min) to afford the title compounds (3aR,5r,6aS)-benzyl 5-benzylhexahydrocyclopenta[c]pyrrole-2(1H)-carboxylate (2) (0.26 g, 10.4%) as colourless liquid [Calculated (M+H): 336.44. Found (M+1): 336.22] and (3aR,5s,6aS)-benzyl 5-benzylhexahydrocyclopenta[c]pyrrole-2(1H)-carboxylate (2A) (0.19 g, 7.6%) as colourless liquid [Calculated (M+H): 336.44. Found (M+1): 336.2]. The stereochemistry given to 2 and 2A are tentative and they are not absolute.

TABLE 16

The following compounds were prepared by the method described above.

| Structure | IUPAC Name | Calculated M + H | Found M + H |
|---|---|---|---|
|  | rac-4-{2-[(3aR,5S,6aS)-5-benzyl-octahydro-cyclopenta[c]pyrrol-2-yl]-1-hydroxyethyl}-2-fluorophenol | 356.45 | 356.3 |
|  | rac-4-{2-[(3aR,5R,6aS)-5-benzyl-octahydro-cyclopenta[c]pyrrol-2-yl]-1-hydroxyethyl}-2-fluorophenol | 356.45 | 356.5 |
|  | 2-[(3aR,5S,6aS)-5-benzyl-octahydro-cyclopenta[c]pyrrol-2-yl]-1-(4-hydroxyphenyl)ethan-1-onefluorophenol | 336.44 | 336.5 |
|  | rac-4-{2-[(3aR,5S,6aS)-5-benzyl-octahydro-cyclopenta[c]pyrrol-2-yl]-1-hydroxyethyl}phenol | 338.46 | 338.5 |
|  | 2-[(3aR,5R,6aS)-5-benzyl-octahydro-cyclopenta[c]pyrrol-2-yl]-1-(4-hydroxyphenyl)ethan-1-one | 336.44 | 336.2 |
|  | rac-4-{2-[(3aR,5R,6aS)-5-benzyl-octahydro-cyclopenta[c]pyrrol-2-yl]-1-hydroxyethyl}phenol | 338.46 | 338.3 |

TABLE 16-continued

The following compounds were prepared by the method described above.

| Structure | IUPAC Name | Calculated M + H | Found M + H |
|---|---|---|---|
| 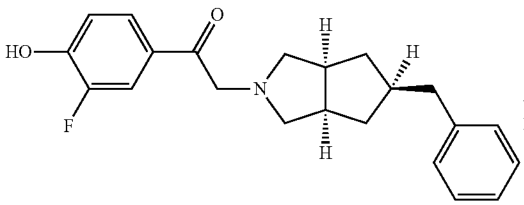 | 2-[(3aR,5S,6aS)-5-benzyl-octahydro-cyclopenta[c]pyrrol-2-yl]-1-(3-fluoro-4-hydroxy-phenyl)ethan-1-one | 354.43 | 354.5 |
| 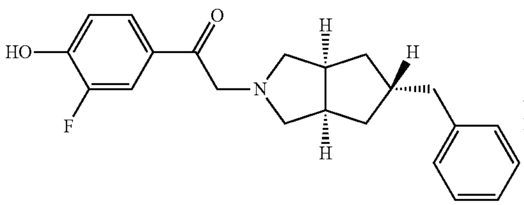 | 2-[(3aR,5R,6aS)-5-benzyl-octahydro-cyclopenta[c]pyrrol-2-yl]-1-(3-fluoro-4-hydroxy-phenyl)ethan-1-one | 354.43 | 354.5 |

Example 47

Preparation of rac-2-((3aR,6aS)-5-benzylhexahydro-cyclopenta[c]pyrrol-2(1H)-yl)-1-(3-(trifluoromethyl)phenyl)ethanol Scheme 47

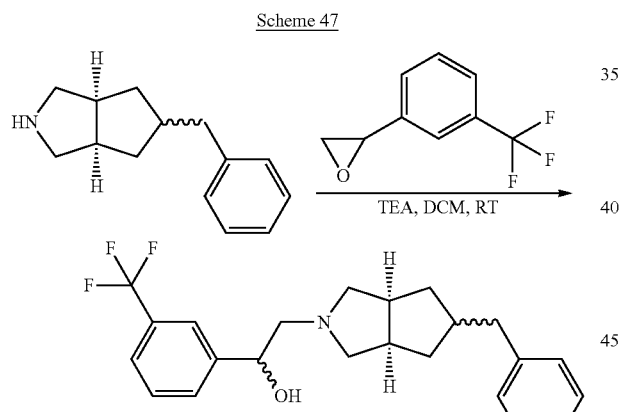

To a solution of (3aR,6aS)-5-benzyloctahydrocyclopenta[c]pyrrole (0.1 g, 0.49 mmol) in dimethyl formamide (0.040 g, 0.19 mmol) in dichloromethane (2 mL) was added 2-(3-(trifluoromethoxy)phenyl)oxirane (0.044 g, 0.22 mmol) and triethylamine (0.041 mL, 0.29 mmol) and resulting solution was stirred at room temperature for 18 h. After completion of reaction (monitored by TLC), the reaction mixture was diluted with water (2 mL) and extracted with dichloromethane (5 mL×2), washed with brine (10 mL), dried over sodium sulfate and concentrated under vacuum to give the crude 2-((3aR,6aS)-5-benzylhexahydrocyclopenta[c]pyrrol-2(1H)-yl)-1-(3-(trifluoromethyl)phenyl)ethanol which was purified by prep HPLC (column: XSelect CSH C-18 Prep (19×250 mm, 5 um), mobile phase: A—5 mM ammonium acetate, B—Acetonitrile, flow mode: gradient, flow: 15 ml/min, gradient T/% B: 0/30, 0.5/30, 15/90, 21/90, 21.5/30, 26/30).

Example 48

Preparation of 5-hydroxy-N-(4-methoxyphenyl)-5-phenylhexahydrocyclopenta[c]pyrrole-2(1H)-carboxamide Scheme 48
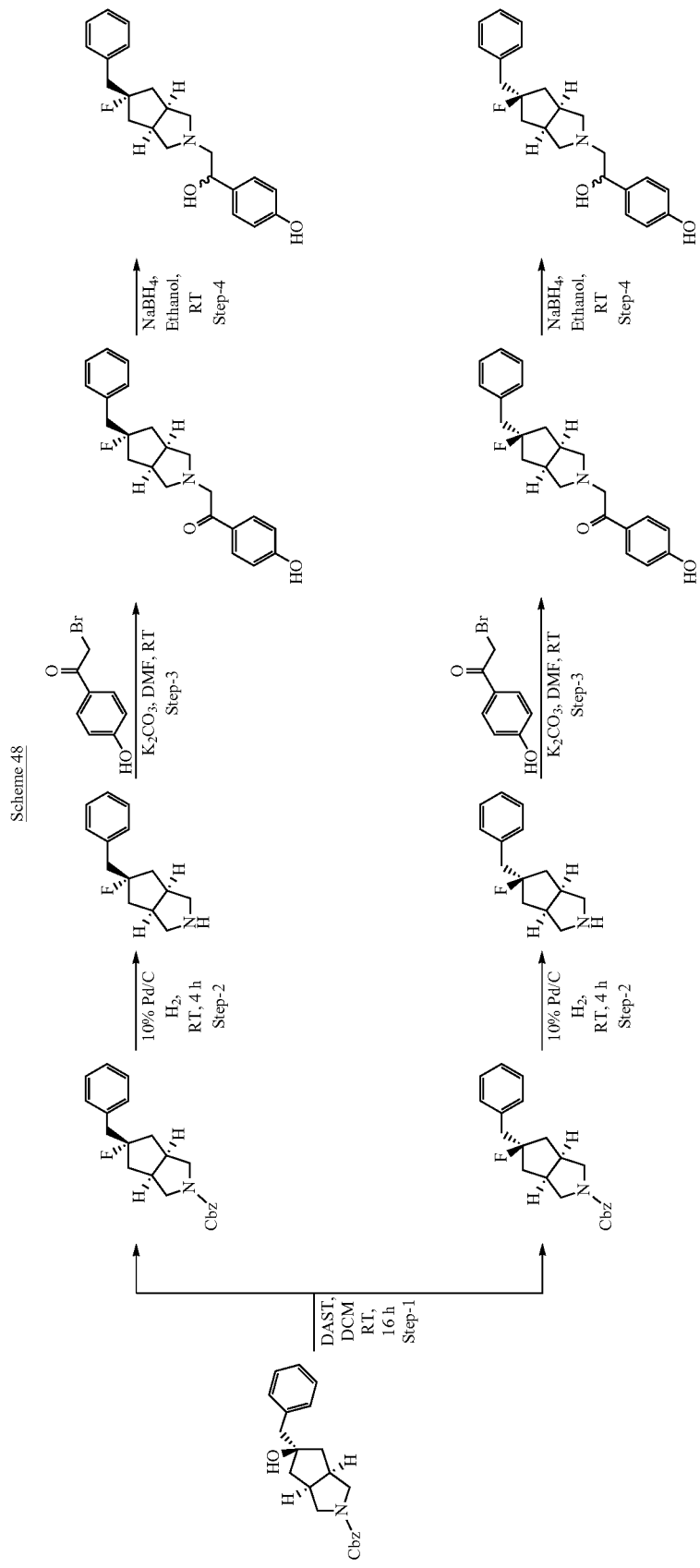

Step-1: Preparation of (3aR,5s,6aS)-benzyl 5-benzyl-5-fluorohexahydrocyclopenta[c]pyrrole-2(1H)-carboxylate (2A) & (3aR,5r,6aS)-benzyl 5-benzyl-5-fluorohexahydrocyclopenta[c]pyrrole-2(1H)-carboxylate (2B)

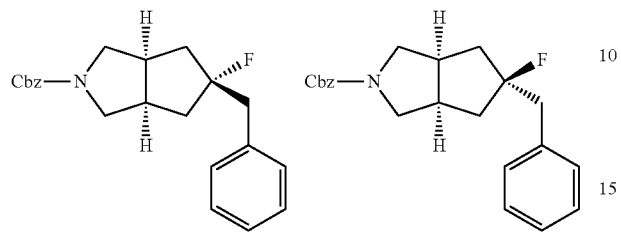

To a stirred solution of (3aR,5r,6aS)-benzyl 5-benzyl-5-hydroxyhexahydrocyclopenta[c]pyrrole-2(1H)-carboxylate (4.0 g, 11.3 mmol) in dichloromethane was added diethylaminosulfur trifluoride (3.3 mL, 25.0 mmol) at room temperature and stirred for 16 h. After completion of reaction (monitored by TLC), the reaction mixture was diluted with water (100 mL), extracted with dichloromethane (100 mL×3). Organic layer was washed with water (50 mL), brine (50 mL), dried over anhydrous sodium sulfate, filtered and evaporated to afford crude product, which was purified by silica gel column chromatography (0-25% ethylacetate/hexane) to obtain the title compound (3aR,5s,6aS)-benzyl 5-benzyl-5-fluorohexahydrocyclopenta[c]pyrrole-2(1H)-carboxylate (2A) (2.8 g, 70% yield) as a colorless semi solid. Calculated (M+H): 354.43. Found (M+1): 354.18 and (3aR,5r,6aS)-benzyl 5-benzyl-5-fluorohexahydrocyclopenta[c]pyrrole-2(1H)-carboxylate (2B) (0.38 g, 9.5% yield) as colorless semi solid. Calculated (M+H): 354.18. Found (M+1): 354.2.

Step-2: Preparation of (3aR,5s,6aS)-5-benzyl-5-fluorooctahydrocyclopenta[c]pyrrole

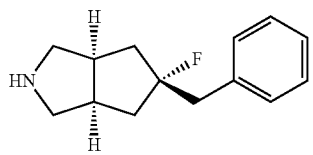 [SMILES: F[C@]1(Cc2ccccc2)C[C@H]2CNC[C@H]2C1]

To a stirred solution of (3aR,5s,6aS)-benzyl 5-benzyl-5-fluorohexahydrocyclopenta[c]pyrrole-2(1H)-carboxylate (0.92 g, 2.6 mol) in ethanol (20 mL), was added 10% Pd/C (0.25 g) under $N_2$ atmosphere. The reaction mixture was subjected to hydrogenation in balloon and stirred for 6 h. After completion of reaction (monitored by TLC), the mixture was filtered through celite bed, washed with methanol. The filtrate was concentrated under vacuum to obtain the title compound (3aR,5s,6aS)-5-benzyl-5-fluorooctahydrocyclopenta[c]pyrrole [0.62 g (crude)] as colorless semi solid. Calculated (M+H): 220.14. Found (M+H): 220.2.

Step-3: Preparation of 2-((3aR,5s,6aS)-5-benzyl-5-fluorohexahydrocyclopenta[c]pyrrol-2(1H)-yl)-1-(4-hydroxyphenyl)ethanone

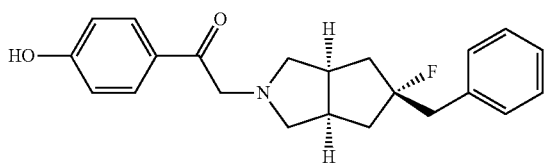

To a stirred solution of (3aR,5s,6aS)-5-benzyl-5-fluorooctahydrocyclopenta[c]pyrrole (0.1 g, 0.46 mmol) in dimethylformamide (5 mL) was added potassium carbonate (0.12 g, 0.91 mmol) and 2-bromo-1-(4-hydroxyphenyl)ethanone (0.078 g, 0.36 mmol) at room temperature. The reaction mixture was stirred at room temperature for 4 h. After completion of reaction (monitored by TLC), the mixture was diluted with cold water (10 mL) and extracted with ethylacetate (30 mL×3). The combined organic layer was washed with cold water (15 mL×2), brine (15 mL), dried over anhydrous sodium sulfate, filtered and concentrated under reduced pressure to afford the crude compound, which was purified by silica gel column chromatography (6% methanol/dichloromethane) to obtain the title compound 2-((3aR,5s,6aS)-5-benzyl-5-fluorohexahydrocyclopenta[c]pyrrol-2(1H)-yl)-1-(4-hydroxyphenyl)ethanone (0.035 g, 22% yield) as a pale yellow solid. Calculated (M+H): 354.18. Found (M+H): 354.2.

TABLE 17

The following compound was prepared by the method described above

| Structure | IUPAC Name | Calculated (M + H) | Found (M + H) |
|---|---|---|---|
| 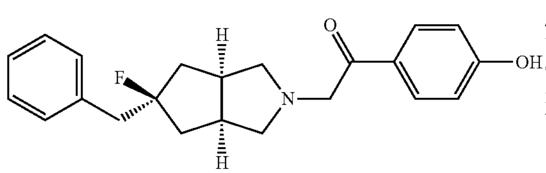 | 4-(2-((3aR,5s,6aS)-5-benzyl-5-fluorohexahydrocyclopenta[c]pyrrol-2(1H)-yl)-1-hydroxyethyl)phenol | 354.18 | 354.4 |

Step-4: Preparation of rac-4-(2-((3aR,5s,6aS)-5-benzyl-5-fluorohexahydrocyclopenta[c]pyrrol-2(1H)-yl)-1-hydroxyethyl)phenol

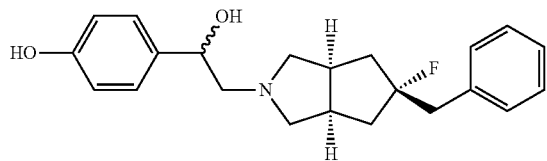

To a stirred solution of 2-((3aR,5s,6aS)-5-benzyl-5-fluorohexahydrocyclopenta[c]pyrrol-2(1H)-yl)-1-(4-hydroxyphenyl)ethanone (0.14 g, 0.3961 mmol) in ethanol was added sodium borohydride (0.14 g, 3.96 mmol) at room temperature and stirred for 6 h. After completion of reaction (monitored by TLC), the solvent was removed under vacuum and the residue was diluted with water (20 mL) and extracted with ethyl acetate (25 mL×3). The combined organic layer was washed with water (25 mL), brine (20 mL), dried over anhydrous sodium sulfate, filtered and concentrated under vacuum to afford the crude compound which was purified by column chromatography using preparative TLC (8% methanol/dichloromethane) to obtain the title compound 4-(2-((3aR,5s,6aS)-5-benzyl-5-fluorohexahydrocyclopenta[c]pyrrol-2(1H)-yl)-1-hydroxyethyl)phenol (0.055 g, 39% yield) as a white solid. Calculated (M+H): 356.19. Found (M+H): 356.5.

TABLE 18

The following compounds were prepared by the method described above.

| Structure | IUPAC Name | Calculated (M + H) | Found (M + H) |
|---|---|---|---|
| 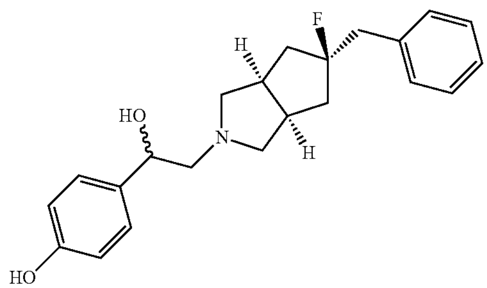 [SMILES: Oc1ccc(C(O)CN2C[C@@H]3C[C@@](F)(Cc4ccccc4)C[C@@H]3C2)cc1] | rac-4-(2-((3aR,5r,6aS)-5-benzyl-5-fluorohexahydrocyclopenta[c]pyrrol-2(1H)-yl)-1-hydroxyethyl)phenol | 356.19 | 356.5 |
| 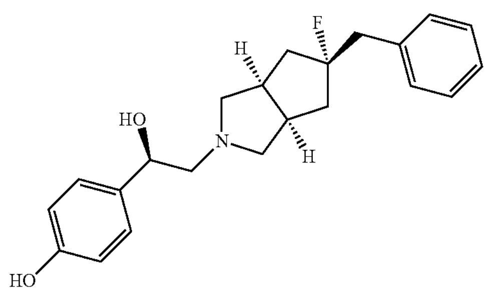 [SMILES: Oc1ccc([C@@H](O)CN2C[C@@H]3C[C@](F)(Cc4ccccc4)C[C@@H]3C2)cc1] | rac-4-((R)-2-((3aR,5S,6aS)-5-benzyl-5-fluorohexahydrocyclopenta[c]pyrrol-2(1H)-yl)-1-hydroxyethyl)phenol | 356.19 | 356.2 |
| 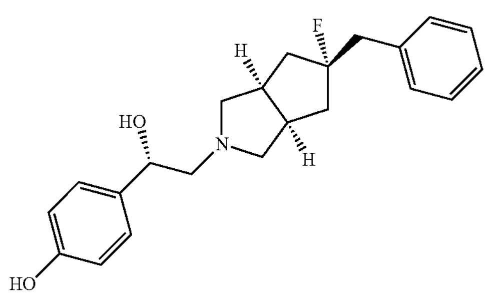 [SMILES: Oc1ccc([C@H](O)CN2C[C@@H]3C[C@](F)(Cc4ccccc4)C[C@@H]3C2)cc1] | rac-4-((S)-2-((3aR,5R,6aS)-5-benzyl-5-fluorohexahydrocyclopenta[c]pyrrol-2(1H)-yl)-1-hydroxyethyl)phenol | 356.19 | 356.2 |

TABLE 18-continued

The following compounds were prepared by the method described above.

| Structure | IUPAC Name | Calculated (M + H) | Found (M + H) |
|---|---|---|---|
| 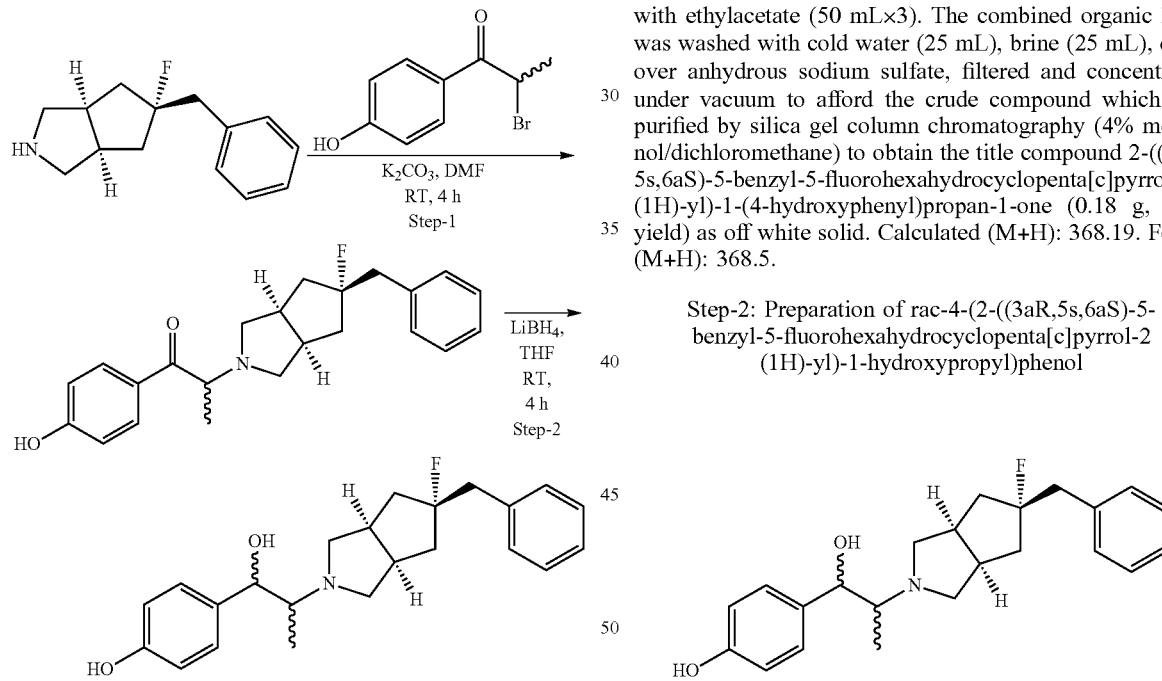 | rac-4-(2-((3aR,5s,6aS)-5-benzyl-5-fluorohexahydro-cyclopenta[c]pyrrol-2(1H)-yl)-1-hydroxyethyl)-2-fluorophenol | 374.19 | 374.5 |

Example 49

Preparation of rac-4-(2-((3aR,5s,6aS)-5-benzyl-5-fluorohexahydrocyclopenta[c]pyrrol-2(1H)-yl)-1-hydroxypropyl)phenol Scheme 49

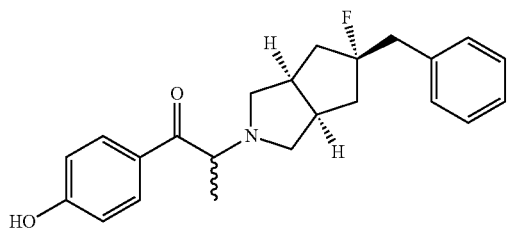 [SMILES: CC(C(=O)c1ccc(O)cc1)N1C[C@@H]2C[C@](F)(Cc3ccccc3)C[C@@H]2C1]

Step-1: Preparation of rac-2-((3aR,5s,6aS)-5-benzyl-5-fluorohexahydrocyclopenta[c]pyrrol-2(1H)-yl)-1-(4-hydroxyphenyl)propan-1-one To a stirred solution of (3aR,5s,6aS)-5-benzyl-5-fluorooctahydrocyclopenta[c]pyrrole (0.31 g, 1.41 mmol) in dimethylformamide (20 mL) was added potassium carbonate (0.39 g, 2.82 mmol) and 2-bromo-1-(4-hydroxyphenyl)propan-1-one (0.32 g, 1.41 mmol) at room temperature and stirred for 4 h. After completion of reaction (monitored by TLC), the mixture was diluted with cold water (30 mL) and extracted with ethylacetate (50 mL×3). The combined organic layer was washed with cold water (25 mL), brine (25 mL), dried over anhydrous sodium sulfate, filtered and concentrated under vacuum to afford the crude compound which was purified by silica gel column chromatography (4% methanol/dichloromethane) to obtain the title compound 2-((3aR,5s,6aS)-5-benzyl-5-fluorohexahydrocyclopenta[c]pyrrol-2(1H)-yl)-1-(4-hydroxyphenyl)propan-1-one (0.18 g, 36% yield) as off white solid. Calculated (M+H): 368.19. Found (M+H): 368.5.

Step-2: Preparation of rac-4-(2-((3aR,5s,6aS)-5-benzyl-5-fluorohexahydrocyclopenta[c]pyrrol-2(1H)-yl)-1-hydroxypropyl)phenol To a stirred suspension of lithium borohydride (0.044 g, 2.04 mmol), in tetrahydrofuran (10 mL) was added 2-((3aR,5s,6aS)-5-benzyl-5-fluorohexahydrocyclopenta[c]pyrrol-2(1H)-yl)-1-(4-hydroxyphenyl)propan-1-one (0.075 g, 0.204 mmol) at room temperature and stirred for 12 h. After completion of reaction (monitored by TLC), the reaction mixture was quenched with ice water (10 mL) and extracted with ethyl acetate (30 ml×3). The combined organic layer was washed with water (10 mL×3), brine (10 mL), dried over anhydrous sodium sulfate, filtered and concentrated to afford the crude compound, which was purified by silica gel column chromatography (6% methanol/dichloromethane) to obtain the title compound 4-(2-((3aR,5s,6aS)-5-benzyl-5-fluorohexahydrocyclopenta[c]pyrrol-2(1H)-yl)-1-hydroxypropyl)phenol (0.035 g, 46% yield) as a white solid. Calculated (M+H): 370.21. Found (M+H): 370.5.

Example 50

Preparation of rac-2-(5-hydroxy-5-phenethylhexahydrocyclopenta[c]pyrrol-2(1H)-yl)-1-(4-hydroxyphenyl)propan-1-one Scheme 50

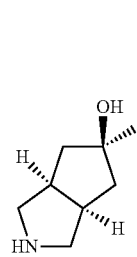 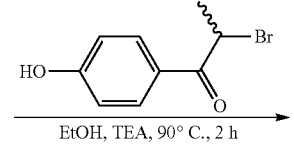

To a solution of 5-phenethyloctahydrocyclopenta[c]pyrrol-5-ol (0.10 g, 0.43 mmol) and 2-bromo-1-(4-hydroxyphenyl)propan-1-one (0.12 g, 0.51 mmol) in ethanol (2 mL) was added triethylamine (0.14 mL, 1.02 mmol) and the resulting suspension was heated to 90° C. and stirred for 2 h. After completion of reaction (monitored by TLC), the reaction was allowed to cool to room temperature, diluted with ethyl acetate (5 mL), washed with water (15 mL×2), dried over sodium sulfate and concentrated to afford the crude 2-(5-hydroxy-5-phenethylhexahydrocyclopenta[c]pyrrol-2(1H)-yl)-1-(4-hydroxyphenyl)propan-1-one which was purified by prep HPLC; (Method: Column: XSelect CSH C-18 Prep (19×250 mm, 5 um), Mobile phase: A—5 mM ammonium Acetate, B—Acetonitrile, Flow mode: Gradient, Flow: 15 ml/min, T/% B: 0.0/30, 0.5/30, 15.0/90, 21.0/90, 21.5/30, 26.0/30).

Example 51

Preparation of rac-2-(1-hydroxy-1-(4-hydroxyphenyl)propan-2-yl)-5-phenethyloctahydrocyclopenta[c]pyrrol-5-ol Scheme 51

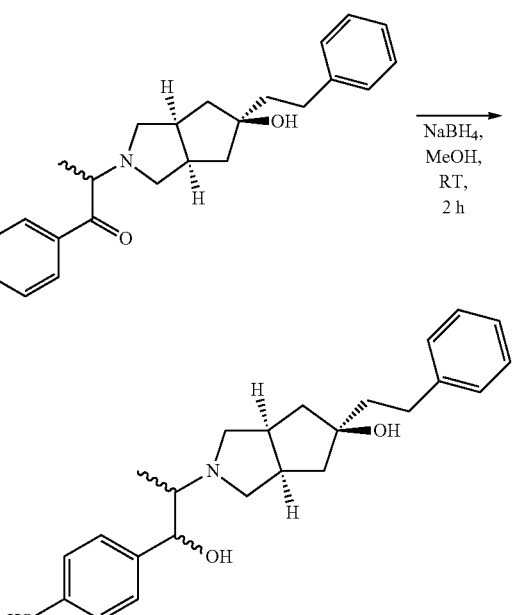

To a solution of 2-(5-hydroxy-5-phenethylhexahydrocyclopenta[c]pyrrol-2(1H)-yl)-1-(4-hydroxyphenyl)propan-1-one (0.070 g, 0.19 mmol) in methanol (3 mL), was added $NaBH_4$ (0.02 g, 0.47 mmol) and the resulting suspension was stirred at room temperature for 2 h. After completion of reaction (monitored by TLC), the reaction mixture was concentrated under vacuum and the residue was dissolved in ethyl acetate (20 mL). The organic layer was washed with brine (15 mL×2), dried over sodium sulfate and concentrated under vacuum to obtain crude 2-(1-hydroxy-1-(4-hydroxyphenyl)propan-2-yl)-5-phenethyloctahydrocyclopenta[c]pyrrol-5-ol, which was purified by prep HPLC; (Method: Column: XSelect CSH C-18 Prep (19×250 mm, 5 um), Mobile phase: A—5 mM ammonium acetate, B—Acetonitrile, Flow mode: Gradient, Flow: 15 ml/min, T/% B: 0.0/30, 0.5/30, 15.0/90, 21.0/90, 21.5/30, 26.0/30).

TABLE 19

The following compounds were prepared by the method described above.

| Structure | IUPAC Name | Calculated M + H | Found M + H |
|---|---|---|---|
| 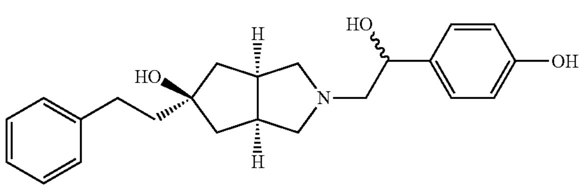 | rac-2-(2-hydroxy-2-(4-hydroxyphenyl)ethyl)-5-phenethyloctahydrocyclopenta[c]pyrrol-5-ol | 368.21 | 368.22 |

Example 52

Preparation of 1-(4-hydroxyphenyl)-2-[(5R)-5-(2-phenylethyl)-octahydrocyclopenta[c]pyrrol-2-yl]propan-1-one Scheme 52

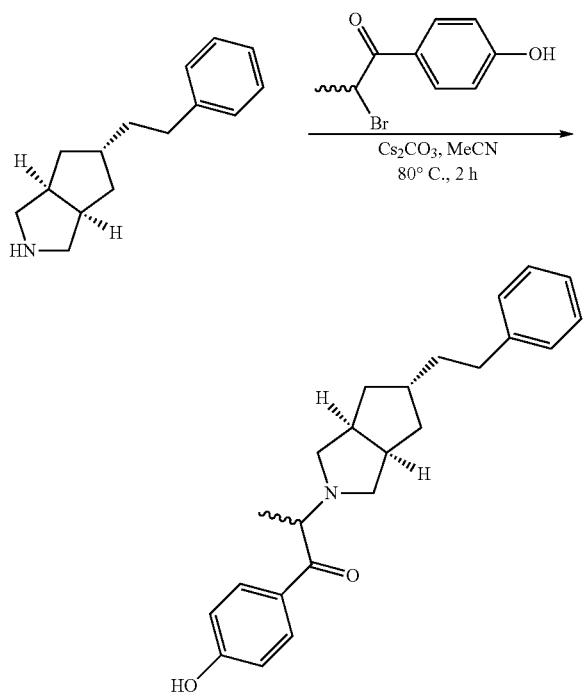

To a solution of 5-phenethyloctahydrocyclopenta[c]pyrrole (0.035 g, 0.16 mmol) and 2-bromo-1-(4-hydroxyphenyl)propan-1-one (0.036 g, 0.16 mmol) in acetonitrile (2 mL) was added $Cs_2CO_3$ (0.16 g, 0.49 mmol) and the resulting suspension was heated to 80° C. and stirred for 2 h. After completion of reaction (monitored by TLC), the reaction mixture was allowed to cool to room temperature and diluted with ethyl acetate (5 mL). The resulting mixture was washed with water (15 mL×2), dried over sodium sulfate and concentrated to afford crude 1-(4-hydroxyphenyl)-2-[(5R)-5-(2-phenylethyl)-octahydrocyclopenta[c]pyrrol-2-yl]propan-1-one, which was purified by prep HPLC; (Method: Column: XSelect CSH C-18 Prep (19×250 mm, 5 um), Mobile phase: A—5 mM ammonium Acetate, B—Acetonitrile, Flow mode: Gradient, Flow: 15 ml/min, T/% B: 0.0/30, 0.5/30, 15.0/90, 21.0/90, 21.5/30, 26.0/30).

TABLE 20

The following compounds were prepared by the method described above

| Structure | IUPAC Name | Calculated M + H | Found M + H |
|---|---|---|---|
| 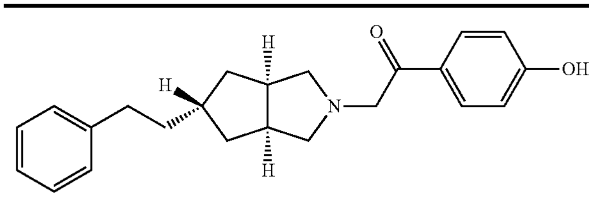 | 1-(4-hydroxyphenyl)-2-(5-phenethylhexahydrocyclo-penta[c]-pyrrol-2(1H)-yl)ethanone | 350.20 | 350.09 |
| 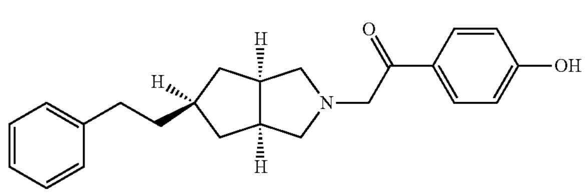 [SMILES: O=C(CN1C[C@H]2C[C@@H](CCc3ccccc3)C[C@H]2C1)c1ccc(O)cc1] | 1-(4-hydroxyphenyl)-2-((3aR,5r,6aS)-5-phenethylhexahydro-cyclopenta[c]pyrrol-2(1H)-yl)ethanone | 350.20 | 350.09 |
| 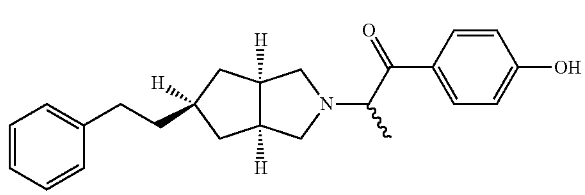 [SMILES: CC(C(=O)c1ccc(O)cc1)N1C[C@H]2C[C@@H](CCc3ccccc3)C[C@H]2C1] | 1-(4-hydroxyphenyl)-2-((3aR,5r,6aS)-5-phenethylhexahydro cyclo-penta[c]pyrrol-2(1H)-yl)propan-1-one | 364.22 | 364.18 |

Example 53

Preparation of 4-(2-(5-benzylhexahydropyrrolo[3,4-c]pyrrol-2(1H)-yl)-1-hydroxyethyl)phenol Scheme 53

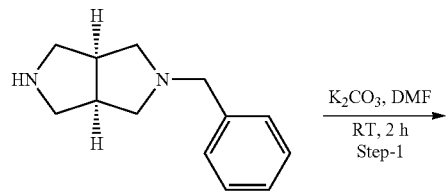

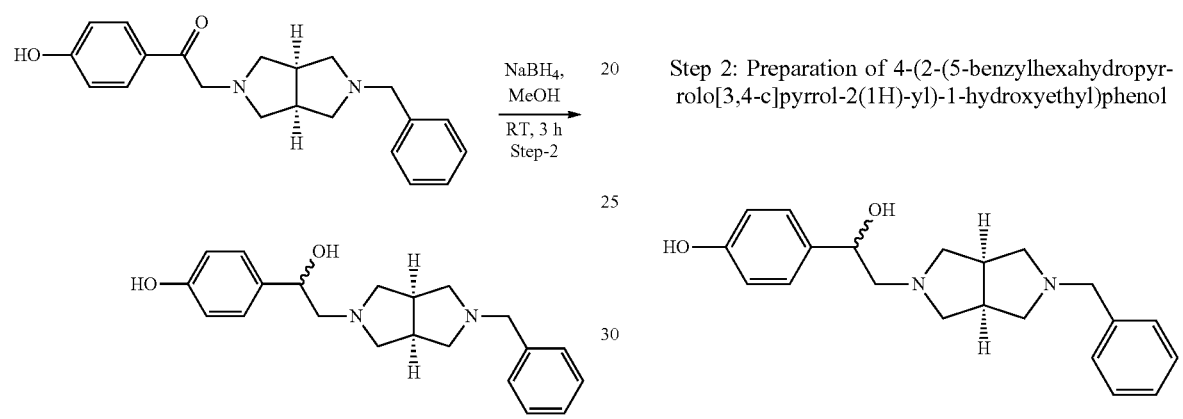

Step 1: Preparation of 2-(5-benzylhexahydropyrrolo[3,4-c]pyrrol-2(1H)-yl)-1-(4-hydroxyphenyl)ethanone 2-bromo-1-(4-hydroxyphenyl)ethanone (0.107 g, 0.494 mmol) was added to a mixture of commercially available 2-benzyloctahydropyrrolo[3,4-c]pyrrole (0.1 g, 0.494 mmol) and potassium carbonate (0.2 g, 1.48 mmol) in DMF (5 mL) at 0° C. and the reaction mixture was stirred at room temperature for 2 h. The suspension was filtered and the filtrate was evaporated. The crude material was purified by combi flash purifier using 8% methanol in dichloromethane to afford the title compound 2-(5-benzylhexahydropyrrolo[3,4-c]pyrrol-2(1H)-yl)-1-(4-hydroxyphenyl)ethanone (0.12 g, 72% yield) as a white solid. Calculated M+H: 337.43. Found M+H: 337.2.

Step 2: Preparation of 4-(2-(5-benzylhexahydropyrrolo[3,4-c]pyrrol-2(1H)-yl)-1-hydroxyethyl)phenol Sodium borohydride (0.112 g, 2.97 mmol) was added to a solution of 2-(5-benzylhexahydropyrrolo[3,4-c]pyrrol-2(1H)-yl)-1-(4-hydroxyphenyl)ethanone (0.1 g, 0.297 mmol) in methanol (5 mL) at 0° C. and the reaction mixture was stirred at room temperature for 3 h. Then the reaction mixture was evaporated and the residue was diluted with water and extracted with dichloromethane (30 mL×2). The combined organic extract was dried over anhydrous sodium sulfate and evaporated to dryness. The crude material was purified by preparative HPLC (analytical conditions: column: zorbax XDB C18 (150 mm×4.6 mm×3.5 μm) mobile phase (A): 0.01% ammonia in water, mobile phase (B): acetonitrile, flow rate: 1.0 mL/min, T/% B: 0/20, 10/70, 25/70, 27/20, 30/20) to afford 4-(2-(5-benzylhexahydropyrrolo[3,4-c]pyrrol-2(1H)-yl)-1-hydroxyethyl)phenol as a white solid (0.03 g, 30.0% yield). Calculated M+H: 339.44. Found M+H: 339.5.

TABLE 21

The following compounds were prepared by the method described above.

| Structure | IUPAC Name | Calculated M + H | Found M + H |
|---|---|---|---|
| 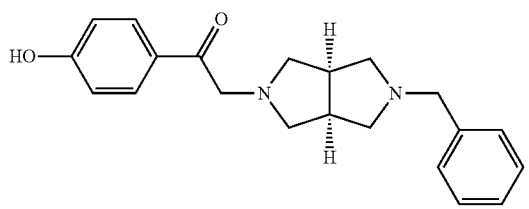 | 2-(5-benzylhexahydropyrrolo[3,4-c]pyrrol-2(1H)-yl)-1-(5-hydroxypyridin-2-yl)ethanone | 338.42 | 338.5 |

TABLE 21-continued

The following compounds were prepared by the method described above.

| Structure | IUPAC Name | Calculated M + H | Found M + H |
|---|---|---|---|
| 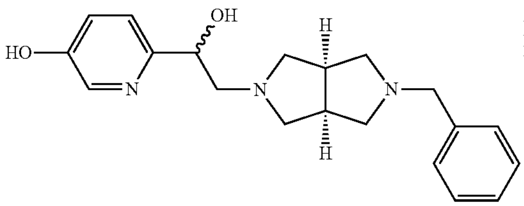 | rac-6-(2-(5-benzylhexahydro-pyrrolo[3,4-c]pyrrol-2(1H)-yl)-1-hydroxy-ethyl)pyridin-3-ol | 340.43 | 340.4 |
| 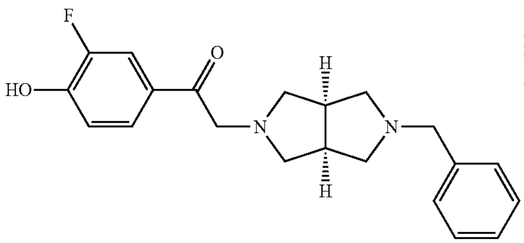 | 2-(5-benzylhexahydro-pyrrolo[3,4-c]pyrrol-2(1H)-yl)-1-(3-fluoro-4-hydroxyphenyl)ethanone | 355.42 | 355.4 |
| 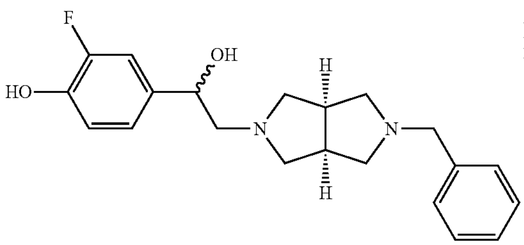 | rac-4-(2-(5-benzylhexahydro-pyrrolo[3,4-c]pyrrol-2(1H)-yl)-1-hydroxyethyl)-2-fluorophenol | 357.43 | 357.5 |

Example 54

Preparation of 6-benzyl-2-(2-hydroxy-2-(4-hydroxyphenyl)ethyl)-2-azaspiro[3.3]heptan-6-ol

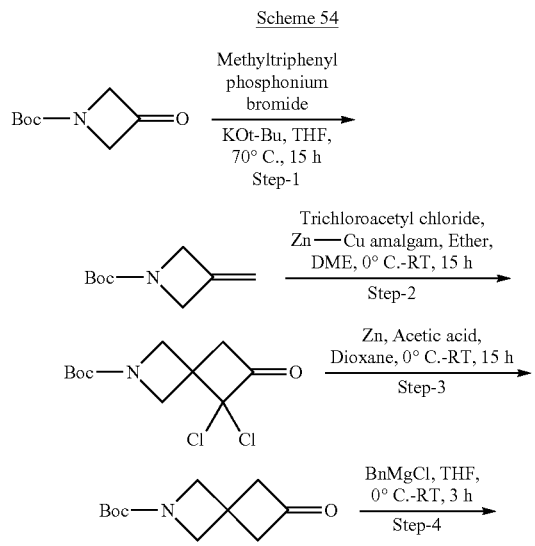

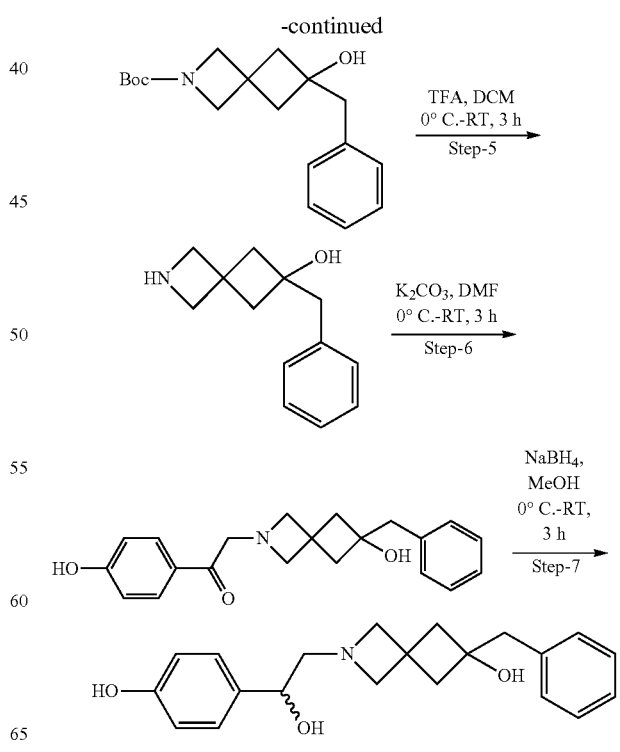

Step 1: Preparation of tert-butyl 3-methyleneazetidine-1-carboxylate

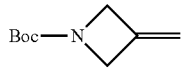

Potassium tert-butoxide (4.27 g, 37.96 mmol) was added to a suspension of methyltriphenylphosphonium bromide (13.56 g, 37.96 mmol) in tetrahydrofuran (80 mL) and the reaction mixture was heated at 70° C. for 4 h. Then the reaction mixture was cooled to 50° C. and added a solution of tert-butyl 3-oxoazetidine-1-carboxylate (5 g, 29.2 mmol) in tetrahydrofuran (20 mL) and heated at 70° C. for 15 h. The reaction mixture was cooled to room temperature and evaporated to dryness. The crude material was purified by combiflash purifier using 4% ethyl acetate in hexane to afford the title compound tert-butyl 3-methyleneazetidine-1-carboxylate (4 g, 80% yield) as a colorless liquid. $^1$H NMR (400 MHz, CDCl$_3$) δ 4.98 (s, 2H), 4.47 (s, 4H), 1.45 (s, 9H).

Step 2: Preparation of tert-butyl 5,5-dichloro-6-oxo-2-azaspiro[3.3]heptane-2-carboxylate

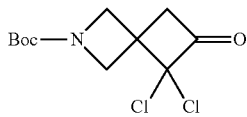

A solution trichloroacetyl chloride (3.32 mL, 29.56 mmol) in 1,2-dimethoxyethane (10 mL) was added dropwise to a mixture of tert-butyl 3-methyleneazetidine-1-carboxylate (1 g, 5.91 mmol) and zinc-copper couple powder (2.32 g, 35.47 mmol) in diethyl ether (20 mL) at 0° C. The reaction mixture was stirred at room temperature for 15 h. The solution was poured into sodium carbonate solution (100 mL), filtered through celite and the filtrate was extracted with ethyl acetate (100 ml×2). The combined organic extract was washed with brine, dried over anhydrous sodium sulfate and evaporated to afford the title compound tert-butyl 5,5-dichloro-6-oxo-2-azaspiro[3.3]heptane-2-carboxylate (1 g, crude) as a black gum. The crude material was directly taken for next step.

Step 3: Preparation tert-butyl 6-oxo-2-azaspiro[3.3]heptane-2-carboxylate

A solution of tert-butyl 5,5-dichloro-6-oxo-2-azaspiro [3.3]heptane-2-carboxylate (1 g, 3.5 mmol) in dioxane (20 mL) was added drop wise to a suspension of zinc powder (0.7 g, 10.71 mmol) in acetic acid (20 mL) at 0° C. and the reaction mixture was stirred at room temperature for 15 h. Then the reaction mixture was filtered through celite, filtrate was basified with 33% sodium hydroxide solution and extracted with ethyl acetate (50 mL×2). The combined organic extract was washed with brine (50 mL), dried over anhydrous sodium sulfate and evaporated. The crude material was purified by combiflash purifier using 30% ethyl acetate in hexane to afford the title compound tert-butyl 6-oxo-2-azaspiro[3.3]heptane-2-carboxylate (0.42 g, 58% yield) as a pale yellow solid. $^1$H NMR (400 MHz, CDCl$_3$) δ 4.12 (s, 4H), 3.28 (s, 4H), 1.45 (s, 9H).

Step 4: Preparation of tert-butyl 6-benzyl-6-hydroxy-2-azaspiro[3.3]heptane-2-carboxylate

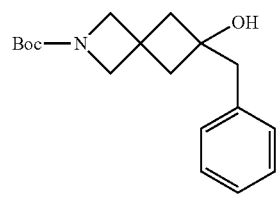 [SMILES: CC(C)(C)OC(=O)N1CC2(C1)CC(O)(Cc1ccccc1)C2]

Benzyl magnesium chloride solution (8.75 mL, 8.75 mmol, 1 M in diethyl ether) was added drop wise to a solution of tert-butyl 6-oxo-2-azaspiro[3.3]heptane-2-carboxylate (0.37 g, 1.75 mmol) in tetrahydrofuran (10 mL) at 0° C. and the reaction mixture was stirred at room temperature for 3 h. The reaction mixture was cooled, quenched with saturated ammonium chloride solution and extracted with ethyl acetate (50 mL×2). The combined organic extract was washed with brine (50 mL), dried over anhydrous sodium sulfate and evaporated. The crude material was purified by combiflash purifier using 30% ethyl acetate in hexane to afford the title compound tert-butyl 6-benzyl-6-hydroxy-2-azaspiro[3.3]heptane-2-carboxylate (0.35 g, 69% yield) as a white solid. Calculated M+H: 304.40. Found M+H: 204.1 (M-boc).

Step 5: Preparation of 6-benzyl-2-azaspiro[3.3]heptan-6-ol

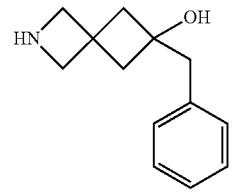 [SMILES: OC1(Cc2ccccc2)CC2(CNC2)C1]

Trifluoroacetic acid (1.0 mL) was added dropwise to a solution of tert-butyl 6-benzyl-6-hydroxy-2-azaspiro[3.3] heptane-2-carboxylate (0.2 g, 0.66 mmol) in dichloromethane (50 mL) at 0° C. and the reaction mixture was stirred at room temperature for 3 h. The solution was evaporated to dryness and the crude material was washed with 50% diethyl ether in hexane and dried to afford the title compound 6-benzyl-2-azaspiro[3.3]heptan-6-ol (0.19 g, crude) as a yellow gum. Calculated M+H: 204.28. Found M+H: 204.2.

Step 6: Preparation of 2-(6-benzyl-6-hydroxy-2-azaspiro[3.3]heptan-2-yl)-1-(4-hydroxyphenyl)ethanone

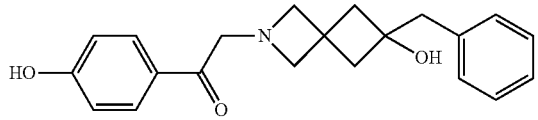 [SMILES: O=C(CN1CC2(C1)CC(O)(Cc1ccccc1)C2)c1ccc(O)cc1]

2-Bromo-1-(4-hydroxyphenyl)ethanone (0.129 g, 0.599 mmol) was added to a mixture of 6-benzyl-2-azaspiro[3.3]heptan-6-ol (0.19 g, 0.599 mmol) and potassium carbonate (0.33 g, 2.39 mmol) in N,N-dimethylformamide (5 mL) at 0° C. and the reaction mixture was stirred at room temperature for 3 h. The reaction mixture was evaporated to dryness. The residue was diluted with water and extracted with ethyl acetate (50 mL×2). The combined organic extract was dried over anhydrous sodium sulfate and evaporated. The crude material was purified by combiflash purifier using 8-10% methanol in dichloromethane to afford the title compound 2-(6-benzyl-6-hydroxy-2-azaspiro[3.3]heptan-2-yl)-1-(4-hydroxyphenyl)ethanone (0.04 g, 20% yield) as a white solid. Calculated M+H: 338.41. Found M+H: 338.3.

Step 7: Preparation of 6-benzyl-2-(2-hydroxy-2-(4-hydroxyphenyl)ethyl)-2-azaspiro[3.3]heptan-6-ol

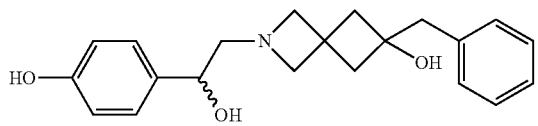 [SMILES: Oc1ccc(C(O)CN2CC3(C2)CC(O)(Cc2ccccc2)C3)cc1]

Sodium borohydride (0.033 g, 0.89 mmol) was added to a solution of 2-(6-benzyl-6-hydroxy-2-azaspiro[3.3]heptan-2-yl)-1-(4-hydroxyphenyl)ethanone (0.03 g, 0.089 mmol) in methanol (5 mL) at 0° C. and the reaction mixture was stirred at room temperature for 3 h. Then solution was evaporated, the residue was diluted with water and extracted with dichloromethane (30 mL×2). The combined organic extract was dried over anhydrous sodium sulfate and evaporated to dryness. The crude material was washed with pentane and dried to afford the title compound 6-benzyl-2-(2-hydroxy-2-(4-hydroxyphenyl)ethyl)-2-azaspiro[3.3]heptan-6-ol (0.02 g, 65% yield) as a white solid. Calculated M+H: 340.43. Found M+H: 340.2.

Example 55

Cell Assay

Cell Culture and plating: HEK293 cells expressing NR1/NR2B (Chantest, Cleveland, Ohio) were grown to 70-80% confluency as an adherent monolayer in standard tissue culture flasks at 37° C., 5% $CO_2$ per supplier's instructions. NR2B expression was induced by incubation with 0.3-0.4 μg/ml tetracycline in the presence of 4 mM ARL-15896 for 18-24 hours under the same growth conditions, then transferred to 30° C. for another 3-5 hours.

After induction, cell culture medium was removed and cells were rinsed once with $Ca^{2+}$ and $Mg^{2+}$-free Dulbecco's phosphate buffered saline. Cells were then removed from the flask using TrypLE™ Express (Life Technologies) according to the manufacturer's instructions and collected to 50 ml centrifuge tubes. Following two washes in $Ca^{2+}/Mg^{2+}$-free HBSS with 20 mM HEPES (HHnoCa), cells were counted and viability assessed using trypan blue. To load cells with $Ca^{2+}$-sensitive dye, they were resuspended in fluo-8 plus Component B (AAT Bioquest Products) diluted in HHnoCa and incubated 15 minutes at 37° C., followed by 30 minutes at room temp (in dark). Cells were then washed and resuspended in HHnoCa to remove extracellular dye and plated in 384-well plates (Falcon, uncoated) at 20,000-30,000 cells/well in a final volume of 25 μl/well.

FDSS Assay: To each well of the plate, 10 μL test compound, control (MK801) or HHnoCa buffer was added to a final concentration of 10 μM with a final concentration of DMSO of 0.1%. Following 10 minutes pre-incubation in the dark, plates are loaded onto the Hamamatsu FDSS 6000. After collecting baseline fluorescence images, 3 μM glutamate, 3 μM glycine, and 1 mM $Ca^{2+}$ in HHnoCa buffer is added to each well, and $Ca^{2+}$ is recorded for 3 minutes. Data were processed by computing ratio of fluorescence at the end of data collection to baseline fluorescence to assess degree of $Ca^{2+}$ influx inhibition relative to that observed in MK801.

Table 30 below provides activity of each compound according to the legend that "++++" indicates inhibition at a concentration <100 nM; "+++" indicates inhibition at a concentration between 100 nM and 1 μM of the disclosed compound; "++" indicates inhibition at a concentration of from 1 μM to 10 μM; and "+" indicates inhibition at a concentration >10 μm.

Table 22 illustrates the NR2B biological activities of the certain compounds

| Cmpd # | Structure | IUPAC Name | NR2B NAM IC50 | Binned Activity |
|---|---|---|---|---|
| 1 | 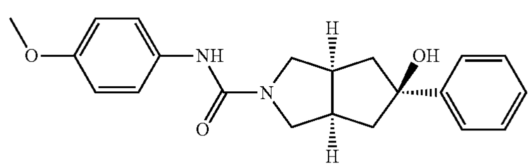 [SMILES: COc1ccc(NC(=O)N2C[C@@H]3C[C@@](O)(c4ccccc4)C[C@@H]3C2)cc1] | 5-hydroxy-N-(4-methoxyphenyl)-5-phenylhexahydrocyclopenta[c]pyrrole-2(1H)-carboxamide | 1.00E−05 | + |

-continued

| Cmpd # | Structure | IUPAC Name | NR2B NAM IC50 | Binned Activity |
|---|---|---|---|---|
| 2 | 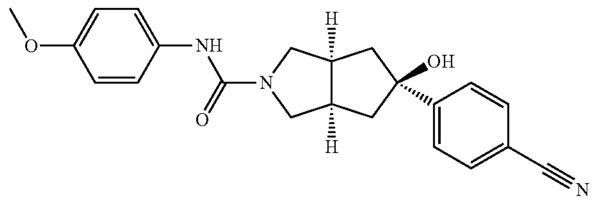 [SMILES: COc1ccc(NC(=O)N2C[C@@H]3C[C@@](O)(c4ccc(C#N)cc4)C[C@@H]3C2)cc1] | 5-(4-cyanophenyl)-5-hydroxy-N-(4-methoxyphenyl)-octahydrocyclopenta[c]pyrrole-2-carboxamide | 1.00E−05 | + |
| 3 | 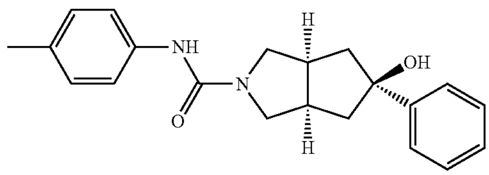 [SMILES: Cc1ccc(NC(=O)N2C[C@@H]3C[C@@](O)(c4ccccc4)C[C@@H]3C2)cc1] | 5-hydroxy-N-(4-methylphenyl)-5-phenyl-octahydrocyclopenta[c]pyrrole-2-carboxamide | 1.00E−05 | + |
| 4 | 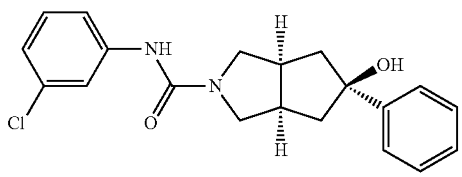 [SMILES: O=C(Nc1cccc(Cl)c1)N1C[C@@H]2C[C@@](O)(c3ccccc3)C[C@@H]2C1] | N-(3-chlorophenyl)-5-hydroxy-5-phenyl-octahydrocyclopenta[c]pyrrole-2-carboxamide | 1.00E−05 | + |
| 5 | 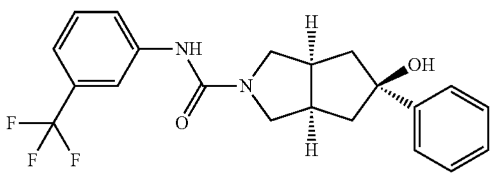 [SMILES: O=C(Nc1cccc(C(F)(F)F)c1)N1C[C@@H]2C[C@@](O)(c3ccccc3)C[C@@H]2C1] | 5-hydroxy-5-phenyl-N-[3-(trifluoromethyl)phenyl]-octahydrocyclopenta[c]pyrrole-2-carboxamide | 1.00E−05 | + |
| 6 | 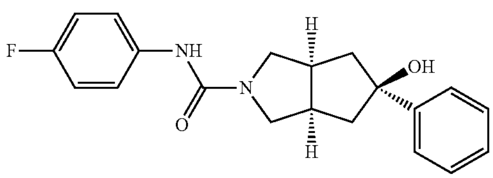 [SMILES: O=C(Nc1ccc(F)cc1)N1C[C@@H]2C[C@@](O)(c3ccccc3)C[C@@H]2C1] | N-(4-fluorophenyl)-5-hydroxy-5-phenyl-octahydrocyclopenta[c]pyrrole-2-carboxamide | 1.00E−05 | + |
| 7 | 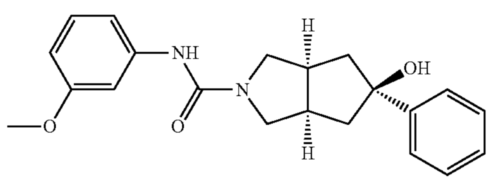 [SMILES: COc1cccc(NC(=O)N2C[C@@H]3C[C@@](O)(c4ccccc4)C[C@@H]3C2)c1] | 5-hydroxy-N-(3-methoxyphenyl)-5-phenyl-octahydrocyclopenta[c]pyrrole-2-carboxamide | 1.00E−05 | + |
| 8 | 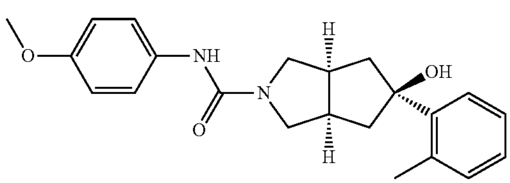 [SMILES: COc1ccc(NC(=O)N2C[C@@H]3C[C@@](O)(c4ccccc4C)C[C@@H]3C2)cc1] | 5-hydroxy-N-(4-methoxyphenyl)-5-(2-methylphenyl)-octahydrocyclopenta[c]pyrrole-2-carboxamide | 1.00E−05 | + |
| 9 | 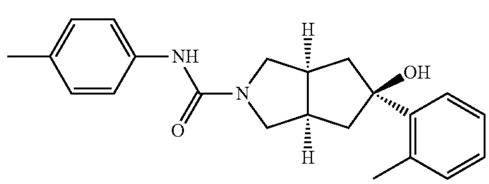 [SMILES: Cc1ccc(NC(=O)N2C[C@@H]3C[C@@](O)(c4ccccc4C)C[C@@H]3C2)cc1] | 5-hydroxy-5-(2-methylphenyl)-N-(4-methylphenyl)-octahydrocyclopenta[c]pyrrole-2-carboxamide | 1.00E−05 | + |

-continued

| Cmpd # | Structure | IUPAC Name | NR2B NAM IC50 | Binned Activity |
|---|---|---|---|---|
| 10 | 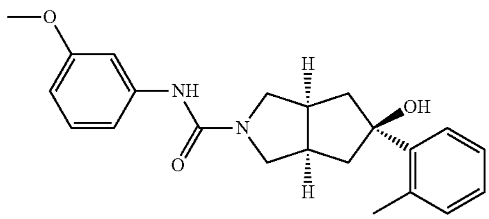 [SMILES: COc1cccc(NC(=O)N2C[C@@H]3C[C@@](O)(c4ccccc4C)C[C@@H]3C2)c1] | 5-hydroxy-N-(3-methoxyphenyl)-5-(2-methylphenyl)-octahydrocyclopenta[c]pyrrole-2-carboxamide | 1.00E−05 | + |
| 11 | 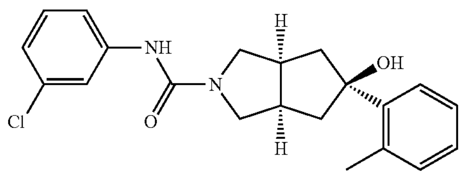 [SMILES: Cc1ccccc1[C@]1(O)C[C@H]2CN(C(=O)Nc3cccc(Cl)c3)C[C@H]2C1] | N-(3-chlorophenyl)-5-hydroxy-5-(2-methylphenyl)-octahydrocyclopenta[c]pyrrole-2-carboxamide | 1.00E−05 | + |
| 12 | 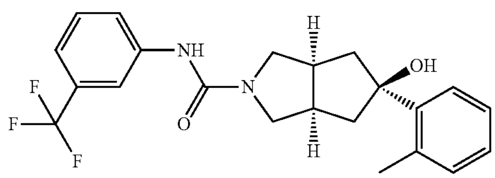 [SMILES: Cc1ccccc1[C@]1(O)C[C@H]2CN(C(=O)Nc3cccc(C(F)(F)F)c3)C[C@H]2C1] | 5-hydroxy-5-(2-methylphenyl)-N-[3-(trifluoromethyl)phenyl]-octahydrocyclopenta[c]pyrrole-2-carboxamide | 1.00E−05 | + |
| 13 | 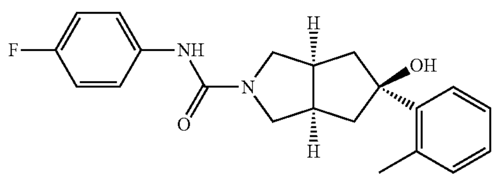 [SMILES: Cc1ccccc1[C@]1(O)C[C@H]2CN(C(=O)Nc3ccc(F)cc3)C[C@H]2C1] | N-(4-fluorophenyl)-5-hydroxy-5-(2-methylphenyl)-octahydrocyclopenta[c]pyrrole-2-carboxamide | 1.00E−05 | + |
| 14 | 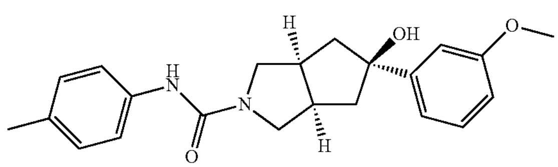 | 5-hydroxy-5-(3-methoxyphenyl)-N-(4-methylphenyl)-octahydrocyclopenta[c]pyrrole-2-carboxamide | 1.00E−05 | + |
| 15 | 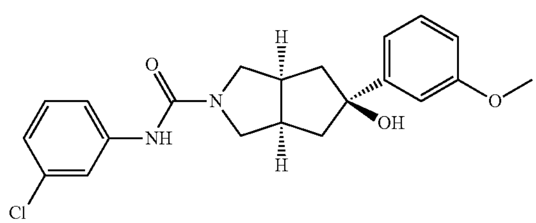 [SMILES: COc1cccc([C@]2(O)C[C@H]3CN(C(=O)Nc4cccc(Cl)c4)C[C@H]3C2)c1] | N-(3-chlorophenyl)-5-hydroxy-5-(3-methoxyphenyl)-octahydrocyclopenta[c]pyrrole-2-carboxamide | 1.00E−05 | + |
| 16 | 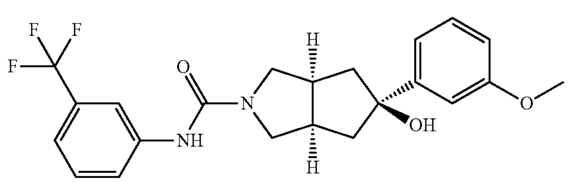 [SMILES: COc1cccc([C@]2(O)C[C@H]3CN(C(=O)Nc4cccc(C(F)(F)F)c4)C[C@H]3C2)c1] | 5-hydroxy-5-(3-methoxyphenyl)-N-[3-(trifluoromethyl)phenyl]-octahydrocyclopenta[c]pyrrole-2-carboxamide | 1.00E−05 | + |
| 17 | 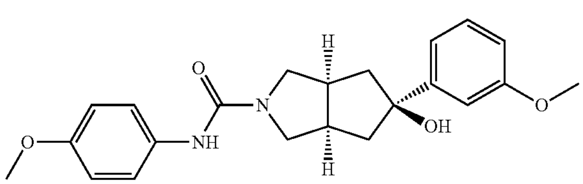 | 5-hydroxy-5-(3-methoxyphenyl)-N-(4-methoxyphenyl)-octahydrocyclopenta[c]pyrrole-2-carboxamide | 1.00E−05 | + |

-continued

| Cmpd # | Structure | IUPAC Name | NR2B NAM IC50 | Binned Activity |
|---|---|---|---|---|
| 18 | 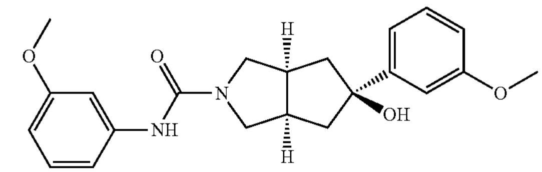 [SMILES: COc1cccc(NC(=O)N2C[C@@H]3C[C@@](O)(c4cccc(OC)c4)C[C@@H]3C2)c1] | 5-hydroxy-N,5-bis(3-methoxyphenyl)-octahydrocyclopenta[c]pyrrole-2-carboxamide | 1.00E−05 | + |
| 19 | 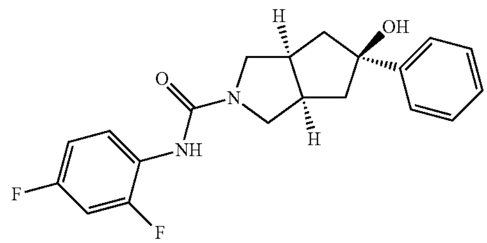 [SMILES: O=C(Nc1ccc(F)cc1F)N1C[C@@H]2C[C@@](O)(c3ccccc3)C[C@@H]2C1] | N-(2,4-difluorophenyl)-5-hydroxy-5-phenyl-octahydrocyclopenta[c]pyrrole-2-carboxamide | 1.00E−05 | + |
| 20 | 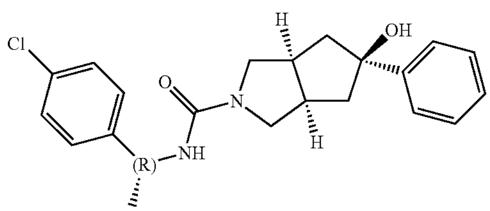 | N-[(1R)-1-(4-chlorophenyl)ethyl]-5-hydroxy-5-phenyl-octahydrocyclopenta[c]pyrrole-2-carboxamide | 1.00E−05 | + |
| 21 | 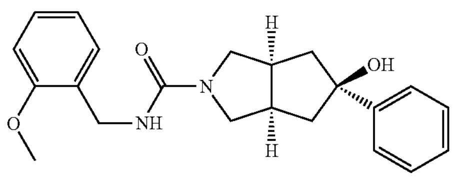 [SMILES: COc1ccccc1CNC(=O)N1C[C@@H]2C[C@@](O)(c3ccccc3)C[C@@H]2C1] | 5-hydroxy-N-[(2-methoxyphenyl)methyl]-5-phenyl-octahydrocyclopenta[c]pyrrole-2-carboxamide | 1.00E−05 | + |
| 22 | 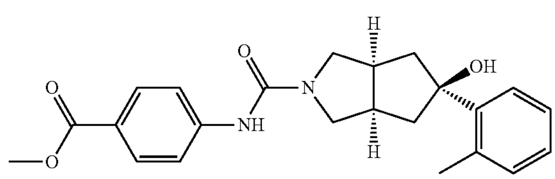 [SMILES: COC(=O)c1ccc(NC(=O)N2C[C@@H]3C[C@@](O)(c4ccccc4C)C[C@@H]3C2)cc1] | Methyl 4-(5-hydroxy-5-(o-tolyl)octahydrocyclopenta[c]pyrrole-2-carboxamido)benzoate | 1.00E−05 | + |
| 23 | 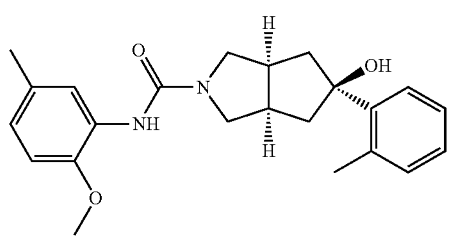 [SMILES: COc1ccc(C)cc1NC(=O)N1C[C@@H]2C[C@@](O)(c3ccccc3C)C[C@@H]2C1] | 5-hydroxy-N-(2-methoxy-5-methylphenyl)-5-(2-methylphenyl)-octahydrocyclopenta[c]pyrrole-2-carboxamide | 1.00E−05 | + |
| 24 | 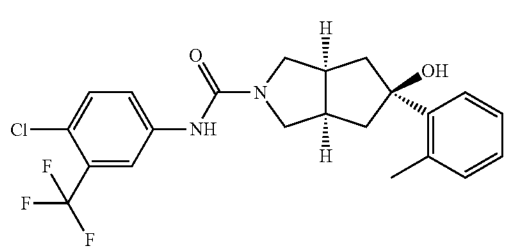 [SMILES: Cc1ccccc1[C@]1(O)C[C@H]2CN(C(=O)Nc3ccc(Cl)c(C(F)(F)F)c3)C[C@H]2C1] | N-[4-chloro-3-(trifluoromethyl)phenyl]-5-hydroxy-5-(2-methylphenyl)-octahydrocyclopenta[c]pyrrole-2-carboxamide | 1.00E−05 | + |

-continued

| Cmpd # | Structure | IUPAC Name | NR2B NAM IC50 | Binned Activity |
|---|---|---|---|---|
| 25 | 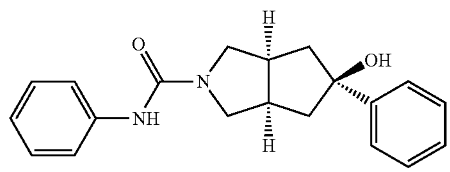 [SMILES: O=C(Nc1ccccc1)N1C[C@@H]2C[C@@](O)(c3ccccc3)C[C@@H]2C1] | 5-hydroxy-N,5-diphenyl-octahydrocyclopenta[c]pyrrole-2-carboxamide | 1.00E−05 | + |
| 26 | 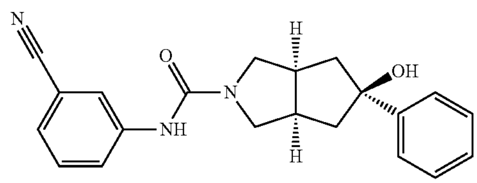 [SMILES: N#Cc1cccc(NC(=O)N2C[C@@H]3C[C@@](O)(c4ccccc4)C[C@@H]3C2)c1] | N-(3-cyanophenyl)-5-hydroxy-5-phenyl-octahydrocyclopenta[c]pyrrole-2-carboxamide | 1.00E−05 | + |
| 27 | 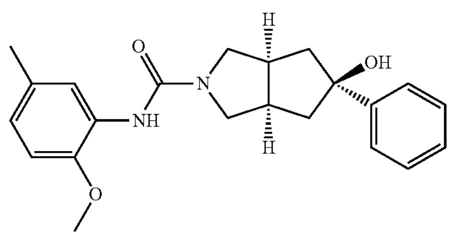 [SMILES: COc1ccc(C)cc1NC(=O)N1C[C@@H]2C[C@@](O)(c3ccccc3)C[C@@H]2C1] | 5-hydroxy-N-(2-methoxy-5-methylphenyl)-5-phenyl-octahydrocyclopenta[c]pyrrole-2-carboxamide | 1.00E−05 | + |
| 28 | 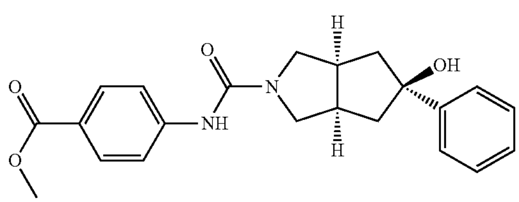 [SMILES: COC(=O)c1ccc(NC(=O)N2C[C@@H]3C[C@@](O)(c4ccccc4)C[C@@H]3C2)cc1] | methyl 4-[({5-hydroxy-5-phenyl-octahydrocyclopenta[c]pyrrol-2-yl}carbonyl)amino]benzoate | 1.00E−05 | + |
| 29 | 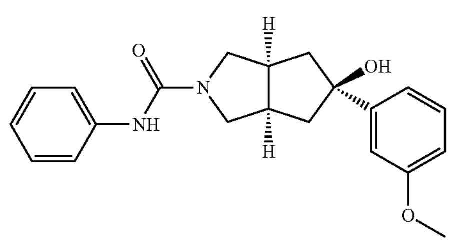 [SMILES: COc1cccc([C@]2(O)C[C@H]3CN(C(=O)Nc4ccccc4)C[C@H]3C2)c1] | 5-hydroxy-5-(3-methoxyphenyl)-N-phenyl-octahydrocyclopenta[c]pyrrole-2-carboxamide | 1.00E−05 | + |
| 30 | 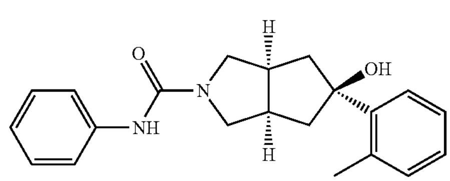 | 5-hydroxy-5-(2-methylphenyl)-N-phenyl-octahydrocyclopenta[c]pyrrole-2-carboxamide | 1.00E−05 | + |
| 31 | 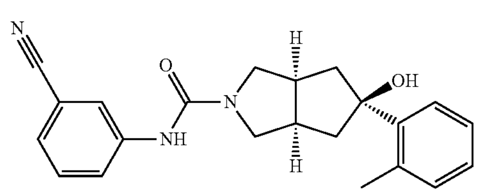 [SMILES: Cc1ccccc1[C@]1(O)C[C@H]2CN(C(=O)Nc3cccc(C#N)c3)C[C@H]2C1] | N-(3-cyanophenyl)-5-hydroxy-5-(2-methylphenyl)-octahydrocyclopenta[c]pyrrole-2-carboxamide | 1.00E−05 | + |

| Cmpd # | Structure | IUPAC Name | NR2B NAM IC50 | Binned Activity |
|---|---|---|---|---|
| 32 | 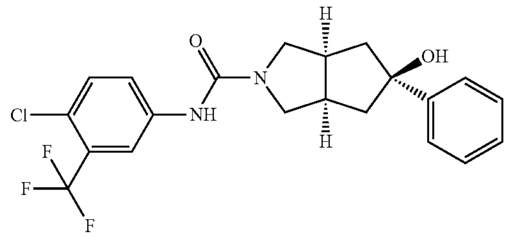 [SMILES: O=C(Nc1ccc(Cl)c(C(F)(F)F)c1)N1C[C@@H]2C[C@@](O)(c3ccccc3)C[C@@H]2C1] | N-[4-chloro-3-(trifluoromethyl)phenyl]-5-hydroxy-5-phenyl-octahydrocyclopenta[c]pyrrole-2-carboxamide | 1.00E−05 | + |
| 33 | 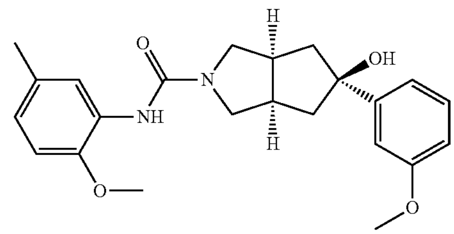 [SMILES: COc1cccc([C@]2(O)C[C@H]3CN(C(=O)Nc4cc(C)ccc4OC)C[C@H]3C2)c1] | 5-hydroxy-N-(2-methoxy-5-methylphenyl)-5-(3-methoxyphenyl)-octahydrocyclopenta[c]pyrrole-2-carboxamide | 1.00E−05 | + |
| 34 | 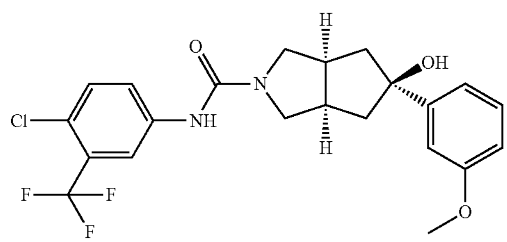 [SMILES: COc1cccc([C@]2(O)C[C@H]3CN(C(=O)Nc4ccc(Cl)c(C(F)(F)F)c4)C[C@H]3C2)c1] | N-[4-chloro-3-(trifluoromethyl)phenyl]-5-hydroxy-5-(3-methoxyphenyl)-octahydrocyclopenta[c]pyrrole-2-carboxamide | 1.00E−05 | + |
| 35 | 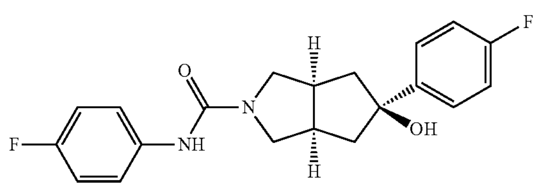 [SMILES: O=C(Nc1ccc(F)cc1)N1C[C@@H]2C[C@@](O)(c3ccc(F)cc3)C[C@@H]2C1] | N,5-bis(4-fluorophenyl)-5-hydroxy-octahydro-cyclopenta[c]pyrrole-2-carboxamide | 1.00E−05 | + |
| 36 | 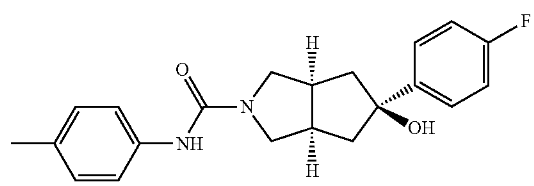 [SMILES: Cc1ccc(NC(=O)N2C[C@@H]3C[C@@](O)(c4ccc(F)cc4)C[C@@H]3C2)cc1] | 5-(4-fluorophenyl)-5-hydroxy-N-(4-methylphenyl)-octahydrocyclopenta[c]pyrrole-2-carboxamide | 1.00E−05 | + |
| 37 | 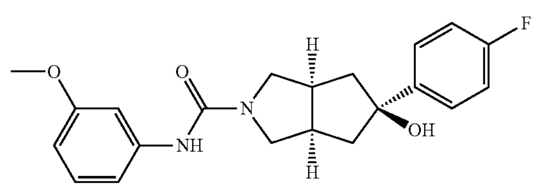 [SMILES: COc1cccc(NC(=O)N2C[C@@H]3C[C@@](O)(c4ccc(F)cc4)C[C@@H]3C2)c1] | 5-(4-fluorophenyl)-5-hydroxy-N-(3-methoxyphenyl)-octahydrocyclopenta[c]pyrrole-2-carboxamide | 1.00E−05 | + |
| 38 | 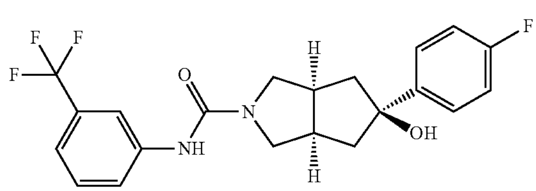 [SMILES: O=C(Nc1cccc(C(F)(F)F)c1)N1C[C@@H]2C[C@@](O)(c3ccc(F)cc3)C[C@@H]2C1] | 5-(4-fluorophenyl)-5-hydroxy-N-[3-(trifluoromethyl)phenyl]-octahydrocyclopenta[c]pyrrole-2-carboxamide | 1.00E−05 | + |

-continued

| Cmpd # | Structure | IUPAC Name | NR2B NAM IC50 | Binned Activity |
|---|---|---|---|---|
| 39 | 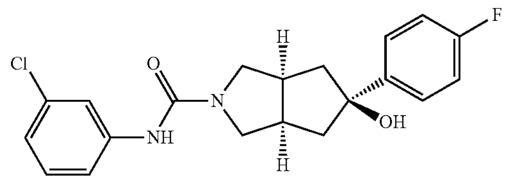 [SMILES: O=C(Nc1cccc(Cl)c1)N1C[C@@H]2C[C@@](O)(c3ccc(F)cc3)C[C@@H]2C1] | N-(3-chlorophenyl)-5-(4-fluorophenyl)-5-hydroxy-octahydrocyclopenta[c]pyrrole-2-carboxamide | 1.00E−05 | + |
| 40 | 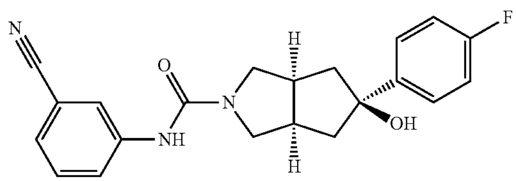 [SMILES: N#Cc1cccc(NC(=O)N2C[C@@H]3C[C@@](O)(c4ccc(F)cc4)C[C@@H]3C2)c1] | N-(3-cyanophenyl)-5-(4-fluorophenyl)-5-hydroxy-octahydrocyclopenta[c]pyrrole-2-carboxamide | 1.00E−05 | + |
| 41 | 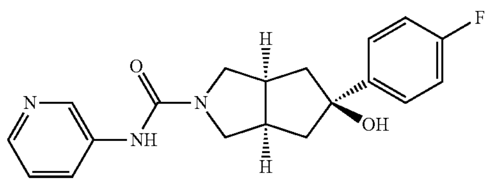 [SMILES: O=C(Nc1cccnc1)N1C[C@@H]2C[C@@](O)(c3ccc(F)cc3)C[C@@H]2C1] | 5-(4-fluorophenyl)-5-hydroxy-N-(pyridin-3-yl)-octahydrocyclopenta[c]pyrrole-2-carboxamide | 1.00E−05 | + |
| 42 | 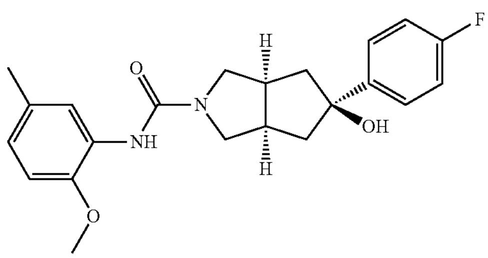 [SMILES: COc1ccc(C)cc1NC(=O)N1C[C@@H]2C[C@@](O)(c3ccc(F)cc3)C[C@@H]2C1] | 5-(4-fluorophenyl)-5-hydroxy-N-(2-methoxy-5-methylphenyl)-octahydrocyclopenta[c]pyrrole-2-carboxamide | 1.00E−05 | + |
| 43 | 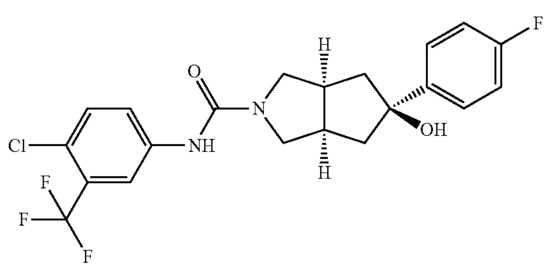 [SMILES: O=C(Nc1ccc(Cl)c(C(F)(F)F)c1)N1C[C@@H]2C[C@@](O)(c3ccc(F)cc3)C[C@@H]2C1] | N-[4-chloro-3-(trifluoromethyl)phenyl]-5-(4-fluorophenyl)-5-hydroxy-octahydrocyclopenta[c]pyrrole-2-carboxamide | 1.00E−05 | + |
| 44 | 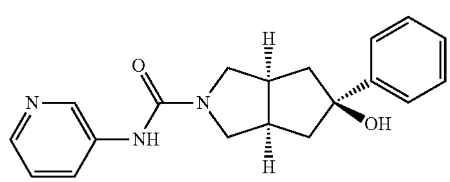 [SMILES: O=C(Nc1cccnc1)N1C[C@@H]2C[C@@](O)(c3ccccc3)C[C@@H]2C1] | 5-hydroxy-5-phenyl-N-(pyridin-3-yl)-octahydrocyclopenta[c]pyrrole-2-carboxamide | 1.00E−05 | + |
| 45 | 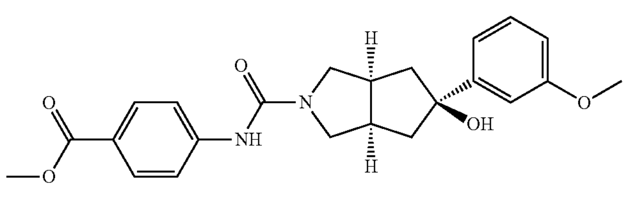 | methyl 4-({[5-hydroxy-5-(3-methoxyphenyl)-octahydrocyclopenta[c]pyrrol-2-yl]carbonyl}amino)benzoate | 1.00E−05 | + |

-continued

| Cmpd # | Structure | IUPAC Name | NR2B NAM IC50 | Binned Activity |
|---|---|---|---|---|
| 46 | 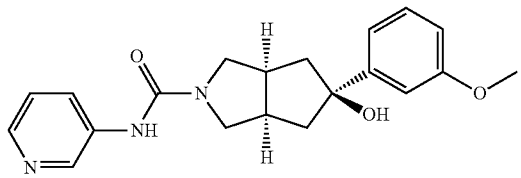 [SMILES: COc1cccc([C@]2(O)C[C@H]3CN(C(=O)Nc4cccnc4)C[C@H]3C2)c1] | 5-hydroxy-5-(3-methoxyphenyl)-N-(pyridin-3-yl)-octahydro-cyclopenta[c]pyrrole-2-carboxamide | 1.00E−05 | + |
| 47 | 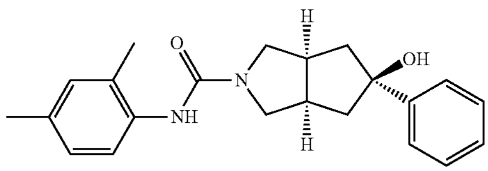 | N-(2,4-dimethylphenyl)-5-hydroxy-5-phenyl-octahydrocyclo-penta[c]pyrrole-2-carboxamide | 1.00E−05 | + |
| 48 | 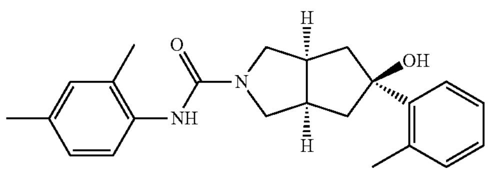 [SMILES: Cc1ccc(NC(=O)N2C[C@@H]3C[C@@](O)(c4ccccc4C)C[C@@H]3C2)c(C)c1] | N-(2,4-dimethylphenyl)-5-hydroxy-5-(2-methylphenyl)-octahydrocyclo-penta[c]pyrrole-2-carboxamide | 1.00E−05 | + |
| 49 | 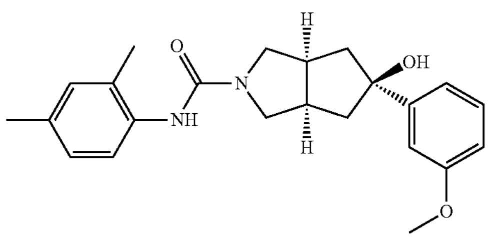 [SMILES: COc1cccc([C@]2(O)C[C@H]3CN(C(=O)Nc4ccc(C)cc4C)C[C@H]3C2)c1] | N-(2,4-dimethylphenyl)-5-hydroxy-5-(3-methoxyphenyl)-octahydrocyclo-penta[c]pyrrole-2-carboxamide | 1.00E−05 | + |
| 50 | 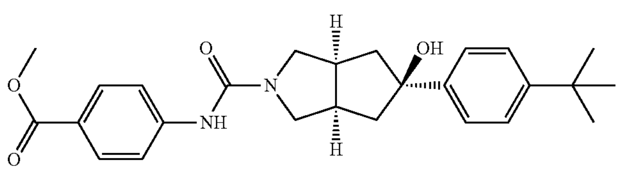 [SMILES: COC(=O)c1ccc(NC(=O)N2C[C@@H]3C[C@@](O)(c4ccc(C(C)(C)C)cc4)C[C@@H]3C2)cc1] | methyl 4-({[5-(4-tert-butylphenyl)-5-hydroxy-octahydrocyclo-penta[c]pyrrol-2-yl]carbonyl}amino)benzoate | 1.00E−05 | + |
| 51 | 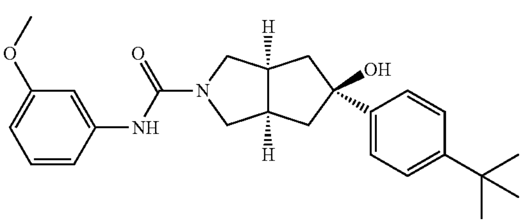 [SMILES: COc1cccc(NC(=O)N2C[C@@H]3C[C@@](O)(c4ccc(C(C)(C)C)cc4)C[C@@H]3C2)c1] | 5-(4-tert-butylphenyl)-5-hydroxy-N-(3-methoxyphenyl)-octahydrocyclo-penta[c]pyrrole-2-carboxamide | 1.00E−05 | + |
| 52 | 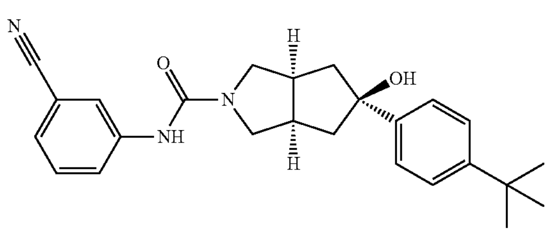 [SMILES: CC(C)(C)c1ccc([C@]2(O)C[C@H]3CN(C(=O)Nc4cccc(C#N)c4)C[C@H]3C2)cc1] | 5-(4-tert-butylphenyl)-N-(3-cyanophenyl)-5-hydroxy-octahydrocyclo-penta[c]pyrrole-2-carboxamide | 1.00E−05 | + |

-continued

| Cmpd # | Structure | IUPAC Name | NR2B NAM IC50 | Binned Activity |
|---|---|---|---|---|
| 53 | 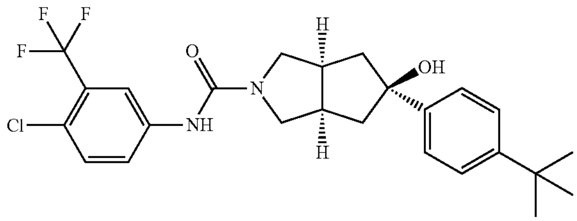 [SMILES: CC(C)(C)c1ccc([C@]2(O)C[C@H]3CN(C(=O)Nc4ccc(Cl)c(C(F)(F)F)c4)C[C@H]3C2)cc1] | 5-(4-tert-butylphenyl)-N-[4-chloro-3-(trifluoromethyl)phenyl]-5-hydroxy-octahydrocyclopenta[c]pyrrole-2-carboxamide | 1.00E−05 | + |
| 54 | 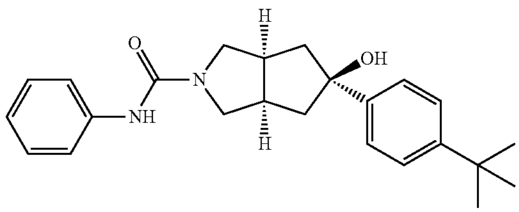 [SMILES: CC(C)(C)c1ccc([C@]2(O)C[C@H]3CN(C(=O)Nc4ccccc4)C[C@H]3C2)cc1] | 5-(4-tert-butylphenyl)-5-hydroxy-N-phenyl-octahydrocyclopenta[c]pyrrole-2-carboxamide | 1.00E−05 | + |
| 55 | 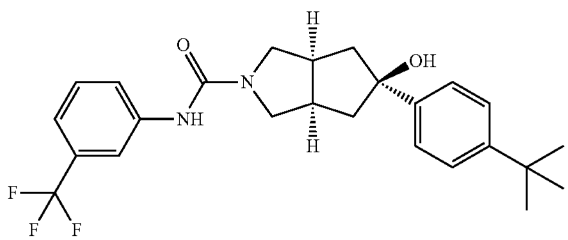 [SMILES: CC(C)(C)c1ccc([C@]2(O)C[C@H]3CN(C(=O)Nc4cccc(C(F)(F)F)c4)C[C@H]3C2)cc1] | 5-(4-tert-butylphenyl)-5-hydroxy-N-[3-(trifluoromethyl)phenyl]-octahydrocyclopenta[c]pyrrole-2-carboxamide | 1.00E−05 | + |
| 56 | 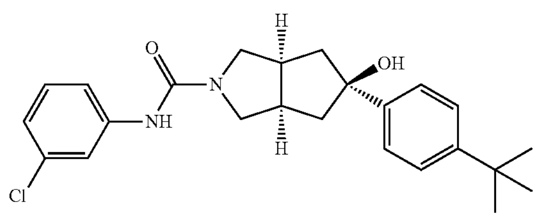 [SMILES: CC(C)(C)c1ccc([C@]2(O)C[C@H]3CN(C(=O)Nc4cccc(Cl)c4)C[C@H]3C2)cc1] | 5-(4-tert-butylphenyl)-N-(3-chlorophenyl)-5-hydroxy-octahydrocyclopenta[c]pyrrole-2-carboxamide | 1.00E−05 | + |
| 57 | 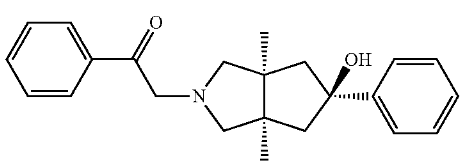 [SMILES: C[C@@]12CN(CC(=O)c3ccccc3)C[C@]1(C)C[C@@](O)(c1ccccc1)C2] | 2-(5-hydroxy-5-phenylhexahydrocyclopenta[c]pyrrol-2(1H)-yl)-1-phenylethanone | 1.00E−05 | + |
| 58 | 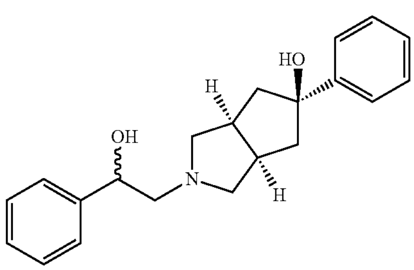 [SMILES: OC(CN1C[C@@H]2C[C@@](O)(c3ccccc3)C[C@@H]2C1)c1ccccc1] | rac-2-(2-hydroxy-2-phenylethyl)-5-phenyloctahydrocyclopenta[c]pyrrol-5-ol | 1.00E−05 | + |
| 59 | 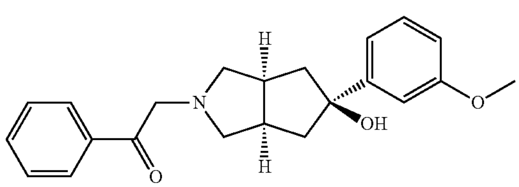 [SMILES: COc1cccc([C@]2(O)C[C@H]3CN(CC(=O)c4ccccc4)C[C@H]3C2)c1] | 2-[5-hydroxy-5-(3-methoxyphenyl)-octahydrocyclopenta[c]pyrrol-2-yl]-1-phenylethan-1-one | 1.00E−05 | + |

-continued

| Cmpd # | Structure | IUPAC Name | NR2B NAM IC50 | Binned Activity |
|---|---|---|---|---|
| 60 | 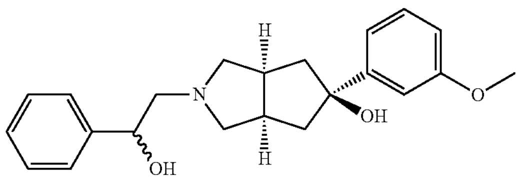 [SMILES: COc1cccc([C@]2(O)C[C@H]3CN(CC(O)c4ccccc4)C[C@H]3C2)c1] | rac-2-(2-hydroxy-2-phenylethyl)-5-(3-methoxyphenyl)-octahydrocyclopenta[c]pyrrol-5-ol | 1.00E−05 | + |
| 61 | 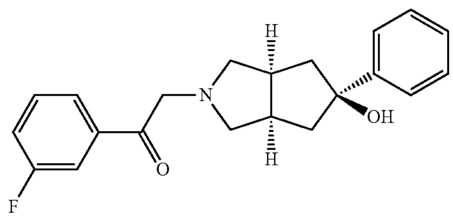 [SMILES: O=C(CN1C[C@@H]2C[C@@](O)(c3ccccc3)C[C@@H]2C1)c1cccc(F)c1] | 1-(3-fluorophenyl)-2-{5-hydroxy-5-phenyl-octahydrocyclopenta[c]pyrrol-2-yl}ethan-1-one | 1.00E−05 | + |
| 62 | 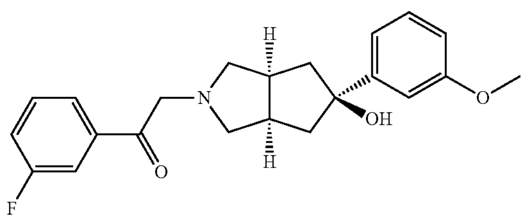 [SMILES: COc1cccc([C@]2(O)C[C@H]3CN(CC(=O)c4cccc(F)c4)C[C@H]3C2)c1] | 1-(3-fluorophenyl)-2-[5-hydroxy-5-(3-methoxyphenyl)-octahydrocyclopenta[c]pyrrol-2-yl]ethan-1-one | 1.00E−05 | + |
| 63 | 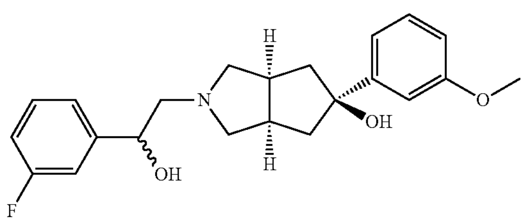 [SMILES: COc1cccc([C@]2(O)C[C@H]3CN(CC(O)c4cccc(F)c4)C[C@H]3C2)c1] | rac-2-[2-(3-fluorophenyl)-2-hydroxyethyl]-5-(3-methoxyphenyl)-octahydrocyclopenta[c]pyrrol-5-ol | 1.00E−05 | + |
| 64 | 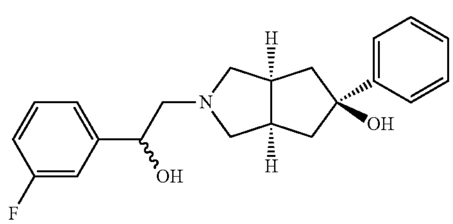 [SMILES: OC(CN1C[C@@H]2C[C@@](O)(c3ccccc3)C[C@@H]2C1)c1cccc(F)c1] | rac-2-[2-(3-fluorophenyl)-2-hydroxyethyl]-5-phenyl-octahydrocyclopenta[c]pyrrol-5-ol | 1.00E−05 | + |
| 65 | | 2-{5-hydroxy-5-phenyl-octahydrocyclopenta[c]pyrrol-2-yl}-1-(4-hydroxyphenyl)ethan-1-one | 1.00E−05 | + |
| 65 | | 2-{5-hydroxy-5-phenyl-octahydrocyclopenta[c]pyrrol-2-yl}-1-(4-methoxyphenyl)ethan-1-one | 1.00E−05 | + |

-continued

| Cmpd # | Structure | IUPAC Name | NR2B NAM IC50 | Binned Activity |
|---|---|---|---|---|
| 66 | 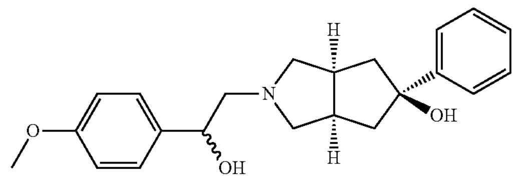 [SMILES: COc1ccc(C(O)CN2C[C@@H]3C[C@@](O)(c4ccccc4)C[C@@H]3C2)cc1] | rac-2-[2-hydroxy-2-(4-methoxyphenyl)ethyl]-5-phenyl-octahydro-cyclopenta[c]pyrrol-5-ol | 1.00E−05 | + |
| 67 | 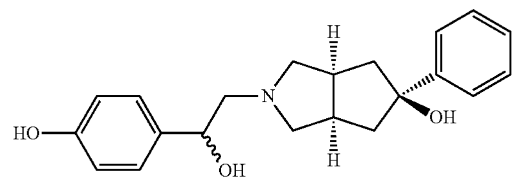 [SMILES: Oc1ccc(C(O)CN2C[C@@H]3C[C@@](O)(c4ccccc4)C[C@@H]3C2)cc1] | rac-2-[2-hydroxy-2-(4-hydroxyphenyl)ethyl]-5-phenyl-octahydrocyclopenta[c]pyrrol-5-ol | 1.00E−05 | + |
| 68 | 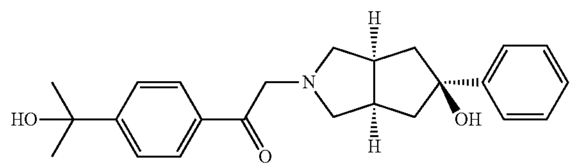 [SMILES: CC(C)(O)c1ccc(C(=O)CN2C[C@@H]3C[C@@](O)(c4ccccc4)C[C@@H]3C2)cc1] | 2-(5-hydroxy-5-phenylhexahydro-cyclopenta[c]pyrrol-2(1H)-yl)-1-(4-(2-hydroxypropan-2-yl)phenyl)ethanone | 1.00E−05 | + |
| 69 | 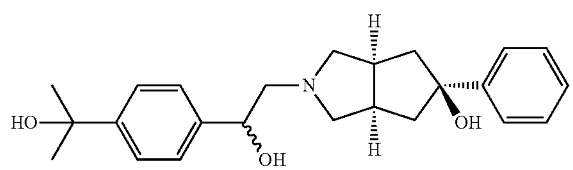 [SMILES: CC(C)(O)c1ccc(C(O)CN2C[C@@H]3C[C@@](O)(c4ccccc4)C[C@@H]3C2)cc1] | rac-2-(2-hydroxy-2-(4-(2-hydroxypropan-2-yl)phenyl)ethyl)-5-phenyloctahydrocyclopenta[c]pyrrol-5-ol | 1.00E−05 | + |
| 70 | 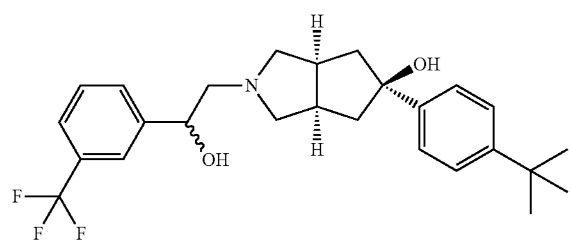 [SMILES: CC(C)(C)c1ccc([C@]2(O)C[C@H]3CN(CC(O)c4cccc(C(F)(F)F)c4)C[C@H]3C2)cc1] | rac-5-(4-(tert-butyl)phenyl)-2-(2-hydroxy-2-(3-(trifluoromethyl)phenyl)ethyl)octahydrocyclopenta[c]pyrrol-5-ol | 1.00E−05 | + |
| 71 | 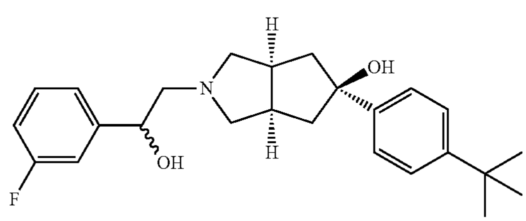 [SMILES: CC(C)(C)c1ccc([C@]2(O)C[C@H]3CN(CC(O)c4cccc(F)c4)C[C@H]3C2)cc1] | rac-5-(4-tert-butylphenyl)-2-[2-(3-fluorophenyl)-2-hydroxyethyl]-octahydrocyclopenta[c]pyrrol-5-ol | 1.00E−05 | + |
| 72 | 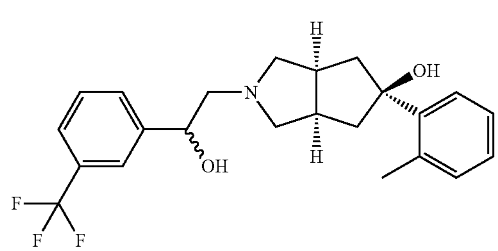 [SMILES: Cc1ccccc1[C@]1(O)C[C@H]2CN(CC(O)c3cccc(C(F)(F)F)c3)C[C@H]2C1] | rac-2-{2-hydroxy-2-[3-(trifluoromethyl)phenyl]ethyl}-5-(2-methylphenyl)-octahydrocyclopenta[c]pyrrol-5-ol | 1.00E−05 | + |

| Cmpd # | Structure | IUPAC Name | NR2B NAM IC50 | Binned Activity |
|---|---|---|---|---|
| 73 | 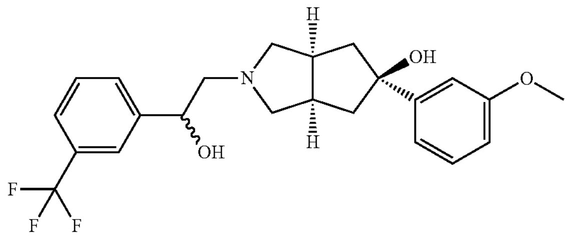 [SMILES: COc1cccc([C@]2(O)C[C@H]3CN(CC(O)c4cccc(C(F)(F)F)c4)C[C@H]3C2)c1] | rac-2-{2-hydroxy-2-[3-(trifluoromethyl)phenyl]ethyl}-5-(3-methoxyphenyl)-octahydrocyclopenta[c]pyrrol-5-ol | 1.00E−05 | + |
| 74 | 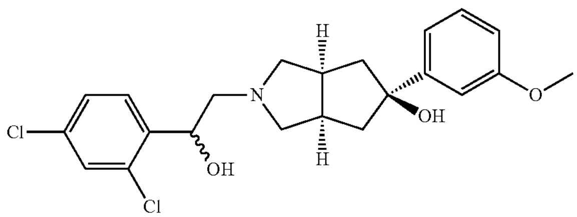 [SMILES: COc1cccc([C@]2(O)C[C@H]3CN(CC(O)c4ccc(Cl)cc4Cl)C[C@H]3C2)c1] | rac-2-[2-(2,4-dichlorophenyl)-2-hydroxyethyl]-5-(3-methoxyphenyl)-octahydrocyclopenta[c]pyrrol-5-ol | 1.00E−05 | + |
| 75 | 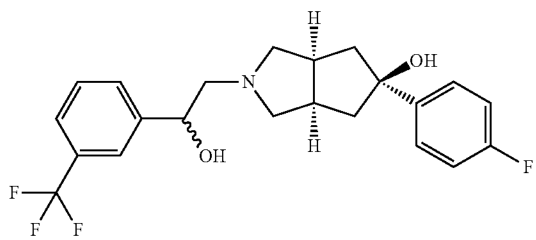 [SMILES: OC(CN1C[C@@H]2C[C@@](O)(c3ccc(F)cc3)C[C@@H]2C1)c1cccc(C(F)(F)F)c1] | rac-5-(4-fluorophenyl)-2-{2-hydroxy-2-[3-(trifluoromethyl)phenyl]ethyl}-octahydrocyclopenta[c]pyrrol-5-ol | 1.00E−05 | + |
| 76 | 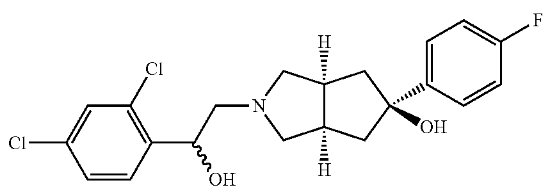 [SMILES: OC(CN1C[C@@H]2C[C@@](O)(c3ccc(F)cc3)C[C@@H]2C1)c1ccc(Cl)cc1Cl] | rac-2-[2-(2,4-dichlorophenyl)-2-hydroxyethyl]-5-(4-fluorophenyl)-octahydrocyclopenta[c]pyrrol-5-ol | 1.00E−05 | + |
| 77 | 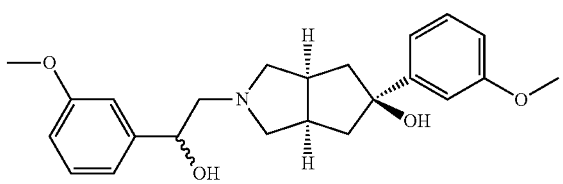 | rac-2-[2-hydroxy-2-(3-methoxyphenyl)ethyl]-5-(3-methoxyphenyl)-octahydrocyclopenta[c]pyrrol-5-ol | 1.00E−05 | + |
| 78 | 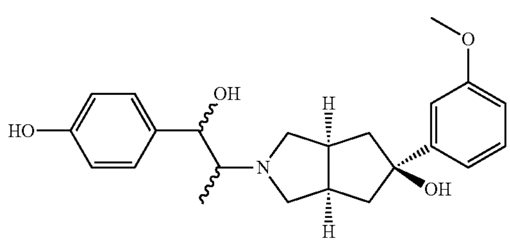 [SMILES: COc1cccc([C@]2(O)C[C@H]3CN(C(C)C(O)c4ccc(O)cc4)C[C@H]3C2)c1] | rac-2-(1-hydroxy-1-(4-hydroxyphenyl)propan-2-yl)-5-(3-methoxyphenyl)octahydrocyclopenta[c]pyrrol-5-ol | 1.00E−05 | + |
| 79 | 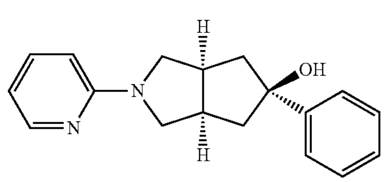 [SMILES: O[C@@]1(c2ccccc2)C[C@H]2CN(c3ccccn3)C[C@H]2C1] | 2-(4-fluorobenzyl)-5-(4-fluorophenyl)octahydrocyclopenta[c]pyrrol-5-ol | 1.00E−05 | + |

| Cmpd # | Structure | IUPAC Name | NR2B NAM IC50 | Binned Activity |
|---|---|---|---|---|
| 80 | 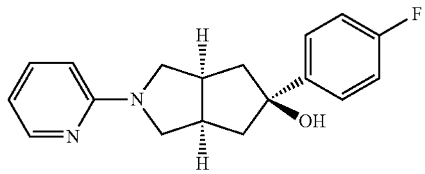 [SMILES: O[C@@]1(c2ccc(F)cc2)C[C@H]2CN(c3ccccn3)C[C@H]2C1] | 5-(4-fluorophenyl)-2-(pyridin-2-yl)-octahydro-cyclopenta[c]pyrrol-5-ol | 1.00E−05 | + |
| 81 | 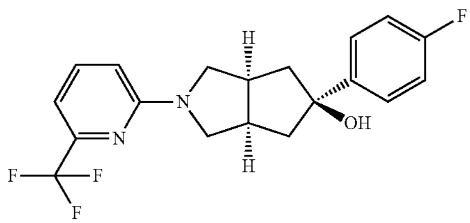 [SMILES: O[C@@]1(c2ccc(F)cc2)C[C@H]2CN(c3cccc(C(F)(F)F)n3)C[C@H]2C1] | 5-(4-fluorophenyl)-2-[6-(trifluoromethyl)pyridin-2-yl]-octahydrocyclopenta[c]pyrrol-5-ol | 1.00E−05 | + |
| 82 | 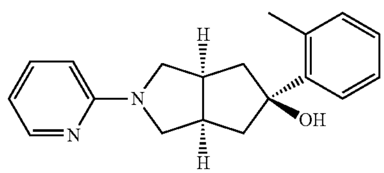 [SMILES: Cc1ccccc1[C@]1(O)C[C@H]2CN(c3ccccn3)C[C@H]2C1] | 5-(2-methylphenyl)-2-(pyridin-2-yl)-octahydro-cyclopenta[c]pyrrol-5-ol | 1.00E−05 | + |
| 83 | 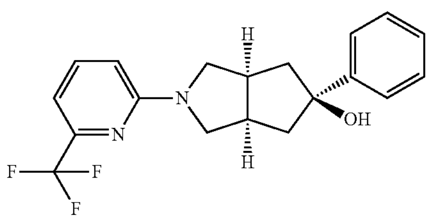 [SMILES: O[C@@]1(c2ccccc2)C[C@H]2CN(c3cccc(C(F)(F)F)n3)C[C@H]2C1] | 5-phenyl-2-[6-(trifluoromethyl)pyridin-2-yl]-octahydrocyclopenta[c]pyrrol-5-ol | 1.00E−05 | + |
| 84 | 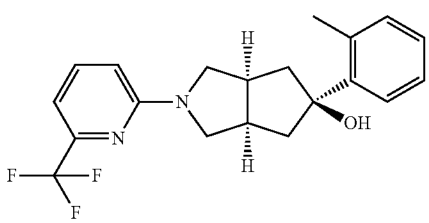 [SMILES: Cc1ccccc1[C@]1(O)C[C@H]2CN(c3cccc(C(F)(F)F)n3)C[C@H]2C1] | 5-(2-methylphenyl)-2-[6-(trifluoromethyl)pyridin-2-yl]-octahydrocyclopenta[c]pyrrol-5-ol | 1.00E−05 | + |
| 85 | 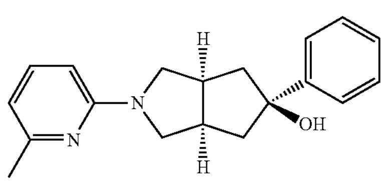 [SMILES: Cc1cccc(N2C[C@@H]3C[C@@](O)(c4ccccc4)C[C@@H]3C2)n1] | 2-(6-methylpyridin-2-yl)-5-phenyl-octahydrocyclopenta[c]pyrrol-5-ol | 1.00E−05 | + |
| 86 | 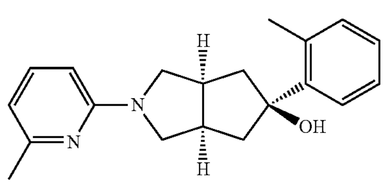 [SMILES: Cc1cccc(N2C[C@@H]3C[C@@](O)(c4ccccc4C)C[C@@H]3C2)n1] | 5-(2-methylphenyl)-2-(6-methylpyridin-2-yl)-octahydrocyclopenta[c]pyrrol-5-ol | 1.00E−05 | + |

| Cmpd # | Structure | IUPAC Name | NR2B NAM IC50 | Binned Activity |
|---|---|---|---|---|
| 87 | 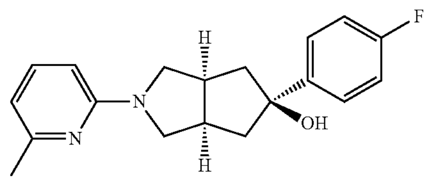 [SMILES: Cc1cccc(N2C[C@@H]3C[C@@](O)(c4ccc(F)cc4)C[C@@H]3C2)n1] | 5-(4-fluorophenyl)-2-(6-methylpyridin-2-yl)-octahydrocyclopenta[c]pyrrol-5-ol | 1.00E−05 | + |
| 88 | 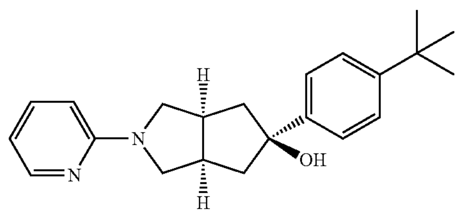 [SMILES: CC(C)(C)c1ccc([C@]2(O)C[C@H]3CN(c4ccccn4)C[C@H]3C2)cc1] | 5-(4-tert-butylphenyl)-2-(pyridin-2-yl)-octahydrocyclopenta[c]pyrrol-5-ol | 1.00E−05 | + |
| 89 | 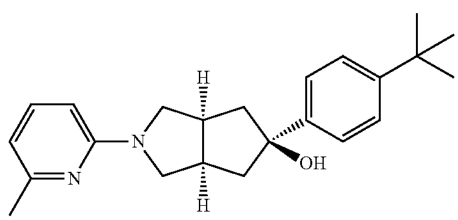 [SMILES: Cc1cccc(N2C[C@@H]3C[C@@](O)(c4ccc(C(C)(C)C)cc4)C[C@@H]3C2)n1] | 5-(4-tert-butylphenyl)-2-(6-methylpyridin-2-yl)-octahydrocyclopenta[c]pyrrol-5-ol | 1.00E−05 | + |
| 90 | 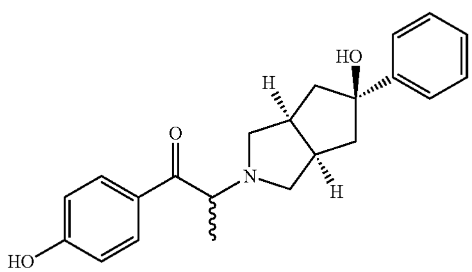 [SMILES: CC(C(=O)c1ccc(O)cc1)N1C[C@@H]2C[C@@](O)(c3ccccc3)C[C@@H]2C1] | rac-2-(5-hydroxy-5-phenylhexahydrocyclopenta[c]pyrrol-2(1H)-yl)-1-(4-hydroxyphenyl)propan-1-one | 1.00E−05 | + |
| 91 | 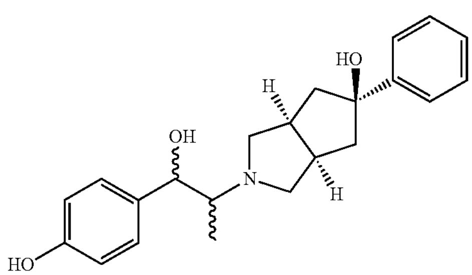 [SMILES: CC(C(O)c1ccc(O)cc1)N1C[C@@H]2C[C@@](O)(c3ccccc3)C[C@@H]2C1] | rac-2-(1-hydroxy-1-(4-hydroxyphenyl)propan-2-yl)-5-phenyloctahydrocyclopenta[c]pyrrol-5-ol | 1.00E−05 | + |
| 92 | 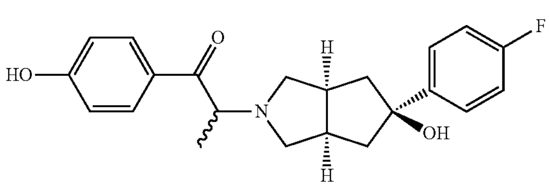 [SMILES: CC(C(=O)c1ccc(O)cc1)N1C[C@@H]2C[C@@](O)(c3ccc(F)cc3)C[C@@H]2C1] | rac-2-[5-(4-fluorophenyl)-5-hydroxy-octahydrocyclopenta[c]pyrrol-2-yl]-1-(4-hydroxyphenyl)propan-1-one | 1.00E−05 | + |

-continued

| Cmpd # | Structure | IUPAC Name | NR2B NAM IC50 | Binned Activity |
|---|---|---|---|---|
| 93 | 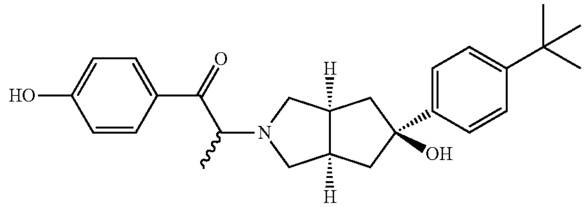 [SMILES: CC(C(=O)c1ccc(O)cc1)N1C[C@@H]2C[C@@](O)(c3ccc(C(C)(C)C)cc3)C[C@@H]2C1] | rac-2-[5-(4-tert-butylphenyl)-5-hydroxy-octahydrocyclopenta[c]pyrrol-2-yl]-1-(4-hydroxyphenyl)propan-1-one | 1.00E−05 | + |
| 94 | 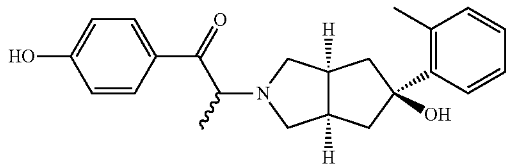 [SMILES: Cc1ccccc1[C@]1(O)C[C@H]2CN(C(C)C(=O)c3ccc(O)cc3)C[C@H]2C1] | rac-2-[5-hydroxy-5-(2-methylphenyl)-octahydrocyclopenta[c]pyrrol-2-yl]-1-(4-hydroxyphenyl)propan-1-one | 1.00E−05 | + |
| 95 | 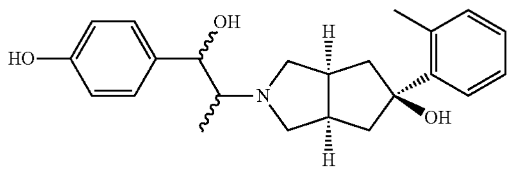 | rac-2-[1-hydroxy-1-(4-hydroxyphenyl)propan-2-yl]-5-(2-methylphenyl)-octahydrocyclopenta[c]pyrrol-5-ol | 1.00E−05 | + |
| 96 | 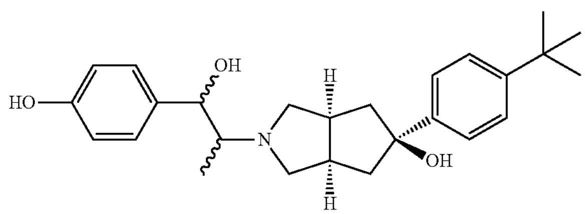 [SMILES: CC(C(O)c1ccc(O)cc1)N1C[C@@H]2C[C@@](O)(c3ccc(C(C)(C)C)cc3)C[C@@H]2C1] | rac-5-(4-tert-butylphenyl)-2-[1-hydroxy-1-(4-hydroxyphenyl)propan-2-yl]-octahydrocyclopenta[c]pyrrol-5-ol | 1.05E−05 | + |
| 97 | 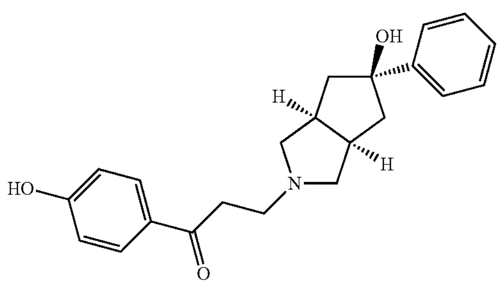 [SMILES: O=C(CCN1C[C@@H]2C[C@@](O)(c3ccccc3)C[C@@H]2C1)c1ccc(O)cc1] | 3-(5-hydroxy-5-phenylhexahydro-cyclopenta[c]pyrrol-2(1H)-yl)-1-(4-hydroxyphenyl)propan-1-one | 1.00E−05 | + |
| 98 | 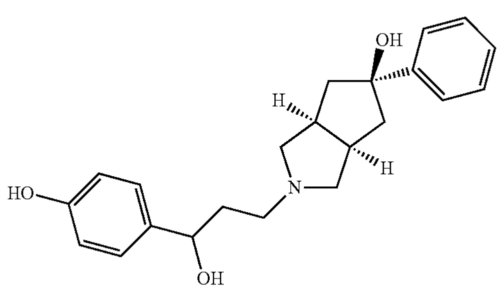 [SMILES: Oc1ccc(C(O)CCN2C[C@@H]3C[C@@](O)(c4ccccc4)C[C@@H]3C2)cc1] | 2-(3-hydroxy-3-(4-hydroxyphenyl)propyl)-5-phenyloctahydrocyclopenta[c]pyrrol-5-ol | 1.00E−05 | + |
| 99 | 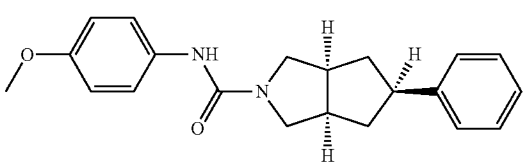 [SMILES: COc1ccc(NC(=O)N2C[C@H]3C[C@@H](c4ccccc4)C[C@H]3C2)cc1] | 2 N-(4-methoxyphenyl)-5-phenylhexahydrocyclopenta[c]pyrrole-2(1H)-carboxamide | 1.00E−05 | + |

| Cmpd # | Structure | IUPAC Name | NR2B NAM IC50 | Binned Activity |
|---|---|---|---|---|
| 100 | 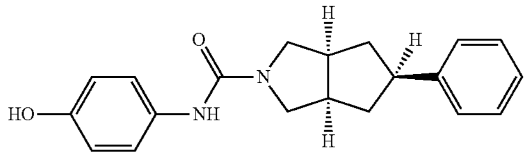 [SMILES: O=C(Nc1ccc(O)cc1)N1C[C@H]2C[C@@H](c3ccccc3)C[C@H]2C1] | N-(4-hydroxyphenyl)-5-phenyl-octahydrocyclopenta[c]pyrrole-2-carboxamide | 1.00E−05 | + |
| 101 | 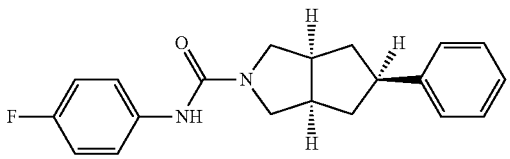 [SMILES: O=C(Nc1ccc(F)cc1)N1C[C@H]2C[C@@H](c3ccccc3)C[C@H]2C1] | N-(4-fluorophenyl)-5-phenyl-octahydrocyclopenta[c]pyrrole-2-carboxamide | 1.00E−05 | + |
| 102 | 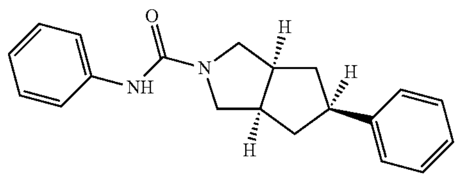 [SMILES: O=C(Nc1ccccc1)N1C[C@H]2C[C@@H](c3ccccc3)C[C@H]2C1] | N,5-diphenyl-octahydrocyclopenta[c]pyrrole-2-carboxamide | 1.00E−05 | + |
| 103 | 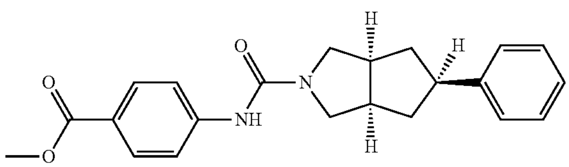 [SMILES: COC(=O)c1ccc(NC(=O)N2C[C@H]3C[C@@H](c4ccccc4)C[C@H]3C2)cc1] | methyl 4-[({5-phenyl-octahydrocyclopenta[c]pyrrol-2-yl}carbonyl)amino]benzoate | 1.00E−05 | + |
| 104 | 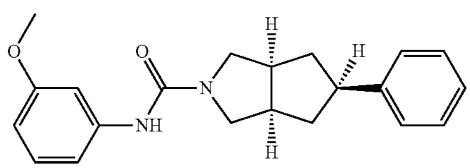 [SMILES: COc1cccc(NC(=O)N2C[C@H]3C[C@@H](c4ccccc4)C[C@H]3C2)c1] | N-(3-methoxyphenyl)-5-phenyl-octahydrocyclopenta[c]pyrrole-2-carboxamide | 1.00E−05 | + |
| 105 | 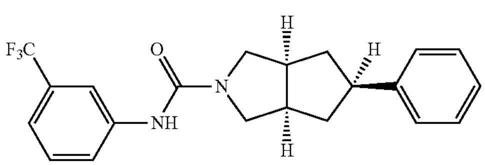 [SMILES: O=C(Nc1cccc(C(F)(F)F)c1)N1C[C@H]2C[C@@H](c3ccccc3)C[C@H]2C1] | 5-phenyl-N-[3-(trifluoromethyl)phenyl]-octahydrocyclopenta[c]pyrrole-2-carboxamide | 1.00E−05 | + |
| 106 | 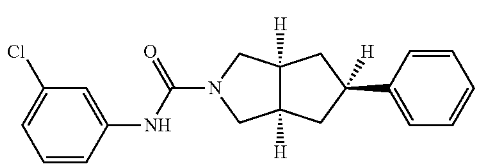 [SMILES: O=C(Nc1cccc(Cl)c1)N1C[C@H]2C[C@@H](c3ccccc3)C[C@H]2C1] | N-(3-chlorophenyl)-5-phenyl-octahydrocyclopenta[c]pyrrole-2-carboxamide | 1.00E−05 | + |
| 107 | 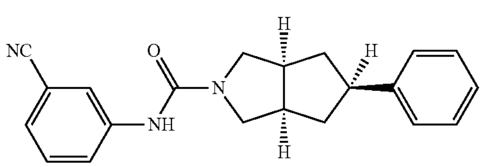 [SMILES: N#Cc1cccc(NC(=O)N2C[C@H]3C[C@@H](c4ccccc4)C[C@H]3C2)c1] | N-(3-cyanophenyl)-5-phenyl-octahydrocyclopenta[c]pyrrole-2-carboxamide | 1.00E−05 | + |
| 108 | 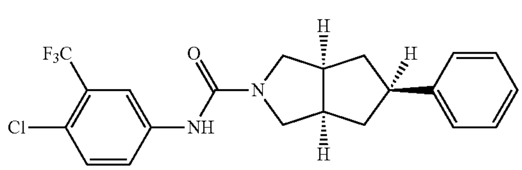 [SMILES: O=C(Nc1ccc(Cl)c(C(F)(F)F)c1)N1C[C@H]2C[C@@H](c3ccccc3)C[C@H]2C1] | N-[4-chloro-3-(trifluoromethyl)phenyl]-5-phenyl-octahydrocyclopenta[c]pyrrole-2-carboxamide | 1.00E−05 | + |

| Cmpd # | Structure | IUPAC Name | NR2B NAM IC50 | Binned Activity |
|---|---|---|---|---|
| 109 | 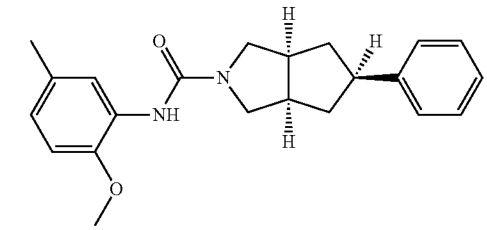 [SMILES: COc1ccc(C)cc1NC(=O)N1C[C@H]2C[C@@H](c3ccccc3)C[C@H]2C1] | N-(2-methoxy-5-methylphenyl)-5-phenyl-octahydrocyclopenta[c]pyrrole-2-carboxamide | 1.00E−05 | + |
| 110 | 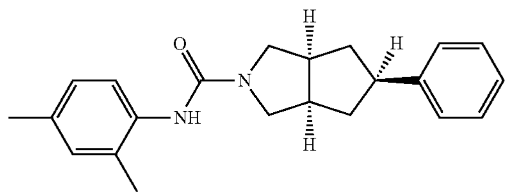 [SMILES: Cc1ccc(NC(=O)N2C[C@H]3C[C@@H](c4ccccc4)C[C@H]3C2)c(C)c1] | N-(2,4-dimethylphenyl)-5-phenyl-octahydrocyclopenta[c]pyrrole-2-carboxamide | 1.00E−05 | + |
| 111 | 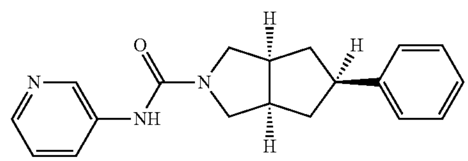 [SMILES: O=C(Nc1cccnc1)N1C[C@H]2C[C@@H](c3ccccc3)C[C@H]2C1] | 5-phenyl-N-(pyridin-3-yl)-octahydrocyclopenta[c]pyrrole-2-carboxamide | 1.00E−05 | + |
| 112 | 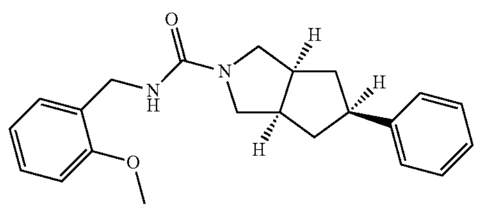 [SMILES: COc1ccccc1CNC(=O)N1C[C@H]2C[C@@H](c3ccccc3)C[C@H]2C1] | N-[(2-methoxyphenyl)methyl]-5-phenyl-octahydrocyclopenta[c]pyrrole-2-carboxamide | 1.00E−05 | + |
| 113 | 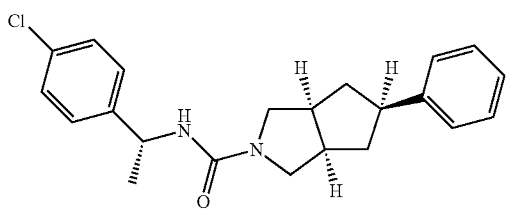 [SMILES: C[C@@H](NC(=O)N1C[C@H]2C[C@@H](c3ccccc3)C[C@H]2C1)c1ccc(Cl)cc1] | N-[(1R)-1-(4-chlorophenyl)ethyl]-5-phenyl-octahydrocyclopenta[c]pyrrole-2-carboxamide | 1.00E−05 | + |
| 114 | 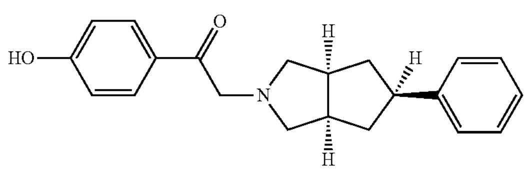 | 1-(4-hydroxyphenyl)-2-(5-phenylhexahydrocyclopenta[c]pyrrol-2(1H)-yl)ethanone | 2.32E−07 | +++ |
| 115 | 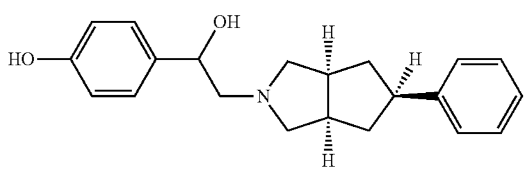 | 4-(1-hydroxy-2-(5-phenylhexahydrocyclopenta[c]pyrrol-2(1H)-yl)ethyl)phenol | 1.00E−05 | + |
| 116 | 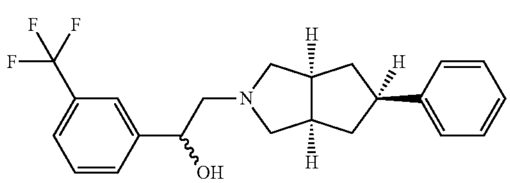 [SMILES: OC(CN1C[C@H]2C[C@@H](c3ccccc3)C[C@H]2C1)c1cccc(C(F)(F)F)c1] | rac-2-(5-phenylhexahydrocyclopenta[c]pyrrol-2(1H)-yl)-1-(3-(trifluoromethyl)phenyl)ethanol | 1.00E−05 | + |

| Cmpd # | Structure | IUPAC Name | NR2B NAM IC50 | Binned Activity |
|---|---|---|---|---|
| 117 | 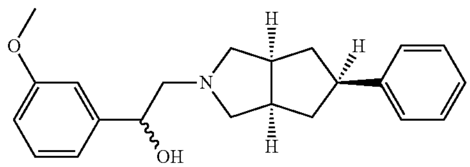 [SMILES: COc1cccc(C(O)CN2C[C@H]3C[C@@H](c4ccccc4)C[C@H]3C2)c1] | rac-1-(3-methoxyphenyl)-2-{5-phenyl-octahydrocyclopenta[c]pyrrol-2-yl}ethan-1-ol | 1.00E−05 | + |
| 118 | 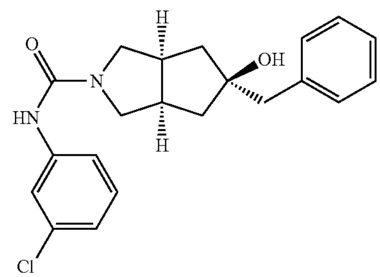 [SMILES: O=C(Nc1cccc(Cl)c1)N1C[C@@H]2C[C@@](O)(Cc3ccccc3)C[C@@H]2C1] | (3aR,5r,6aS)-5-benzyl-N-(3-chlorophenyl)-5-hydroxyhexahydrocyclopenta[c]pyrrole-2(1H)-carboxamide | 1.00E−05 | + |
| 119 | 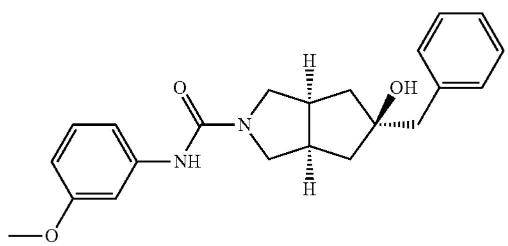 [SMILES: COc1cccc(NC(=O)N2C[C@@H]3C[C@@](O)(Cc4ccccc4)C[C@@H]3C2)c1] | (3aR,5r,6aS)-5-benzyl-5-hydroxy-N-(3-methoxyphenyl)hexahydrocyclopenta[c]pyrrole-2(1H)-carboxamide | 1.00E−05 | + |
| 120 | 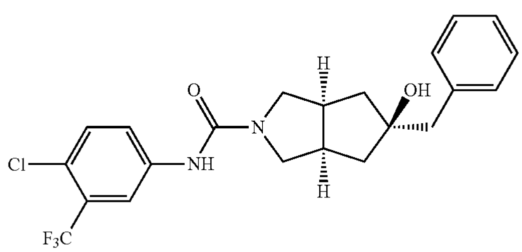 [SMILES: O=C(Nc1ccc(Cl)c(C(F)(F)F)c1)N1C[C@@H]2C[C@@](O)(Cc3ccccc3)C[C@@H]2C1] | (3aR,5r,6aS)-5-benzyl-N-(4-chloro-3-(trifluoromethyl)phenyl)-5-hydroxyhexahydrocyclopenta[c]pyrrole-2(1H)-carboxamide | 1.00E−05 | + |
| 121 | 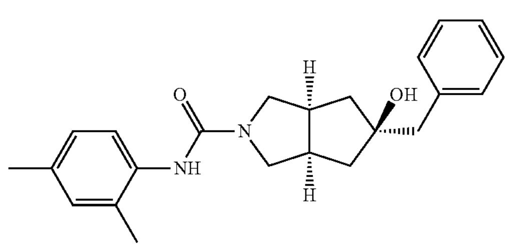 [SMILES: Cc1ccc(NC(=O)N2C[C@@H]3C[C@@](O)(Cc4ccccc4)C[C@@H]3C2)c(C)c1] | (3aR,5r,6aS)-5-benzyl-N-(2,4-dimethylphenyl)-5-hydroxyhexahydrocyclopenta[c]pyrrole-2(1H)-carboxamide | 1.00E−05 | + |
| 122 | 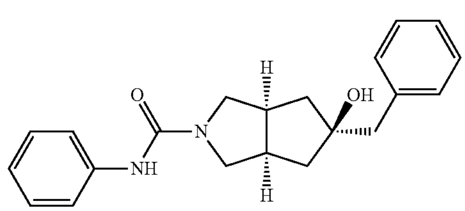 [SMILES: O=C(Nc1ccccc1)N1C[C@@H]2C[C@@](O)(Cc3ccccc3)C[C@@H]2C1] | (3aR,5r,6aS)-5-benzyl-5-hydroxy-N-phenylhexahydrocyclopenta[c]pyrrole-2(1H)-carboxamide | 1.00E−05 | + |

| Cmpd # | Structure | IUPAC Name | NR2B NAM IC50 | Binned Activity |
|---|---|---|---|---|
| 123 | 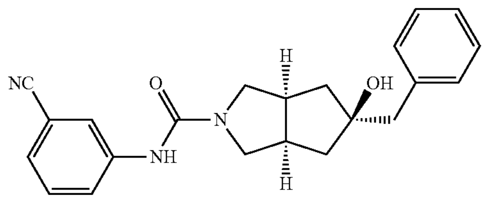 [SMILES: N#Cc1cccc(NC(=O)N2C[C@@H]3C[C@@](O)(Cc4ccccc4)C[C@@H]3C2)c1] | (3aR,5r,6aS)-5-benzyl-N-(3-cyanophenyl)-5-hydroxyhexahydrocyclopenta[c]pyrrole-2(1H)-carboxamide | 1.00E−05 | + |
| 124 | 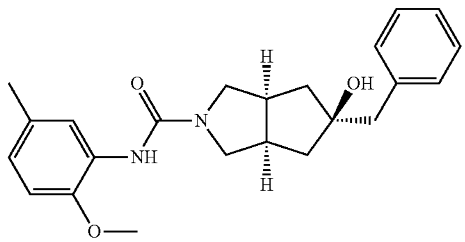 [SMILES: COc1ccc(C)cc1NC(=O)N1C[C@@H]2C[C@@](O)(Cc3ccccc3)C[C@@H]2C1] | (3aR,5r,6aS)-5-benzyl-5-hydroxy-N-(2-methoxy-5-methyl-phenyl)hexahydro-cyclopenta[c]pyrrole-2(1H)-carboxamide | 1.00E−05 | + |
| 125 | 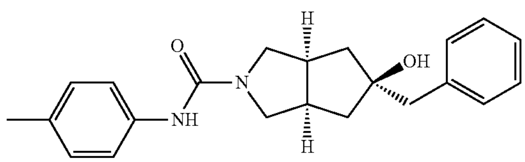 [SMILES: Cc1ccc(NC(=O)N2C[C@@H]3C[C@@](O)(Cc4ccccc4)C[C@@H]3C2)cc1] | (3aR,5r,6aS)-5-benzyl-5-hydroxy-N-(p-tolyl)hexahydrocyclopenta[c]pyrrole-2(1H)-carboxamide | 1.00E−05 | + |
| 126 | 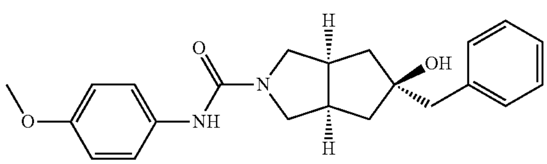 [SMILES: COc1ccc(NC(=O)N2C[C@@H]3C[C@@](O)(Cc4ccccc4)C[C@@H]3C2)cc1] | (3aR,5r,6aS)-5-benzyl-5-hydroxy-N-(4-methoxyphenyl)hexahydrocyclopenta[c]pyrrole-2(1H)-carboxamide | 1.00E−05 | + |
| 127 | 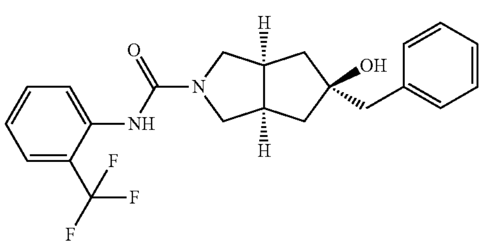 [SMILES: O=C(Nc1ccccc1C(F)(F)F)N1C[C@@H]2C[C@@](O)(Cc3ccccc3)C[C@@H]2C1] | (3aR,5r,6aS)-5-benzyl-5-hydroxy-N-(2-(trifluoromethyl)phenyl)hexahydro-cyclopenta[c]pyrrole-2(1H)-carboxamide | 1.00E−05 | + |
| 128 | 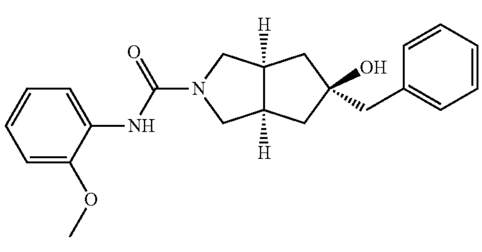 [SMILES: COc1ccccc1NC(=O)N1C[C@@H]2C[C@@](O)(Cc3ccccc3)C[C@@H]2C1] | (3aR,5r,6aS)-5-benzyl-5-hydroxy-N-(2-methoxyphenyl)hexahydrocyclopenta[c]pyrrole-2(1H)-carboxamide | 1.00E−05 | + |
| 129 | 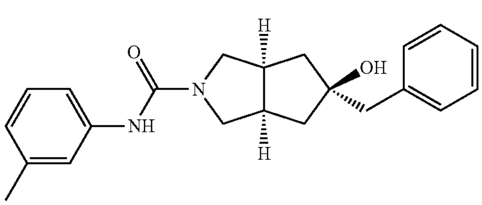 [SMILES: Cc1cccc(NC(=O)N2C[C@@H]3C[C@@](O)(Cc4ccccc4)C[C@@H]3C2)c1] | (3aR,5r,6aS)-5-benzyl-5-hydroxy-N-(m-tolyl)hexahydrocyclopenta[c]pyrrole-2(1H)-carboxamide | 1.00E−05 | + |

| Cmpd # | Structure | IUPAC Name | NR2B NAM IC50 | Binned Activity |
|---|---|---|---|---|
| 130 | 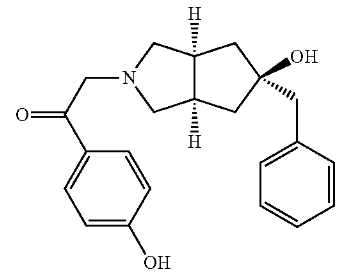 [SMILES: O=C(CN1C[C@@H]2C[C@@](O)(Cc3ccccc3)C[C@@H]2C1)c1ccc(O)cc1] | 2-((3aR,5r,6aS)-5-benzyl-5-hydroxyhexahydrocyclopenta[c]pyrrol-2(1H)-yl)-1-(4-hydroxyphenyl)ethanone | 4.41E−08 | ++++ |
| 131 | 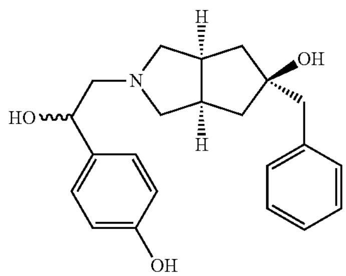 [SMILES: Oc1ccc(C(O)CN2C[C@@H]3C[C@@](O)(Cc4ccccc4)C[C@@H]3C2)cc1] | rac-(3aR,5r,6aS)-5-benzyl-2-(2-hydroxy-2-(4-hydroxyphenyl)ethyl)octahydrocyclopenta[c]pyrrol-5-ol | 2.55E−08 | ++++ |
| 132 | 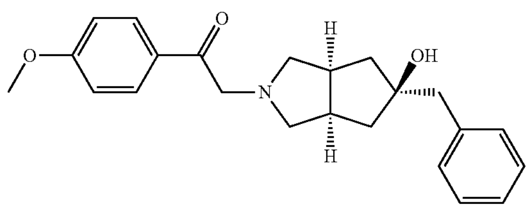 [SMILES: COc1ccc(C(=O)CN2C[C@@H]3C[C@@](O)(Cc4ccccc4)C[C@@H]3C2)cc1] | 2-((3aR,5r,6aS)-5-benzyl-5-hydroxyhexahydrocyclopenta[c]pyrrol-2(1H)-yl)-1-(4-methoxyphenyl)ethanone | 1.00E−05 | + |
| 133 | 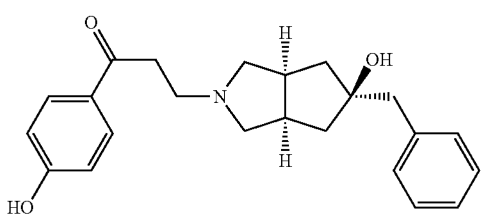 [SMILES: O=C(CCN1C[C@@H]2C[C@@](O)(Cc3ccccc3)C[C@@H]2C1)c1ccc(O)cc1] | 3-((3aR,5r,6aS)-5-benzyl-5-hydroxyhexahydrocyclopenta[c]pyrrol-2(1H)-yl)-1-(4-hydroxyphenyl)propan-1-one | 7.05E−06 | ++ |
| 134 | 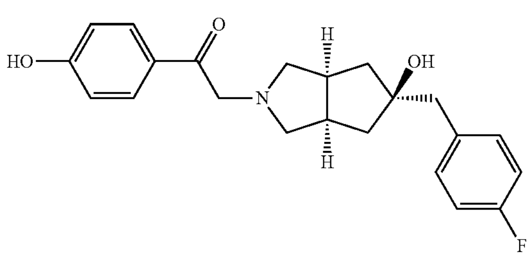 [SMILES: O=C(CN1C[C@@H]2C[C@@](O)(Cc3ccc(F)cc3)C[C@@H]2C1)c1ccc(O)cc1] | 2-((3aR,5r,6aS)-5-(4-fluorobenzyl)-5-hydroxyhexahydrocyclopenta[c]pyrrol-2(1H)-yl)-1-(4-hydroxyphenyl)ethanone | 4.32E−08 | ++++ |
| 135 | 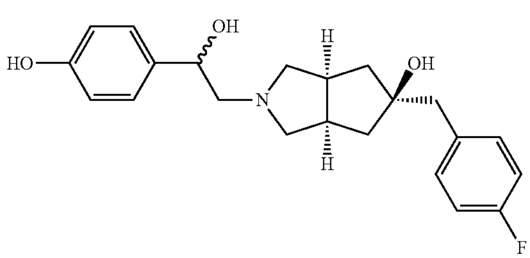 [SMILES: Oc1ccc(C(O)CN2C[C@@H]3C[C@@](O)(Cc4ccc(F)cc4)C[C@@H]3C2)cc1] | rac-(3aR,5r,6aS)-5-(4-fluorobenzyl)-2-(2-hydroxy-2-(4-hydroxyphenyl)ethyl)octahydrocyclopenta[c]pyrrol-5-ol | 2.71E−08 | ++++ |

-continued

| Cmpd # | Structure | IUPAC Name | NR2B NAM IC50 | Binned Activity |
|---|---|---|---|---|
| 136 | 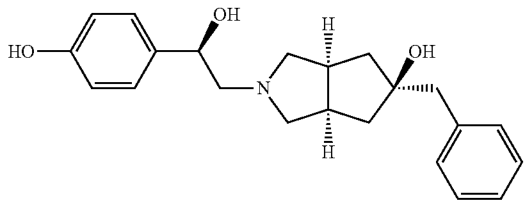 [SMILES: Oc1ccc([C@@H](O)CN2C[C@@H]3C[C@@](O)(Cc4ccccc4)C[C@@H]3C2)cc1] | (3aR,5R,6aS)-5-benzyl-2-((R)-2-hydroxy-2-(4-hydroxyphenyl)ethyl)octahydrocyclopenta[c]pyrrol-5-ol | 2.37E−08 | ++++ |
| 137 | 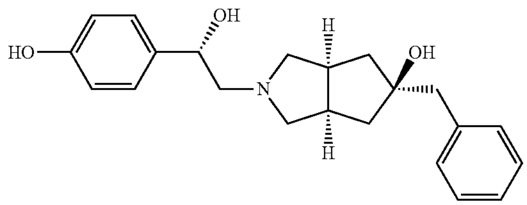 [SMILES: Oc1ccc([C@H](O)CN2C[C@@H]3C[C@@](O)(Cc4ccccc4)C[C@@H]3C2)cc1] | (3aR,5S,6aS)-5-benzyl-2-((S)-2-hydroxy-2-(4-hydroxyphenyl)ethyl)octahydrocyclopenta[c]pyrrol-5-ol | 2.04E−08 | ++++ |
| 138 | 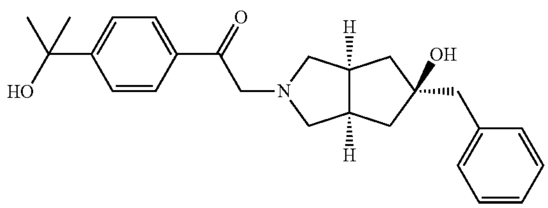 [SMILES: CC(C)(O)c1ccc(C(=O)CN2C[C@@H]3C[C@@](O)(Cc4ccccc4)C[C@@H]3C2)cc1] | 2-((3aR,5r,6aS)-5-benzyl-5-hydroxyhexahydrocyclopenta[c]pyrrol-2(1H)-yl)-1-(4-(2-hydroxypropan-2-yl)phenyl)ethanone | 1.00E−05 | + |
| 139 | 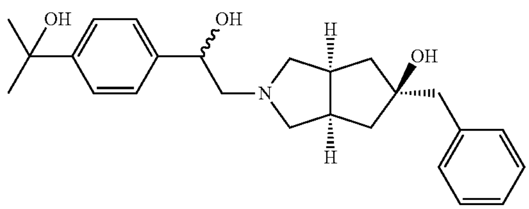 [SMILES: CC(C)(O)c1ccc(C(O)CN2C[C@@H]3C[C@@](O)(Cc4ccccc4)C[C@@H]3C2)cc1] | rac-(3aR,5r,6aS)-5-benzyl-2-(2-hydroxy-2-(4-(2-hydroxypropan-2-yl)phenyl)ethyl)octahydrocyclopenta[c]pyrrol-5-ol | 1.00E−05 | + |
| 140 | 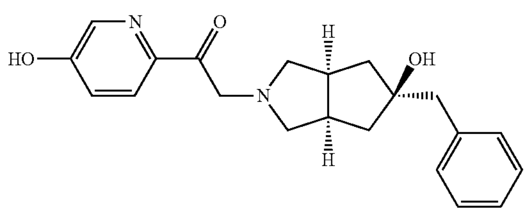 [SMILES: O=C(CN1C[C@@H]2C[C@@](O)(Cc3ccccc3)C[C@@H]2C1)c1ccc(O)cn1] | 2-((3aR,5r,6aS)-5-benzyl-5-hydroxyhexahydrocyclopenta[c]pyrrol-2(1H)-yl)-1-(5-hydroxypyridin-2-yl)ethanone | 6.94E−06 | ++ |
| 141 | 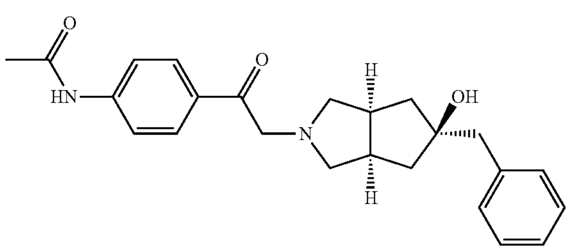 [SMILES: CC(=O)Nc1ccc(C(=O)CN2C[C@@H]3C[C@@](O)(Cc4ccccc4)C[C@@H]3C2)cc1] | N-(4-(2-((3aR,5r,6aS)-5-benzyl-5-hydroxy-hexahydrocyclopenta[c]pyrrol-2(1H)-yl)acetyl)phenyl)acetamide | 1.00E−05 | + |
| 142 | 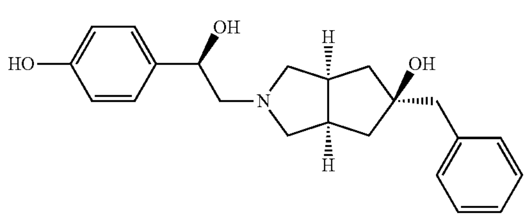 [SMILES: Oc1ccc([C@@H](O)CN2C[C@@H]3C[C@@](O)(Cc4ccccc4)C[C@@H]3C2)cc1] | (3aR,5R,6aS)-5-benzyl-2-((R)-2-hydroxy-2-(4-hydroxyphenyl)ethyl)octahydrocyclopenta[c]pyrrol-5-ol | 2.37E−08 | ++++ |

-continued

| Cmpd # | Structure | IUPAC Name | NR2B NAM IC50 | Binned Activity |
|---|---|---|---|---|
| 143 | 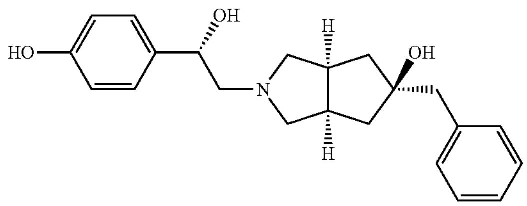 [SMILES: Oc1ccc([C@H](O)CN2C[C@@H]3C[C@@](O)(Cc4ccccc4)C[C@@H]3C2)cc1] | (3aR,5S,6aS)-5-benzyl-2-((S)-2-hydroxy-2-(4-hydroxyphenyl)ethyl)octahydrocyclopenta[c]pyrrol-5-ol | 2.04E−08 | ++++ |
| 144 | 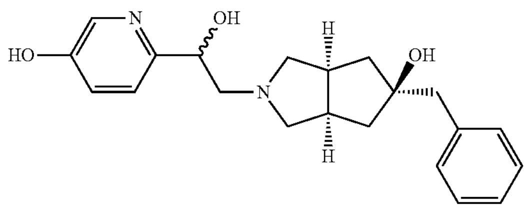 | rac-(3aR,5r,6aS)-5-benzyl-2-(2-hydroxy-2-(5-hydroxypyridin-2-yl)ethyl)octahydrocyclopenta[c]pyrrol-5-ol | 2.68E−08 | ++++ |
| 145 | 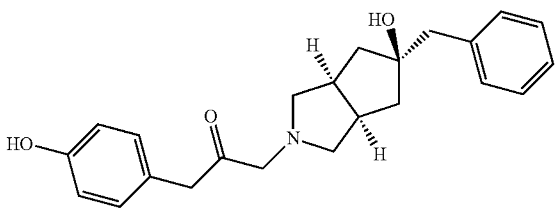 [SMILES: O=C(Cc1ccc(O)cc1)CN1C[C@@H]2C[C@@](O)(Cc3ccccc3)C[C@@H]2C1] | 1-((3aR,5r,6aS)-5-benzyl-5-hydroxyhexahydrocyclopenta[c]pyrrol-2(1H)-yl)-3-(4-hydroxyphenyl)propan-2-one | 1.00E−05 | + |
| 146 | 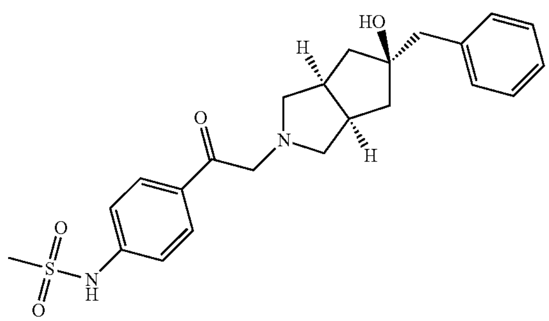 [SMILES: CS(=O)(=O)Nc1ccc(C(=O)CN2C[C@@H]3C[C@@](O)(Cc4ccccc4)C[C@@H]3C2)cc1] | N-(4-(2-((3aR,5r,6aS)-5-benzyl-5-hydroxyhexahydrocyclopenta[c]pyrrol-2(1H)-yl)acetyl)phenyl)methanesulfonamide | 3.26E−07 | +++ |
| 147 | 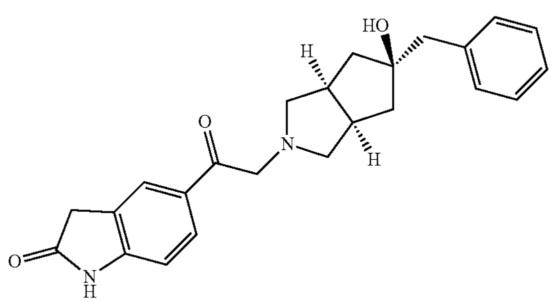 [SMILES: O=C1Cc2cc(C(=O)CN3C[C@@H]4C[C@@](O)(Cc5ccccc5)C[C@@H]4C3)ccc2N1] | 5-(2-((3aR,5r,6aS)-5-benzyl-5-hydroxyhexahydrocyclopenta[c]pyrrol-2(1H)-yl)acetyl)indolin-2-one | 3.52E−07 | +++ |
| 148 | 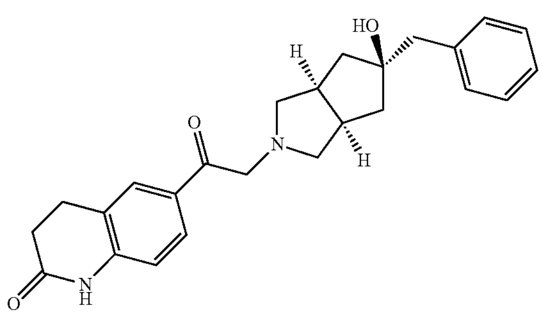 [SMILES: O=C1CCc2cc(C(=O)CN3C[C@@H]4C[C@@](O)(Cc5ccccc5)C[C@@H]4C3)ccc2N1] | 6-(2-((3aR,5r,6aS)-5-benzyl-5-hydroxyhexahydrocyclopenta[c]pyrrol-2(1H)-yl)acetyl)-3,4-dihydroquinolin-2(1H)-one | 1.37E−07 | +++ |

| Cmpd # | Structure | IUPAC Name | NR2B NAM IC50 | Binned Activity |
|---|---|---|---|---|
| 149 | 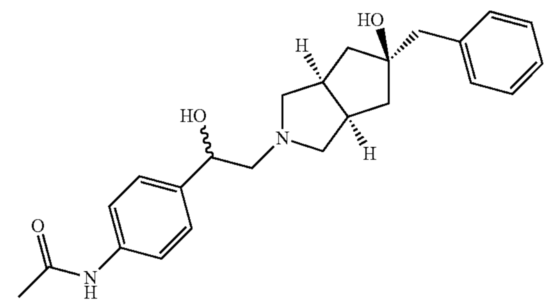 [SMILES: CC(=O)Nc1ccc(C(O)CN2C[C@@H]3C[C@@](O)(Cc4ccccc4)C[C@@H]3C2)cc1] | rac-N-(4-(2-((3aR,5r,6aS)-5-benzyl-5-hydroxyhexahydro-cyclopenta[c]pyrrol-2(1H)-yl)-1-hydroxy-ethyl)phenyl)acetamide | 2.31E−06 | ++ |
| 150 | 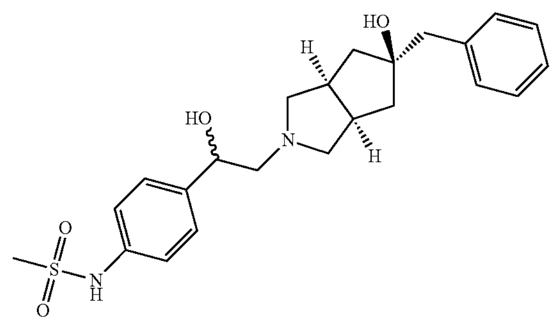 [SMILES: CS(=O)(=O)Nc1ccc(C(O)CN2C[C@@H]3C[C@@](O)(Cc4ccccc4)C[C@@H]3C2)cc1] | rac-N-(4-(2-((3aR,5r,6aS)-5-benzyl-5-hydroxyhexahydrocyclo-penta[c]pyrrol-2(1H)-yl)-1-hydroxyethyl)phenyl)methanesulfonamide | 4.70E−08 | ++++ |
| 151 | 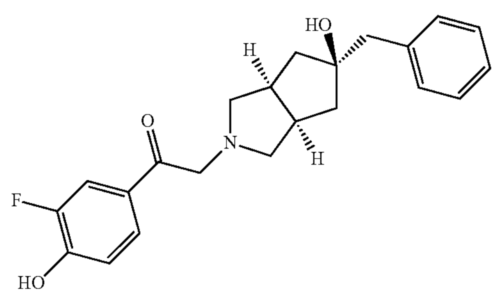 [SMILES: O=C(CN1C[C@@H]2C[C@@](O)(Cc3ccccc3)C[C@@H]2C1)c1ccc(O)c(F)c1] | 2-((3aR,5r,6aS)-5-benzyl-5-hydroxyhexahydrocyclo-penta[c]pyrrol-2(1H)-yl)-1-(3-fluoro-4-hydroxy-phenyl)ethanone | 3.72E−07 | +++ |
| 152 | 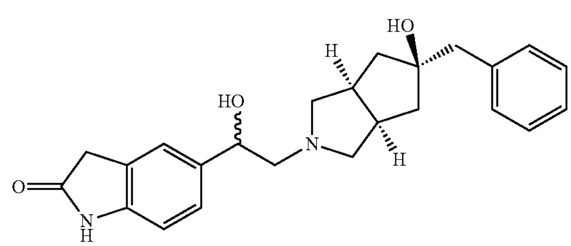 [SMILES: O=C1Cc2cc(C(O)CN3C[C@@H]4C[C@@](O)(Cc5ccccc5)C[C@@H]4C3)ccc2N1] | rac-5-(2-((3aR,5r,6aS)-5-benzyl-5-hydroxy-hexahydrocyclo-penta[c]pyrrol-2(1H)-yl)-1-hydroxyethyl)indolin-2-one | 1.43E−07 | +++ |
| 153 | 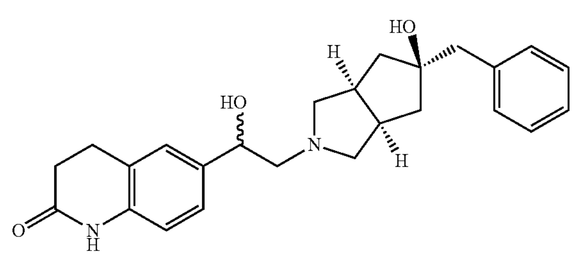 [SMILES: O=C1CCc2cc(C(O)CN3C[C@@H]4C[C@@](O)(Cc5ccccc5)C[C@@H]4C3)ccc2N1] | rac-6-(2-((3aR,5r,6aS)-5-benzyl-5-hydroxy-hexahydrocyclo-penta[c]pyrrol-2(1H)-yl)-1-hydroxyethyl)-3,4-dihydroquinolin-2(1H)-one | 4.02E−08 | ++++ |

| Cmpd # | Structure | IUPAC Name | NR2B NAM IC50 | Binned Activity |
|---|---|---|---|---|
| 154 | 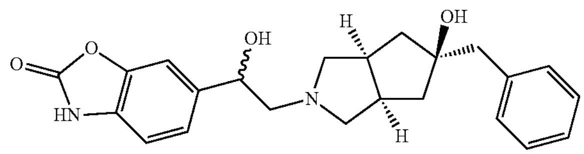 [SMILES: O=c1[nH]c2ccc(C(O)CN3C[C@@H]4C[C@@](O)(Cc5ccccc5)C[C@@H]4C3)cc2o1] | rac-6-(2-((3aR,5r,6aS)-5-benzyl-5-hydroxy-hexahydrocyclopenta[c]pyrrol-2(1H)-yl)-1-hydroxy-ethyl)benzo[d]oxazol-2(3H)-one | 5.24E−08 | ++++ |
| 155 | 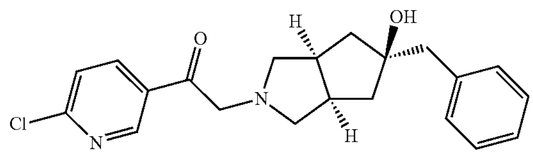 [SMILES: O=C(CN1C[C@@H]2C[C@@](O)(Cc3ccccc3)C[C@@H]2C1)c1ccc(Cl)nc1] | 2-((3aR,5r,6aS)-5-benzyl-5-hydroxyhexahydrocyclopenta[c]pyrrol-2(1H)-yl)-1-(6-chloropyridin-3-yl)ethanone | 1.00E−05 | + |
| 156 | 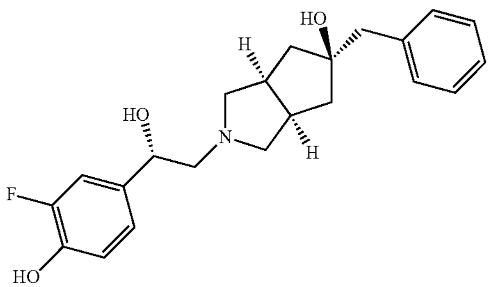 [SMILES: Oc1ccc([C@H](O)CN2C[C@@H]3C[C@@](O)(Cc4ccccc4)C[C@@H]3C2)cc1F] | (3aR,5S,6aS)-5-benzyl-2-((S)-2-(3-fluoro-4-hydroxyphenyl)-2-hydroxyethyl)octahydro-cyclopenta[c]pyrrol-5-ol | 3.05E−08 | ++++ |
| 157 | 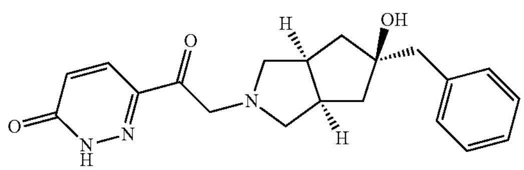 [SMILES: O=C(CN1C[C@@H]2C[C@@](O)(Cc3ccccc3)C[C@@H]2C1)c1ccc(=O)[nH]n1] | 6-(2-((3aR,5r,6aS)-5-benzyl-5-hydroxyhexahydrocyclopenta[c]pyrrol-2(1H)-yl)acetyl)pyridazin-3(2H)-one | 1.00E−05 | + |
| 158 | 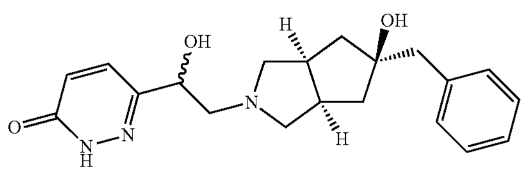 [SMILES: O=c1ccc(C(O)CN2C[C@@H]3C[C@@](O)(Cc4ccccc4)C[C@@H]3C2)n[nH]1] | rac-6-(2-((3aR,5r,6aS)-5-benzyl-5-hydroxyhexahydrocyclopenta[c]pyrrol-2(1H)-yl)-1-hydroxy-ethyl)pyridazin-3(2H)-one | 1.00E−05 | + |
| 159 | 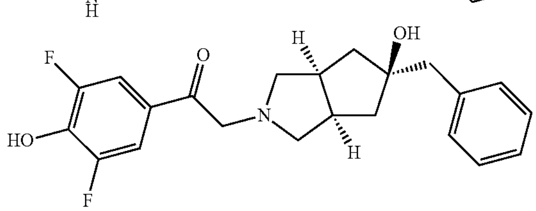 | 2-((3aR,5r,6aS)-5-benzyl-5-hydroxyhexahydrocyclopenta[c]pyrrol-2(1H)-yl)-1-(3,5-difluoro-4-hydroxyphenyl)ethanone | 1.16E−05 | + |
| 160 | 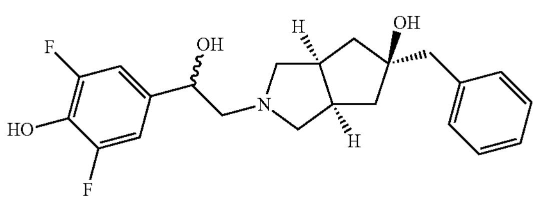 [SMILES: Oc1c(F)cc(C(O)CN2C[C@@H]3C[C@@](O)(Cc4ccccc4)C[C@@H]3C2)cc1F] | rac-(3aR,5r,6aS)-5-benzyl-2-(2-(3,5-difluoro-4-hydroxyphenyl)-2-hydroxyethyl)octahydro-cyclopenta[c]pyrrol-5-ol | 9.81E−08 | ++++ |
| 161 | 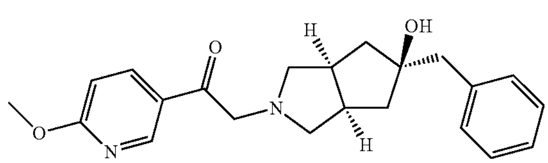 [SMILES: COc1ccc(C(=O)CN2C[C@@H]3C[C@@](O)(Cc4ccccc4)C[C@@H]3C2)cn1] | 2-((3aR,5r,6aS)-5-benzyl-5-hydroxyhexahydrocyclopenta[c]pyrrol-2(1H)-yl)-1-(6-methoxypyridin-3-yl)ethanone | 1.00E−05 | + |

| Cmpd # | Structure | IUPAC Name | NR2B NAM IC50 | Binned Activity |
|---|---|---|---|---|
| 162 | 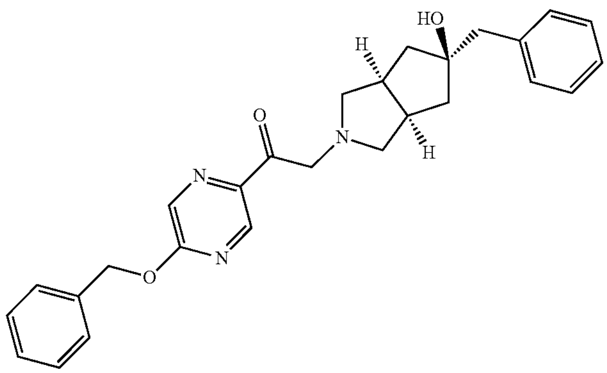 [SMILES: O=C(CN1C[C@@H]2C[C@@](O)(Cc3ccccc3)C[C@@H]2C1)c1cnc(OCc2ccccc2)cn1] | 2-((3aR,5r,6aS)-5-benzyl-5-hydroxyhexahydrocyclopenta[c]pyrrol-2(1H)-yl)-1-(5-(benzyloxy)pyrazin-2-yl)ethanone | 1.00E−05 | + |
| 163 | 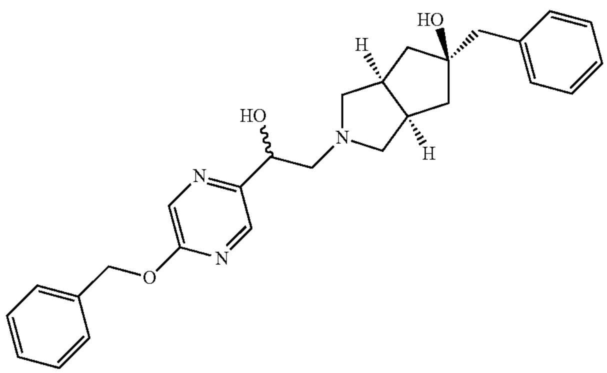 [SMILES: OC(CN1C[C@@H]2C[C@@](O)(Cc3ccccc3)C[C@@H]2C1)c1cnc(OCc2ccccc2)cn1] | rac-(3aR,5r,6aS)-5-benzyl-2-(2-(5-(benzyloxy)pyrazin-2-yl)-2-hydroxyethyl(octahydrocyclopenta[c]pyrrol-5-ol | 1.00E−05 | + |
| 1646 | 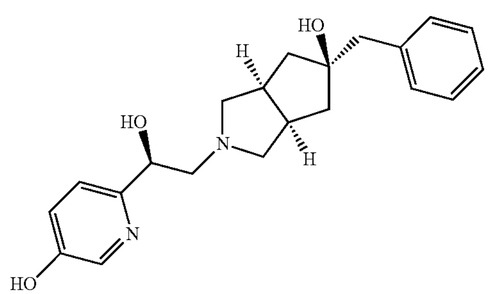 [SMILES: Oc1ccc([C@@H](O)CN2C[C@@H]3C[C@@](O)(Cc4ccccc4)C[C@@H]3C2)nc1] | (3aR,5S,6aS)-5-benzyl-2-((S)-2-hydroxy-2-(5-hydroxypyridin-2-yl)ethyl)octahydrocyclopenta[c]pyrrol-5-ol | 3.81E−08 | ++++ |
| 165 | 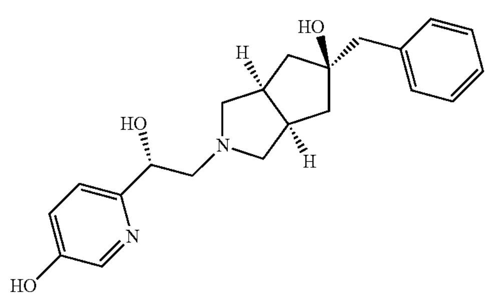 [SMILES: Oc1ccc([C@H](O)CN2C[C@@H]3C[C@@](O)(Cc4ccccc4)C[C@@H]3C2)nc1] | (3aR,5R,6aS)-5-benzyl-2-((R)-2-hydroxy-2-(5-hydroxypyridin-2-yl)ethyl)octahydrocyclopenta[c]pyrrol-5-ol | 3.37E−08 | ++++ |
| 166 | 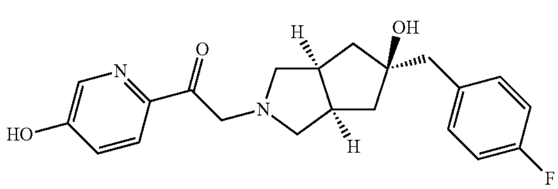 [SMILES: O=C(CN1C[C@@H]2C[C@@](O)(Cc3ccc(F)cc3)C[C@@H]2C1)c1ccc(O)cn1] | 2-((3aR,5r,6aS)-5-(4-fluorobenzyl)-5-hydroxyhexahydrocyclopenta[c]pyrrol-2(1H)-yl)-1-(5-hydroxypyridin-2-yl)ethanone | 6.40E−06 | ++ |

-continued

| Cmpd # | Structure | IUPAC Name | NR2B NAM IC50 | Binned Activity |
|---|---|---|---|---|
| 167 | 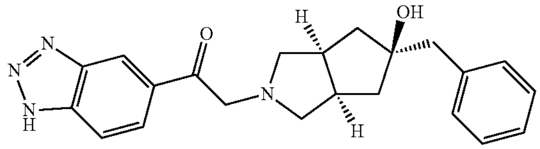 [SMILES: O=C(CN1C[C@@H]2C[C@@](O)(Cc3ccccc3)C[C@@H]2C1)c1ccc2[nH]nnc2c1] | 2-[(3aR,5R,6aS)-5-benzyl-5-hydroxy-octahydrocyclopenta[c]pyrrol-2-yl]-1-(1H-1,2,3-benzotriazol-5-yl)ethan-1-one | 1.00E−05 | + |
| 168 | 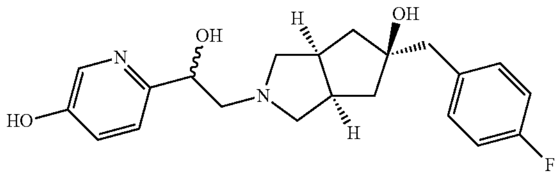 [SMILES: Oc1ccc(C(O)CN2C[C@@H]3C[C@@](O)(Cc4ccc(F)cc4)C[C@@H]3C2)nc1] | rac-(3aR,5r,6aS)-5-(4-fluorobenzyl)-2-(2-hydroxy-2-(5-hydroxypyridin-2-yl)ethyl)octahydrocyclopenta[c]pyrrol-5-ol | 1.78E−08 | ++++ |
| 169 | 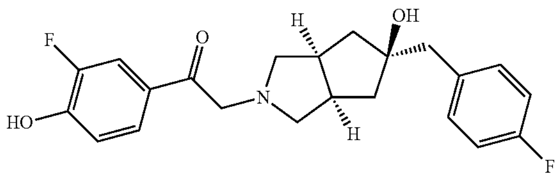 [SMILES: O=C(CN1C[C@@H]2C[C@@](O)(Cc3ccc(F)cc3)C[C@@H]2C1)c1ccc(O)c(F)c1] | 1-(3-fluoro-4-hydroxyphenyl)-2-((3aR,5r,6aS)-5-(4-fluorobenzyl)-5-hydroxyhexahydrocyclopenta[c]pyrrol-2(1H)-yl)ethanone | 1.17E−07 | +++ |
| 170 | 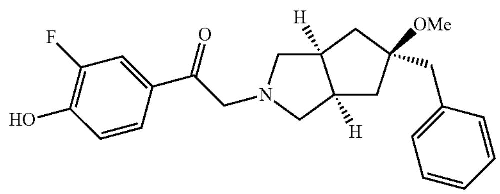 | 2-((3aR,5r,6aS)-5-benzyl-5-methoxyhexahydrocyclopenta[c]pyrrol-2(1H)-yl)-1-(3-fluoro-4-hydroxyphenyl)ethanone | 1.32E−07 | +++ |
| 171 | 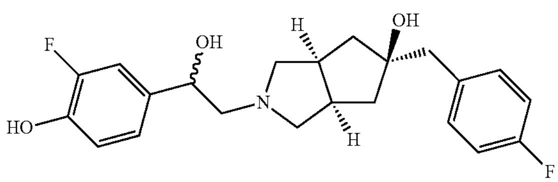 [SMILES: Oc1ccc(C(O)CN2C[C@@H]3C[C@@](O)(Cc4ccc(F)cc4)C[C@@H]3C2)cc1F] | rac-(3aR,5r,6aS)-2-(2-(3-fluoro-4-hydroxyphenyl)-2-hydroxyethyl)-5-(4-fluorobenzyl)octahydrocyclopenta[c]pyrrol-5-ol | 2.21E−08 | ++++ |
| 172 | 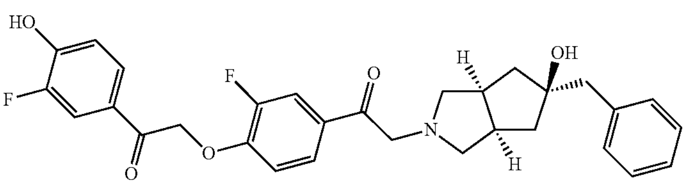 [SMILES: O=C(COc1ccc(C(=O)CN2C[C@@H]3C[C@@](O)(Cc4ccccc4)C[C@@H]3C2)cc1F)c1ccc(O)c(F)c1] | 2-((3aR,5r,6aS)-5-benzyl-5-hydroxyhexahydrocyclopenta[c]pyrrol-2(1H)-yl)-1-(3-fluoro-4-(2-(3-fluoro-4-hydroxyphenyl)-2-oxoethoxy)phenyl)ethanone | 1.00E−05 | + |
| 173 | 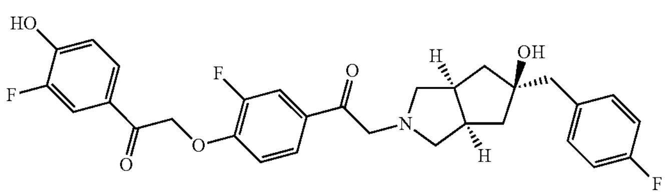 [SMILES: O=C(COc1ccc(C(=O)CN2C[C@@H]3C[C@@](O)(Cc4ccc(F)cc4)C[C@@H]3C2)cc1F)c1ccc(O)c(F)c1] | 2-(2-fluoro-4-(2-((3aR,5r,6aS)-5-(4-fluorobenzyl)-5-hydroxyhexahydrocyclopenta[c]pyrrol-2(1H)-yl)acetyl)phenoxy)-1-(3-fluoro-4-hydroxyphenyl)ethanone | 1.00E−05 | + |
| 174 | 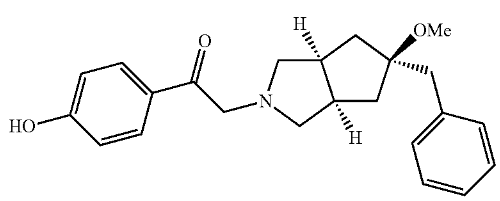 [SMILES: CO[C@@]1(Cc2ccccc2)C[C@H]2CN(CC(=O)c3ccc(O)cc3)C[C@H]2C1] | 2-((3aR,5r,6aS)-5-benzyl-5-methoxyhexahydrocyclopenta[c]pyrrol-2(1H)-yl)-1-(4-hydroxyphenyl)ethanone | 5.72E−08 | ++++ |

| Cmpd # | Structure | IUPAC Name | NR2B NAM IC50 | Binned Activity |
|---|---|---|---|---|
| 175 | 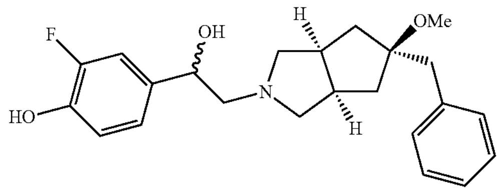 [SMILES: CO[C@@]1(Cc2ccccc2)C[C@H]2CN(CC(O)c3ccc(O)c(F)c3)C[C@H]2C1] | rac-4-(2-((3aR,5r,6aS)-5-benzyl-5-methoxy-hexahydrocyclopenta[c]pyrrol-2(1H)-yl)-1-hydroxyethyl)-2-fluorophenol | 3.24E−08 | ++++ |
| 176 | 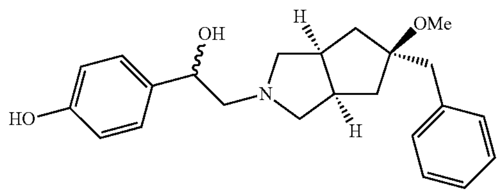 [SMILES: CO[C@@]1(Cc2ccccc2)C[C@H]2CN(CC(O)c3ccc(O)cc3)C[C@H]2C1] | rac-4-(2-((3aR,5r,6aS)-5-benzyl-5-methoxy-hexahydrocyclopenta[c]pyrrol-2(1H)-yl)-1-hydroxyethyl)phenol | 3.24E−08 | ++++ |
| 177 | 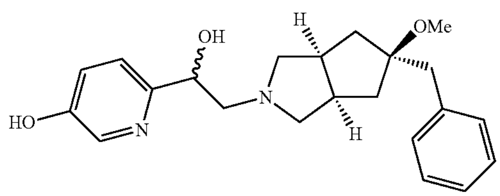 [SMILES: CO[C@@]1(Cc2ccccc2)C[C@H]2CN(CC(O)c3ccc(O)cn3)C[C@H]2C1] | rac-6-(2-((3aR,5r,6aS)-5-benzyl-5-methoxy-hexahydrocyclopenta[c]pyrrol-2(1H)-yl)-1-hydroxyethyl)pyridin-3-ol | 3.16E−08 | ++++ |
| 178 | 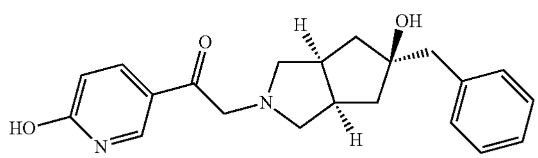 [SMILES: O=C(CN1C[C@@H]2C[C@@](O)(Cc3ccccc3)C[C@@H]2C1)c1ccc(O)nc1] | 2-[(3aR,5R,6aS)-5-benzyl-5-hydroxy-octahydrocyclopenta[c]pyrrol-2-yl]-1-(6-hydroxypyridin-3-yl)ethan-1-one | 1.00E−05 | + |
| 179 | 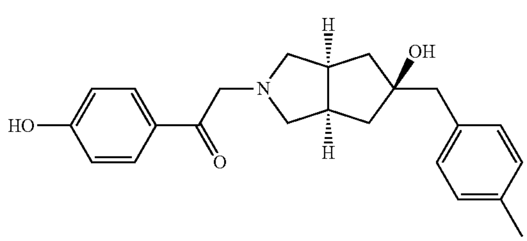 [SMILES: Cc1ccc(C[C@]2(O)C[C@H]3CN(CC(=O)c4ccc(O)cc4)C[C@H]3C2)cc1] | 2-((3aR,5r,6aS)-5-hydroxy-5-(4-methylbenzyl)hexahydrocyclopenta[c]pyrrol-2(1H)-yl)-1-(4-hydroxyphenyl)ethanone | 7.98E−08 | ++++ |
| 180 | 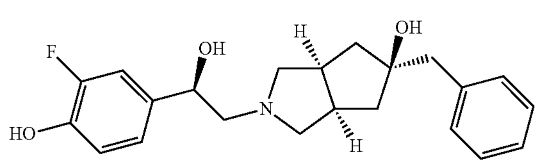 [SMILES: Oc1ccc([C@@H](O)CN2C[C@@H]3C[C@@](O)(Cc4ccccc4)C[C@@H]3C2)cc1F] | (3aR,5R,6aS)-5-benzyl-2-((R)-2-(3-fluoro-4-hydroxyphenyl)-2-hydroxyethyl)octahydrocyclopenta[c]pyrrol-5-ol | 2.23E−08 | ++++ |
| | | (3aR,5S,6aS)-5-benzyl-2-((S)-2-(3-fluoro-4-hydroxyphenyl)-2-hydroxyethyl)octahydrocyclopenta[c]pyrrol-5-ol | 2.28E−08 | ++++ |
| 181 | 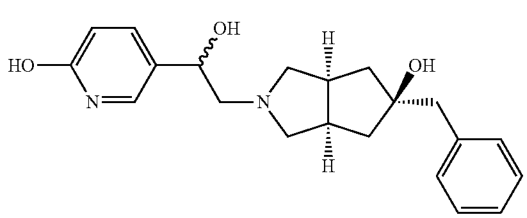 [SMILES: Oc1ccc(C(O)CN2C[C@@H]3C[C@@](O)(Cc4ccccc4)C[C@@H]3C2)cn1] | rac-5-{2-[(3aR,5R,6aS)-5-benzyl-5-hydroxy-octahydrocyclopenta[c]pyrrol-2-yl]-1-hydroxyethyl}pyridin-2-ol | 1.00E−05 | + |

-continued

| Cmpd # | Structure | IUPAC Name | NR2B NAM IC50 | Binned Activity |
|---|---|---|---|---|
| 182 | 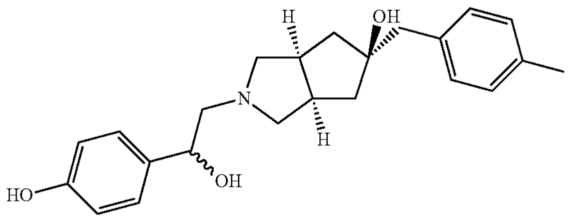 [SMILES: Cc1ccc(C[C@]2(O)C[C@H]3CN(CC(O)c4ccc(O)cc4)C[C@H]3C2)cc1] | rac-(3aR,5R,6aS)-2-[2-hydroxy-2-(4-hydroxyphenyl)ethyl]-5-[(4-methylphenyl)methyl]-octahydrocyclopenta[c]pyrrol-5-ol | 4.15E−08 | ++++ |
| 183 | 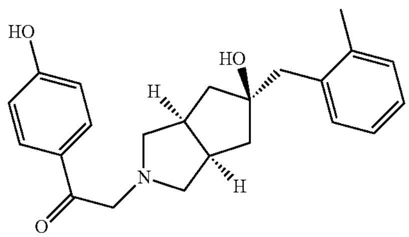 [SMILES: Cc1ccccc1C[C@]1(O)C[C@H]2CN(CC(=O)c3ccc(O)cc3)C[C@H]2C1] | 2-((3aR,5r,6aS)-5-hydroxy-5-(2-methylbenzyl)hexahydrocyclopenta[c]pyrrol-2(1H)-yl)-1-(4-hydroxyphenyl)ethanone | 1.45E−07 | +++ |
| 184 | 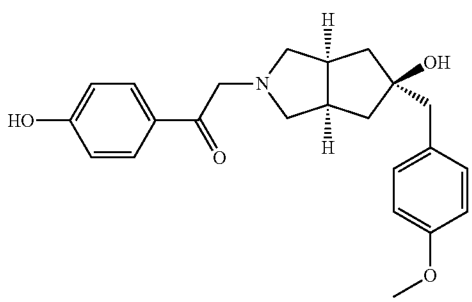 [SMILES: COc1ccc(C[C@]2(O)C[C@H]3CN(CC(=O)c4ccc(O)cc4)C[C@H]3C2)cc1] | 2-[(3aR,5R,6aS)-5-hydroxy-5-[(4-methoxyphenyl)methyl]-octahydrocyclopenta[c]pyrrol-2-yl]-1-(4-hydroxyphenyl)ethan-1-one | 4.33E−08 | ++++ |
| 185 | 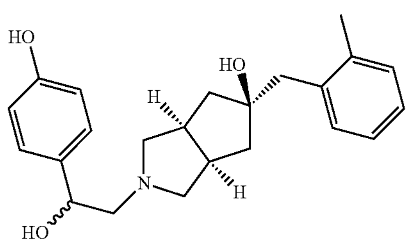 [SMILES: Cc1ccccc1C[C@]1(O)C[C@H]2CN(CC(O)c3ccc(O)cc3)C[C@H]2C1] | rac-(3aR,5r,6aS)-2-(2-hydroxy-2-(4-hydroxyphenyl)ethyl)-5-(2-methylbenzyl)octahydrocyclopenta[c]pyrrol-5-ol | 3.49E−08 | ++++ |
| 186 | 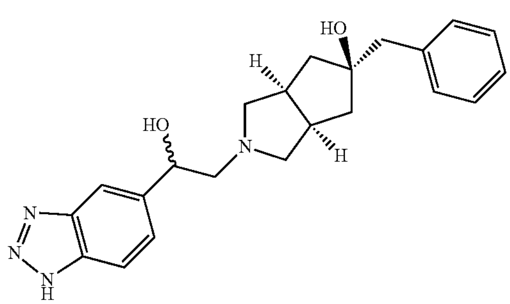 [SMILES: OC(CN1C[C@@H]2C[C@@](O)(Cc3ccccc3)C[C@@H]2C1)c1ccc2[nH]nnc2c1] | rac-(3aR,5R,6aS)-2-[2-(1H-1,2,3-benzotriazol-5-yl)-2-hydroxyethyl]-5-benzyl-octahydrocyclopenta[c]pyrrol-5-ol | 7.48E−07 | +++ |

| Cmpd # | Structure | IUPAC Name | NR2B NAM IC50 | Binned Activity |
|---|---|---|---|---|
| 187 | 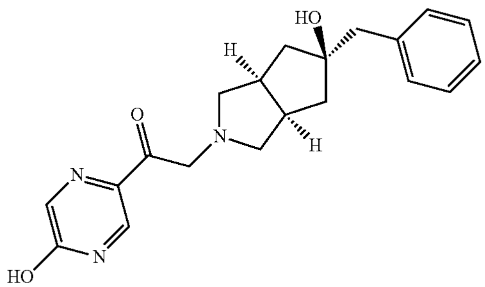 [SMILES: O=C(CN1C[C@@H]2C[C@@](O)(Cc3ccccc3)C[C@@H]2C1)c1cnc(O)cn1] | 2-((3aR,5r,6aS)-5-benzyl-5-hydroxyhexahydrocyclopenta[c]pyrrol-2(1H)-yl)-1-(5-hydroxypyrazin-2-yl)ethanone | 1.00E−05 | + |
| 188 | 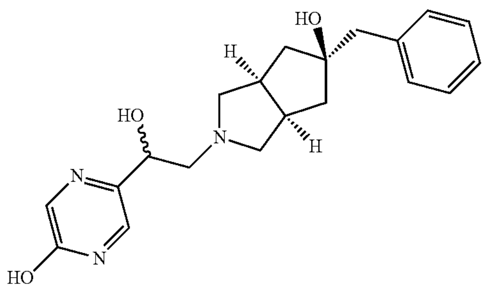 [SMILES: Oc1cnc(C(O)CN2C[C@@H]3C[C@@](O)(Cc4ccccc4)C[C@@H]3C2)cn1] | rac-(3aR,5r,6aS)-5-benzyl-2-(2-hydroxy-2-(5-hydroxypyrazin-2-yl)ethyl)octahydrocyclopenta[c]pyrrol-5-ol | 1.00E−05 | + |
| 189 | 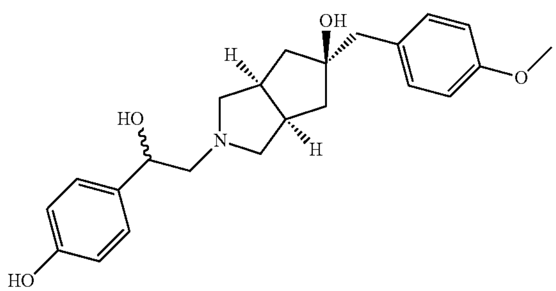 [SMILES: COc1ccc(C[C@]2(O)C[C@H]3CN(CC(O)c4ccc(O)cc4)C[C@H]3C2)cc1] | rac-(3aR,5r,6aS)-2-(2-hydroxy-2-(4-hydroxyphenyl)ethyl)-5-(4-methoxybenzyl)octahydrocyclopenta[c]pyrrol-5-ol | 4.74E−08 | ++++ |
| 190 | 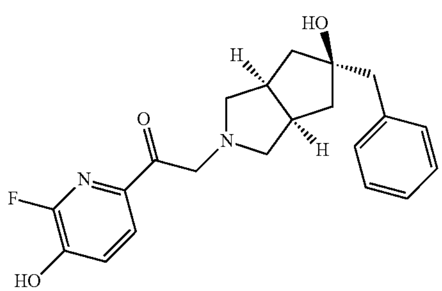 [SMILES: O=C(CN1C[C@@H]2C[C@@](O)(Cc3ccccc3)C[C@@H]2C1)c1ccc(O)c(F)n1] | 2-((3aR,5r,6aS)-5-benzyl-5-hydroxyhexahydrocyclopenta[c]pyrrol-2(1H)-yl)-1-(6-fluoro-5-hydroxypyridin-2-yl)ethanone | 1.00E−05 | + |
| 191 | 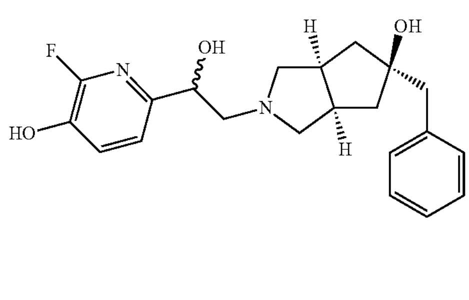 [SMILES: Oc1ccc(C(O)CN2C[C@@H]3C[C@@](O)(Cc4ccccc4)C[C@@H]3C2)nc1F] | rac-(3aR,5r,6aS)-5-benzyl-2-(2-(6-fluoro-5-hydroxypyridin-2-yl)-2-hydroxyethyl)octahydrocyclopenta[c]pyrrol-5-ol | 1.71E−07 | +++ |

-continued

| Cmpd # | Structure | IUPAC Name | NR2B NAM IC50 | Binned Activity |
|---|---|---|---|---|
| 192 | 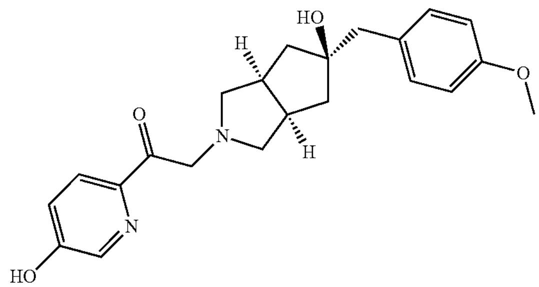 [SMILES: COc1ccc(C[C@]2(O)C[C@H]3CN(CC(=O)c4ccc(O)cn4)C[C@H]3C2)cc1] | 2-[(3aR,5R,6aS)-5-hydroxy-5-[(4-methoxyphenyl)methyl]-octahydrocyclo-penta[c]pyrrol-2-yl]-1-(5-hydroxypyridin-2-yl)ethan-1-one | 7.61E−06 | ++ |
| 193 | 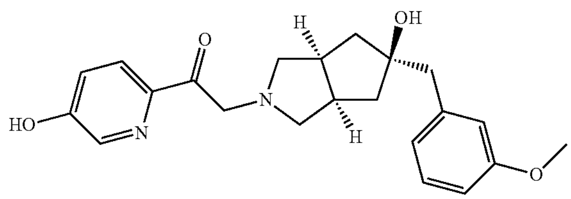 [SMILES: COc1cccc(C[C@]2(O)C[C@H]3CN(CC(=O)c4ccc(O)cn4)C[C@H]3C2)c1] | 2-((3aR,5r,6aS)-5-hydroxy-5-(3-methoxybenzyl)hexahydro-cyclopenta[c]pyrrol-2(1H)-yl)-1-(5-hydroxypyridin-2-yl)ethanone | 1.00E−05 | + |
| 194 | 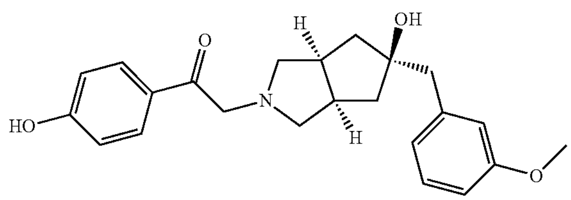 [SMILES: COc1cccc(C[C@]2(O)C[C@H]3CN(CC(=O)c4ccc(O)cc4)C[C@H]3C2)c1] | 2-((3aR,5r,6aS)-5-hydroxy-5-(3-methoxy-benzyl)hexahydrocyclo-penta[c]pyrrol-2(1H)-yl)-1-(4-hydroxy-phenyl)ethanone | 9.81E−08 | ++++ |
| 195 | 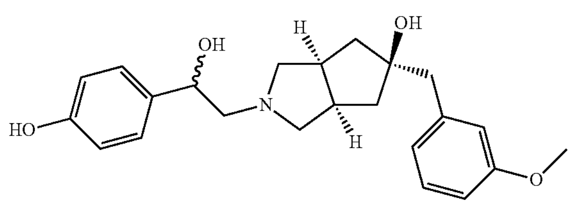 [SMILES: COc1cccc(C[C@]2(O)C[C@H]3CN(CC(O)c4ccc(O)cc4)C[C@H]3C2)c1] | rac-(3aR,5r,6aS)-2-(2-hydroxy-2-(4-hydroxyphenyl)ethyl)-5-(3-methoxybenzyl)octahydro-cyclopenta[c]pyrrol-5-ol | 2.87E−08 | ++++ |
| 196 | 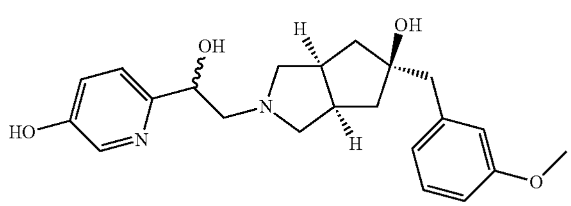 [SMILES: COc1cccc(C[C@]2(O)C[C@H]3CN(CC(O)c4ccc(O)cn4)C[C@H]3C2)c1] | rac-((3aR,5r,6aS)-2-(2-hydroxy-2-(5-hydroxypyridin-2-yl)ethyl)-5-(3-methoxy-benzyl)octahydrocyclo-penta[c]pyrrol-5-ol | 6.60E−08 | ++++ |
| 197 | 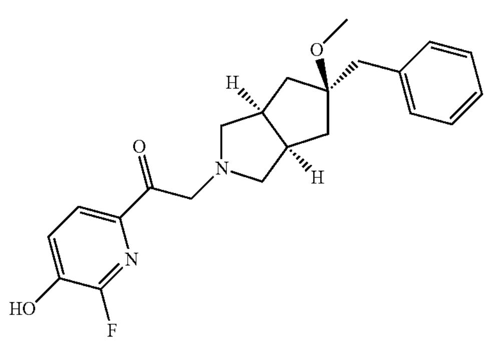 [SMILES: CO[C@@]1(Cc2ccccc2)C[C@H]2CN(CC(=O)c3ccc(O)c(F)n3)C[C@H]2C1] | 2-((3aR,5r,6aS)-5-benzyl-5-methoxyhexahydro-cyclopenta[c]pyrrol-2(1H)-yl)-1-(6-fluoro-5-hydroxypyridin-2-yl)ethanone | 1.00E−05 | + |

| Cmpd # | Structure | IUPAC Name | NR2B NAM IC50 | Binned Activity |
|---|---|---|---|---|
| 198 | 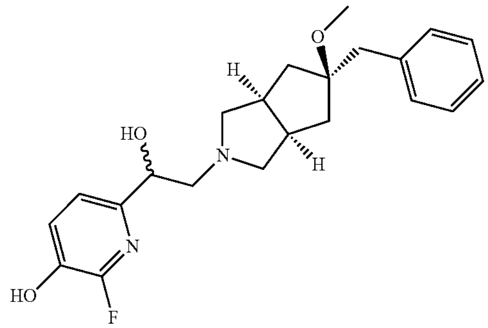 [SMILES: CO[C@@]1(Cc2ccccc2)C[C@H]2CN(CC(O)c3ccc(O)c(F)n3)C[C@H]2C1] | rac-6-(2-((3aR,5r,6aS)-5-benzyl-5-methoxy-hexahydrocyclopenta[c]pyrrol-2(1H)-yl)-1-hydroxyethyl)-2-fluoropyridin-3-ol | 4.76E−07 | +++ |
| 199 | 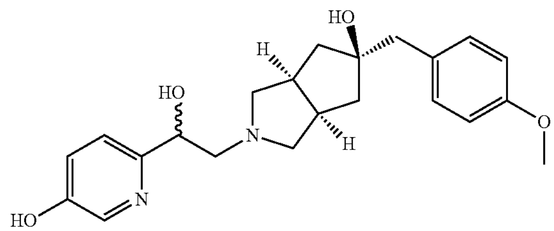 [SMILES: COc1ccc(C[C@]2(O)C[C@H]3CN(CC(O)c4ccc(O)cn4)C[C@H]3C2)cc1] | rac-6-{2-[(3aR,5R,6aS)-5-hydroxy-5-[(4-methoxyphenyl)methyl]-octahydrocyclopenta[c]pyrrol-2-yl]-1-hydroxyethyl}pyridin-3-ol | 3.63E−08 | ++++ |
| 200 | 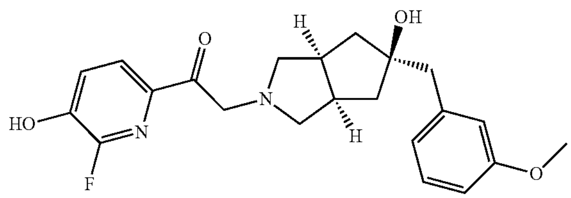 [SMILES: COc1cccc(C[C@]2(O)C[C@H]3CN(CC(=O)c4ccc(O)c(F)n4)C[C@H]3C2)c1] | 1-(6-fluoro-5-hydroxypyridin-2-yl)-2-((3aR,5r,6aS)-5-hydroxy-5-(3-methoxybenzyl)hexahydrocyclopenta[c]pyrrol-2(1H)-yl)ethanone | 1.00E−05 | + |
| 201 | 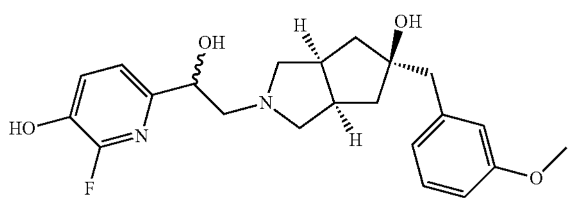 [SMILES: COc1cccc(C[C@]2(O)C[C@H]3CN(CC(O)c4ccc(O)c(F)n4)C[C@H]3C2)c1] | rac-(3aR,5r,6aS)-2-(2-(6-fluoro-5-hydroxypyridin-2-yl)-2-hydroxyethyl)-5-(3-methoxybenzyl)octahydrocyclopenta[c]pyrrol-5-ol | 3.82E−07 | +++ |
| 202 | 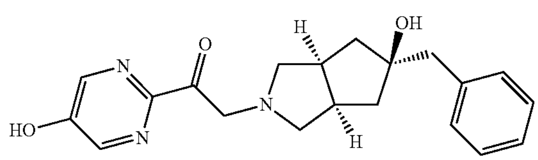 [SMILES: O=C(CN1C[C@@H]2C[C@@](O)(Cc3ccccc3)C[C@@H]2C1)c1ncc(O)cn1] | 2-[(3aR,5R,6aS)-5-benzyl-5-hydroxy-octahydrocyclopenta[c]pyrrol-2-yl]-1-(5-hydroxypyrimidin-2-yl)ethan-1-one | 1.00E−05 | + |
| 203 | 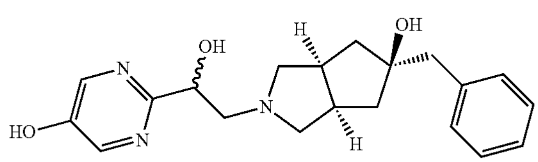 [SMILES: Oc1cnc(C(O)CN2C[C@@H]3C[C@@](O)(Cc4ccccc4)C[C@@H]3C2)nc1] | rac-2-{2-[(3aR,5R,6aS)-5-benzyl-5-hydroxy-octahydrocyclopenta[c]pyrrol-2-yl]-1-hydroxyethyl}pyrimidin-5-ol | 3.40E−06 | ++ |
| 204 | 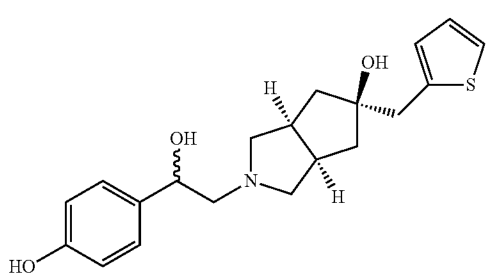 [SMILES: Oc1ccc(C(O)CN2C[C@@H]3C[C@@](O)(Cc4cccs4)C[C@@H]3C2)cc1] | rac-(3aR,5r,6aS)-2-(2-hydroxy-2-(4-hydroxyphenyl)ethyl)-5-(thiophen-2-ylmethyl)octahydrocyclopenta[c]pyrrol-5-ol | 1.26E−08 | ++++ |

| Cmpd # | Structure | IUPAC Name | NR2B NAM IC50 | Binned Activity |
|---|---|---|---|---|
| 205 | 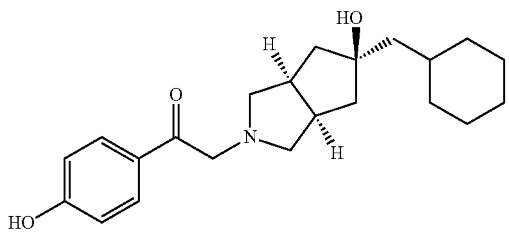 [SMILES: O=C(CN1C[C@@H]2C[C@@](O)(CC3CCCCC3)C[C@@H]2C1)c1ccc(O)cc1] | 2-[(3aR,5R,6aS)-5-(cyclohexylmethyl)-5-hydroxy-octahydro-cyclopenta[c]pyrrol-2-yl]-1-(4-hydroxy-phenyl)ethan-1-one | 3.46E−07 | +++ |
| 206 | 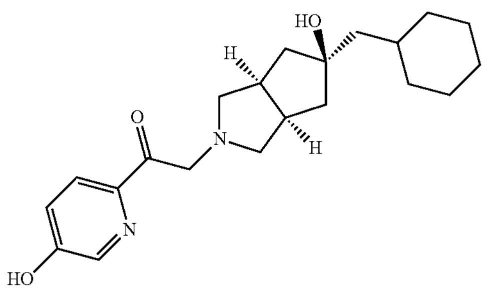 [SMILES: O=C(CN1C[C@@H]2C[C@@](O)(CC3CCCCC3)C[C@@H]2C1)c1ccc(O)cn1] | 2-[(3aR,5R,6aS)-5-(cyclohexylmethyl)-5-hydroxy-octahydro-cyclopenta[c]pyrrol-2-yl]-1-(5-hydroxypyridin-2-yl)ethan-1-one | 1.00E−05 | + |
| 207 | 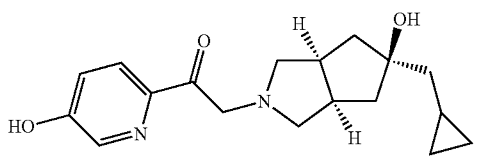 [SMILES: O=C(CN1C[C@@H]2C[C@@](O)(CC3CC3)C[C@@H]2C1)c1ccc(O)cn1] | 2-((3aR,5r,6aS)-5-(cyclopropylmethyl)-5-hydroxyhexahydrocyclopenta[c]pyrrol-2(1H)-yl)-1-(5-hydroxypyridin-2-yl)ethanone | 1.00E−05 | + |
| 208 | 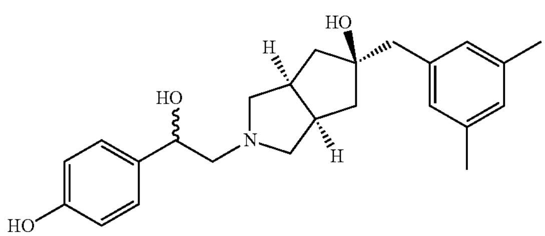 [SMILES: Cc1cc(C)cc(C[C@]2(O)C[C@H]3CN(CC(O)c4ccc(O)cc4)C[C@H]3C2)c1] | rac-6-{2-[(3aR,5R,6aS)-5-[(3,5-dimethyl-phenyl)methyl]-5-hydroxy-octahydrocyclopenta[c]pyrrol-2-yl]-1-hydroxyethyl}pyridin-3-ol-3-ol | 6.66E−07 | +++ |
| 209 | 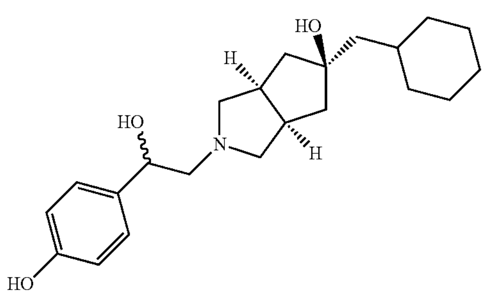 [SMILES: Oc1ccc(C(O)CN2C[C@@H]3C[C@@](O)(CC4CCCCC4)C[C@@H]3C2)cc1] | rac-(3aR,5R,6aS)-5-(cyclohexylmethyl)-2-[2-hydroxy-2-(4-hydroxyphenyl)ethyl]-octahydrocyclopenta[c]pyrrol-5-ol | 4.10E−07 | +++ |
| 210 | 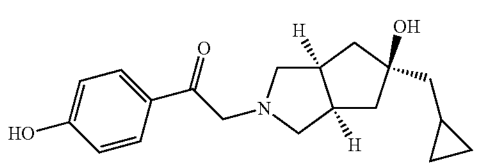 [SMILES: O=C(CN1C[C@@H]2C[C@@](O)(CC3CC3)C[C@@H]2C1)c1ccc(O)cc1] | 2-((3aR,5r,6aS)-5-(cyclopropylmethyl)-5-hydroxyhexahydrocyclopenta[c]pyrrol-2(1H)-yl)-1-(4-hydroxy-phenyl)ethanone | 1.00E−05 | + |
| 211 | 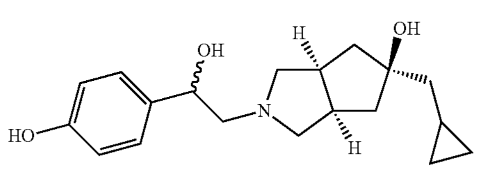 [SMILES: Oc1ccc(C(O)CN2C[C@@H]3C[C@@](O)(CC4CC4)C[C@@H]3C2)cc1] | rac-(3aR,5r,6aS)-5-(cyclopropylmethyl)-2-(2-hydroxy-2-(4-hydroxyphenyl)ethyl)octahydrocyclopenta[c]pyrrol-5-ol | 1.00E−05 | + |

| Cmpd # | Structure | IUPAC Name | NR2B NAM IC50 | Binned Activity |
|---|---|---|---|---|
| 212 | 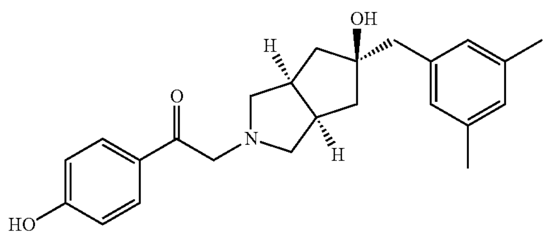 [SMILES: Cc1cc(C)cc(C[C@]2(O)C[C@H]3CN(CC(=O)c4ccc(O)cc4)C[C@H]3C2)c1] | 2-[(3aR,5R,6aS)-5-[(3,5-dimethylphenyl)methyl]-5-hydroxy-octahydro-cyclopenta[c]pyrrol-2-yl]-1-(4-hydroxy-phenyl)ethan-1-one | 1.00E−05 | + |
| 213 | 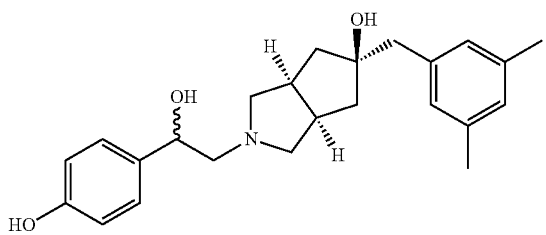 [SMILES: Cc1cc(C)cc(C[C@]2(O)C[C@H]3CN(CC(O)c4ccc(O)cc4)C[C@H]3C2)c1] | rac-(3aR,5R,6aS)-5-[(3,5-dimethylphenyl)methyl]-2-[2-hydroxy-2-(4-hydroxyphenyl)ethyl]-octahydrocyclo-penta[c]pyrrol-5-ol | 5.66E−07 | +++ |
| 214 | 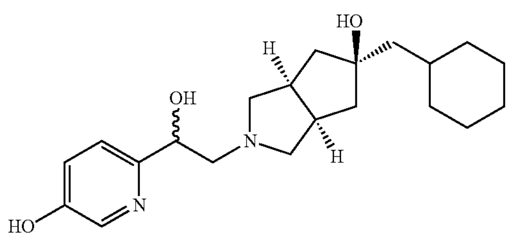 [SMILES: Oc1ccc(C(O)CN2C[C@@H]3C[C@@](O)(CC4CCCCC4)C[C@@H]3C2)nc1] | rac-6-{2-[(3aR,5R,6aS)-5-(cyclohexylmethyl)-5-hydroxy-octahydrocyclo-penta[c]pyrrol-2-yl]-1-hydroxyethyl}pyridin-3-ol | 2.63E−06 | ++ |
| 215 | 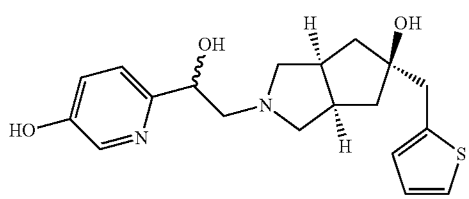 [SMILES: Oc1ccc(C(O)CN2C[C@@H]3C[C@@](O)(Cc4cccs4)C[C@@H]3C2)nc1] | rac-2-(2-hydroxy-2-(5-hydroxypyridin-2-yl)ethyl)-5-(thiophen-2-ylmethyl)octahydrocyclo-penta[c]pyrrol-5-ol | 2.57E−08 | ++++ |
| 216 | 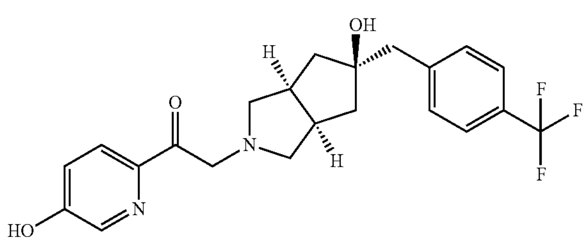 [SMILES: O=C(CN1C[C@@H]2C[C@@](O)(Cc3ccc(C(F)(F)F)cc3)C[C@@H]2C1)c1ccc(O)cn1] | 2-[(3aR,5R,6aS)-5-hydroxy-5-{[4-(trifluoro-methyl)phenyl]methyl}-octahydrocyclo-penta[c]pyrrol-2-yl]-1-(5-hydroxypyridin-2-yl)ethan-1-one | 8.03E−07 | +++ |
| 217 | 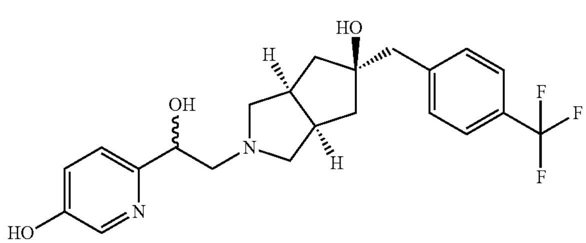 [SMILES: Oc1ccc(C(O)CN2C[C@@H]3C[C@@](O)(Cc4ccc(C(F)(F)F)cc4)C[C@@H]3C2)nc1] | rac-6-{2-[(3aR,5R,6aS)-5-hydroxy-5-{[4-(trifluoromethyl)phenyl]methyl}-octahydrocyclo-penta[c]pyrrol-2-yl]-1-hydroxyethyl}pyridin-3-ol | 3.60E−08 | ++++ |

-continued

| Cmpd # | Structure | IUPAC Name | NR2B NAM IC50 | Binned Activity |
|---|---|---|---|---|
| 218 | 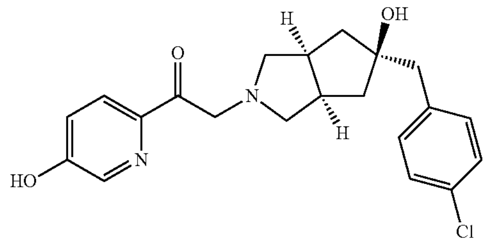 [SMILES: O=C(CN1C[C@@H]2C[C@@](O)(Cc3ccc(Cl)cc3)C[C@@H]2C1)c1ccc(O)cn1] | 2-((3aR,5r,6aS)-5-(4-chlorobenzyl)-5-hydroxyhexahydrocyclopenta[c]pyrrol-2(1H)-yl)-1-(5-hydroxypyridin-2-yl)ethanone | 3.74E−07 | +++ |
| 219 | 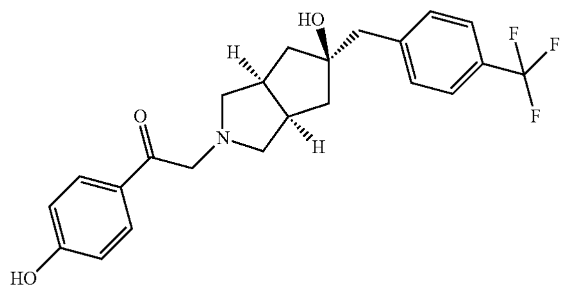 [SMILES: O=C(CN1C[C@@H]2C[C@@](O)(Cc3ccc(C(F)(F)F)cc3)C[C@@H]2C1)c1ccc(O)cc1] | 2-[(3aR,5R,6aS)-5-hydroxy-5-{[4-(trifluoromethyl)phenyl]methyl}-octahydrocyclopenta[c]pyrrol-2-yl]-1-(4-hydroxyphenyl)ethan-1-one | 1.25E−07 | +++ |
| 220 | 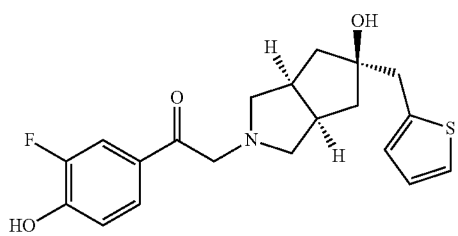 [SMILES: O=C(CN1C[C@@H]2C[C@@](O)(Cc3cccs3)C[C@@H]2C1)c1ccc(O)c(F)c1] | 1-(3-fluoro-4-hydroxyphenyl)-2-(5-hydroxy-5-(thiophen-2-ylmethyl)hexahydrocyclopenta[c]pyrrol-2(1H)-yl)ethanone | 1.11E−07 | +++ |
| 221 | 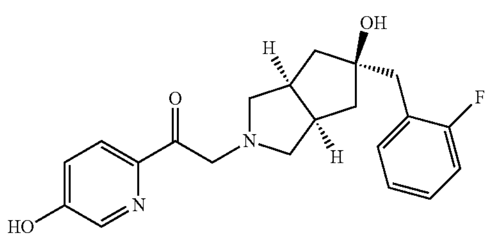 [SMILES: O=C(CN1C[C@@H]2C[C@@](O)(Cc3ccccc3F)C[C@@H]2C1)c1ccc(O)cn1] | 2-(5-(2-fluorobenzyl)-5-hydroxyhexahydrocyclopenta[c]pyrrol-2(1H)-yl)-1-(5-hydroxypyridin-2-yl)ethanone | 9.98E−07 | +++ |
| 222 | 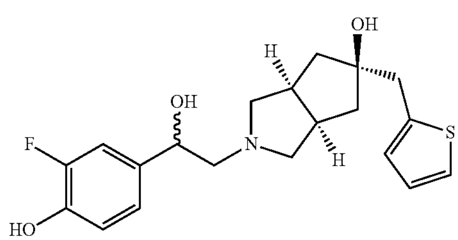 [SMILES: Oc1ccc(C(O)CN2C[C@@H]3C[C@@](O)(Cc4cccs4)C[C@@H]3C2)cc1F] | rac-2-(2-(3-fluoro-4-hydroxyphenyl)-2-hydroxyethyl)-5-(thiophen-2-ylmethyl)octahydrocyclopenta[c]pyrrol-5-ol | 1.93E−08 | ++++ |
| 223 | 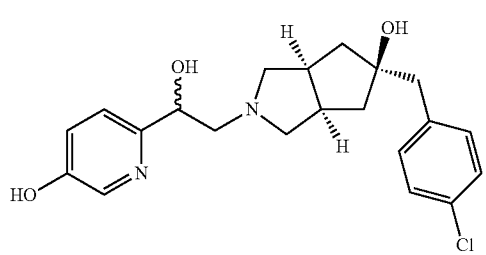 [SMILES: Oc1ccc(C(O)CN2C[C@@H]3C[C@@](O)(Cc4ccc(Cl)cc4)C[C@@H]3C2)nc1] | rac-(3aR,5r,6aS)-5-(4-chlorobenzyl)-2-(2-hydroxy-2-(5-hydroxypyridin-2-yl)ethyl)octahydrocyclopenta[c]pyrrol-5-ol | 1.15E−08 | ++++ |

-continued

| Cmpd # | Structure | IUPAC Name | NR2B NAM IC50 | Binned Activity |
|---|---|---|---|---|
| 224 | 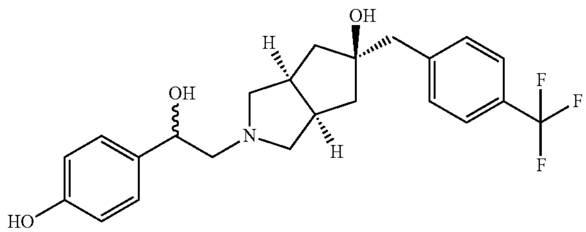 [SMILES: Oc1ccc(C(O)CN2C[C@@H]3C[C@@](O)(Cc4ccc(C(F)(F)F)cc4)C[C@@H]3C2)cc1] | rac-(3aR,5R,6aS)-2-[2-hydroxy-2-(4-hydroxyphenyl)ethyl]-5-{[4-(trifluoromethyl)phenyl]methyl}-octahydrocyclopenta[c]pyrrol-5-ol | 8.48E−08 | ++++ |
| 225 | 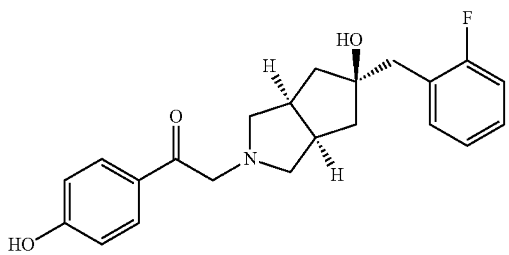 [SMILES: O=C(CN1C[C@@H]2C[C@@](O)(Cc3ccccc3F)C[C@@H]2C1)c1ccc(O)cc1] | 2-((3aR,5r,6aS)-5-(2-fluorobenzyl)-5-hydroxyhexahydrocyclopenta[c]pyrrol-2(1H)-yl)-1-(4-hydroxyphenyl)ethanone | 2.73E−08 | ++++ |
| 226 | 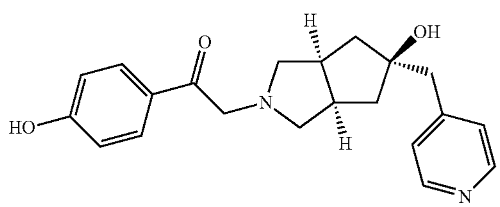 [SMILES: O=C(CN1C[C@@H]2C[C@@](O)(Cc3ccncc3)C[C@@H]2C1)c1ccc(O)cc1] | 2-((3aR,5r,6aS)-5-hydroxy-5-(pyridin-4-ylmethyl)hexahydrocyclopenta[c]pyrrol-2(1H)-yl)-1-(4-hydroxyphenyl)ethanone | 3.89E−06 | ++ |
| 227 | 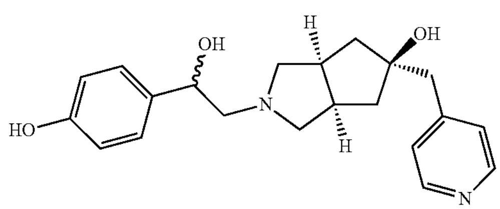 [SMILES: Oc1ccc(C(O)CN2C[C@@H]3C[C@@](O)(Cc4ccncc4)C[C@@H]3C2)cc1] | rac-(3aR,5r,6aS)-2-(2-hydroxy-2-(4-hydroxyphenyl)ethyl)-5-(pyridin-4-ylmethyl)octahydrocyclopenta[c]pyrrol-5-ol | 3.15E−06 | ++ |
| 228 | 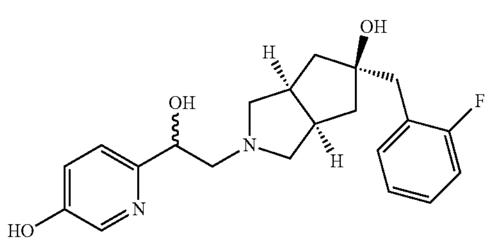 | rac-5-(2-fluorobenzyl)-2-(2-hydroxy-2-(5-hydroxypyridin-2-yl)ethyl)octahydrocyclopenta[c]pyrrol-5-olyl)ethanone | 4.09E−08 | ++++ |
| 229 | 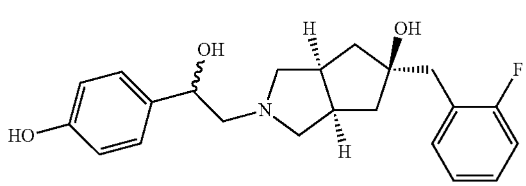 [SMILES: Oc1ccc(C(O)CN2C[C@@H]3C[C@@](O)(Cc4ccccc4F)C[C@@H]3C2)cc1] | rac-(3aR,5r,6aS)-5-(2-fluorobenzyl)-2-(2-hydroxy-2-(4-hydroxyphenyl)ethyl)octahydrocyclopenta[c]pyrrol-5-ol | 1.55E−08 | ++++ |

-continued

| Cmpd # | Structure | IUPAC Name | NR2B NAM IC50 | Binned Activity |
|---|---|---|---|---|
| 230 | 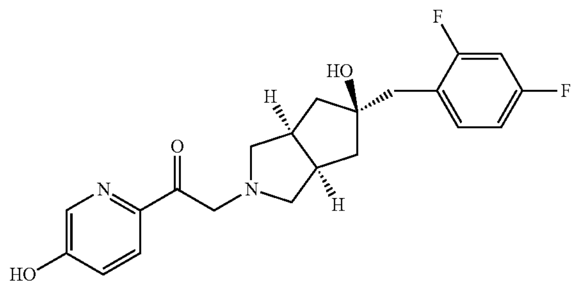 [SMILES: O=C(CN1C[C@@H]2C[C@@](O)(Cc3ccc(F)cc3F)C[C@@H]2C1)c1ccc(O)cn1] | 2-((3aR,5r,6aS)-5-(2,4-difluorobenzyl)-5-hydroxyhexahydrocyclopenta[c]pyrrol-2(1H)-yl)-1-(5-hydroxypyridin-2-yl)ethanone | 2.16E−06 | ++ |
| 231 | 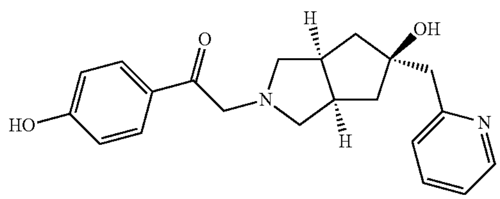 [SMILES: O=C(CN1C[C@@H]2C[C@@](O)(Cc3ccccn3)C[C@@H]2C1)c1ccc(O)cc1] | 2-((3aR,5r,6aS)-5-hydroxy-5-(pyridin-2-ylmethyl)hexahydrocyclopenta[c]pyrrol-2(1H)-yl)-1-(4-hydroxyphenyl)ethanone | 9.65E−07 | +++ |
| 232 | 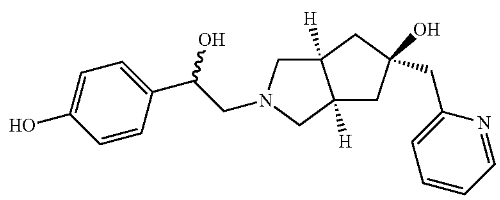 | rac-(3aR,5r,6aS)-2-(2-hydroxy-2-(4-hydroxyphenyl)ethyl)-5-(pyridin-2-ylmethyl)octahydrocyclopenta[c]pyrrol-5-ol | 6.69E−07 | +++ |
| 233 | 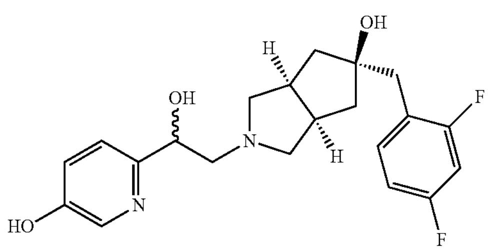 [SMILES: Oc1ccc(C(O)CN2C[C@@H]3C[C@@](O)(Cc4ccc(F)cc4F)C[C@@H]3C2)nc1] | rac-(3aR,5r,6aS)-5-(2,4-difluorobenzyl)-2-(2-hydroxy-2-(5-hydroxypyridin-2-yl)ethyl)octahydrocyclopenta[c]pyrrol-5-ol | 2.99E−08 | ++++ |
| 234 | 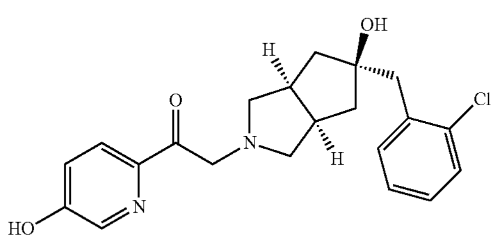 [SMILES: O=C(CN1C[C@@H]2C[C@@](O)(Cc3ccccc3Cl)C[C@@H]2C1)c1ccc(O)cn1] | 2-((3aR,5r,6aS)-5-(2-chlorobenzyl)-5-hydroxyhexahydrocyclopenta[c]pyrrol-2(1H)-yl)-1-(5-hydroxypyridin-2-yl)ethanone | 1.99E−06 | ++ |
| 235 | 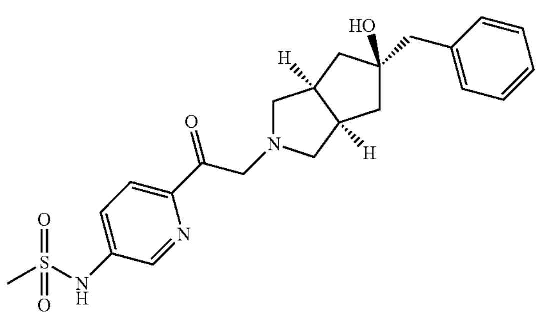 [SMILES: CS(=O)(=O)Nc1ccc(C(=O)CN2C[C@@H]3C[C@@](O)(Cc4ccccc4)C[C@@H]3C2)nc1] | N-(6-(2-((3aR,5r,6aS)-5-benzyl-5-hydroxyhexahydrocyclopenta[c]pyrrol-2(1H)-yl)acetyl)pyridin-3-yl)methanesulfonamide | 1.00E−05 | + |

| Cmpd # | Structure | IUPAC Name | NR2B NAM IC50 | Binned Activity |
|---|---|---|---|---|
| 236 | 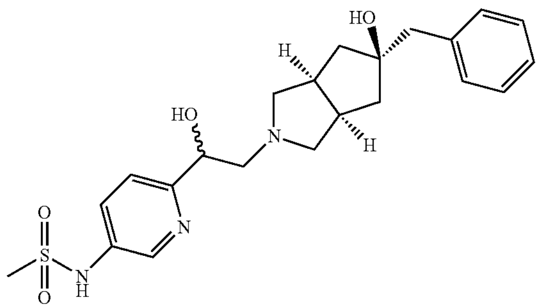 [SMILES: CS(=O)(=O)Nc1ccc(C(O)CN2C[C@@H]3C[C@@](O)(Cc4ccccc4)C[C@@H]3C2)nc1] | rac-N-(6-(2-((3aR,5r,6aS)-5-benzyl-5-hydroxyhexahydrocyclopenta[c]pyrrol-2(1H)-yl)-1-hydroxyethyl)pyridin-3-yl)methanesulfonamide | 1.14E−07 | +++ |
| 237 | 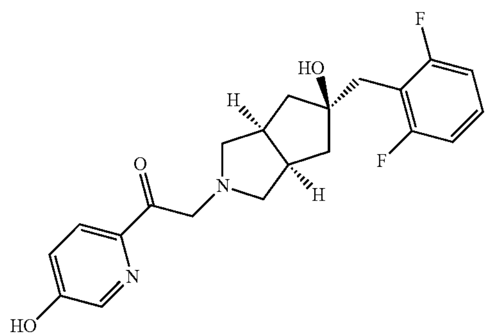 [SMILES: O=C(CN1C[C@@H]2C[C@@](O)(Cc3c(F)cccc3F)C[C@@H]2C1)c1ccc(O)cn1] | 2-[(3aR,5R,6aS)-5-[(2,6-difluorophenyl)methyl]-5-hydroxy-octahydro-cyclopenta[c]pyrrol-2-yl]-1-(5-hydroxypyridin-2-yl)ethan-1-one | 1.91E−06 | ++ |
| 238 | 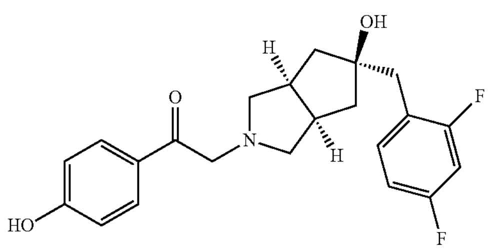 [SMILES: O=C(CN1C[C@@H]2C[C@@](O)(Cc3ccc(F)cc3F)C[C@@H]2C1)c1ccc(O)cc1] | 2-(5-(2,4-difluorobenzyl)-5-hydroxyhexahydrocyclopenta[c]pyrrol-2(1H)-yl)-1-(4-hydroxyphenyl)ethanone | 5.16E−08 | ++++ |
| 239 | 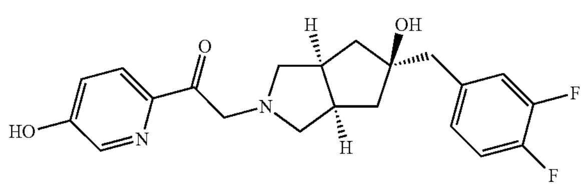 [SMILES: O=C(CN1C[C@@H]2C[C@@](O)(Cc3ccc(F)c(F)c3)C[C@@H]2C1)c1ccc(O)cn1] | 2-((3aR,5r,6aS)-5-(3,4-difluorobenzyl)-5-hydroxyhexahydrocyclopenta[c]pyrrol-2(1H)-yl)-1-(5-hydroxypyridin-2-yl)ethanone | 1.00E−05 | + |
| 240 | 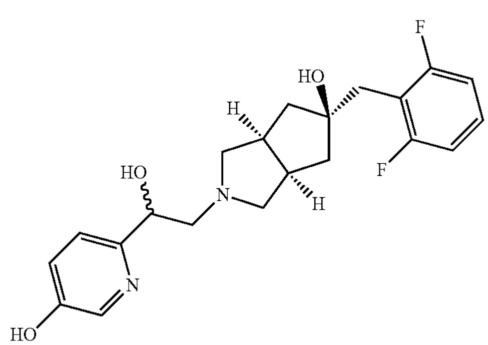 [SMILES: Oc1ccc(C(O)CN2C[C@@H]3C[C@@](O)(Cc4c(F)cccc4F)C[C@@H]3C2)nc1] | rac-6-{2-[(3aR,5R,6aS)-5-[(2,6-difluorophenyl)methyl]-5-hydroxy-octahydrocyclopenta[c]pyrrol-2-yl]-1-hydroxyethyl}pyridin-3-ol | 6.96E−08 | ++++ |

| Cmpd # | Structure | IUPAC Name | NR2B NAM IC50 | Binned Activity |
|---|---|---|---|---|
| 241 | 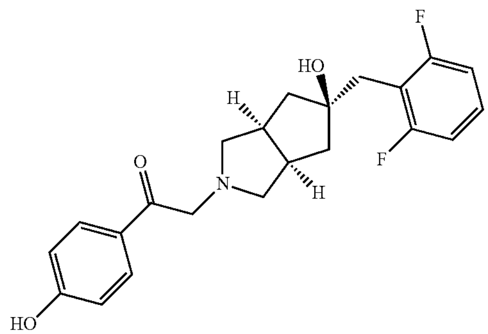 [SMILES: O=C(CN1C[C@@H]2C[C@@](O)(Cc3c(F)cccc3F)C[C@@H]2C1)c1ccc(O)cc1] | 2-[(3aR,5R,6aS)-5-[(2,6-difluorophenyl)methyl]-5-hydroxy-octahydro-cyclopenta[c]pyrrol-2-yl]-1-(4-hydroxy-phenyl)ethan-1-one | 1.18E−07 | +++ |
| 242 | 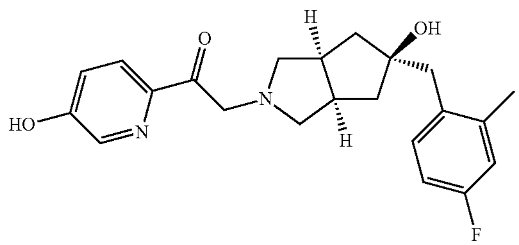 [SMILES: Cc1cc(F)ccc1C[C@]1(O)C[C@H]2CN(CC(=O)c3ccc(O)cn3)C[C@H]2C1] | 2-((3aR,5r,6aS)-5-(4-fluoro-2-methylbenzyl)-5-hydroxyhexahydrocyclopenta[c]pyrrol-2(1H)-yl)-1-(5-hydroxypyridin-2-yl)ethanone | 2.71E−06 | ++ |
| 243 | 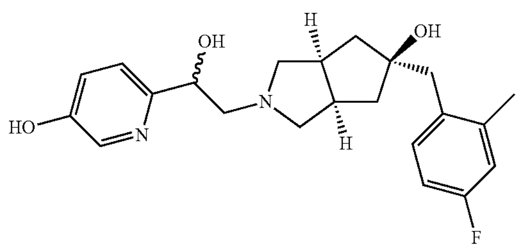 [SMILES: Cc1cc(F)ccc1C[C@]1(O)C[C@H]2CN(CC(O)c3ccc(O)cn3)C[C@H]2C1] | rac-(3aR,5r,6aS)-5-(4-fluoro-2-methylbenzyl)-2-(2-hydroxy-2-(5-hydroxypyridin-2-yl)ethyl)octahydrocyclopenta[c]pyrrol-5-ol | 7.57E−08 | ++++ |
| 244 | 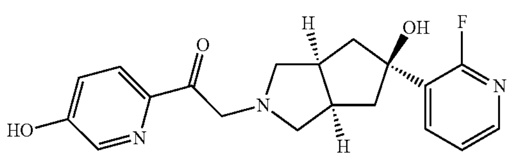 [SMILES: O=C(CN1C[C@@H]2C[C@@](O)(c3cccnc3F)C[C@@H]2C1)c1ccc(O)cn1] | 2-((3aR,6aS)-5-(2-fluoropyridin-3-yl)-5-hydroxyhexahydrocyclopenta[c]pyrrol-2(1H)-yl)-1-(5-hydroxypyridin-2-yl)ethanone | 1.00E−05 | + |
| 245 | 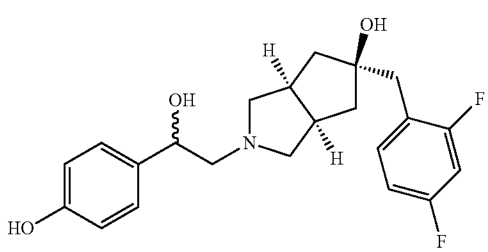 [SMILES: Oc1ccc(C(O)CN2C[C@@H]3C[C@@](O)(Cc4ccc(F)cc4F)C[C@@H]3C2)cc1] | rac-5-(2,4-difluorobenzyl)-2-(2-hydroxy-2-(4-hydroxyphenyl)ethyl)octahydrocyclopenta[c]pyrrol-5-ol | 2.38E−08 | ++++ |
| 246 | 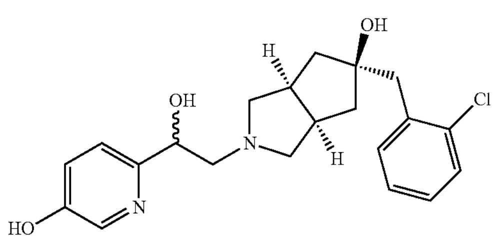 [SMILES: Oc1ccc(C(O)CN2C[C@@H]3C[C@@](O)(Cc4ccccc4Cl)C[C@@H]3C2)nc1] | rac-(3aR,5r,6aS)-5-(2-chlorobenzyl)-2-(2-hydroxy-2-(5-hydroxypyridin-2-yl)ethyl)octahydrocyclopenta[c]pyrrol-5-ol | 5.03E−08 | ++++ |

| Cmpd # | Structure | IUPAC Name | NR2B NAM IC50 | Binned Activity |
|---|---|---|---|---|
| 247 | 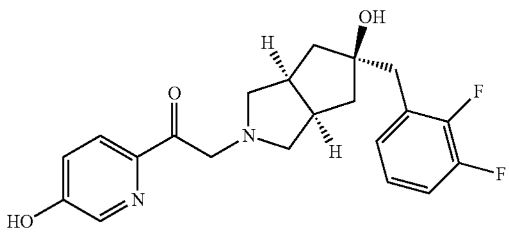 [SMILES: O=C(CN1C[C@@H]2C[C@@](O)(Cc3cccc(F)c3F)C[C@@H]2C1)c1ccc(O)cn1] | 2-((3aR,5r,6aS)-5-(2,3-difluorobenzyl)-5-hydroxyhexahydrocyclopenta[c]pyrrol-2(1H)-yl)-1-(5-hydroxypyridin-2-yl)ethanone | 3.06E−06 | ++ |
| 248 | 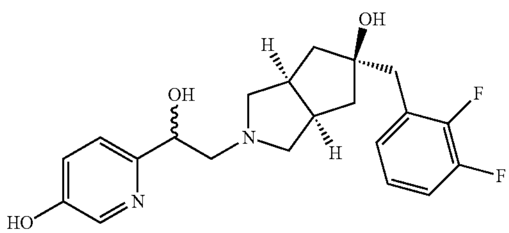 [SMILES: Oc1ccc(C(O)CN2C[C@@H]3C[C@@](O)(Cc4cccc(F)c4F)C[C@@H]3C2)nc1] | rac-(3aR,5r,6aS)-5-(2,3-difluorobenzyl)-2-(2-hydroxy-2-(5-hydroxypyridin-2-yl)ethyl)octahydrocyclopenta[c]pyrrol-5-ol | 4.76E−08 | ++++ |
| 249 | 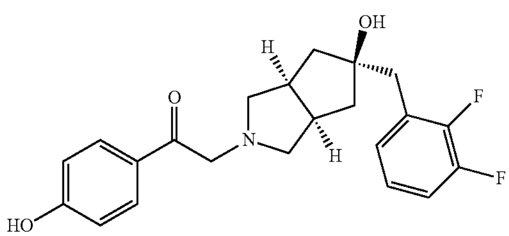 [SMILES: O=C(CN1C[C@@H]2C[C@@](O)(Cc3cccc(F)c3F)C[C@@H]2C1)c1ccc(O)cc1] | 2-((3aR,5r,6aS)-5-(2,3-difluorobenzyl)-5-hydroxyhexahydrocyclopenta[c]pyrrol-2(1H)-yl)-1-(4-hydroxyphenyl)ethanone | 1.10E−07 | +++ |
| 250 | 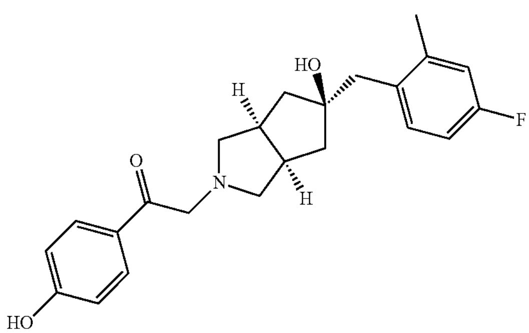 [SMILES: Cc1cc(F)ccc1C[C@]1(O)C[C@H]2CN(CC(=O)c3ccc(O)cc3)C[C@H]2C1] | 2-((3aR,5r,6aS)-5-(4-fluoro-2-methylbenzyl)-5-hydroxyhexahydrocyclopenta[c]pyrrol-2(1H)-yl)-1-(4-hydroxyphenyl)ethanone | 1.37E−07 | +++ |
| 251 | 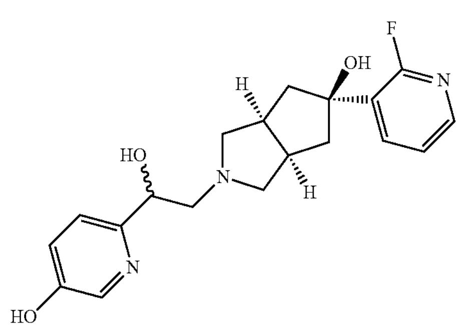 [SMILES: Oc1ccc(C(O)CN2C[C@@H]3C[C@@](O)(c4cccnc4F)C[C@@H]3C2)nc1] | rac-(3aR,6aS)-5-(2-fluoropyridin-3-yl)-2-(2-hydroxy-2-(5-hydroxypyridin-2-yl)ethyl)octahydrocyclopenta[c]pyrrol-5-ol | 1.00E−05 | + |

| Cmpd # | Structure | IUPAC Name | NR2B NAM IC50 | Binned Activity |
|---|---|---|---|---|
| 252 | 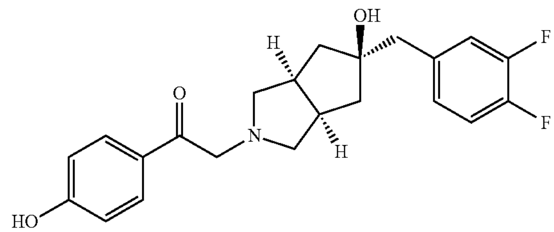 [SMILES: O=C(CN1C[C@@H]2C[C@@](O)(Cc3ccc(F)c(F)c3)C[C@@H]2C1)c1ccc(O)cc1] | 2-((3aR,5r,6aS)-5-(3,4-difluorobenzyl)-5-hydroxyhexahydrocyclopenta[c]pyrrol-2(1H)-yl)-1-(4-hydroxyphenyl)ethanone | 8.53E−08 | ++++ |
| 253 | 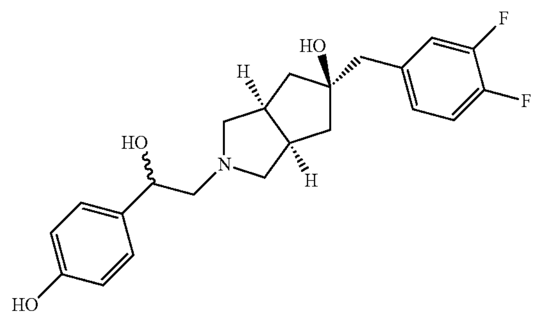 [SMILES: Oc1ccc(C(O)CN2C[C@@H]3C[C@@](O)(Cc4ccc(F)c(F)c4)C[C@@H]3C2)cc1] | rac-(3aR,5r,6aS)-5-(3,4-difluorobenzyl)-2-(2-hydroxy-2-(4-hydroxyphenyl)ethyl)octahydrocyclopenta[c]pyrrol-5-ol | 3.15E−08 | ++++ |
| 254 | 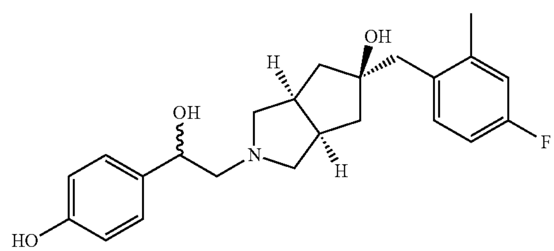 [SMILES: Cc1cc(F)ccc1C[C@]1(O)C[C@H]2CN(CC(O)c3ccc(O)cc3)C[C@H]2C1] | rac-(3aR,5r,6aS)-5-(4-fluoro-2-methylbenzyl)-2-(2-hydroxy-2-(4-hydroxyphenyl)ethyl)octahydrocyclopenta[c]pyrrol-5-ol | 4.25E−08 | ++++ |
| 255 | 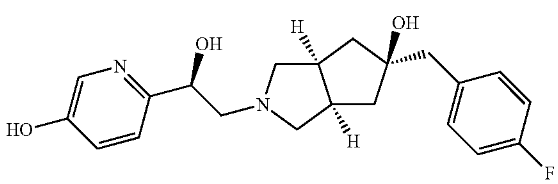 [SMILES: Oc1ccc([C@@H](O)CN2C[C@@H]3C[C@@](O)(Cc4ccc(F)cc4)C[C@@H]3C2)nc1] | (3aR,5S,6aS)-5-(4-fluorobenzyl)-2-((S)-2-hydroxy-2-(5-hydroxypyridin-2-yl)ethyl)octahydrocyclopenta[c]pyrrol-5-ol | 2.40E−08 | ++++ |
| 256 | 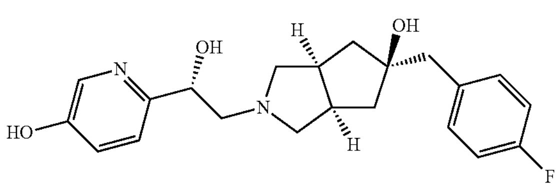 [SMILES: Oc1ccc([C@H](O)CN2C[C@@H]3C[C@@](O)(Cc4ccc(F)cc4)C[C@@H]3C2)nc1] | (3aR,5R,6aS)-5-(4-fluorobenzyl)-2-((R)-2-hydroxy-2-(5-hydroxypyridin-2-yl)ethyl)octahydrocyclopenta[c]pyrrol-5-ol | 3.17E−08 | ++++ |
| 257 | 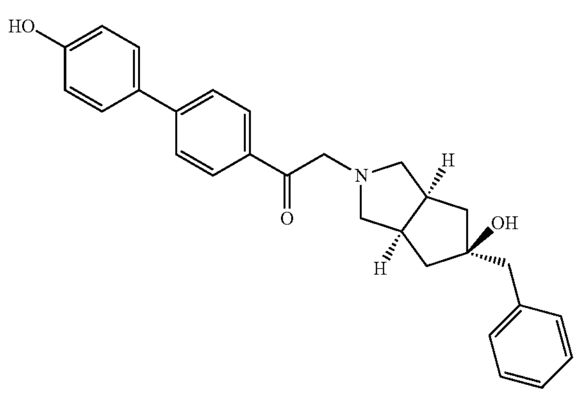 [SMILES: O=C(CN1C[C@@H]2C[C@@](O)(Cc3ccccc3)C[C@@H]2C1)c1ccc(-c2ccc(O)cc2)cc1] | 2-((3aR,5r,6aS)-5-benzyl-5-hydroxyhexahydrocyclopenta[c]pyrrol-2(1H)-yl)-1-(4'-hydroxy-[1,1'-biphenyl]-4-yl)ethanone | 1.00E−05 | + |

-continued

| Cmpd # | Structure | IUPAC Name | NR2B NAM IC50 | Binned Activity |
|---|---|---|---|---|
| 258 | 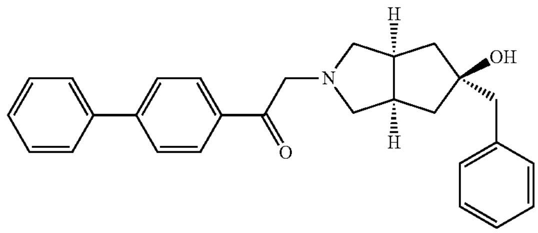 | 1-([1,1'-biphenyl]-4-yl)-2-((3aR,5r,6aS)-5-benzyl-5-hydroxyhexahydrocyclopenta[c]pyrrol-2(1H)-yl)ethanone | 1.00E−05 | + |
| 259 | 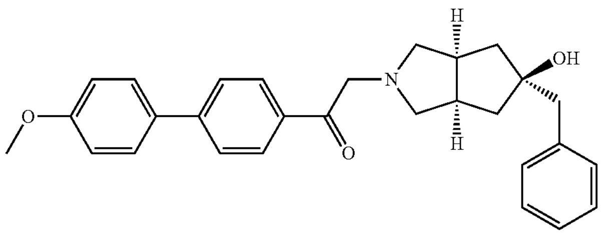 [SMILES: COc1ccc(-c2ccc(C(=O)CN3C[C@@H]4C[C@@](O)(Cc5ccccc5)C[C@@H]4C3)cc2)cc1] | 2-((3aR,5r,6aS)-5-benzyl-5-hydroxyhexahydrocyclopenta[c]pyrrol-2(1H)-yl)-1-(4'-methoxy-[1,1'-biphenyl]-4-yl)ethanone | 1.00E−05 | + |
| 260 | 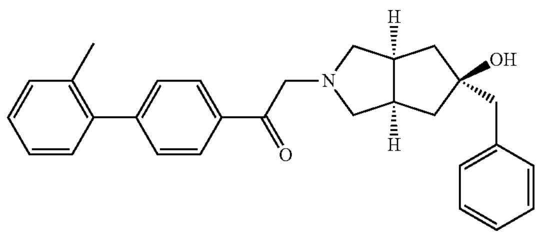 [SMILES: Cc1ccccc1-c1ccc(C(=O)CN2C[C@@H]3C[C@@](O)(Cc4ccccc4)C[C@@H]3C2)cc1] | 2-((3aR,5r,6aS)-5-benzyl-5-hydroxyhexahydrocyclopenta[c]pyrrol-2(1H)-yl)-1-(2'-methyl-[1,1'-biphenyl]-4-yl)ethanone | 1.00E−05 | + |
| 261 | 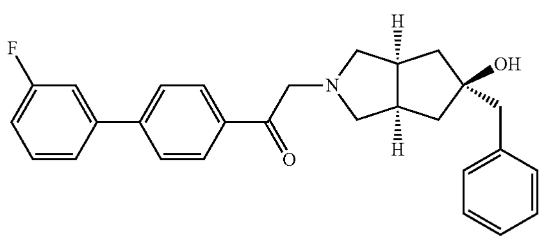 [SMILES: O=C(CN1C[C@@H]2C[C@@](O)(Cc3ccccc3)C[C@@H]2C1)c1ccc(-c2cccc(F)c2)cc1] | 2-((3aR,5r,6aS)-5-benzyl-5-hydroxyhexahydrocyclopenta[c]pyrrol-2(1H)-yl)-1-(3'-fluoro-[1,1'-biphenyl]-4-yl)ethanone | 1.00E−05 | + |
| 262 | 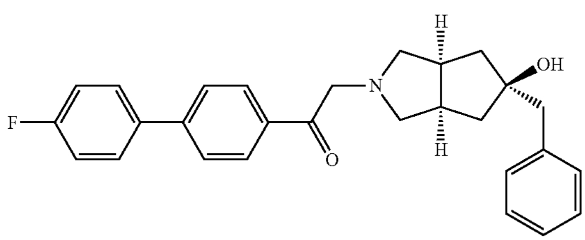 [SMILES: O=C(CN1C[C@@H]2C[C@@](O)(Cc3ccccc3)C[C@@H]2C1)c1ccc(-c2ccc(F)cc2)cc1] | 2-((3aR,5r,6aS)-5-benzyl-5-hydroxyhexahydrocyclopenta[c]pyrrol-2(1H)-yl)-1-(4'-fluoro-[1,1'-biphenyl]-4-yl)ethanone | 1.00E−05 | + |
| 263 | 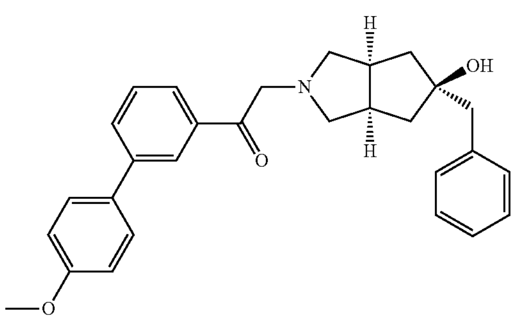 [SMILES: COc1ccc(-c2cccc(C(=O)CN3C[C@@H]4C[C@@](O)(Cc5ccccc5)C[C@@H]4C3)c2)cc1] | 2-((3aR,5r,6aS)-5-benzyl-5-hydroxyhexahydrocyclopenta[c]pyrrol-2(1H)-yl)-1-(4'-methoxy-[1,1'-biphenyl]-3-yl)ethanone | 1.00E−05 | + |

-continued

| Cmpd # | Structure | IUPAC Name | NR2B NAM IC50 | Binned Activity |
|---|---|---|---|---|
| 264 | 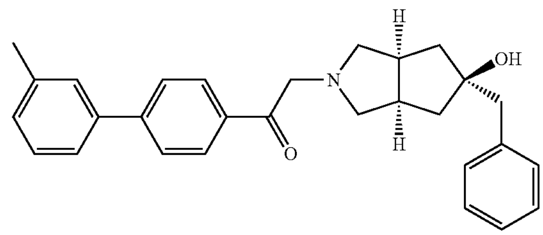 [SMILES: Cc1cccc(-c2ccc(C(=O)CN3C[C@@H]4C[C@@](O)(Cc5ccccc5)C[C@@H]4C3)cc2)c1] | 2-((3aR,5r,6aS)-5-benzyl-5-hydroxyhexahydrocyclopenta[c]pyrrol-2(1H)-yl)-1-(3'-methyl-[1,1'-biphenyl]-4-yl)ethanone | 1.00E−05 | + |
| 265 | 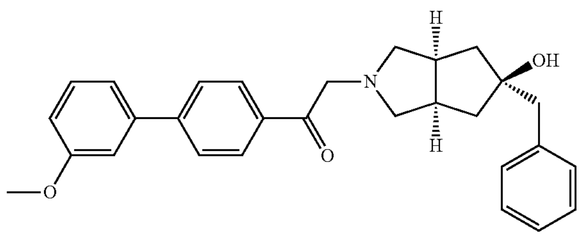 [SMILES: COc1cccc(-c2ccc(C(=O)CN3C[C@@H]4C[C@@](O)(Cc5ccccc5)C[C@@H]4C3)cc2)c1] | 2-((3aR,5r,6aS)-5-benzyl-5-hydroxyhexahydrocyclopenta[c]pyrrol-2(1H)-yl)-1-(3'-methoxy-[1,1'-biphenyl]-4-yl)ethanone | 1.00E−05 | + |
| 266 | 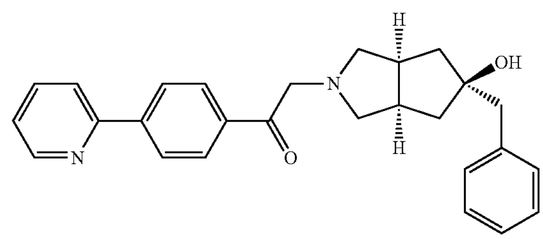 [SMILES: O=C(CN1C[C@@H]2C[C@@](O)(Cc3ccccc3)C[C@@H]2C1)c1ccc(-c2ccccn2)cc1] | 2-((3aR,5r,6aS)-5-benzyl-5-hydroxyhexahydrocyclopenta[c]pyrrol-2(1H)-yl)-1-(4-(pyridin-2-yl)phenyl)ethanone | 1.00E−05 | + |
| 267 | 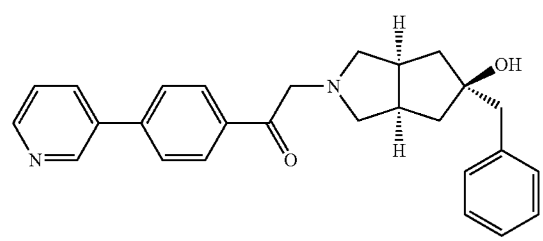 [SMILES: O=C(CN1C[C@@H]2C[C@@](O)(Cc3ccccc3)C[C@@H]2C1)c1ccc(-c2cccnc2)cc1] | 2-((3aR,5r,6aS)-5-benzyl-5-hydroxyhexahydrocyclopenta[c]pyrrol-2(1H)-yl)-1-(4-(pyridin-3-yl)phenyl)ethanone | 1.00E−05 | + |
| 268 | 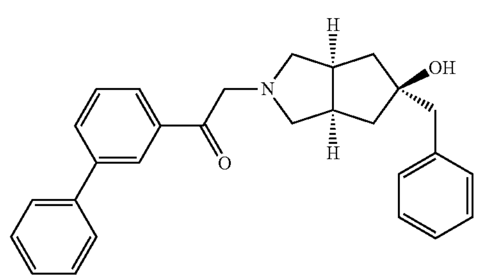 [SMILES: O=C(CN1C[C@@H]2C[C@@](O)(Cc3ccccc3)C[C@@H]2C1)c1cccc(-c2ccccc2)c1] | 1-([1,1'-biphenyl]-3-yl)-2-((3aR,5r,6aS)-5-benzyl-5-hydroxyhexahydrocyclopenta[c]pyrrol-2(1H)-yl)ethanone | 1.00E−05 | + |
| 269 | 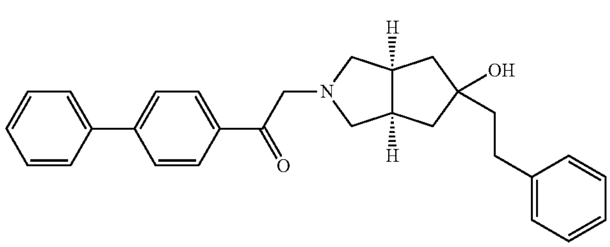 [SMILES: O=C(CN1C[C@@H]2CC(O)(CCc3ccccc3)C[C@@H]2C1)c1ccc(-c2ccccc2)cc1] | 2-[5-hydroxy-5-(2-phenylethyl)-octahydrocyclopenta[c]pyrrol-2-yl]-1-(4-phenylphenyl)ethan-1-one | 1.00E−05 | + |

-continued

| Cmpd # | Structure | IUPAC Name | NR2B NAM IC50 | Binned Activity |
|---|---|---|---|---|
| 270 | 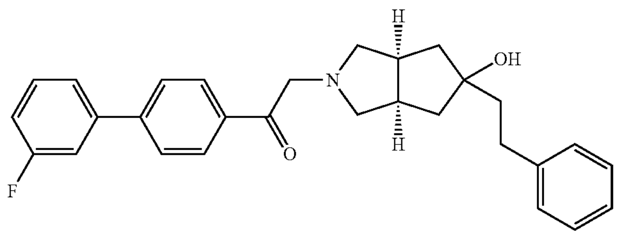 [SMILES: O=C(CN1C[C@@H]2CC(O)(CCc3ccccc3)C[C@@H]2C1)c1ccc(-c2cccc(F)c2)cc1] | 1-[4-(3-fluorophenyl)phenyl]-2-[5-hydroxy-5-(2-phenylethyl)-octahydro-cyclopenta[c]pyrrol-2-yl]ethan-1-one | 1.00E−05 | + |
| 271 | 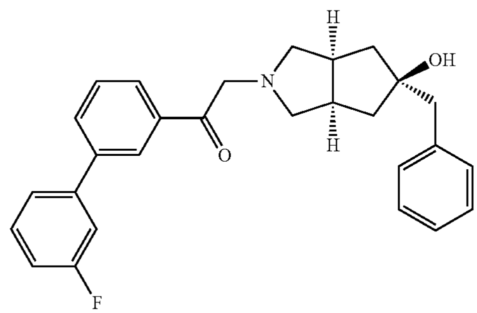 [SMILES: O=C(CN1C[C@@H]2C[C@@](O)(Cc3ccccc3)C[C@@H]2C1)c1cccc(-c2cccc(F)c2)c1] | 2-((3aR,5r,6aS)-5-benzyl-5-hydroxyhexahydrocyclopenta[c]pyrrol-2(1H)-yl)-1-(3'-fluoro-[1,1'-biphenyl]-3-yl)ethanone | 1.00E−05 | + |
| 272 | 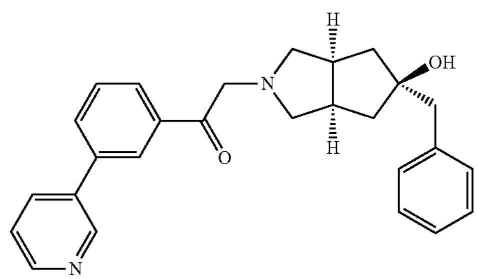 [SMILES: O=C(CN1C[C@@H]2C[C@@](O)(Cc3ccccc3)C[C@@H]2C1)c1cccc(-c2cccnc2)c1] | 2-((3aR,5r,6aS)-5-benzyl-5-hydroxyhexahydrocyclopenta[c]pyrrol-2(1H)-yl)-1-(3-(pyridin-3-yl)phenyl)ethanone | 1.00E−05 | + |
| 273 | 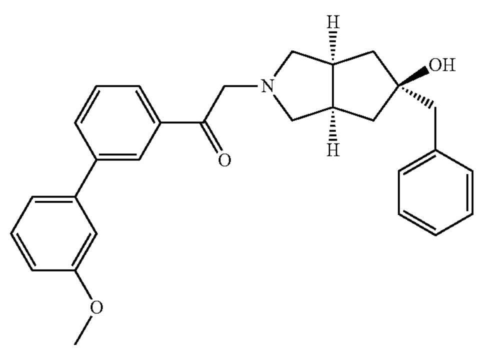 [SMILES: COc1cccc(-c2cccc(C(=O)CN3C[C@@H]4C[C@@](O)(Cc5ccccc5)C[C@@H]4C3)c2)c1] | 2-((3aR,5r,6aS)-5-benzyl-5-hydroxyhexahydrocyclopenta[c]pyrrol-2(1H)-yl)-1-(3'-methoxy-[1,1'-biphenyl]-3-yl)ethanone | 1.00E−05 | + |
| 274 | 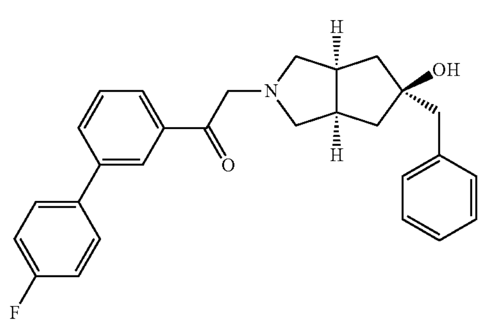 [SMILES: O=C(CN1C[C@@H]2C[C@@](O)(Cc3ccccc3)C[C@@H]2C1)c1cccc(-c2ccc(F)cc2)c1] | 2-((3aR,5r,6aS)-5-benzyl-5-hydroxyhexahydrocyclopenta[c]pyrrol-2(1H)-yl)-1-(4'-fluoro-[1,1'-biphenyl]-3-yl)ethanone | 1.00E−05 | + |

| Cmpd # | Structure | IUPAC Name | NR2B NAM IC50 | Binned Activity |
|---|---|---|---|---|
| 275 | 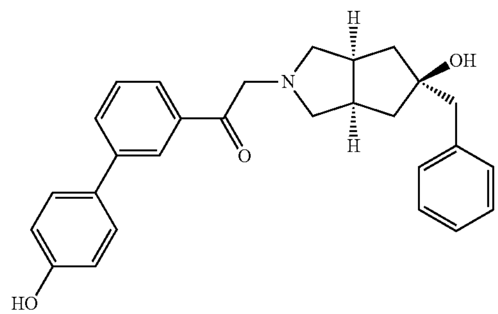 [SMILES: O=C(CN1C[C@@H]2C[C@@](O)(Cc3ccccc3)C[C@@H]2C1)c1cccc(-c2ccc(O)cc2)c1] | 2-((3aR,5r,6aS)-5-benzyl-5-hydroxyhexahydrocyclo-penta[c]pyrrol-2(1H)-yl)-1-(4'-hydroxy-[1,1'-biphenyl]-3-yl)ethanone | 1.00E−05 | + |
| 276 | 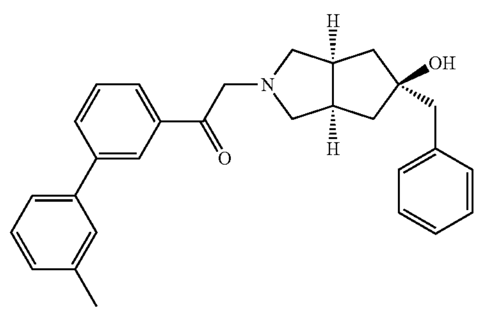 [SMILES: Cc1cccc(-c2cccc(C(=O)CN3C[C@@H]4C[C@@](O)(Cc5ccccc5)C[C@@H]4C3)c2)c1] | 2-((3aR,5r,6aS)-5-benzyl-5-hydroxyhexahydrocyclo-penta[c]pyrrol-2(1H)-yl)-1-(3'-methyl-[1,1'-biphenyl]-3-yl)ethanone | 1.00E−05 | + |
| 277 | 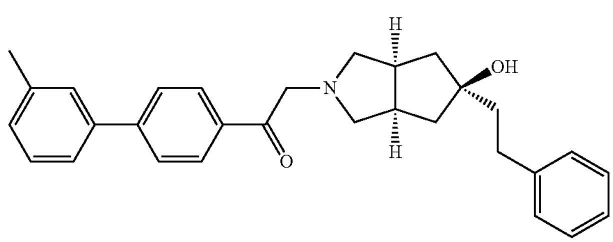 [SMILES: Cc1cccc(-c2ccc(C(=O)CN3C[C@@H]4C[C@@](O)(CCc5ccccc5)C[C@@H]4C3)cc2)c1] | 2-[5-hydroxy-5-(2-phenylethyl)-octahydro-cyclopenta[c]pyrrol-2-yl]-1-[4-(3-methylphenyl)phenyl]ethan-1-one | 1.00E−05 | + |
| 278 | 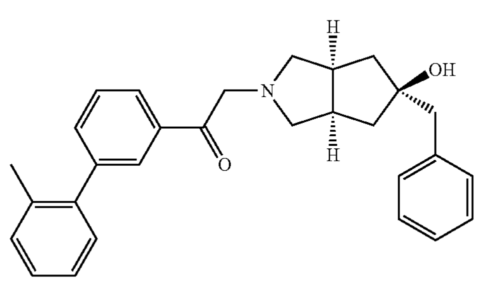 [SMILES: Cc1ccccc1-c1cccc(C(=O)CN2C[C@@H]3C[C@@](O)(Cc4ccccc4)C[C@@H]3C2)c1] | 2-((3aR,5r,6aS)-5-benzyl-5-hydroxyhexahydrocyclo-penta[c]pyrrol-2(1H)-yl)-1-(2'-methyl-[1,1'-biphenyl]-3-yl)ethanone | 1.00E−05 | + |
| 279 | 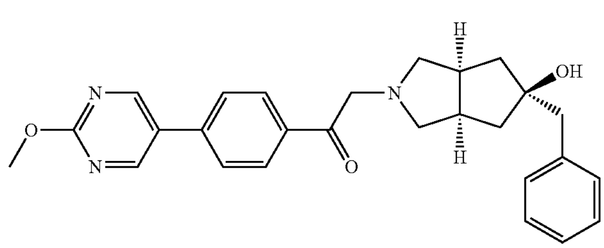 | 2-((3aR,5r,6aS)-5-benzyl-5-hydroxyhexahydrocyclo-penta[c]pyrrol-2(1H)-yl)-1-(4-(2-methoxypyrimidin-5-yl)phenyl)ethanone | 1.00E−05 | + |

-continued

| Cmpd # | Structure | IUPAC Name | NR2B NAM IC50 | Binned Activity |
|---|---|---|---|---|
| 280 | 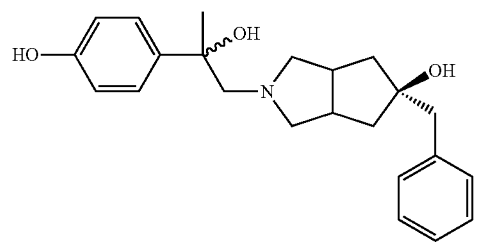 | rac-(3aR,5R,6aS)-5-benzyl-2-[2-hydroxy-2-(4-hydroxyphenyl)propyl]-octahydrocyclopenta[c]pyrrol-5-ol | 4.30E−08 | ++++ |
| 281 | 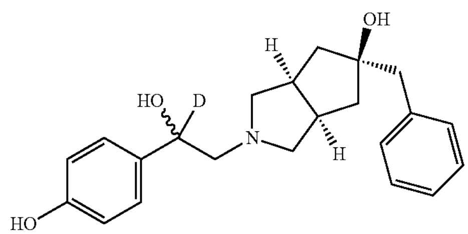 [SMILES: [2H]C(O)(CN1C[C@@H]2C[C@@](O)(Cc3ccccc3)C[C@@H]2C1)c1ccc(O)cc1] | deuterated rac-(3aR,6aS)-5-benzyl-2-((S)-2-hydroxy-2-(4-hydroxyphenyl)ethyl)octahydrocyclopenta[c]pyrrol-5-ol | 1.74E−08 | ++++ |
| 282 | 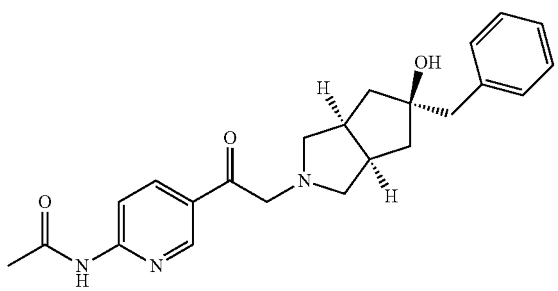 [SMILES: CC(=O)Nc1ccc(C(=O)CN2C[C@@H]3C[C@@](O)(Cc4ccccc4)C[C@@H]3C2)cn1] | N-(5-(2-((3aR,5r,6aS)-5-benzyl-5-hydroxyhexahydrocyclopenta[c]pyrrol-2(1H)-yl)acetyl)pyridin-2-yl)acetamide | 1.00E−05 | + |
| 283 | 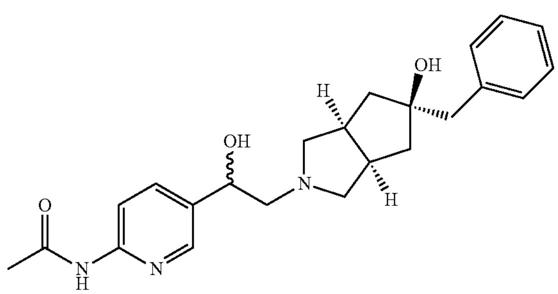 [SMILES: CC(=O)Nc1ccc(C(O)CN2C[C@@H]3C[C@@](O)(Cc4ccccc4)C[C@@H]3C2)cn1] | rac-N-(5-(2-((3aR,5r,6aS)-5-benzyl-5-hydroxyhexahydrocyclopenta[c]pyrrol-2(1H)-yl)-1-hydroxyethyl)pyridin-2-yl)acetamide | 1.00E−05 | + |
| 284 | 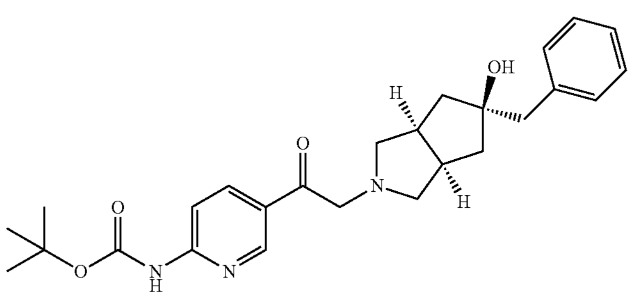 [SMILES: CC(C)(C)OC(=O)Nc1ccc(C(=O)CN2C[C@@H]3C[C@@](O)(Cc4ccccc4)C[C@@H]3C2)cn1] | tert-butyl (5-(2-(5-benzyl-5-hydroxyhexahydrocyclopenta[c]pyrrol-2(1H)-yl)acetyl)pyridin-2-yl)carbamate | 1.00E−05 | + |

| Cmpd # | Structure | IUPAC Name | NR2B NAM IC50 | Binned Activity |
|---|---|---|---|---|
| 285 | 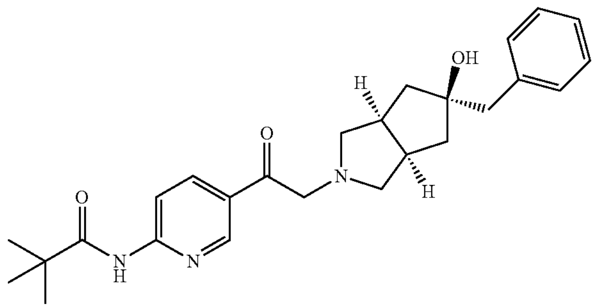 [SMILES: CC(C)(C)C(=O)Nc1ccc(C(=O)CN2C[C@@H]3C[C@@](O)(Cc4ccccc4)C[C@@H]3C2)cn1] | N-(5-(2-(5-benzyl-5-hydroxyhexahydrocyclopenta[c]pyrrol-2(1H)-yl)acetyl)pyridin-2-yl)pivalamide | 1.00E−05 | + |
| 286 | 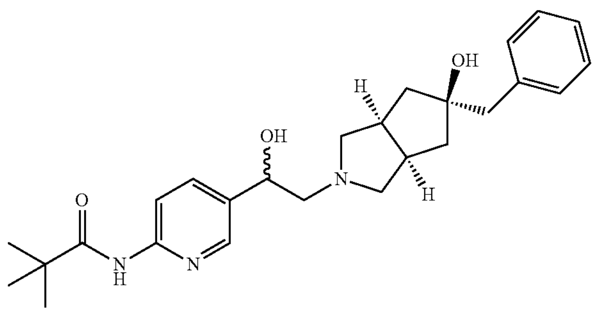 [SMILES: CC(C)(C)C(=O)Nc1ccc(C(O)CN2C[C@@H]3C[C@@](O)(Cc4ccccc4)C[C@@H]3C2)cn1] | rac-N-(5-(2-(5-benzyl-5-hydroxyhexahydrocyclopenta[c]pyrrol-2(1H)-yl)-1-hydroxyethyl)pyridin-2-yl)pivalamide | 1.00E−05 | + |
| 287 | 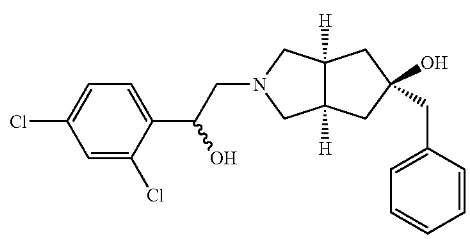 [SMILES: OC(CN1C[C@@H]2C[C@@](O)(Cc3ccccc3)C[C@@H]2C1)c1ccc(Cl)cc1Cl] | rac-(3aR,5r,6aS)-5-benzyl-2-(2-(2,4-dichlorophenyl)-2-hydroxyethyl)octahydrocyclopenta[c]pyrrol-5-ol | 1.00E−05 | + |
| 288 | 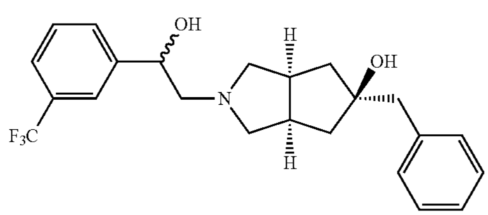 [SMILES: OC(CN1C[C@@H]2C[C@@](O)(Cc3ccccc3)C[C@@H]2C1)c1cccc(C(F)(F)F)c1] | rac-(3aR,5r,6aS)-5-benzyl-2-(2-hydroxy-2-(3-(trifluoromethyl)phenyl)ethyl)octahydrocyclopenta[c]pyrrol-5-ol | 1.00E−05 | + |
| 289 | 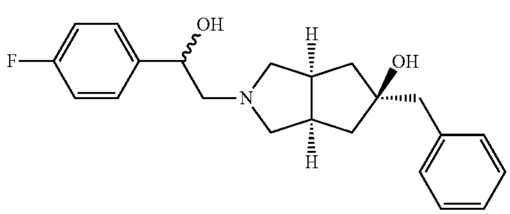 [SMILES: OC(CN1C[C@@H]2C[C@@](O)(Cc3ccccc3)C[C@@H]2C1)c1ccc(F)cc1] | rac-(3aR,5r,6aS)-5-benzyl-2-(2-(4-fluorophenyl)-2-hydroxyethyl)octahydrocyclopenta[c]pyrrol-5-ol | 1.00E−05 | + |
| 290 | 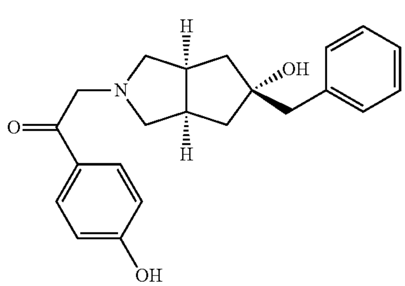 [SMILES: O=C(CN1C[C@@H]2C[C@](O)(Cc3ccccc3)C[C@@H]2C1)c1ccc(O)cc1] | 2-((3aR,5r,6aS)-5-benzyl-5-hydroxyhexahydrocyclopenta[c]pyrrol-2(1H)-yl)-1-(4-hydroxyphenyl)ethanone | 7.66E−08 | ++++ |

| Cmpd # | Structure | IUPAC Name | NR2B NAM IC50 | Binned Activity |
|---|---|---|---|---|
| 2291 | 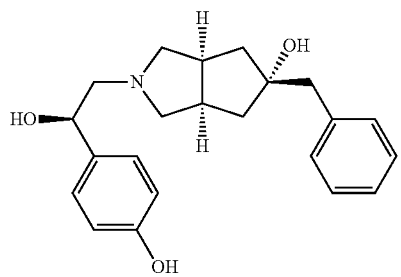 [SMILES: Oc1ccc([C@@H](O)CN2C[C@@H]3C[C@](O)(Cc4ccccc4)C[C@@H]3C2)cc1] | (3aR,5R,6aS)-5-benzyl-2-((R)-2-hydroxy-2-(4-hydroxyphenyl)ethyl)octahydrocyclopenta[c]pyrrol-5-ol | 3.32E−07 | +++ |
| 292 | 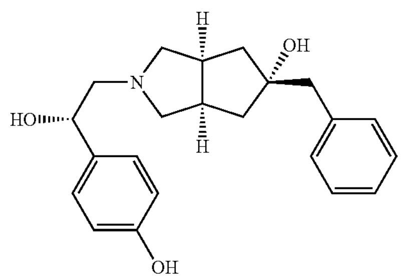 [SMILES: Oc1ccc([C@H](O)CN2C[C@@H]3C[C@](O)(Cc4ccccc4)C[C@@H]3C2)cc1] | (3aR,5S,6aS)-5-benzyl-2-((S)-2-hydroxy-2-(4-hydroxyphenyl)ethyl)octahydrocyclopenta[c]pyrrol-5-ol | 4.71E−06 | ++ |
| 293 | 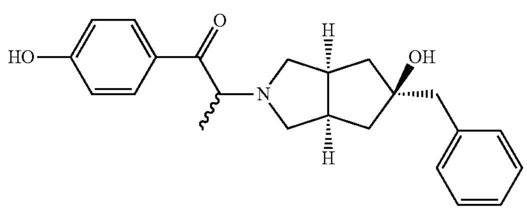 [SMILES: CC(C(=O)c1ccc(O)cc1)N1C[C@@H]2C[C@@](O)(Cc3ccccc3)C[C@@H]2C1] | rac-2-((3aR,5r,6aS)-5-benzyl-5-hydroxy-hexahydrocyclopenta[c]pyrrol-2(1H)-yl)-1-(4-hydroxyphenyl)propan-1-one | 1.00E−07 | +++ |
| 294 | 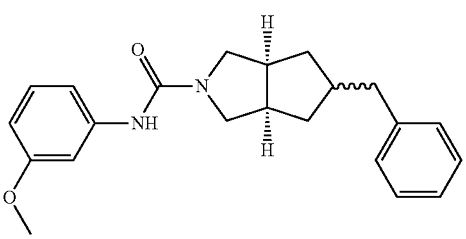 [SMILES: COc1cccc(NC(=O)N2C[C@H]3CC(Cc4ccccc4)C[C@H]3C2)c1] | (3aR,6aS)-5-benzyl-N-(3-methoxyphenyl)hexahydrocyclopenta[c]pyrrole-2(1H)-carboxamide | 1.00E−05 | + |
| 295 | 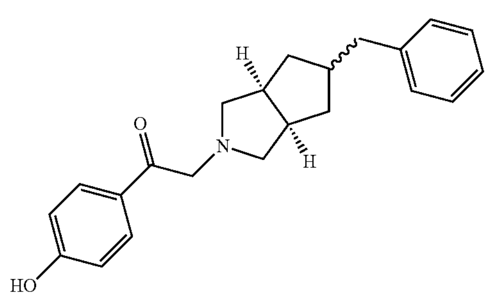 [SMILES: O=C(CN1C[C@H]2CC(Cc3ccccc3)C[C@H]2C1)c1ccc(O)cc1] | 2-((3aR,6aS)-5-benzyl-hexahydrocyclopenta[c]pyrrol-2(1H)-yl)-1-(4-hydroxyphenyl)ethanone | 5.17E−08 | ++++ |
| 296 | 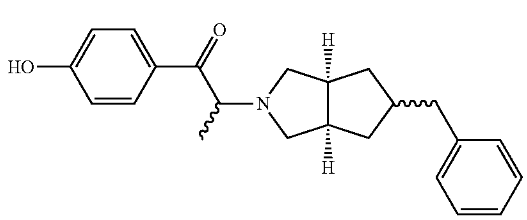 [SMILES: CC(C(=O)c1ccc(O)cc1)N1C[C@H]2CC(Cc3ccccc3)C[C@H]2C1] | rac-2-((3aR,6aS)-5-benzylhexahydrocyclopenta[c]pyrrol-2(1H)-yl)-1-(4-hydroxyphenyl)propan-1-one | 1.25E−07 | +++ |

-continued

| Cmpd # | Structure | IUPAC Name | NR2B NAM IC50 | Binned Activity |
|---|---|---|---|---|
| 297 | 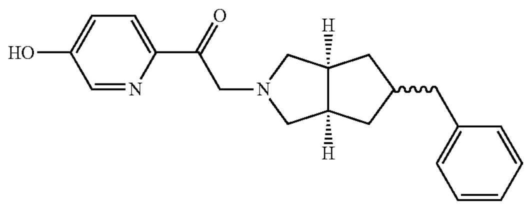 [SMILES: O=C(CN1C[C@H]2CC(Cc3ccccc3)C[C@H]2C1)c1ccc(O)cn1] | 2-{5-benzyl-octahydrocyclopenta[c]pyrrol-2-yl}-1-(5-hydroxypyridin-2-yl)ethan-1-one | 7.92E−07 | +++ |
| 298 | 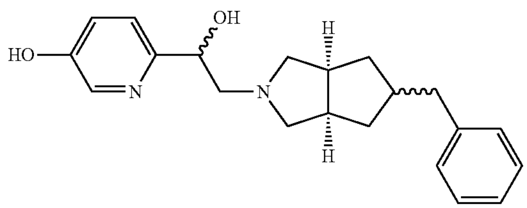 [SMILES: Oc1ccc(C(O)CN2C[C@H]3CC(Cc4ccccc4)C[C@H]3C2)nc1] | rac-6-(2-{5-benzyl-octahydrocyclopenta[c]pyrrol-2-yl}-1-hydroxyethyl)pyridin-3-ol | 2.24E−08 | ++++ |
| 299 | 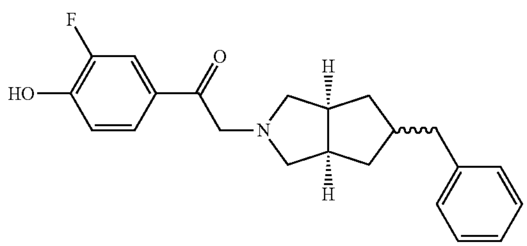 [SMILES: O=C(CN1C[C@H]2CC(Cc3ccccc3)C[C@H]2C1)c1ccc(O)c(F)c1] | 2-{5-benzyl-octahydro-cyclopenta[c]pyrrol-2-yl}-1-(3-fluoro-4-hydroxyphenyl)ethan-1-one | 7.81E−08 | ++++ |
| 300 | 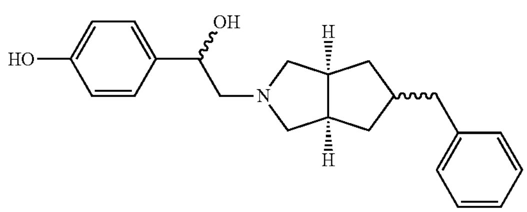 | rac-4-(2-((3aR,6aS)-5-benzylhexahydrocyclopenta[c]pyrrol-2(1H)-yl)-1-hydroxyethyl)phenol | 1.39E−08 | ++++ |
| 301 | 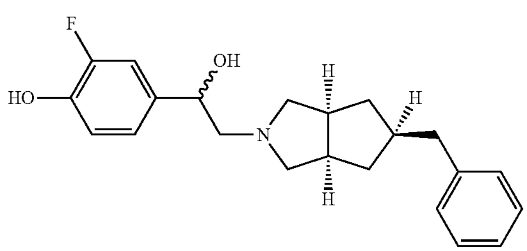 [SMILES: Oc1ccc(C(O)CN2C[C@H]3C[C@@H](Cc4ccccc4)C[C@H]3C2)cc1F] | rac-4-{2-[(3aR,5S,6aS)-5-benzyl-octahydrocyclopenta[c]pyrrol-2-yl]-1-hydroxyethyl}-2-fluorophenol | 1.22E−08 | ++++ |
| 302 | 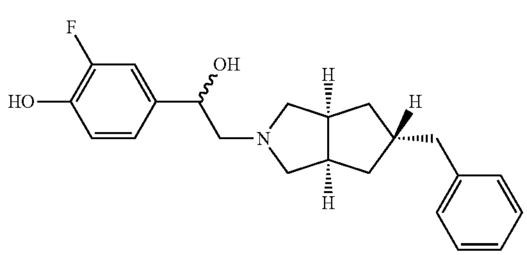 [SMILES: Oc1ccc(C(O)CN2C[C@H]3C[C@H](Cc4ccccc4)C[C@H]3C2)cc1F] | rac-4-{2-[(3aR,5R,6aS)-5-benzyl-octahydrocyclopenta[c]pyrrol-2-yl]-1-hydroxyethyl}-2-fluorophenol | 2.01E−08 | ++++ |

-continued

| Cmpd # | Structure | IUPAC Name | NR2B NAM IC50 | Binned Activity |
|---|---|---|---|---|
| 303 | 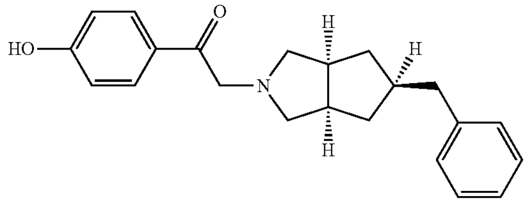 [SMILES: O=C(CN1C[C@H]2C[C@@H](Cc3ccccc3)C[C@H]2C1)c1ccc(O)cc1] | 2-[(3aR,5S,6aS)-5-benzyl-octahydro-cyclopenta[c]pyrrol-2-yl]-1-(4-hydroxy-phenyl)ethan-1-onefluorophenol | 3.88E−08 | ++++ |
| 304 | 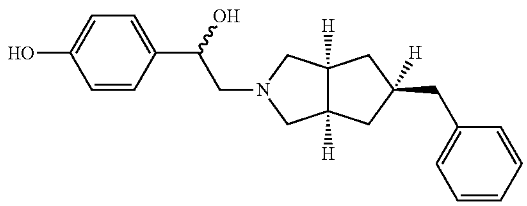 [SMILES: Oc1ccc(C(O)CN2C[C@H]3C[C@@H](Cc4ccccc4)C[C@H]3C2)cc1] | rac-4-{2-[(3aR,5S,6aS)-5-benzyl-octahydro-cyclopenta[c]pyrrol-2-yl]-1-hydroxy-ethyl}phenol | 1.68E−08 | ++++ |
| 305 | 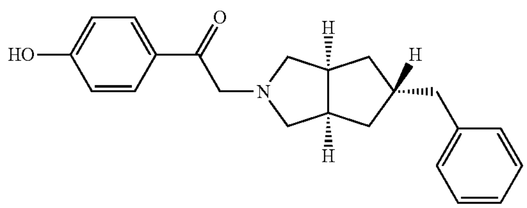 [SMILES: O=C(CN1C[C@H]2C[C@H](Cc3ccccc3)C[C@H]2C1)c1ccc(O)cc1] | 2-[(3aR,5R,6aS)-5-benzyl-octahydrocyclo-penta[c]pyrrol-2-yl]-1-(4-hydroxyphenyl)ethan-1-one | 5.35E−08 | ++++ |
| 306 | 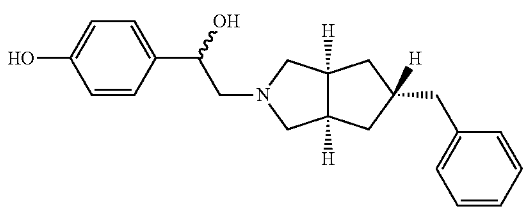 [SMILES: Oc1ccc(C(O)CN2C[C@H]3C[C@H](Cc4ccccc4)C[C@H]3C2)cc1] | rac-4-{2-[(3aR,5R,6aS)-5-benzyl-octahydro-cyclopenta[c]pyrrol-2-yl]-1-hydroxyethyl}phenol | 1.17E−08 | ++++ |
| 307 | 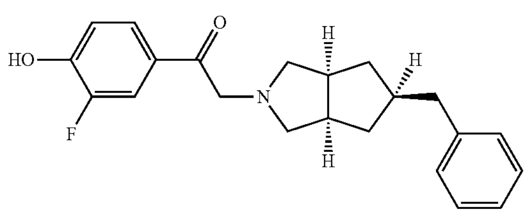 [SMILES: O=C(CN1C[C@H]2C[C@@H](Cc3ccccc3)C[C@H]2C1)c1ccc(O)c(F)c1] | 2-[(3aR,5S,6aS)-5-benzyl-octahydrocyclo-penta[c]pyrrol-2-yl]-1-(3-fluoro-4-hydroxy-phenyl)ethan-1-one | 4.12E−08 | ++++ |
| 308 | 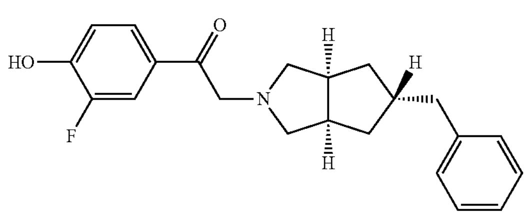 [SMILES: O=C(CN1C[C@H]2C[C@H](Cc3ccccc3)C[C@H]2C1)c1ccc(O)c(F)c1] | 2-[(3aR,5R,6aS)-5-benzyl-octahydrocyclo-penta[c]pyrrol-2-yl]-1-(3-fluoro-4-hydroxy-phenyl)ethan-1-one | 5.22E−08 | ++++ |
| 309 | 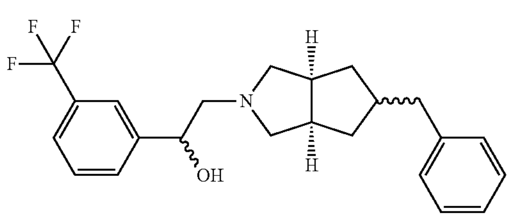 [SMILES: OC(CN1C[C@H]2CC(Cc3ccccc3)C[C@H]2C1)c1cccc(C(F)(F)F)c1] | rac-2-((3aR,6aS)-5-benzylhexahydrocyclo-penta[c]pyrrol-2(1H)-yl)-1-(3-(trifluoro-methyl)phenyl)ethanol | 1.00E−05 | + |

-continued

| Cmpd # | Structure | IUPAC Name | NR2B NAM IC50 | Binned Activity |
|---|---|---|---|---|
| 310 | 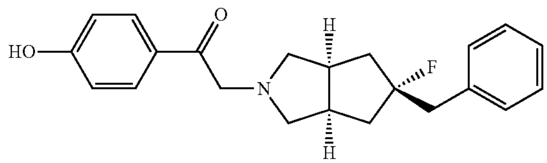 [SMILES: O=C(CN1C[C@@H]2C[C@](F)(Cc3ccccc3)C[C@@H]2C1)c1ccc(O)cc1] | 2-((3aR,5s,6aS)-5-benzyl-5-fluorohexahydrocyclopenta[c]pyrrol-2(1H)-yl)-1-(4-hydroxyphenyl)ethanone | 1.75E−07 | +++ |
| 311 | 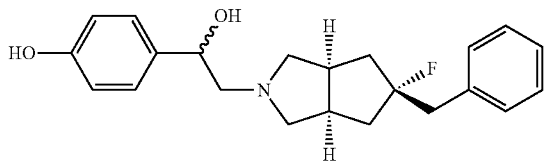 [SMILES: Oc1ccc(C(O)CN2C[C@@H]3C[C@](F)(Cc4ccccc4)C[C@@H]3C2)cc1] | rac-4-(2-((3aR,5s,6aS)-5-benzyl-5-fluorohexahydrocyclopenta[c]pyrrol-2(1H)-yl)-1-hydroxyethyl)phenol | 4.48E−07 | +++ |
| 312 | 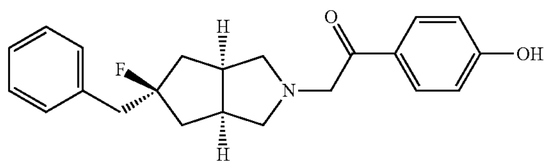 [SMILES: O=C(CN1C[C@@H]2C[C@@](F)(Cc3ccccc3)C[C@@H]2C1)c1ccc(O)cc1] | 4-(2-((3aR,5s,6aS)-5-benzyl-5-fluorohexahydrocyclopenta[c]pyrrol-2(1H)-yl)-1-hydroxyethyl)phenol | 9.30E−08 | ++++ |
| 313 | 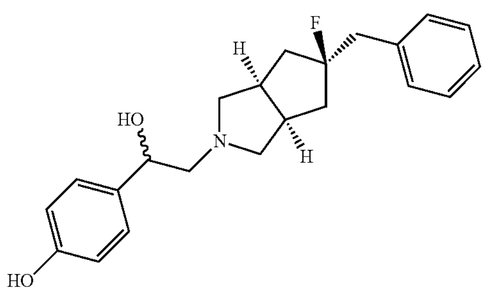 [SMILES: Oc1ccc(C(O)CN2C[C@@H]3C[C@@](F)(Cc4ccccc4)C[C@@H]3C2)cc1] | rac-4-(2-((3aR,5r,6aS)-5-benzyl-5-fluorohexahydrocyclopenta[c]pyrrol-2(1H)-yl)-1-hydroxyethyl)phenol | 2.69E−08 | ++++ |
| 314 | 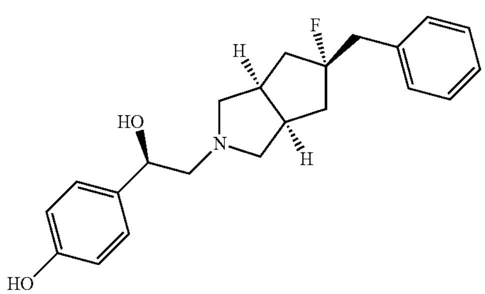 [SMILES: Oc1ccc([C@@H](O)CN2C[C@@H]3C[C@](F)(Cc4ccccc4)C[C@@H]3C2)cc1] | 4-((R)-2-((3aR,5S,6aS)-5-benzyl-5-fluorohexahydrocyclopenta[c]pyrrol-2(1H)-yl)-1-hydroxyethyl)phenol | 4.14E−07 | +++ |
| 315 | 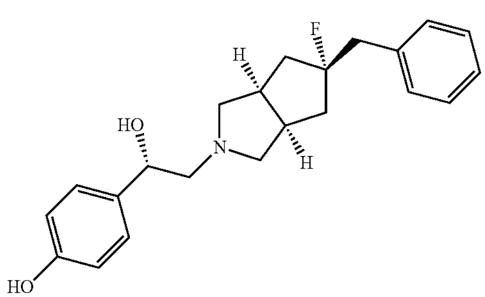 [SMILES: Oc1ccc([C@H](O)CN2C[C@@H]3C[C@](F)(Cc4ccccc4)C[C@@H]3C2)cc1] | 4-((S)-2-((3aR,5R,6aS)-5-benzyl-5-fluorohexahydrocyclopenta[c]pyrrol-2(1H)-yl)-1-hydroxyethyl)phenol | 3.24E−07 | +++ |

-continued

| Cmpd # | Structure | IUPAC Name | NR2B NAM IC50 | Binned Activity |
|---|---|---|---|---|
| 316 | 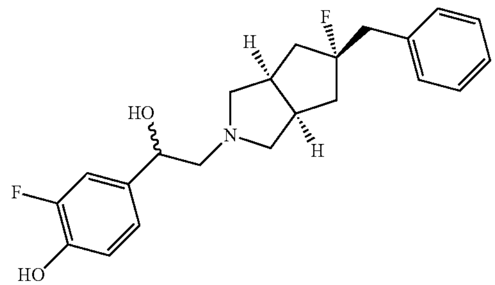 [SMILES: Oc1ccc(C(O)CN2C[C@@H]3C[C@](F)(Cc4ccccc4)C[C@@H]3C2)cc1F] | rac-4-(2-((3aR,5s,6aS)-5-benzyl-5-fluorohexahydro-cyclopenta[c]pyrrol-2(1H)-yl)-1-hydroxy-ethyl)-2-fluorophenol | 3.64E−08 | ++++ |
| 317 | 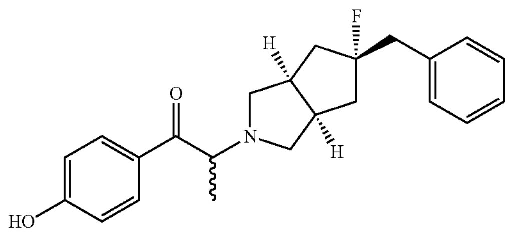 [SMILES: CC(C(=O)c1ccc(O)cc1)N1C[C@@H]2C[C@](F)(Cc3ccccc3)C[C@@H]2C1] | rac-2-((3aR,5s,6aS)-5-benzyl-5-fluoro-hexahydrocyclo-penta[c]pyrrol-2(1H)-yl)-1-(4-hydroxy-phenyl)propan-1-one | 2.84E−07 | +++ |
| 318 | 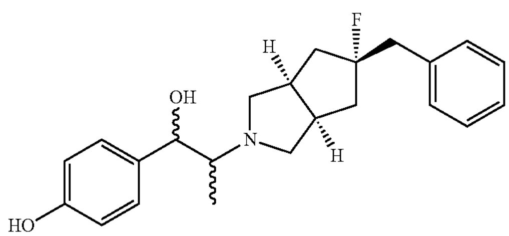 [SMILES: CC(C(O)c1ccc(O)cc1)N1C[C@@H]2C[C@](F)(Cc3ccccc3)C[C@@H]2C1] | rac-4-(2-((3aR,5s,6aS)-5-benzyl-5-fluoro-hexahydrocyclo-penta[c]pyrrol-2(1H)-yl)-1-hydroxypropyl)phenol | 1.28E−05 | + |
| 319 | 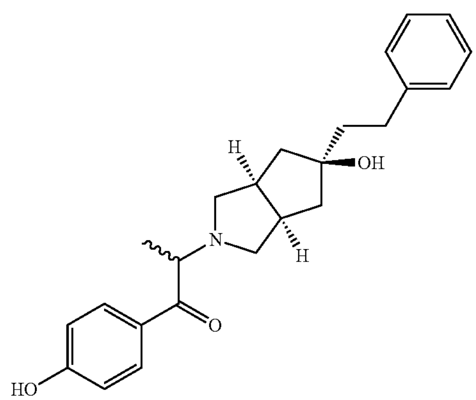 [SMILES: CC(C(=O)c1ccc(O)cc1)N1C[C@@H]2C[C@@](O)(CCc3ccccc3)C[C@@H]2C1] | rac-2-(5-hydroxy-5-phenethylhexahydrocyclo-penta[c]pyrrol-2(1H)-yl)-1-(4-hydroxy-phenyl)propan-1-one | 4.97E−07 | +++ |
| 320 | 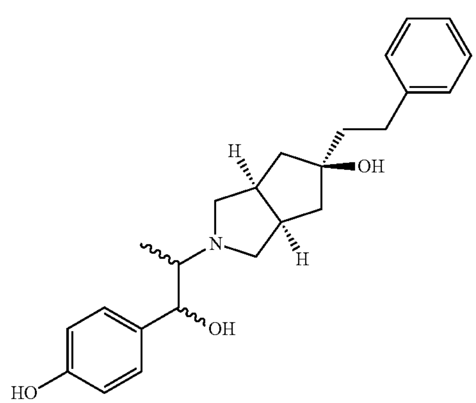 [SMILES: CC(C(O)c1ccc(O)cc1)N1C[C@@H]2C[C@@](O)(CCc3ccccc3)C[C@@H]2C1] | rac-2-(1-hydroxy-1-(4-hydroxyphenyl)propan-2-yl)-5-phenethyl-octahydrocyclo-penta[c]pyrrol-5-ol | 2.05E−06 | ++ |

-continued

| Cmpd # | Structure | IUPAC Name | NR2B NAM IC50 | Binned Activity |
|---|---|---|---|---|
| 321 | 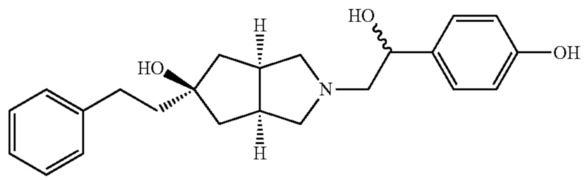 [SMILES: Oc1ccc(C(O)CN2C[C@@H]3C[C@@](O)(CCc4ccccc4)C[C@@H]3C2)cc1] | rac-2-(2-hydroxy-2-(4-hydroxyphenyl)ethyl)-5-phenethyloctahydrocyclopenta[c]pyrrol-5-ol | 1.00E−05 | + |
| 322 | 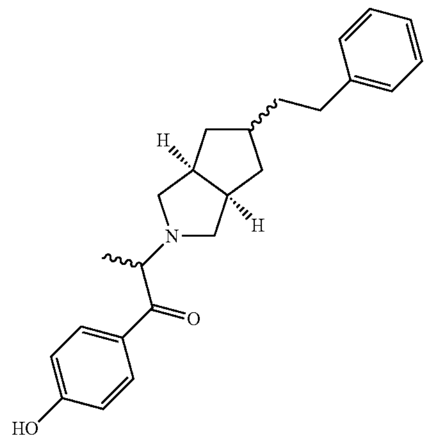 [SMILES: CC(C(=O)c1ccc(O)cc1)N1C[C@H]2CC(CCc3ccccc3)C[C@H]2C1] | rac-1-(4-hydroxyphenyl)-2-[(5R)-5-(2-phenylethyl)-octahydrocyclopenta[c]pyrrol-2-yl]propan-1-one | 5.33E−07 | +++ |
| 323 | 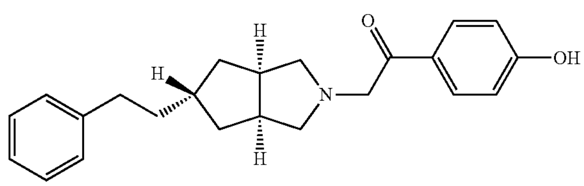 [SMILES: O=C(CN1C[C@H]2C[C@H](CCc3ccccc3)C[C@H]2C1)c1ccc(O)cc1] | 1-(4-hydroxyphenyl)-2-(5-phenethylhexahydrocyclopenta[c]pyrrol-2(1H)-yl)ethanone | 4.26E−07 | +++ |
| 324 | 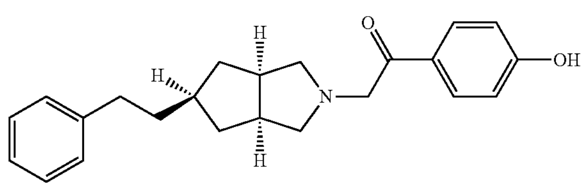 [SMILES: O=C(CN1C[C@H]2C[C@@H](CCc3ccccc3)C[C@H]2C1)c1ccc(O)cc1] | 1-(4-hydroxyphenyl)-2-((3aR,5r,6aS)-5-phenethylhexahydrocyclopenta[c]pyrrol-2(1H)-yl)ethanone | 2.15E−07 | +++ |
| 325 | 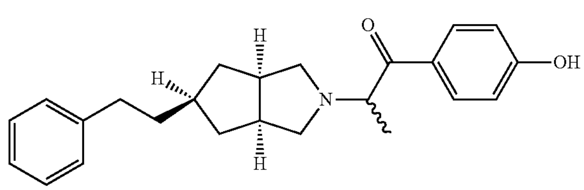 [SMILES: CC(C(=O)c1ccc(O)cc1)N1C[C@H]2C[C@@H](CCc3ccccc3)C[C@H]2C1] | 1-(4-hydroxyphenyl)-2-((3aR,5r,6aS)-5-phenethylhexahydrocyclopenta[c]pyrrol-2(1H)-yl)propan-1-one | 1.92E−07 | +++ |
| 326 | 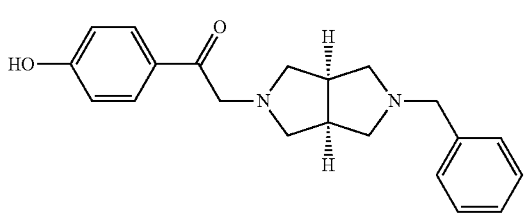 | 2-(5-benzyl-hexahydropyrrolo[3,4-c]pyrrol-2(1H)-yl)-1-(4-hydroxyphenyl)ethanone | 6.82E−07 | +++ |

-continued

| Cmpd # | Structure | IUPAC Name | NR2B NAM IC50 | Binned Activity |
|---|---|---|---|---|
| 327 | 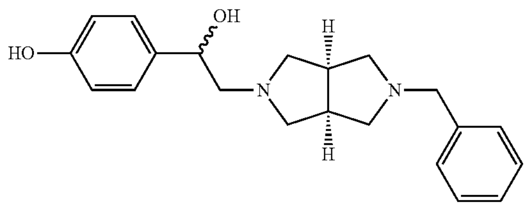 | rac-4-(2-(5-benzyl-hexahydropyrrolo[3,4-c]pyrrol-2(1H)-yl)-1-hydroxyethyl)phenol | 1.39E−07 | +++ |
| 328 | 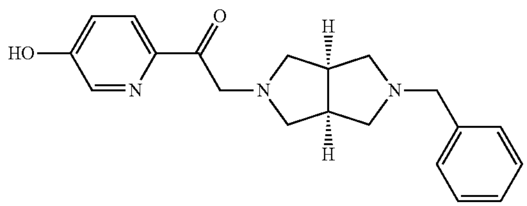 | 2-(5-benzyl-hexahydropyrrolo[3,4-c]pyrrol-2(1H)-yl)-1-(5-hydroxypyridin-2-yl)ethanone | 1.00E−05 | + |
| 329 | 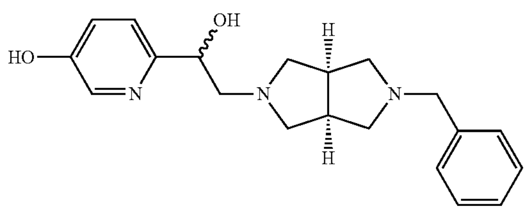 | rac-6-(2-(5-benzyl-hexahydropyrrolo[3,4-c]pyrrol-2(1H)-yl)-1-hydroxyethyl)pyridin-3-ol | 3.80E−07 | +++ |
| 340 | 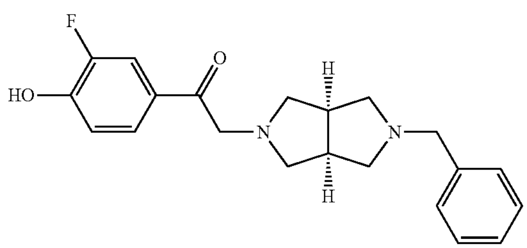 | 2-(5-benzyl-hexahydropyrrolo[3,4-c]pyrrol-2(1H)-yl)-1-(3-fluoro-4-hydroxyphenyl)ethanone | 1.00E−05 | + |
| 341 | 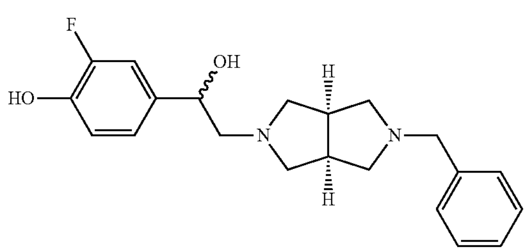 [SMILES: Oc1ccc(C(O)CN2C[C@H]3CN(Cc4ccccc4)C[C@H]3C2)cc1F] | rac-4-(2-(5-benzyl-hexahydropyrrolo[3,4-c]pyrrol-2(1H)-yl)-1-hydroxyethyl)-2-fluorophenol | 7.43E−08 | ++++ |
| 342 | 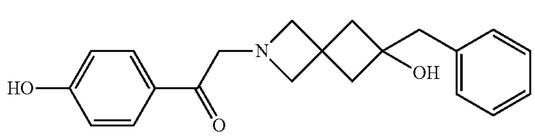 [SMILES: O=C(CN1CC2(C1)CC(O)(Cc1ccccc1)C2)c1ccc(O)cc1] | 2-(6-benzyl-6-hydroxy-2-azaspiro[3.3]heptan-2-yl)-1-(4-hydroxy-phenyl)ethanone | 2.67E−06 | ++ |
| 343 | 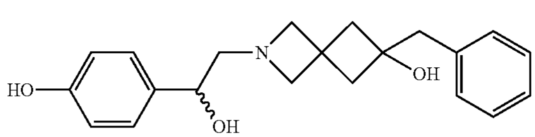 [SMILES: Oc1ccc(C(O)CN2CC3(C2)CC(O)(Cc2ccccc2)C3)cc1] | rac-6-benzyl-2-(2-hydroxy-2-(4-hydroxyphenyl)ethyl)-2-azaspiro[3.3]heptan-6-ol | 5.06E−07 | +++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula I:

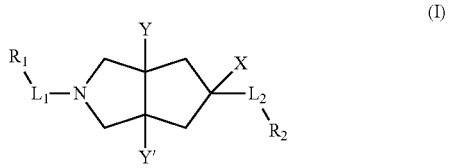

(I)

or pharmaceutically acceptable salt, tautomer, or stereoisomer thereof
wherein:
$L_1$ is straight or branched $C_2$-$C_4$ alkyl optionally substituted with one or more substituents selected from the group consisting of OH, D, $OR_{10}$, $NH_2$, $NHR_{10}$, and $N(R_{10})(R_{10'})$, provided that no more than one oxygen or nitrogen is attached to any carbon;
or
$L_1$ is selected from the group consisting of —CO—$C_1$-$C_2$alkylenyl-, —S(O)$_2$—, —S(O)$_2$NH—, —C(O)NH—, —C(O)NR$_{10}$—, —$C_1$-$C_3$alkylenyl-C(O)—$C_1$-$C_3$alkylenyl-, and a bond, wherein the $C_1$-$C_2$ alkylenyl and $C_1$-$C_3$ alkylenyl is optionally substituted with $C_1$-$C_4$ alkyl;
Each $R_{10}$ and $R_{10'}$ is independently selected from the group consisting of H; O—$C_1$-$C_5$ alkyl; $C_1$-$C_6$ alkyl optionally substituted with one or more substituents selected from the group consisting of OH, O—$C_1$-$C_5$ alkyl, —OP(O)(OH)$_2$, OP(O)O$_2^{-2}$M$_2$, —OC(O)alkyl, —OC(O)Oalkyl, and aryl; and cycloalkyl optionally substituted with one or more substituents selected from the group consisting of OH and O—$C_1$-$C_5$ alkyl;
provided that no more than one oxygen is attached to any carbon of $R_{10}$ and $R_{10'}$;
M is a monovalent metal cation;
$R_1$ is aryl optionally substituted with one or more substituents selected from the group consisting of OH, CN, halogen, —O—$R_{10}$, —OP(O)(OH)$_2$, OP(O)O$_2^{-2}$M$_2$, —SH, —S—$R_{10}$, $C_1$-$C_5$ alkyl, branched alkyl, —$C_1$-$C_6$haloalkyl, NH$_2$, NHR$_{10}$, —$C_1$-$C_6$hydroxyalkyl, N(R$_{10}$)(NR$_{10'}$), —NHS(O)$_2$R$_{10}$, —O-alkylaryl, —O—(CH$_2$)—C(O)-aryl, and NHCOR$_{10}$; M is a monovalent metal cation; or
$R_1$ is cycloalkyl;
X is selected from the group consisting of H, halogen, OH, O—$C_1$-$C_6$ alkyl, O-branched alkyl, $C_1$-$C_5$ straight alkyl and $C_1$-$C_5$ branched alkyl;
Y and Y' are independently H, F, or methyl;
$L_2$ is —(CH$_2$)$_n$— or —(CHR$_{11}$)$_n$—, or a bond;
Each $R_{11}$ is independently selected from the group consisting of H, —$C_1$-$C_5$ alkylenyl-, —C(O)—$C_1$-$C_5$alkylenyl-, and -alkylenyl-CO-alkylenyl-;
$R_2$ is $C_3$-$C_8$cycloalkyl; phenyl, or naphthyl, each of which is optionally substituted with one or more substituents selected from the group consisting of halogen, OH, $C_1$-$C_6$alkyl, OR$_{10}$, CN, NH$_2$, NHR$_{10}$, N(R$_{10}$)(R$_{10'}$), SH, SR$_{10}$, SOR$_{10}$, SO$_2$R$_{10}$, SO$_2$NHR$_{10}$, SO$_2$N(R$_{10}$)(R$_{10'}$), CONH$_2$, CONR$_{10}$, and CON(R$_{10}$)(R$_{10'}$); and
n is 1, 2, or 3.

2. The compound of claim 1 wherein $R_1$ is aryl substituted with one or more substituents selected from the group consisting of OH, OR$_{10}$, SH, SR$_{10}$, NH$_2$, NHR$_{10}$ and NHCOR$_{10}$.

3. The compound of claim 1 wherein $R_1$ is aryl substituted with one substituent selected from the group consisting of OH, OR$_{10}$, SH, SR$_{10}$, NH$_2$, NHR$_{10}$ and NHCOR$_{10}$.

4. The compound of claim 1 wherein Y and Y' are hydrogen.

5. The compound of claim 1 wherein $L_2$ is a bond.

6. The compound of claim 1 wherein $R_2$ is phenyl optionally substituted with one or more halogen, OH, OR$_{10}$, CN, NH$_2$, NHR$_{10}$, N(R$_{10}$)(R$_{10'}$), SH, SR$_{10}$, SOR$_{10}$, SO$_2$R$_{10}$, SO$_2$NHR$_{10}$, SO$_2$N(R$_{10}$)(R$_{10'}$), CONH$_2$, CONR$_{10}$, CON(R$_{10}$)(R$_{10'}$).

7. The compound of claim 1 wherein $R_2$ is phenyl substituted with one or more halogen.

8. The compound of claim 1 wherein $L_1$ is branched $C_2$-$C_4$ alkyl substituted with one or more substituents selected from the group consisting of OH, OR$_{10}$, NH$_2$, NHR$_{10}$, and N(R$_{10}$)(R$_{10'}$) provided that no more than one oxygen or nitrogen is attached to any carbon of $L_1$.

9. The compound of claim 1 wherein $L_1$ is straight $C_1$-$C_5$ alkyl substituted with one or more substituents selected from the group consisting of OH, OR$_{10}$, NH$_2$, NHR$_{10}$, and N(R$_{10}$)(R$_{10'}$) provided that no more than one oxygen or nitrogen is attached to any carbon of $L_1$.

10. A compound of claim 1 of Formula (Ia):

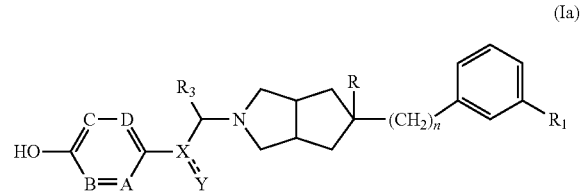

(Ia)

or pharmaceutically acceptable salt, tautomer, or stereoisomer thereof
wherein:
A, B, C and D are CH;
X is CH or C;
Y is OH or O;
$R_3$ is H or CH$_3$
n is 0, 1, or 2;
R is H, OH or F; and
$R_1$ is H or F.

11. The compound of claim 10 wherein X and Y form a carbonyl, or X is CH and Y is OH.

12. The compound of claim 10 wherein $R_3$ is H; R is H or OH.

13. A compound of claim 1 of Formula (Ib):

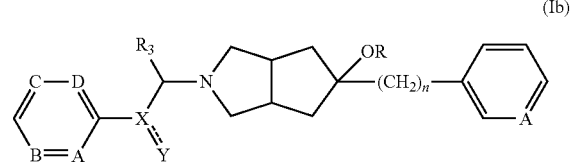

(Ib)

or pharmaceutically acceptable salt, tautomer, or stereoisomer thereof
wherein:
A, B, C, and D are independently $CR_x$;
X is CH or C;
Y is OH or O;
$R_3$ is H
n is 0, 1, or 2;
R is H, or $CH_3$; and
$R_x$ is H, $C_{1-6}$ alkyl, halogen, —OH, or —$OC_{1-6}$ alkyl.

14. A compound of claim 1 of Formula (Ic):

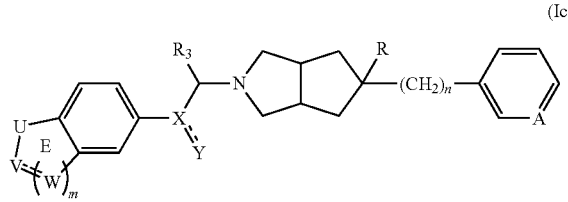

(Ic)

or pharmaceutically acceptable salt, tautomer, or stereoisomer thereof
wherein:
A is $CR_x$;
U is C=O, or $C(R_x)_m$;
V is C=O, or $C(R_x)_m$;
each W is independently C=O, or $C(R_x)_m$;
------- is an optional double bond which allows the E ring to be partially or fully saturated;
X is CH or C;
Y is OH or O;
$R_3$ is H;
n is 0, 1, or 2;
each m is independently 1 or 2;
R is H, OH, or $CH_3$;
$R_x$ is H, $C_{1-6}$ alkyl, halogen, —OH, or —$OC_{1-6}$ alkyl; and
$R_y$ is H, or $C_{1-6}$ alkyl.

15. A compound of claim 1 of Formula (Id):

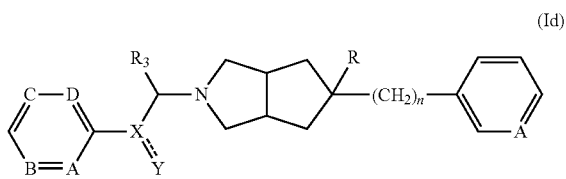

(Id)

or pharmaceutically acceptable salt, tautomer, or stereoisomer thereof
wherein:
A, B, C, and D are independently $CR_x$;
X is CH or C;
Y is OH or O;
$R_3$ is H;
n is 0, 1, or 2;
R is F;
$R_x$ is H, $C_{1-6}$ alkyl, halogen, —OH, or —$OC_{1-6}$ alkyl.

16. A compound of claim 1 of Formula (Ie):

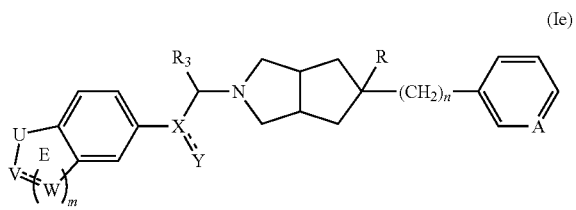

(Ie)

or pharmaceutically acceptable salt, tautomer, or stereoisomer thereof
wherein:
A is $CR_x$;
U is C=O, or $C(R_x)_m$;
V is C=O, or $C(R_x)_m$;
each W is independently C=O, or $C(R_x)_m$;
------- is an optional double bond which allows the E ring to be partially or fully saturated;
X is CH or C;
Y is OH or O;
$R_3$ is H;
n is 0, 1, or 2;
each m is independently 1 or 2;
R is H, OH, or $CH_3$;
$R_x$ is H, $C_{1-6}$ alkyl, halogen, —OH, or —$OC_{1-6}$ alkyl; and
$R_y$ is H, or $C_{1-6}$ alkyl.

17. A compound selected from the group consisting of
5-hydroxy-N-(4-methoxyphenyl)-5-phenylhexahydrocyclopenta[c]pyrrole-2(1H)-carboxamide;
5-(4-cyanophenyl)-5-hydroxy-N-(4-methoxyphenyl)-octahydrocyclopenta[c]pyrrole-2-carboxamide;
5-hydroxy-N-(4-methylphenyl)-5-phenyl-octahydrocyclopenta[c]pyrrole-2-carboxamide;
N-(3-chlorophenyl)-5-hydroxy-5-phenyl-octahydrocyclopenta[c]pyrrole-2-carboxamide;
5-hydroxy-5-phenyl-N-[3-(trifluoromethyl)phenyl]-octahydrocyclopenta[c]pyrrole-2-carboxamide;
N-(4-fluorophenyl)-5-hydroxy-5-phenyl-octahydrocyclopenta[c]pyrrole-2-carboxamide;
5-hydroxy-N-(3-methoxyphenyl)-5-phenyl-octahydrocyclopenta[c]pyrrole-2-carboxamide;
5-hydroxy-N-(4-methoxyphenyl)-5-(2-methylphenyl)-octahydrocyclopenta[c]pyrrole-2-carboxamide;
5-hydroxy-5-(2-methylphenyl)-N-(4-methylphenyl)-octahydrocyclopenta[c]pyrrole-2-carboxamide;
5-hydroxy-N-(3-methoxyphenyl)-5-(2-methylphenyl)-octahydrocyclopenta[c]pyrrole-2-carboxamide;
N-(3-chlorophenyl)-5-hydroxy-5-(2-methylphenyl)-octahydrocyclopenta[c]pyrrole-2-carboxamide;
5-hydroxy-5-(2-methylphenyl)-N-[3-(trifluoromethyl)phenyl]-octahydrocyclopenta[c]pyrrole-2-carboxamide;
N-(4-fluorophenyl)-5-hydroxy-5-(2-methylphenyl)-octahydrocyclopenta[c]pyrrole-2-carboxamide;
5-hydroxy-5-(3-methoxyphenyl)-N-(4-methylphenyl)-octahydrocyclopenta[c]pyrrole-2-carboxamide;
N-(3-chlorophenyl)-5-hydroxy-5-(3-methoxyphenyl)-octahydrocyclopenta[c]pyrrole-2-carboxamide;
5-hydroxy-5-(3-methoxyphenyl)-N-[3-(trifluoromethyl)phenyl]-octahydrocyclopenta[c]pyrrole-2-carboxamide;

5-hydroxy-5-(3-methoxyphenyl)-N-(4-methoxyphenyl)-octahydrocyclopenta[c]pyrrole-2-carboxamide;
5-hydroxy-N,5-bis(3-methoxyphenyl)-octahydrocyclopenta[c]pyrrole-2-carboxamide;
N-(2,4-difluorophenyl)-5-hydroxy-5-phenyl-octahydrocyclopenta[c]pyrrole-2-carboxamide;
N-[(1R)-1-(4-chlorophenyl)ethyl]-5-hydroxy-5-phenyl-octahydrocyclopenta[c]pyrrole-2-carboxamide;
5-hydroxy-N-[(2-methoxyphenyl)methyl]-5-phenyl-octahydrocyclopenta[c]pyrrole-2-carboxamide;
Methyl 4-(5-hydroxy-5-(o-tolyl)octahydrocyclopenta[c]pyrrole-2-carboxamido)benzoate;
5-hydroxy-N-(2-methoxy-5-methylphenyl)-5-(2-methylphenyl)-octahydrocyclopenta[c]pyrrole-2-carboxamide;
N-[4-chloro-3-(trifluoromethyl)phenyl]-5-hydroxy-5-(2-methylphenyl)-octahydrocyclopenta[c]pyrrole-2-carboxamide;
5-hydroxy-N,5-diphenyl-octahydrocyclopenta[c]pyrrole-2-carboxamide;
N-(3-cyanophenyl)-5-hydroxy-5-phenyl-octahydrocyclopenta[c]pyrrole-2-carboxamide;
5-hydroxy-N-(2-methoxy-5-methylphenyl)-5-phenyl-octahydrocyclopenta[c]pyrrole-2-carboxamide;
methyl 4-[({5-hydroxy-5-phenyl-octahydrocyclopenta[c]pyrrol-2-yl}carbonyl)amino]benzoate;
5-hydroxy-5-(3-methoxyphenyl)-N-phenyl-octahydrocyclopenta[c]pyrrole-2-carboxamide;
5-hydroxy-5-(2-methylphenyl)-N-phenyl-octahydrocyclopenta[c]pyrrole-2-carboxamide;
N-(3-cyanophenyl)-5-hydroxy-5-(2-methylphenyl)-octahydrocyclopenta[c]pyrrole-2-carboxamide;
N-[4-chloro-3-(trifluoromethyl)phenyl]-5-hydroxy-5-phenyl-octahydrocyclopenta[c]pyrrole-2-carboxamide;
5-hydroxy-N-(2-methoxy-5-methylphenyl)-5-(3-methoxyphenyl)-octahydrocyclopenta[c]pyrrole-2-carboxamide;
N-[4-chloro-3-(trifluoromethyl)phenyl]-5-hydroxy-5-(3-methoxyphenyl)-octahydrocyclopenta[c]pyrrole-2-carboxamide;
N,5-bis(4-fluorophenyl)-5-hydroxy-octahydrocyclopenta[c]pyrrole-2-carboxamide;
5-(4-fluorophenyl)-5-hydroxy-N-(4-methylphenyl)-octahydrocyclopenta[c]pyrrole-2-carboxamide;
5-(4-fluorophenyl)-5-hydroxy-N-(3-methoxyphenyl)-octahydrocyclopenta[c]pyrrole-2-carboxamide;
5-(4-fluorophenyl)-5-hydroxy-N-[3-(trifluoromethyl)phenyl]-octahydrocyclopenta[c]pyrrole-2-carboxamide;
N-(3-chlorophenyl)-5-(4-fluorophenyl)-5-hydroxy-octahydrocyclopenta[c]pyrrole-2-carboxamide;
N-(3-cyanophenyl)-5-(4-fluorophenyl)-5-hydroxy-octahydrocyclopenta[c]pyrrole-2-carboxamide;
5-(4-fluorophenyl)-5-hydroxy-N-(2-methoxy-5-methylphenyl)-octahydrocyclopenta[c]pyrrole-2-carboxamide;
N-[4-chloro-3-(trifluoromethyl)phenyl]-5-(4-fluorophenyl)-5-hydroxy-octahydrocyclopenta[c]pyrrole-2-carboxamide;
methyl 4-({[5-hydroxy-5-(3-methoxyphenyl)-octahydrocyclopenta[c]pyrrol-2-yl]carbonyl}amino)benzoate;
N-(2,4-dimethylphenyl)-5-hydroxy-5-phenyl-octahydrocyclopenta[c]pyrrole-2-carboxamide;
N-(2,4-dimethylphenyl)-5-hydroxy-5-(2-methylphenyl)-octahydrocyclopenta[c]pyrrole-2-carboxamide;
N-(2,4-dimethylphenyl)-5-hydroxy-5-(3-methoxyphenyl)-octahydrocyclopenta[c]pyrrole-2-carboxamide;
methyl 4-({[5-(4-tert-butylphenyl)-5-hydroxy-octahydrocyclopenta[c]pyrrol-2-yl]carbonyl}amino)benzoate;
5-(4-tert-butylphenyl)-5-hydroxy-N-(3-methoxyphenyl)-octahydrocyclopenta[c]pyrrole-2-carboxamide;
5-(4-tert-butylphenyl)-N-(3-cyanophenyl)-5-hydroxy-octahydrocyclopenta[c]pyrrole-2-carboxamide;
5-(4-tert-butylphenyl)-N-[4-chloro-3-(trifluoromethyl)phenyl]-5-hydroxy-octahydrocyclopenta[c]pyrrole-2-carboxamide;
5-(4-tert-butylphenyl)-5-hydroxy-N-phenyl-octahydrocyclopenta[c]pyrrole-2-carboxamide;
5-(4-tert-butylphenyl)-5-hydroxy-N-[3-(trifluoromethyl)phenyl]-octahydrocyclopenta[c]pyrrole-2-carboxamide;
5-(4-tert-butylphenyl)-N-(3-chlorophenyl)-5-hydroxy-octahydrocyclopenta[c]pyrrole-2-carboxamide;
2-(5-hydroxy-5-phenylhexahydrocyclopenta[c]pyrrol-2(1H)-yl)-1-phenylethanone;
rac-2-(2-hydroxy-2-phenylethyl)-5-phenyloctahydrocyclopenta[c]pyrrol-5-ol;
2-[5-hydroxy-5-(3-methoxyphenyl)-octahydrocyclopenta[c]pyrrol-2-yl]-1-phenylethan-1-one;
rac-2-(2-hydroxy-2-phenylethyl)-5-(3-methoxyphenyl)-octahydrocyclopenta[c]pyrrol-5-ol;
1-(3-fluorophenyl)-2-{5-hydroxy-5-phenyl-octahydrocyclopenta[c]pyrrol-2-yl}ethan-1-one;
1-(3-fluorophenyl)-2-[5-hydroxy-5-(3-methoxyphenyl)-octahydrocyclopenta[c]pyrrol-2-yl]ethan-1-one;
rac-2-[2-(3-fluorophenyl)-2-hydroxyethyl]-5-(3-methoxyphenyl)-octahydrocyclopenta[c]pyrrol-5-ol;
rac-2-[2-(3-fluorophenyl)-2-hydroxyethyl]-5-phenyl-octahydrocyclopenta[c]pyrrol-5-ol;
2-{5-hydroxy-5-phenyl-octahydrocyclopenta[c]pyrrol-2-yl}-1-(4-hydroxyphenyl)ethan-1-one;
2-{5-hydroxy-5-phenyl-octahydrocyclopenta[c]pyrrol-2-yl}-1-(4-methoxyphenyl)ethan-1-one;
rac-2-[2-hydroxy-2-(4-methoxyphenyl)ethyl]-5-phenyl-octahydrocyclopenta[c]pyrrol-5-ol;
rac-2-[2-hydroxy-2-(4-hydroxyphenyl)ethyl]-5-phenyl-octahydrocyclopenta[c]pyrrol-5-ol;
2-(5-hydroxy-5-phenylhexahydrocyclopenta[c]pyrrol-2(1H)-yl)-1-(4-(2-hydroxypropan-2-yl)phenyl)ethanone;
rac-2-(2-hydroxy-2-(4-(2-hydroxypropan-2-yl)phenyl)ethyl)-5-phenyloctahydrocyclopenta[c]pyrrol-5-ol;
rac-5-(4-(tert-butyl)phenyl)-2-(2-hydroxy-2-(3-(trifluoromethyl)phenyl)ethyl)octahydrocyclopenta[c]pyrrol-5-ol;
rac-5-(4-tert-butylphenyl)-2-[2-(3-fluorophenyl)-2-hydroxyethyl]-octahydrocyclopenta[c]pyrrol-5-ol;
rac-2-{2-hydroxy-2-[3-(trifluoromethyl)phenyl]ethyl}-5-(2-methylphenyl)-octahydrocyclopenta[c]pyrrol-5-ol;
rac-2-{2-hydroxy-2-[3-(trifluoromethyl)phenyl]ethyl}-5-(3-methoxyphenyl)-octahydrocyclopenta[c]pyrrol-5-ol;
rac-2-[2-(2,4-dichlorophenyl)-2-hydroxyethyl]-5-(3-methoxyphenyl)-octahydrocyclopenta[c]pyrrol-5-ol;
rac-5-(4-fluorophenyl)-2-{2-hydroxy-2-[3-(trifluoromethyl)phenyl]ethyl}-octahydrocyclopenta[c]pyrrol-5-ol;
rac-2-[2-(2,4-dichlorophenyl)-2-hydroxyethyl]-5-(4-fluorophenyl)-octahydrocyclopenta[c]pyrrol-5-ol;
rac-2-[2-hydroxy-2-(3-methoxyphenyl)ethyl]-5-(3-methoxyphenyl)-octahydrocyclopenta[c]pyrrol-5-ol;
rac-2-(1-hydroxy-1-(4-hydroxyphenyl)propan-2-yl)-5-(3-methoxyphenyl)octahydrocyclopenta[c]pyrrol-5-ol;

2-(4-fluorobenzyl)-5-(4-fluorophenyl)octahydrocyclopenta[c]pyrrol-5-ol;
rac-2-(5-hydroxy-5-phenylhexahydrocyclopenta[c]pyrrol-2(1H)-yl)-1-(4-hydroxyphenyl)propan-1-one;
rac-2-(1-hydroxy-1-(4-hydroxyphenyl)propan-2-yl)-5-phenyloctahydrocyclopenta[c]pyrrol-5-ol;
rac-2-[5-(4-fluorophenyl)-5-hydroxy-octahydrocyclopenta[c]pyrrol-2-yl]-1-(4-hydroxyphenyl)propan-1-one;
rac-2-[5-(4-tert-butylphenyl)-5-hydroxy-octahydrocyclopenta[c]pyrrol-2-yl]-1-(4-hydroxyphenyl)propan-1-one;
rac-2-[5-hydroxy-5-(2-methylphenyl)-octahydrocyclopenta[c]pyrrol-2-yl]-1-(4-hydroxyphenyl)propan-1-one;
rac-2-[1-hydroxy-1-(4-hydroxyphenyl)propan-2-yl]-5-(2-methylphenyl)-octahydrocyclopenta[c]pyrrol-5-ol;
rac-5-(4-tert-butylphenyl)-2-[1-hydroxy-1-(4-hydroxyphenyl)propan-2-yl]-octahydrocyclopenta[c]pyrrol-5-ol;
(5-hydroxy-5-phenylhexahydrocyclopenta[c]pyrrol-2(1H)-yl)(4-hydroxyphenyl)methanone;
3-(5-hydroxy-5-phenylhexahydrocyclopenta[c]pyrrol-2(1H)-yl)-1-(4-hydroxyphenyl)propan-1-one;
2-(3-hydroxy-3-(4-hydroxyphenyl)propyl)-5-phenyloctahydrocyclopenta[c]pyrrol-5-ol;
2N-(4-methoxyphenyl)-5-phenylhexahydrocyclopenta[c]pyrrole-2(1H)-carboxamide;
N-(4-hydroxyphenyl)-5-phenyl-octahydrocyclopenta[c]pyrrole-2-carboxamide;
N-(4-fluorophenyl)-5-phenyl-octahydrocyclopenta[c]pyrrole-2-carboxamide;
N,5-diphenyl-octahydrocyclopenta[c]pyrrole-2-carboxamide;
methyl 4-[({5-phenyl-octahydrocyclopenta[c]pyrrol-2-yl}carbonyl)amino]benzoate;
N-(3-methoxyphenyl)-5-phenyl-octahydrocyclopenta[c]pyrrole-2-carboxamide;
5-phenyl-N-[3-(trifluoromethyl)phenyl]-octahydrocyclopenta[c]pyrrole-2-carboxamide;
N-(3-chlorophenyl)-5-phenyl-octahydrocyclopenta[c]pyrrole-2-carboxamide;
N-(3-cyanophenyl)-5-phenyl-octahydrocyclopenta[c]pyrrole-2-carboxamide;
N-[4-chloro-3-(trifluoromethyl)phenyl]-5-phenyl-octahydrocyclopenta[c]pyrrole-2-carboxamide;
N-(2-methoxy-5-methylphenyl)-5-phenyl-octahydrocyclopenta[c]pyrrole-2-carboxamide;
N-(2,4-dimethylphenyl)-5-phenyl-octahydrocyclopenta[c]pyrrole-2-carboxamide;
N-[(2-methoxyphenyl)methyl]-5-phenyl-octahydrocyclopenta[c]pyrrole-2-carboxamide;
N-[(1R)-1-(4-chlorophenyl)ethyl]-5-phenyl-octahydrocyclopenta[c]pyrrole-2-carboxamide;
1-(4-hydroxyphenyl)-2-(5-phenylhexahydrocyclopenta[c]pyrrol-2(1H)-yl)ethanone;
4-(1-hydroxy-2-(5-phenylhexahydrocyclopenta[c]pyrrol-2(1H)-yl)ethyl)phenol;
rac-2-(5-phenylhexahydrocyclopenta[c]pyrrol-2(1H)-yl)-1-(3-(trifluoromethyl)phenyl)ethanol;
rac-1-(3-methoxyphenyl)-2-{5-phenyl-octahydrocyclopenta[c]pyrrol-2-yl}ethan-1-ol;
(3aR,5r,6aS)-5-benzyl-N-(3-chlorophenyl)-5-hydroxyhexahydrocyclopenta[c]pyrrole-2(1H)-carboxamide;
(3aR,5r,6aS)-5-benzyl-5-hydroxy-N-(3-methoxyphenyl)hexahydrocyclopenta[c]pyrrole-2(1H)-carboxamide;
(3aR,5r,6aS)-5-benzyl-N-(4-chloro-3-(trifluoromethyl)phenyl)-5-hydroxyhexahydrocyclopenta[c]pyrrole-2(1H)-carboxamide;
(3aR,5r,6aS)-5-benzyl-N-(2,4-dimethylphenyl)-5-hydroxyhexahydrocyclopenta[c]pyrrole-2(1H)-carboxamide;
(3aR,5r,6aS)-5-benzyl-5-hydroxy-N-phenylhexahydrocyclopenta[c]pyrrole-2(1H)-carboxamide;
(3aR,5r,6aS)-5-benzyl-N-(3-cyanophenyl)-5-hydroxyhexahydrocyclopenta[c]pyrrole-2(1H)-carboxamide;
(3aR,5r,6aS)-5-benzyl-5-hydroxy-N-(2-methoxy-5-methylphenyl)hexahydrocyclopenta[c]pyrrole-2(1H)-carboxamide;
(3aR,5r,6aS)-5-benzyl-5-hydroxy-N-(p-tolyl)hexahydrocyclopenta[c]pyrrole-2(1H)-carboxamide
(3aR,5r,6aS)-5-benzyl-5-hydroxy-N-(4-methoxyphenyl)hexahydrocyclopenta[c]pyrrole-2(1H)-carboxamide;
(3aR,5r,6aS)-5-benzyl-5-hydroxy-N-(2-(trifluoromethyl)phenyl)hexahydrocyclopenta[c]pyrrole-2(1H)-carboxamide;
(3aR,5r,6aS)-5-benzyl-5-hydroxy-N-(2-methoxyphenyl)hexahydrocyclopenta[c]pyrrole-2(1H)-carboxamide;
(3aR,5r,6aS)-5-benzyl-5-hydroxy-N-(m-tolyl)hexahydrocyclopenta[c]pyrrole-2(1H)-carboxamide;
2-((3aR,5r,6aS)-5-benzyl-5-hydroxyhexahydrocyclopenta[c]pyrrol-2(1H)-yl)-1-(4-hydroxyphenyl)ethanone;
rac-(3aR,5r,6aS)-5-benzyl-2-(2-hydroxy-2-(4-hydroxyphenyl)ethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(4-methoxyphenyl)ethanone;
3-((3aR,5r,6aS)-5-benzyl-5-hydroxyhexahydrocyclopenta[c]pyrrol-2(1H)-yl)-1-(4-hydroxyphenyl)propan-1-one;
2-((3aR,5r,6aS)-5-(4-fluorobenzyl)-5-hydroxyhexahydrocyclopenta[c]pyrrol-2(1H)-yl)-1-(4-hydroxyphenyl)ethanone;
rac-(3aR,5r,6aS)-5-(4-fluorobenzyl)-2-(2-hydroxy-2-(4-hydroxyphenyl)ethyl)octahydrocyclopenta[c]pyrrol-5-ol;
(3aR,5R,6aS)-5-benzyl-2-((R)-2-hydroxy-2-(4-hydroxyphenyl)ethyl)octahydrocyclopenta[c]pyrrol-5-ol;
(3aR,5S,6aS)-5-benzyl-2-((S)-2-hydroxy-2-(4-hydroxyphenyl)ethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(4-(2-hydroxypropan-2-yl)phenyl)ethanone;
rac-(3aR,5r,6aS)-5-benzyl-2-(2-hydroxy-2-(4-(2-hydroxypropan-2-yl)phenyl)ethyl)octahydrocyclopenta[c]pyrrol-5-ol;
N-(4-(2-((3aR,5r,6aS)-5-benzyl-5-hydroxyhexahydrocyclopenta[c]pyrrol-2(1H)-yl)acetyl)phenyl)acetamide;
(3aR,5R,6aS)-5-benzyl-2-((R)-2-hydroxy-2-(4-hydroxyphenyl)ethyl)octahydrocyclopenta[c]pyrrol-5-ol;
(3aR,5S,6aS)-5-benzyl-2-((S)-2-hydroxy-2-(4-hydroxyphenyl)ethyl)octahydrocyclopenta[c]pyrrol-5-ol;
1-((3aR,5r,6aS)-5-benzyl-5-hydroxyhexahydrocyclopenta[c]pyrrol-2(1H)-yl)-3-(4-hydroxyphenyl)propan-2-one;
N-(4-(2-((3aR,5r,6aS)-5-benzyl-5-hydroxyhexahydrocyclopenta[c]pyrrol-2(1H)-yl)acetyl)phenyl)methanesulfonamide;
rac-N-(4-(2-((3aR,5r,6aS)-5-benzyl-5-hydroxyhexahydrocyclopenta[c]pyrrol-2(1H)-yl)-1-hydroxyethyl)phenyl)acetamide;

rac-N-(4-(2-((3aR,5r,6aS)-5-benzyl-5-hydroxyhexahydrocyclopenta[c]pyrrol-2(1H)-yl)-1-hydroxyethyl)phenyl)methanesulfonamide;
2-((3aR,5r,6aS)-5-benzyl-5-hydroxyhexahydrocyclopenta[c]pyrrol-2(1H)-yl)-1-(3-fluoro-4-hydroxyphenyl)ethanone;
(3aR,5S,6aS)-5-benzyl-2-((S)-2-(3-fluoro-4-hydroxyphenyl)-2-hydroxyethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(3,5-difluoro-4-hydroxyphenyl)ethanone;
rac-(3aR,5r,6aS)-5-benzyl-2-(2-(3,5-difluoro-4-hydroxyphenyl)-2-hydroxyethyl)octahydrocyclopenta[c]pyrrol-5-ol;
1-(3-fluoro-4-hydroxyphenyl)-2-((3aR,5r,6aS)-5-(4-fluorobenzyl)-5-hydroxyhexahydrocyclopenta[c]pyrrol-2(1H)-yl)ethanone;
2-((3aR,5r,6aS)-5-benzyl-5-methoxyhexahydrocyclopenta[c]pyrrol-2(1H)-yl)-1-(3-fluoro-4-hydroxyphenyl)ethanone;
rac-(3aR,5r,6aS)-2-(2-(3-fluoro-4-hydroxyphenyl)-2-hydroxyethyl)-5-(4-fluorobenzyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(3-fluoro-4-(2-(3-fluoro-4-hydroxyphenyl)-2-oxoethoxy)phenyl)ethanone;
2-(2-fluoro-4-(2-((3aR,5r,6aS)-5-(4-fluorobenzyl)-5-hydroxyhexahydrocyclopenta[c]pyrrol-2(1H)-yl)acetyl)phenoxy)-1-(3-fluoro-4-hydroxyphenyl)ethanone;
2-((3aR,5r,6aS)-5-benzyl-5-methoxyhexahydrocyclopenta[c]pyrrol-2(1H)-yl)-1-(4-hydroxyphenyl)ethanone;
rac-4-(2-((3aR,5r,6aS)-5-benzyl-5-methoxyhexahydrocyclopenta[c]pyrrol-2(1H)-yl)-1-hydroxyethyl)-2-fluorophenol;
rac-4-(2-((3aR,5r,6aS)-5-benzyl-5-methoxyhexahydrocyclopenta[c]pyrrol-2(1H)-yl)-1-hydroxyethyl)phenol;
2-((3aR,5r,6aS)-5-hydroxy-5-(4-methylbenzyl)hexahydrocyclopenta[c]pyrrol-2(1H)-yl)-1-(4-hydroxyphenyl)ethanone;
(3aR,5R,6aS)-5-benzyl-2-((R)-2-(3-fluoro-4-hydroxyphenyl)-2-hydroxyethyl)octahydrocyclopenta[c]pyrrol-5-ol;
(3aR,5S,6aS)-5-benzyl-2-((S)-2-(3-fluoro-4-hydroxyphenyl)-2-hydroxyethyl)octahydrocyclopenta[c]pyrrol-5-ol;
rac-(3aR,5R,6aS)-2-[2-hydroxy-2-(4-hydroxyphenyl)ethyl]-5-[(4-methylphenyl)methyl]-octahydrocyclopenta[c]pyrrol-5-ol;
2-((3aR,5r,6aS)-5-hydroxy-5-(2-methylbenzyl)hexahydrocyclopenta[c]pyrrol-2(1H)-yl)-1-(4-hydroxyphenyl)ethanone;
2-[(3aR,5R,6aS)-5-hydroxy-5-[(4-methoxyphenyl)methyl]-octahydrocyclopenta[c]pyrrol-2-yl]-1-(4-hydroxyphenyl)ethan-1-one;
rac-(3aR,5r,6aS)-2-(2-hydroxy-2-(4-hydroxyphenyl)ethyl)-5-(2-methylbenzyl)octahydrocyclopenta[c]pyrrol-5-ol;
rac-(3aR,5r,6aS)-2-(2-hydroxy-2-(4-hydroxyphenyl)ethyl)-5-(4-methoxybenzyl)octahydrocyclopenta[c]pyrrol-5-ol;
2-((3aR,5r,6aS)-5-hydroxy-5-(3-methoxybenzyl)hexahydrocyclopenta[c]pyrrol-2(1H)-yl)-1-(4-hydroxyphenyl)ethanone;
rac-(3aR,5r,6aS)-2-(2-hydroxy-2-(4-hydroxyphenyl)ethyl)-5-(3-methoxybenzyl)octahydrocyclopenta[c]pyrrol-5-ol;
2-[(3aR,5R,6aS)-5-(cyclohexylmethyl)-5-hydroxy-octahydrocyclopenta[c]pyrrol-2-yl]-1-(4-hydroxyphenyl)ethan-1-one;
rac-(3aR,5R,6aS)-5-(cyclohexylmethyl)-2-[2-hydroxy-2-(4-hydroxyphenyl)ethyl]-octahydrocyclopenta[c]pyrrol-5-ol;
2-((3aR,5r,6aS)-5-(cyclopropylmethyl)-5-hydroxyhexahydrocyclopenta[c]pyrrol-2(1H)-yl)-1-(4-hydroxyphenyl)ethanone;
rac-(3aR,5r,6aS)-5-(cyclopropylmethyl)-2-(2-hydroxy-2-(4-hydroxyphenyl)ethyl)octahydrocyclopenta[c]pyrrol-5-ol;
2-[(3aR,5R,6aS)-5-[(3,5-dimethylphenyl)methyl]-5-hydroxy-octahydrocyclopenta[c]pyrrol-2-yl]-1-(4-hydroxyphenyl)ethan-1-one;
rac-(3aR,5R,6aS)-5-[(3,5-dimethylphenyl)methyl]-2-[2-hydroxy-2-(4-hydroxyphenyl)ethyl]-octahydrocyclopenta[c]pyrrol-5-ol;
2-[(3aR,5R,6aS)-5-hydroxy-5-{[4-(trifluoromethyl)phenyl]methyl}-octahydrocyclopenta[c]pyrrol-2-yl]-1-(4-hydroxyphenyl)ethan-1-one;
rac-(3aR,5R,6aS)-2-[2-hydroxy-2-(4-hydroxyphenyl)ethyl]-5-{[4-(trifluoromethyl)phenyl]methyl}-octahydrocyclopenta[c]pyrrol-5-ol;
2-((3aR,5r,6aS)-5-(2-fluorobenzyl)-5-hydroxyhexahydrocyclopenta[c]pyrrol-2(1H)-yl)-1-(4-hydroxyphenyl)ethanone;
rac-(3aR,5r,6aS)-5-(2-fluorobenzyl)-2-(2-hydroxy-2-(4-hydroxyphenyl)ethyl)octahydrocyclopenta[c]pyrrol-5-ol;
2-(5-(2,4-difluorobenzyl)-5-hydroxyhexahydrocyclopenta[c]pyrrol-2(1H)-yl)-1-(4-hydroxyphenyl)ethanone;
2-[(3aR,5R,6aS)-5-[(2,6-difluorophenyl)methyl]-5-hydroxy-octahydrocyclopenta[c]pyrrol-2-yl]-1-(4-hydroxyphenyl)ethan-1-one;
rac-5-(2,4-difluorobenzyl)-2-(2-hydroxy-2-(4-hydroxyphenyl)ethyl)octahydrocyclopenta[c]pyrrol-5-ol;
2-((3aR,5r,6aS)-5-(2,3-difluorobenzyl)-5-hydroxyhexahydrocyclopenta[c]pyrrol-2(1H)-yl)-1-(4-hydroxyphenyl)ethanone;
2-((3aR,5r,6aS)-5-(4-fluoro-2-methylbenzyl)-5-hydroxyhexahydrocyclopenta[c]pyrrol-2(1H)-yl)-1-(4-hydroxyphenyl)ethanone;
2-((3aR,5r,6aS)-5-(3,4-difluorobenzyl)-5-hydroxyhexahydrocyclopenta[c]pyrrol-2(1H)-yl)-1-(4-hydroxyphenyl)ethanone;
rac-(3aR,5r,6aS)-5-(3,4-difluorobenzyl)-2-(2-hydroxy-2-(4-hydroxyphenyl)ethyl)octahydrocyclopenta[c]pyrrol-5-ol;
rac-(3aR,5r,6aS)-5-(4-fluoro-2-methylbenzyl)-2-(2-hydroxy-2-(4-hydroxyphenyl)ethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(4'-hydroxy-[1,1'-biphenyl]-4-yl)ethanone;
1-([1,1'-biphenyl]-4-yl)-2-((3aR,5r,6aS)-5-benzyl-5-hydroxyhexahydrocyclopenta[c]pyrrol-2(1H)-yl)ethanone;
2-((3aR,5r,6aS)-5-benzyl-5-hydroxyhexahydrocyclopenta[c]pyrrol-2(1H)-yl)-1-(4'-methoxy-[1,1'-biphenyl]-4-yl)ethanone;

2-((3aR,5r,6aS)-5-benzyl-5-hydroxyhexahydrocyclopenta[c]pyrrol-2(1H)-yl)-1-(2'-methyl-[1,1'-biphenyl]-4-yl)ethanone;
2-((3aR,5r,6aS)-5-benzyl-5-hydroxyhexahydrocyclopenta[c]pyrrol-2(1H)-yl)-1-(3'-fluoro-[1,1'-biphenyl]-4-yl)ethanone;
2-((3aR,5r,6aS)-5-benzyl-5-hydroxyhexahydrocyclopenta[c]pyrrol-2(1H)-yl)-1-(4'-fluoro-[1,1'-biphenyl]-4-yl)ethanone;
2-((3aR,5r,6aS)-5-benzyl-5-hydroxyhexahydrocyclopenta[c]pyrrol-2(1H)-yl)-1-(4'-methoxy-[1,1'-biphenyl]-3-yl)ethanone;
2-((3aR,5r,6aS)-5-benzyl-5-hydroxyhexahydrocyclopenta[c]pyrrol-2(1H)-yl)-1-(3'-methyl-[1,1'-biphenyl]-4-yl)ethanone;
2-((3aR,5r,6aS)-5-benzyl-5-hydroxyhexahydrocyclopenta[c]pyrrol-2(1H)-yl)-1-(3'-methoxy-[1,1'-biphenyl]-4-yl)ethanone;
1-([1,1'-biphenyl]-3-yl)-2-((3aR,5r,6aS)-5-benzyl-5-hydroxyhexahydrocyclopenta[c]pyrrol-2(1H)-yl)ethanone;
2-[5-hydroxy-5-(2-phenylethyl)-octahydrocyclopenta[c]pyrrol-2-yl]-1-(4-phenylphenyl)ethan-1-one;
1-[4-(3-fluorophenyl)phenyl]-2-[5-hydroxy-5-(2-phenylethyl)-octahydrocyclopenta[c]pyrrol-2-yl]ethan-1-one;
2-((3aR,5r,6aS)-5-benzyl-5-hydroxyhexahydrocyclopenta[c]pyrrol-2(1H)-yl)-1-(3'-fluoro-[1,1'-biphenyl]-3-yl)ethanone;
2-((3aR,5r,6aS)-5-benzyl-5-hydroxyhexahydrocyclopenta[c]pyrrol-2(1H)-yl)-1-(3'-methoxy-[1,1'-biphenyl]-3-yl)ethanone;
2-((3aR,5r,6aS)-5-benzyl-5-hydroxyhexahydrocyclopenta[c]pyrrol-2(1H)-yl)-1-(4'-fluoro-[1,1'-biphenyl]-3-yl)ethanone;
2-((3aR,5r,6aS)-5-benzyl-5-hydroxyhexahydrocyclopenta[c]pyrrol-2(1H)-yl)-1-(4'-hydroxy-[1,1'-biphenyl]-3-yl)ethanone;
2-((3aR,5r,6aS)-5-benzyl-5-hydroxyhexahydrocyclopenta[c]pyrrol-2(1H)-yl)-1-(3'-methyl-[1,1'-biphenyl]-3-yl)ethanone;
2-[5-hydroxy-5-(2-phenylethyl)-octahydrocyclopenta[c]pyrrol-2-yl]-1-[4-(3-methylphenyl)phenyl]ethan-1-one;
2-((3aR,5r,6aS)-5-benzyl-5-hydroxyhexahydrocyclopenta[c]pyrrol-2(1H)-yl)-1-(2'-methyl-[1,1'-biphenyl]-3-yl)ethanone;
rac-(3aR,5R,6aS)-5-benzyl-2-[2-hydroxy-2-(4-hydroxyphenyl)propyl]-octahydrocyclopenta[c]pyrrol-5-ol;
deuterated rac-(3aR,6aS)-5-benzyl-2-((S)-2-hydroxy-2-(4-hydroxyphenyl)ethyl)octahydrocyclopenta[c]pyrrol-5-ol;
rac-(3aR,5r,6aS)-5-benzyl-2-(2-(2,4-dichlorophenyl)-2-hydroxyethyl)octahydrocyclopenta[c]pyrrol-5-ol;
rac-(3aR,5r,6aS)-5-benzyl-2-(2-hydroxy-2-(3-(trifluoromethyl)phenyl)ethyl)octahydrocyclopenta[c]pyrrol-5-ol;
rac-(3aR,5r,6aS)-5-benzyl-2-(2-(4-fluorophenyl)-2-hydroxyethyl)octahydrocyclopenta[c]pyrrol-5-ol;
2-((3aR,5r,6aS)-5-benzyl-5-hydroxyhexahydrocyclopenta[c]pyrrol-2(1H)-yl)-1-(4-hydroxyphenyl)ethanone;
(3aR,5R,6aS)-5-benzyl-2-((R)-2-hydroxy-2-(4-hydroxyphenyl)ethyl)octahydrocyclopenta[c]pyrrol-5-ol;
(3aR,5S,6aS)-5-benzyl-2-((S)-2-hydroxy-2-(4-hydroxyphenyl)ethyl)octahydrocyclopenta[c]pyrrol-5-ol;
rac-2-((3aR,5r,6aS)-5-benzyl-5-hydroxyhexahydrocyclopenta[c]pyrrol-2(1H)-yl)-1-(4-hydroxyphenyl)propan-1-one;
(3aR,6aS)-5-benzyl-N-(3-methoxyphenyl)hexahydrocyclopenta[c]pyrrole-2(1H)-carboxamide;
2-((3aR,6aS)-5-benzylhexahydrocyclopenta[c]pyrrol-2(1H)-yl)-1-(4-hydroxyphenyl)ethanone;
rac-2-((3aR,6aS)-5-benzylhexahydrocyclopenta[c]pyrrol-2(1H)-yl)-1-(4-hydroxyphenyl)propan-1-one;
2-{5-benzyl-octahydrocyclopenta[c]pyrrol-2-yl}-1-(3-fluoro-4-hydroxyphenyl)ethan-1-one;
rac-4-(2-((3aR,6aS)-5-benzylhexahydrocyclopenta[c]pyrrol-2(1H)-yl)-1-hydroxyethyl)phenol;
rac-4-{2-[(3aR,5S,6aS)-5-benzyl-octahydrocyclopenta[c]pyrrol-2-yl]-1-hydroxyethyl}-2-fluorophenol;
rac-4-{2-[(3aR,5R,6aS)-5-benzyl-octahydrocyclopenta[c]pyrrol-2-yl]-1-hydroxyethyl}-2-fluorophenol;
2-[(3aR,5S,6aS)-5-benzyl-octahydrocyclopenta[c]pyrrol-2-yl]-1-(4-hydroxyphenyl)ethan-1-onefluorophenol;
rac-4-{2-[(3aR,5S,6aS)-5-benzyl-octahydrocyclopenta[c]pyrrol-2-yl]-1-hydroxyethyl}phenol;
2-[(3aR,5R,6aS)-5-benzyl-octahydrocyclopenta[c]pyrrol-2-yl]-1-(4-hydroxyphenyl)ethan-1-one;
rac-4-{2-[(3aR,5R,6aS)-5-benzyl-octahydrocyclopenta[c]pyrrol-2-yl]-1-hydroxyethyl}phenol;
2-[(3aR,5S,6aS)-5-benzyl-octahydrocyclopenta[c]pyrrol-2-yl]-1-(3-fluoro-4-hydroxyphenyl)ethan-1-one;
2-[(3aR,5R,6aS)-5-benzyl-octahydrocyclopenta[c]pyrrol-2-yl]-1-(3-fluoro-4-hydroxyphenyl)ethan-1-one;
rac-2-((3aR,6aS)-5-benzylhexahydrocyclopenta[c]pyrrol-2(1H)-yl)-1-(3-(trifluoromethyl)phenyl)ethanol;
2-((3aR,5s,6aS)-5-benzyl-5-fluorohexahydrocyclopenta[c]pyrrol-2(1H)-yl)-1-(4-hydroxyphenyl)ethanone;
rac-4-(2-((3aR,5s,6aS)-5-benzyl-5-fluorohexahydrocyclopenta[c]pyrrol-2(1H)-yl)-1-hydroxyethyl)phenol;
4-(2-((3aR,5s,6aS)-5-benzyl-5-fluorohexahydrocyclopenta[c]pyrrol-2(1H)-yl)-1-hydroxyethyl)phenol;
rac-4-(2-((3aR,5r,6aS)-5-benzyl-5-fluorohexahydrocyclopenta[c]pyrrol-2(1H)-yl)-1-hydroxyethyl)phenol;
4-((R)-2-((3aR,5S,6aS)-5-benzyl-5-fluorohexahydrocyclopenta[c]pyrrol-2(1H)-yl)-1-hydroxyethyl)phenol;
4-((S)-2-((3aR,5R,6aS)-5-benzyl-5-fluorohexahydrocyclopenta[c]pyrrol-2(1H)-yl)-1-hydroxyethyl)phenol;
rac-4-(2-((3aR,5s,6aS)-5-benzyl-5-fluorohexahydrocyclopenta[c]pyrrol-2(1H)-yl)-1-hydroxyethyl)-2-fluorophenol;
rac-2-((3aR,5s,6aS)-5-benzyl-5-fluorohexahydrocyclopenta[c]pyrrol-2(1H)-yl)-1-(4-hydroxyphenyl)propan-1-one;
rac-4-(2-((3aR,5s,6aS)-5-benzyl-5-fluorohexahydrocyclopenta[c]pyrrol-2(1H)-yl)-1-hydroxypropyl)phenol;
rac-2-(5-hydroxy-5-phenethylhexahydrocyclopenta[c]pyrrol-2(1H)-yl)-1-(4-hydroxyphenyl)propan-1-one;
rac-2-(1-hydroxy-1-(4-hydroxyphenyl)propan-2-yl)-5-phenethyloctahydrocyclopenta[c]pyrrol-5-ol;
rac-2-(2-hydroxy-2-(4-hydroxyphenyl)ethyl)-5-phenethyloctahydrocyclopenta[c]pyrrol-5-ol;
rac-1-(4-hydroxyphenyl)-2-[(5R)-5-(2-phenylethyl)-octahydrocyclopenta[c]pyrrol-2-yl]propan-1-one;
1-(4-hydroxyphenyl)-2-(5-phenethylhexahydrocyclopenta[c]pyrrol-2(1H)-yl)ethanone;
1-(4-hydroxyphenyl)-2-((3aR,5r,6aS)-5-phenethylhexahydrocyclopenta[c]pyrrol-2(1H)-yl)ethanone; and
1-(4-hydroxyphenyl)-2-((3aR,5r,6aS)-5-phenethylhexahydrocyclopenta[c]pyrrol-2(1H)-yl)propan-1-one.

18. A pharmaceutical composition comprising a compound of claim 1 or a pharmaceutically acceptable salt thereof.

* * * * *